US012708638B2

(12) United States Patent
Hermans et al.

(10) Patent No.: US 12,708,638 B2
(45) Date of Patent: Aug. 18, 2026

(54) SEMICARBAZONE-BASED SAPONIN CONJUGATE

(71) Applicant: SAPREME TECHNOLOGIES B.V., Bilthoven (NL)

(72) Inventors: Guy Hermans, Bilthoven (NL); Ruben Postel, Bilthoven (NL); Helmus Van De Langemheen, Putten (NL); Mazdak Asadian Birjand, Berlin (DE)

(73) Assignee: Sapreme Technologies B.V., Bilthoven (NL)

( * ) Notice: Subject to any disclaimer, the term of this patent is extended or adjusted under 35 U.S.C. 154(b) by 436 days.

(21) Appl. No.: 18/044,950

(22) PCT Filed: Sep. 9, 2021

(86) PCT No.: PCT/NL2021/050550

§ 371 (c)(1),
(2) Date: Mar. 10, 2023

(87) PCT Pub. No.: WO2022/055352

PCT Pub. Date: Mar. 17, 2022

(65) Prior Publication Data

US 2024/0066045 A1 Feb. 29, 2024

(30) Foreign Application Priority Data

Sep. 10, 2020 (NL) .................................... 2026442
Jan. 26, 2021 (NL) .................................... 2027405

(51) Int. Cl.
*A61K 31/7034* (2006.01)
*A61K 47/68* (2017.01)
*A61P 3/06* (2006.01)
*A61P 35/00* (2006.01)

(52) U.S. Cl.
CPC ...... *A61K 31/7034* (2013.01); *A61K 47/6803* (2017.08); *A61P 3/06* (2018.01); *A61P 35/00* (2018.01); *A61K 2121/00* (2013.01)

(58) Field of Classification Search
CPC . A61K 31/7034; A61K 47/554; C07H 15/256
See application file for complete search history.

(56) References Cited

U.S. PATENT DOCUMENTS 5,856,571 A 1/1999 Berninger et al.

FOREIGN PATENT DOCUMENTS

| | | | |
|---|---|---|---|
| CN | 103102385 | A | 5/2013 |
| CN | 111690033 | A | 9/2020 |
| CN | 112209988 | A | 1/2021 |
| WO | WO 1993/05789 | A1 | 4/1993 |
| WO | WO 1996/40263 | A2 | 12/1996 |
| WO | WO 2011/054811 | A1 | 5/2011 |
| WO | WO 2015/071388 | A1 | 5/2015 |
| WO | WO 2015/113922 | A1 | 8/2015 |
| WO | WO 2020/126064 | A1 | 6/2020 |
| WO | WO 2020/126600 | A1 | 6/2020 |
| WO | WO 2020/126604 | A1 | 6/2020 |
| WO | WO 2020/126609 | A2 | 6/2020 |
| WO | WO 2020/126610 | A1 | 6/2020 |
| WO | WO 2020/126620 | A2 | 6/2020 |
| WO | WO 2020/126626 | A1 | 6/2020 |
| WO | WO 2020/126627 | A1 | 6/2020 |
| WO | WO 2020/126609 | A3 | 8/2020 |
| WO | WO 2020/126610 | A9 | 9/2020 |
| WO | WO 2021/014019 | A1 | 1/2021 |
| WO | WO 2021/014026 | A2 | 1/2021 |
| WO | WO 2021/014026 | A3 | 3/2021 |
| WO | WO 2021/259506 | A1 | 12/2021 |
| WO | WO 2021/259507 | A1 | 12/2021 |
| WO | WO 2021/259508 | A1 | 12/2021 |

(Continued)

OTHER PUBLICATIONS

Bachran, C. et al. "Saponins in Tumor Therapy," Mini Reviews in Medicinal Chemistry, vol. 8, No. 6, Jun. 1, 2008, pp. 575-584.
Elliott, D. et al. Sapogenins. Part VII "The structure of quillaic acid and its relation to echinocystic acid," Journal of the Chemical Society, Jan. 1, 1940, pp. 612-617.
Emirdağ-Öztürk, S. et al. "Synthesis, antimicrobial and cytotoxic activities, and structure-activity relationships of gypsogenin derivatives against human cancer cells," European Journal of Medicinal Chemistry, vol. 82, Jul. 2014, pp. 565-573.

(Continued)

*Primary Examiner* — Layla D Berry
(74) *Attorney, Agent, or Firm* — Ipsilon USA—NLO

(57) ABSTRACT

The invention relates to a saponin derivative based on a saponin comprising a triterpene aglycone and at least one of a first saccharide chain and a second saccharide chain linked to the aglycone core structure, wherein the saponin derivative comprises an aglycone core structure comprising an aldehyde functional group which has been transformed to a semicarbazone functional group. The invention also relates to a first pharmaceutical composition comprising the saponin derivative of the invention. In addition, the invention relates to a pharmaceutical combination comprising the first pharmaceutical composition of the invention and a second pharmaceutical composition comprising for example an ADC or a GalNAc-oligonucleotide conjugate. The invention also relates to the first pharmaceutical composition or the pharmaceutical combination of the invention, for use as a medicament, or use in the treatment or prophylaxis of a cancer or an auto-immune disease, a cardiovascular disease or hypercholesterolemia, or in a method for lowering LDL-cholesterol in the circulation of a subject. The invention also relates to a saponin conjugate comprising a proteinaceous molecule, capable of binding to a cell, and optionally comprising an effector moiety such as an oligonucleotide. The invention also relates to a saponin conjugate comprising GalNAc and an oligonucleotide.

11 Claims, 77 Drawing Sheets

Specification includes a Sequence Listing.

(56) References Cited

FOREIGN PATENT DOCUMENTS

| | | | |
|---|---|---|---|
| WO | WO 2021/259925 | A1 | 12/2021 |
| WO | WO 2021/259928 | A2 | 12/2021 |
| WO | WO 2021/259944 | A1 | 12/2021 |
| WO | WO 2021/260054 | A2 | 12/2021 |
| WO | WO 2021/260061 | A2 | 12/2021 |
| WO | WO 2021/261992 | A1 | 12/2021 |
| WO | WO 2021/261995 | A1 | 12/2021 |
| WO | WO 2021/261996 | A2 | 12/2021 |
| WO | WO 2021/261998 | A1 | 12/2021 |

OTHER PUBLICATIONS

Emirdağ-Öztürk, S. et al. Synthesis, characterization, and in vitro anti-neoplastic activity of gypsogenin derivatives. Bio-organic Chemistry, vol. 53, Apr. 2014, pp. 15-23.

Fuchs, H. et al. "Glycosylated triterpenoids as endosomal escape enhancers in targeted tumor therapies," Biomedicines, vol. 5, No. 2, Mar. 29, 2017, 25 pages.

Gilabert-Oriol, R et al. "Modified trastuzumab and cetuximab mediate efficient toxin delivery while retaining antibody-dependent cell-mediated cytotoxicity in target cells," Molecular Pharmaceutics, vol. 10, No. 11, Nov. 4, 2013, pp. 4347-4357.

PCT International Search Report and Written Opinion, PCT Application No. PCT/NL2021/050550, Jan. 25, 2022, 16 pages.

Ruzicka, L. et al. "Polyterpene und Polyterpenoide CXX. Umwandlung der Oleanolsäure in beta-Amyrin und Erythro-diol," Helvetica Chimica Acta, vol. 20, No. 1, Jan. 1, 1937, pp. 1553-1556.

Ruzicka, L. et al. "Zur Kenntnis der Triterpene: Bereitung des epi-β-Amyrins aus α-Boswellinsäure und aus β-Amyron," Helvetica Chimica Acta, vol. 24, No. 1, 1941, 248-252.

Sewing, S. et al. "GalNAc Conjugation Attenuates the Cytotoxicity of Antisense Oligonucleotide Drugs in Renal Tubular Cells." Molecular Therapy: Nucleic Acids, vol. 14, No. 1, Mar. 2019, pp. 67-79.

Weng, A. et al. "The toxin component of targeted anti-tumor toxins determines their efficacy increase by saponins," Molecular Oncology, vol. 6, No. 3, Jun. 2012, pp. 323-332.

Xu, R. et al. "On the origins of triterpenoid skeletal diversity." Phytochemistry, vol. 65, No. 3, Feb. 2004, pp. 261-291.

Yu, B. et al. "Antibody-drug conjugates in clinical trials for lymphoid malignancies and multiple myeloma," Journal of Hematology & Oncology, vol. 12, No. 94, Dec. 2019, pp. 1-17.

Morpholine-4-carbohydrazide

1-Cbz-piperazine intermediate 1 intermediate 2 intermediate 2

6-maleimidocaproic acid intermediate 3

2-mercaptoethanol

A

B

A

B

A

B

A

B

A

B

A

B

A

B

A

B

A

B

C

A

B

C

B

Intermediate 5

Intermediate 6

D

Intermediate 7

=

1
2
3
Intermediate 1
4
Trifunctional linker
3
5
Intermediate 2

6

7

Intermediate 3

8

5

8

9

Intermediate 4

10

11

12

Intermediate 5

9

12

13

TFL-(L-hydrazone-SO1861)-(L-BNA)-(trivalent GalNAc)

1

14

15

Intermediate 6

16

15

Intermediate 7

17

17

18

19

Intermediate 8

Trifunctional linker

4

8

Intermediate 9

20

20

12

Intermediate 10

21

TFL-(dendron(L-hydrazone-SO1861)4)-(L-BNA)-(trivalent GalNAc)

22

E (continued)

21

19

23

24

Intermediate 12

25

B (continued)

18

24

TFL-(dendron(L-hydrazone-SO1861)8)-(L-BNA)-(trivalent GalNAc)

26

C (continued)

21

25

27

28

29

4

TFL-(L-semicarbazone-SO1861)-(L-BNA)-(trivalent GalNAc)

30

12

31

Intermediate 16
Intermediate 17
Intermediate 18
Intermediate 19
32
33
34
35
36
36
37
1
=

38

37

Intermediate 20

39

39

18

Intermediate 21

40

Intermediate 3

8

Intermediate 22

41

Trifunctional linker

4

41

Intermediate 23

20

Intermediate 24

E (continued)

40

20

TFL-(dendron(L-hydrazone-SO1861)4)-(L-BNA)-(trivalent GalNAc)

12

41

42

Intermediate 25

44

A (continued)

43

37

Intermediate 26

45

B (continued)

18

44

Intermediate 27

46

C (continued)

45

20

TFL-(dendron(L-hydrazone-SO1861)8)-(L-BNA)-(trivalent GalNAc)

12

47

48

49

Intermediate 28

50

50

3

20

Trivalent linker-(L-SPT001)-(blocked TCO)-(trivalent GalNAc)

51

20

57

Intermediate 29

58

58

12

59

Trivalent linker-(blocked DBCO)-(L-BNA oligo)-(trivalent GalNAc)

Hydrazone linker

Semicarbazone linker 13, 13a, 51

22, 22a, 52

26, 26a, 53

59, 59a 31, 31a, 54

42, 42a, 55

47, 47a, 56

13, 22. 26, 31, 42, 47, 59

13a, 22a,, 26a, 31a, 42a, 47a. 59a 51, 52, 53, 54, 55, 56

Trifunctional linker

4

Targeting ligand

41

Effector

12

Enhancers

Hydrazone linker

3

19

25

Semicarbazone linker

28

40

45

Blocking agents for controls

5

50

12a

SEMICARBAZONE-BASED SAPONIN CONJUGATE

CROSS-REFERENCE TO RELATED APPLICATIONS

This application is the National Stage of International Application No. PCT/NL2021/050550, filed on Sep. 9, 2021, which claims the benefit of and priority to Netherlands Patent Application No. 2026442, filed on Sep. 10, 2020; and Netherlands Patent Application No. 2027405, filed on Jan. 26, 2021, the contents of which are incorporated by reference in their entirety.

SEQUENCE LISTING

The instant application contains a Sequence Listing which has been submitted electronically and is hereby incorporated by reference in its entirety. Said ASCII copy, created on Mar. 9, 2023, is named 55041_US_CRF_Sequence_Listing.txt, and is 4,688 bytes in size.

TECHNOLOGICAL FIELD

The invention relates to a saponin derivative based on a saponin comprising a triterpene aglycone and at least one saccharide chain linked to the aglycone core structure, wherein the saponin derivative comprises an aglycone core structure comprising an aldehyde functional group which has been transformed to a semicarbazone functional group. The invention also relates to a first pharmaceutical composition comprising the saponin derivative of the invention. In addition, the invention relates to a pharmaceutical combination comprising the first pharmaceutical composition of the invention and a second pharmaceutical composition comprising a conjugate of a cell-surface molecule binding-molecule and an effector moiety, such as any one or more of an antibody-effector moiety conjugate, an receptor-ligand-effector moiety conjugate, an antibody-toxin conjugate, a receptor-ligand-toxin conjugate, an antibody-drug conjugate, a receptor-ligand-drug conjugate, an antibody-nucleic acid conjugate or a receptor-ligand-nucleic acid conjugate (such as a receptor-ligand-oligonucleotide conjugate, wherein for example the oligonucleotide is an AON such as a BNA or an siRNA, and wherein the receptor ligand is for example EGF or at least one GalNAc moiety). The invention also relates to the first pharmaceutical composition or the therapeutic combination comprising the first pharmaceutical composition of the invention, for use as a medicament, or for use in the treatment or prophylaxis of a cancer or an auto-immune disease or a cardiovascular disease or hypercholesterolemia, or for use in a method for decreasing the level of LDL, preferably LDL-cholesterol, in the blood of a subject. Furthermore, the invention relates to an in vitro or ex vivo method for transferring a molecule such as an effector molecule or, when part of a conjugate, an effector moiety, from outside a cell to inside said cell, comprising contacting said cell with the molecule and with a saponin derivative of the invention. The invention also relates to a saponin conjugate comprising a cell-surface molecule binding-molecule such as a proteinaceous molecule or a non-proteinaceous molecule such as a receptor ligand such as at least one GalNAc moiety, capable of binding to said cell, covalently bound to the saponin, wherein the saponin conjugate is based on the saponin derivative of the invention. The invention also relates to a pharmaceutical combination comprising a third pharmaceutical composition comprising the saponin conjugate of the invention and a fourth pharmaceutical composition comprising an active pharmaceutical ingredient such as a conjugate of a cell-surface molecule binding-molecule and an effector moiety, for example an ADC or an AOC or a conjugate of a receptor ligand, such as at least one GalNAc moiety, and an oligonucleotide, or the invention also relates to a pharmaceutical composition comprising the saponin conjugate of the invention and a conjugate of a cell-surface molecule binding-molecule and an effector moiety such as a conjugate of a receptor ligand, such as at least one GalNAc moiety, and an oligonucleotide. In addition, the invention relates to the pharmaceutical combination of the invention or the pharmaceutical composition of the invention, for use as a medicament, or for use in the treatment or the prophylaxis of a cancer or an auto-immune disease or a cardiovascular disease or hypercholesterolemia, or for use in a method for decreasing the level of LDL-cholesterol in the blood of a subject. The invention also relates to a saponin derivative in which at least one GalNAc moiety, an oligonucleotide and at least one saponin molecule are covalently bound together, wherein the saponin derivative is based on a saponin comprising a triterpene aglycone and at least one saccharide chain linked to the aglycone core structure, wherein the saponin derivative comprises an aglycone core structure comprising an aldehyde functional group which has been transformed to a semicarbazone functional group (also referred to as 'semicarbazone bond'). An aspect of the invention relates to the saponin derivative encompassing GalNAc, an oligonucleotide and one or more saponin moieties, for use as a medicament or for use in a method for the treatment or prophylaxis of a cardiovascular disease or hypercholesterolemia, or for use in a method for lowering LDL-cholesterol in the blood of a subject.

BACKGROUND OF THE INVENTION

Targeted tumor therapy is a cancer treatment that uses drugs to target specific genes and proteins that are involved in the growth and survival of cancer cells. Immunotoxins, which are targeted toxins that contain an antibody as targeting moiety, are very promising because they combine the specificity of an antibody against tumor-specific antigens, which enables them to channel the toxin to the aimed point of action, and can introduce additionally cell killing mechanisms such as antibody-dependent cell-mediated cytotoxicity and complement-dependent cytotoxicity. To exhibit its effect, the toxin needs to be released into the cytosol after internalization. A major drawback is that the targeting moiety which bears the payload is often not fully internalized, directly recycled to the surface after internalization, or degraded in lysosomes, therewith hampering the sufficient delivery of the payload into the cell cytosol. To ensure a toxic payload concentration for tumor cells and to overcome insufficient cytosolic entry, high serum levels of the targeted toxin are required often resulting in severe side effects, in particular including immunogenicity and vascular leak syndrome. Thus, a sufficiently wide therapeutic window remains a concern when treating cancer patients with antibody-drug conjugates (ADCs).

To cope with the drawback of insufficient cytosolic entry, several strategies were developed relating to for example the redirection of toxins to endogenous cellular membrane transport complexes of the biosynthetic pathway, disruption of endosomes, attenuation of the membrane integrity of endosomal membranes, or use of cell penetrating peptides.

For example, glycosylated triterpenes such as saponins were found to act as endosomal escape enhancers for targeted toxins, such as ribosome-inactivating proteins (RIPs), in tumor therapy. Structural-activity relationship analysis of saponins revealed that the presence of inter alia an aldehyde at the C-4 position appears to be beneficial for the ability of saponins to enhance the cytotoxicity of RIPs (see Formula (1) with $A^1$=H or OH and $A^2$=a polysaccharide moiety).

Formula (1)

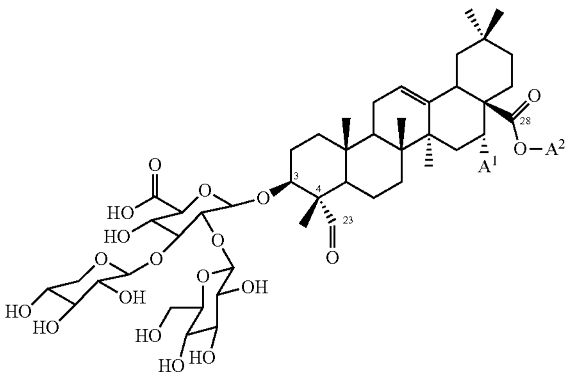

Especially, saponin SO1861 (Formula (2), sometimes also referred to as SPT001 or SPT1 or SPT), a triterpenoid saponin, was identified as a potent molecule in order to enhance the endosomal escape of tumor-cell targeted toxins. A dual effect for the enhancer mechanism is postulated: first, a direct increase of the endosomal escape resulting in caspase-dependent apoptosis that is, second, combined with lysosomal-mediated cell death pathways, which are triggered after the release of cathepsins and other hydrolytic enzymes following destruction of lysosomal membranes.

larly, when administered to a patient in need of anti-tumor therapy, is of concern when for example the optimal dosing regimen and route and frequency of administration are considered.

All characteristics of the chemical composition of the saponins themselves, including the structure of the triterpene backbone, a pentacyclic C30 terpene skeleton (also known as sapogenin or aglycone), number and length of saccharide side chains as well as type and linkage variants of the sugar residues linked to the backbone, contribute to the hemolytic potential and/or cytotoxicity of such saponins.

The saponins are per se not target-specific when the endosome and the cytosol of cells are considered, and saponins expectedly and most often distribute in a (human) subject with other kinetics than the targeted toxins, even when the same route of administration would be considered for a combination of a saponin and e.g. an ADC. Thus, after application to a patient in need thereof of a therapeutic combination comprising e.g. an ADC and a saponin, the saponin molecules can be found in any organ connoting that specificity is only mediated by the targeted toxin. Distribution of saponins in the whole body (systemic distribution) requires higher concentrations for a successful treatment when compared to specific accumulation in target cells as is achieved for the ADC. Hence, the toxicity of the modified saponins needs to be low enough for a successful application in view of the systemic application of saponins in the body, in order to achieve a suitable therapeutic window.

Therefore, there is a still a need to improve the therapeutic index when co-administration of a saponin together with e.g. an ADC is considered: need for better controlling (or better: lowering) the cytotoxicity of saponins while at the same time maintaining sufficient efficacy when potentiation of the cytotoxic effect of an ADC is considered.

Formula (2)

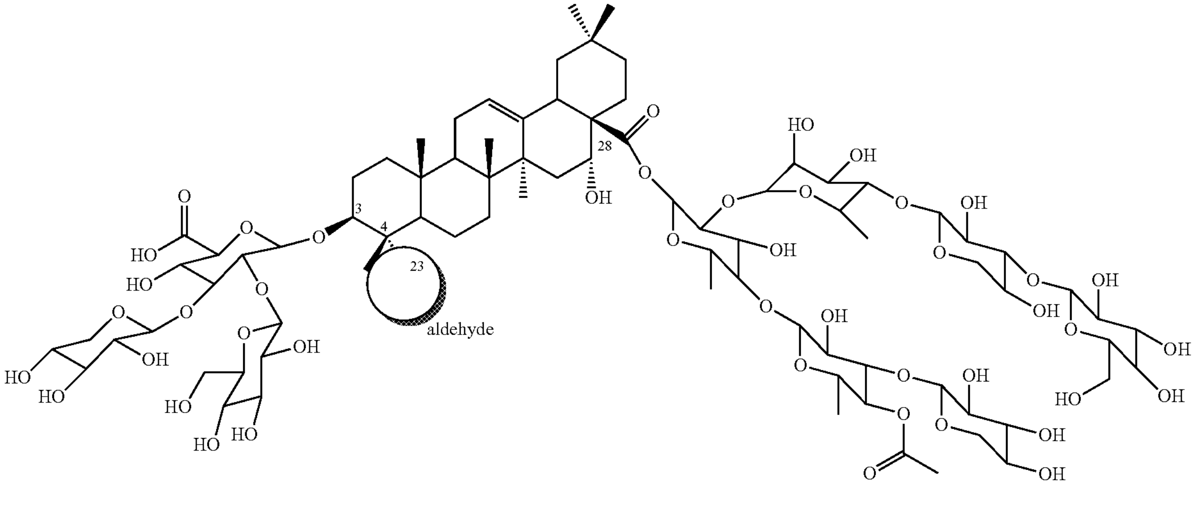

The application of saponins as endosomal escape enhancers is based on the recognition that these saponins have the ability to rupture erythrocyte membranes. However, at the very same time, cell rupturing activity of saponins contribute to (the risk for) side effects when a subject is treated with such saponins, therewith influencing optimal therapeutic windows in view of limiting therapeutic index. Indeed toxicity of such saponins, extracellularly and/or intracellu- ADCs are mainly composed of an antibody, a cytotoxic moiety such as a payload, and a linker. Several novel strategies have been proposed and carried out in the design and development of new ADCs to overcome the existing problems, targeting each of the components of ADCs. For example, by identification and validation of adequate antigenic targets for the antibody component, by selecting antigens which have high expression levels in tumor and little or no expression in normal tissues, antigens which are present on the cell surface to be accessible to the circulating ADCs, and antigens which allow internalizing of ADCs into the cell after binding; and alternative mechanisms of activity; design and optimize linkers which enhance the solubility and the drug-to-antibody ratio (DAR) of ADCs and overcome resistance induced by proteins that can transport the chemotherapeutic agent out of the cells; enhance the DAR ratio by inclusion of more payloads, select and optimize antibodies to improve antibody homogeneity and developability. In addition to the technological development of ADCs, new clinical and translational strategies are also being deployed to maximize the therapeutic index, such as, change dosing schedules through fractionated dosing; perform bio-distribution studies; include biomarkers to optimize patient selection, to capture response signals early and monitor the duration and depth of response, and to inform combination studies.

An example of ADCs with clinical potential are those ADCs such as brentuximab vedotin, inotuzumab ozogamicin, moxetumomab pasudotox, and polatuzumab vedotin, which are evaluated as a treatment option for lymphoid malignancies and multiple myeloma. Polatuzumab vedotin, binding to CD79b on (malignant) B-cells, and pinatuzumab vedotin, binding to CD22, are tested in clinical trials wherein the ADCs each were combined with co-administered rituximab, a monoclonal antibody binding to CD20 and not provided with a payload [B. Yu and D. Liu, *Antibody-drug conjugates in clinical trials for lymphoid malignancies and multiple myeloma*; Journal of Hematology & Oncology (2019) 12:94]. Combinations of monoclonal antibodies such as these examples are yet a further approach and attempt to arrive at the 'magic bullet' which combines many or even all of the aforementioned desired characteristics of ADCs.

Meanwhile in the past few decades, nucleic acid-based therapeutics are under development. Therapeutic nucleic acids can be based on deoxyribonucleic acid (DNA) or ribonucleic acid (RNA), anti-sense oligonucleotides (ASOs, AONs), and short interfering RNAs (siRNAs), microRNAs, and DNA and RNA aptamers, for approaches such as gene therapy, RNA interference (RNAi). Many of them share the same fundamental basis of action by inhibition of either DNA or RNA expression or degradation of mRNA, thereby preventing expression of disease-related abnormal proteins. The largest number of clinical trials is being carried out in the field of gene therapy, with almost 2600 ongoing or completed clinical trials worldwide but with only about 4% entering phase 3. This is followed by clinical trials with ASOs. Similarly to ADCs, despite the large number of techniques being explored, therapeutic nucleic acids share two major issues during clinical development: delivery into cells and off-target effects (often resulting in intolerable adverse events and side effects). For instance, ASOs such as peptide nucleic acid (PNA), phosphoramidate morpholino oligomer (PMO), locked nucleic acid (LNA) and other bridged nucleic acids (BNA), are being investigated as an attractive strategy to inhibit specifically target genes and especially those genes that are difficult to target with small molecule inhibitors or neutralizing antibodies. Currently, the efficacy of different ASOs is being studied in many neurodegenerative diseases such as Huntington's disease, Parkinson's disease, Alzheimer's disease, and amyotrophic lateral sclerosis and also in several cancer stages. The application of ASOs as potential therapeutic agents requires safe and effective methods for their delivery to the cytoplasm and/or nucleus of the target cells and tissues. Although the clinical relevance of ASOs has been demonstrated, inefficient cellular uptake, both in vitro and in vivo, limit the efficacy of ASOs and has been a barrier to therapeutic development. Cellular uptake can be <2% of the dose resulting in too low ASO concentration at the active site for an effective and sustained outcome. This consequently requires an increase of the administered dose which induces off-target effects. Most common side-effects are activation of the complement cascade, the inhibition of the clotting cascade and toll-like receptor mediated stimulation of the immune system.

Chemotherapeutics are most commonly small molecules, however, their efficacy is hampered by the severe off-target side toxicity, as well as their poor solubility, rapid clearance and limited tumor exposure. Scaffold-small-molecule drug conjugates such as polymer-drug conjugates (PDCs) are macromolecular constructs with pharmacologically activity, which comprises one or more molecules of a small-molecule drug bound to a carrier scaffold (e.g. polyethylene glycol (PEG)).

Such conjugate principle has attracted much attention and has been under investigation for several decades. The majority of conjugates of small-molecule drugs under pre-clinical or clinical development are for oncological indications. However, up-to-date only one drug not related to cancer has been approved (Movantik, a PEG oligomer conjugate of opioid antagonist naloxone, AstraZeneca) for opioid-induced constipation in patients with chronic pain in 2014, which is a non-oncology indication. Translating application of drug-scaffold conjugates into treatment of human subjects provided little clinical success so far. For example, PK1 (N-(2-hydroxypropyl)methacrylamide (HPMA) copolymer doxorubicin; development by Pharmacia, Pfizer) showed great anti-cancer activity in both solid tumors and leukemia in murine models, and was under clinical investigation for oncological indications. Despite that it demonstrated significant reduction of nonspecific toxicity and improved pharmacokinetics in man, improvements in anticancer efficacy turned out to be marginal in patients, and as a consequence further development of PK1 was discontinued.

The failure of scaffold-small-molecule drug conjugates is at least partially attributed to its poor accumulation at the tumor site. For example, while in murine models PK1 showed 45-250 times higher accumulation in the tumor than in healthy tissues (liver, kidney, lung, spleen, and heart), accumulation in tumor was only observed in a small subset of patients in the clinical trial.

A potential solution to the aforementioned problems is application of nanoparticle systems for drug delivery such as liposomes. Liposomes are sphere-shaped vesicles consisting of one or more phospholipid bilayers, which are spontaneously formed when phospholipids are dispersed in water. The amphiphilicity characteristics of the phospholipids provide it with the properties of self-assembly, emulsifying and wetting characteristics, and these properties can be employed in the design of new drugs and new drug delivery systems. Drug encapsulated in a liposomal delivery system may convey several advantages over a direct administration of the drug, such as an improvement and control over pharmacokinetics and pharmacodynamics, tissue targeting property, decreased toxicity and enhanced drug activity. An example of such success is liposome-encapsulated form of a small molecule chemotherapy agent doxorubicin (Doxil: a pegylated liposome-encapsulated form of doxorubicin; Myocet: a non-pegylated liposomal doxorubicin), which have been approved for clinical use.

Therefore, a solution still needs to be found that allows for drug therapies such as anti-tumor therapies and anti-autoimmune disease therapies (e.g. rheumatoid arthritis treatment options) and, generally, gene-silencing therapies, applicable for non-systemic use when desired, wherein the drug has for example an acceptable safety profile, little to no off-target activity, sufficient efficacy, sufficiently low clearance rate from the patient's body, a sufficiently wide therapeutic window, etc.

SUMMARY OF THE INVENTION

According to the inventors the saponin derivatives according to the invention, wherein the aldehyde functional group is transformed to a semicarbazone functional group according to formula (I) are not known in the art.

(I)

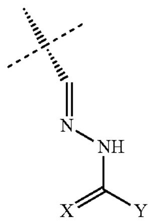

Here, X=O, P or S, and $Y=NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H; or

Y=

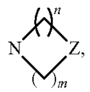

wherein n and m each are an integer independently selected from 1, 2, or 3, $Z=CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b (II)a

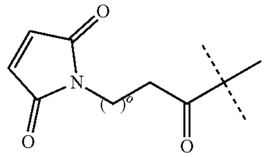

(II)b

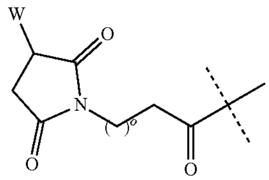

or an azide moiety according to formula (II)c (II)c

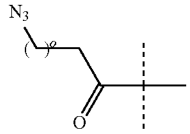

wherein o is an integer selected from 0-10, preferably 2-7, more preferably 4-6, and W is a thiol functional group according to formula (III)

(III)

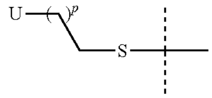

wherein U=SH, $NH_2$ or OH and p is an integer selected from 0-4, preferably 1-3, more preferably 1 or 2.

Surprisingly, the inventors have found that these saponin derivatives have one or more of the following benefits:

i) a reduced toxicity when cell viability is considered of cells contacted with the saponin derivatives, ii) increased activity when potentiation of an effector moiety, e.g. toxin cytotoxicity or AON (e.g. BNA) mediated gene silencing, is considered (without wishing to be bound by any theory: relating to similar or improved endosomal escape enhancing activity of the modified saponin) and/or iii) reduced hemolytic activity, when compared with the toxicity, activity and haemolytic activity of unmodified saponin (non-derivatized saponin). Therewith, the inventors provide saponin derivatives with an improved therapeutic window, since the ratio between IC50 values for cell toxicity and e.g. IC50 values for toxin potentiation or IC50 values for gene silencing is increased, and/or since the ratio between IC50 values for saponin haemolytic activity and e.g. IC50 values for toxin potentiation or IC50 values for gene silencing is increased.

In addition, the inventors surprisingly established (tumor) cell killing by contacting such cells with a saponin conjugate of the current invention based on a saponin derivative of the current invention e.g. comprising a ligand such as an antibody or a GalNAc moiety, for a cell-surface molecule such as a receptor such as ASGPR (when the ligand is at least one GalNAc moiety in the saponin conjugate), together with an ADC such as an antibody-protein toxin conjugate or a conjugate comprising a GalNAc moiety and an oligonucleotide, despite the medium to low expression of the cell-surface receptor targeted by the cell-surface molecule binding-molecule (e.g. antibody, one or more GalNAc moieties) comprised by the saponin conjugate and/or despite the medium to low expression of the cell-surface receptor targeted by the ADC or by the GalNAc/oligonucleotide conjugate. The saponin derivative and the saponin conjugate of the invention comprise the semicarbazone functional group. For example, in a comparative example, such cell killing when cells are contacted with the ADC could not be established or only to a lower extent, when a saponin conjugate comprising the same cell-surface molecule binding-molecule (e.g. antibody) but comprising a hydrazone functional group (=N—N(H)—C(O)—) instead of the semicarbazone functional group, was contacted with the cells. Therewith, the inventors now provide for a more potent saponin derivative and saponin conjugate, when the activation or potentiating of an effector moiety such as an effector moiety comprised by an ADC or AOC or comprised by a GalNAc/oligonucleotide conjugate, is considered.

Furthermore, the inventors have found that the saponin derivatives according to the invention comprising the semicarbazone functional group hydrolyses more rapidly and in a higher amount towards the corresponding native saponin comprising a “free” aldehyde functional group, as compared to saponin derivatives comprising a hydrazone functional group (=N—N(H)—C(O)—) known in the art, under acidic conditions which are the conditions present in endosomes and/or lysosomes of mammalian cells, in particular of human cells. This has the benefit that a lower amount of the saponin derivatives according to the invention should be administered to a patient in need of potentiation of e.g. an ADC or an AOC or a GalNAc/oligonucleotide conjugate, to obtain the same amount of native saponin comprising the “free” aldehyde to act as endosomal escape enhancer for targeted toxins or targeted oligonucleotides, compared to the required amount of saponin derivative comprising the hydrazone functional group (=N—N(H)—C(O)—). Without wishing to be bound by any theory, faster release of the saponin comprising the aldehyde functional group from the saponin derivative that comprises the semicarbazone functional group according to the invention, when compared to release of the saponin comprising the aldehyde functional group from the saponin derivative that comprises the hydrazone functional group, is at the basis for the improved activity of the saponin conjugate of the invention comprising a saponin derivative of the invention, wherein the activity is the potentiation of the effector moiety activity inside the cytosol or nucleus of the targeted cell by endosomal escape enhancement.

An aspect of the invention relates to a saponin derivative based on a saponin comprising a triterpene aglycone core structure and at least one of a first saccharide chain ‘$R^1$’ and a second saccharide chain ‘$R^2$’ linked to the aglycone core structure, wherein the saponin derivative comprises an aglycone core structure comprising an aldehyde group, wherein the aldehyde group is transformed into a semicarbazone functional group according to formula (I)

(I)

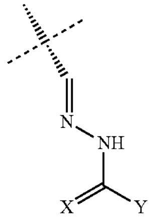

wherein $R^1$ and $R^2$ are independently selected from hydrogen, a monosaccharide, a linear oligosaccharide and a branched oligosaccharide, X=O, P or S, and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H, or

Y=

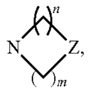

wherein n and m each are an integer independently selected from 1, 2, or 3,

Z=$CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b (II)a

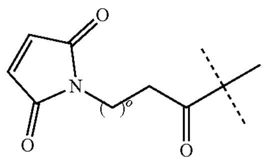

(II)b

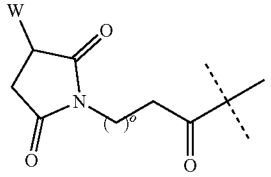

or an azide moiety according to formula (II)c (II)c

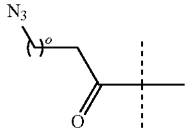

wherein o is an integer selected from 0-10, preferably 2-7, more preferably 4-6, and W is a thiol functional group according to formula (III)

(III)

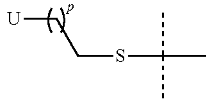

wherein U=SH, $NH_2$ or OH and p is an integer selected from 0-4, preferably 1-3, more preferably 1 or 2.

Preferred is the saponin derivative according to the invention, wherein the saponin on which the saponin derivative is based is a monodesmosidic or bi-desmosidic triterpene saponin belonging to the type of a 12,13-dehydrooleanane with the aldehyde group in position C-23 and optionally comprising a glucuronic acid group in a carbohydrate substituent at the C-3beta-OH group of the saponin, preferably a bi-desmosidic triterpene saponin belonging to the type of a 12,13-dehydrooleanane with the aldehyde group in position C-23 and comprising a glucuronic acid group in a carbohydrate substituent at the C-3beta-OH group of the saponin.

Typically, the saponin derivative according to the invention is according to formula (IV):

(IV)

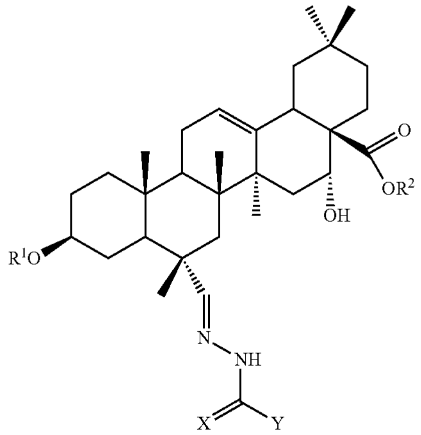

wherein $R^1$ and $R^2$ are independently selected from hydrogen, a monosaccharide, a linear oligosaccharide and a branched oligosaccharide, X=O, P or S, and $Y=NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H; or

Y=

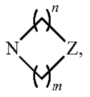

wherein n and m each are an integer independently selected from 1, 2 or 3;

$Z=CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, or a maleimide moiety according to formula (II)a or formula (II)b (II)a

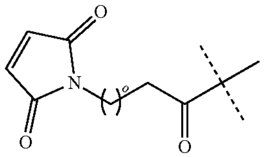

-continued (II)b

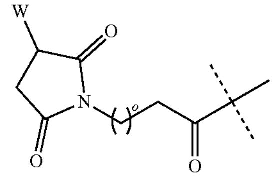

or an azide moiety according to formula (II)c (II)c

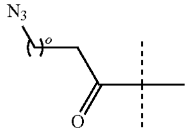

wherein o is an integer selected from 0-10, preferably 2-7, more preferably 4-6 and W is a thiol functional group according to formula (III)

(III)

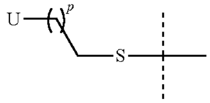

wherein U=SH, $NH_2$ or OH and p is an integer selected from 0-4, preferably 1-3, more preferably 1 or 2.

Preferred is the saponin derivative according to the invention, wherein X=O.

Also preferred is the saponin derivative according to the invention, wherein Y=

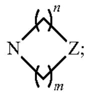

n and m each are an integer independently selected from 1, 2 or 3; and $Z=CH_2$, O, S, P or $NR^5$; and wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, or a maleimide moiety according to formula (II)a or formula (II)b (II)a

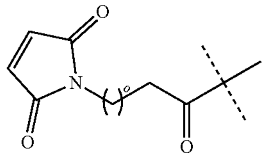

-continued (II)b

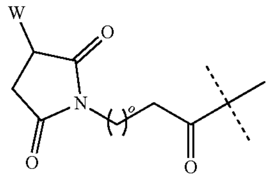

or an azide moiety according to formula (II)c (II)c

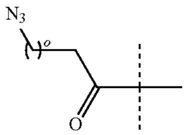

wherein o is an integer selected from 0-10, preferably 2-7, more preferably 4-6 and W is a thiol functional group according to formula (III)

(III)

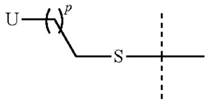

wherein U=SH, $NH_2$ or OH and p is an integer selected from 0-4, preferably 1-3, more preferably 1 or 2.

A saponin derivative according to the invention is a saponin derivative wherein Y=

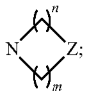

n and m each are an integer independently selected from 1, 2 or 3; and

Z=O or NR;

wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, or a maleimide moiety according to formula (II)a or formula (II)b (II)a

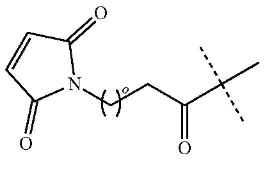

-continued (II)b

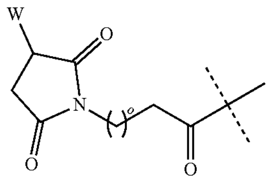

or an azide moiety according to formula (II)c (II)c

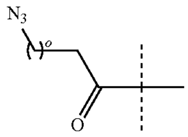

wherein o is an integer selected from 0-10, preferably 2-7, more preferably 4-6 and W is a thiol functional group according to formula (III)

(III)

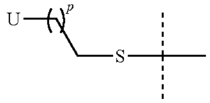

wherein U=SH, $NH_2$ or OH and p is an integer selected from 0-4, preferably 1-3, more preferably 1 or 2.

Preferred is the saponin derivative of the invention, wherein Y=

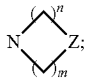

n and m each are an integer independently selected from 1, 2 or 3; and

Z=O or NR;

wherein $R^5$ represents H, or a covalently bound linker, or a maleimide moiety according to formula (II)a or formula (II)b (II)a

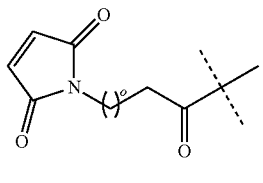

(II)b

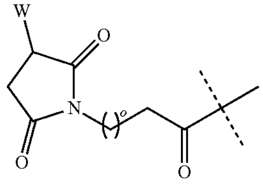

or an azide moiety according to formula (II)c (II)c

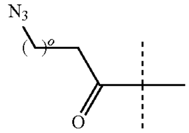

wherein o is an integer selected from 0-10, preferably 2-7, more preferably 4-6 and W is a thiol functional group according to formula (III)

(III)

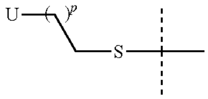

wherein U=SH, $NH_2$ or OH, preferably $NH_2$ or OH, more preferably OH; and p is an integer selected from 0-4, preferably 1-3, more preferably 1 or 2.

Particular saponin derivatives according to the invention are saponin derivatives, wherein n=1 and m=1, or n=2 and m=1, or n=2 and m=2, or n=3 and m=2, or n=3 and m=3;

preferably wherein n=2 and m=2.

A saponin derivative according to the invention is the saponin derivative according to molecule (AA):

(AA)

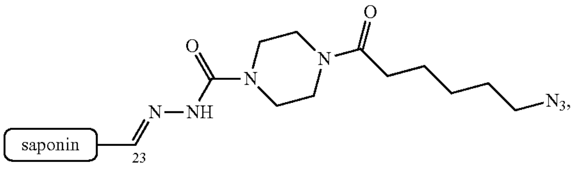

wherein

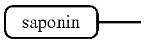

represents a saponin moiety according to formula (SM):

(SM)

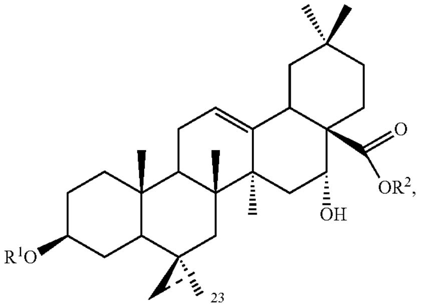

wherein $R^1$ and $R^2$ are independently selected from hydrogen, a monosaccharide, a linear oligosaccharide and a branched oligosaccharide, and wherein the saponin moiety according to formula (SM) is based on a saponin comprising an aldehyde group in position C-23. Preferably, the saponin derivative of molecule (AA) is based on SO1861, SO1832 or QS-21, more preferably SO1861 or SO1832, most preferably SO1861.

A saponin derivative according to the invention is the saponin derivative according to molecule (BB):

(BB)

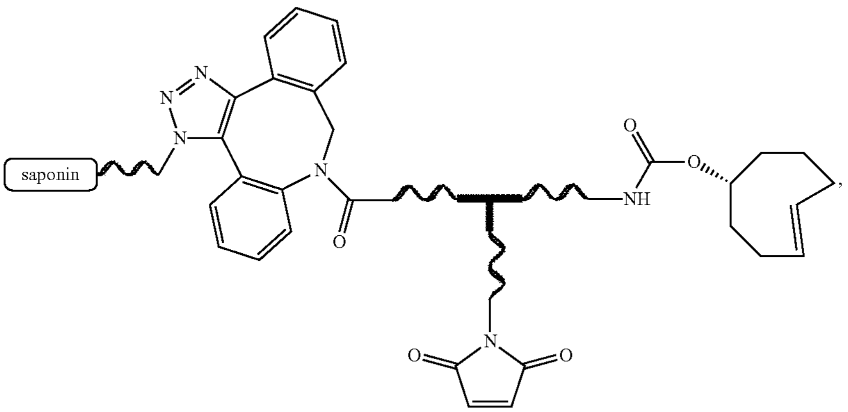

which molecule (BB) is the covalent conjugation product obtained by the covalent conjugation of the saponin derivative according to molecule (AA) with the tri-functional linker according to formula (XXI):

(XXI)

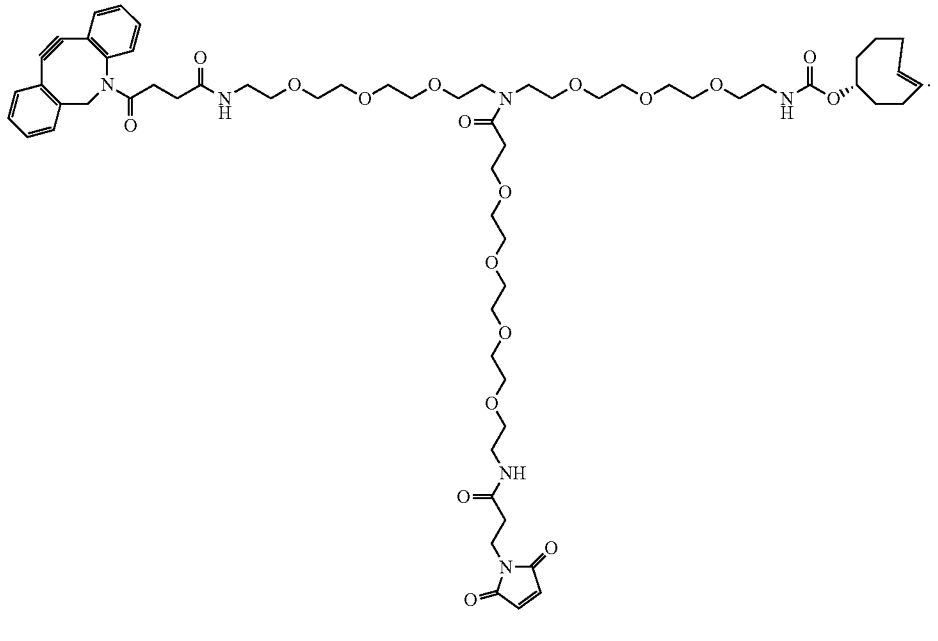

Preferably, the saponin derivative of molecule (BB) is based on SO1861, SO1832 or QS-21, more preferably SO1861 or SO1832, most preferably SO1861.

A saponin conjugate according to the invention is the saponin conjugate according to molecule (CC):

(CC)

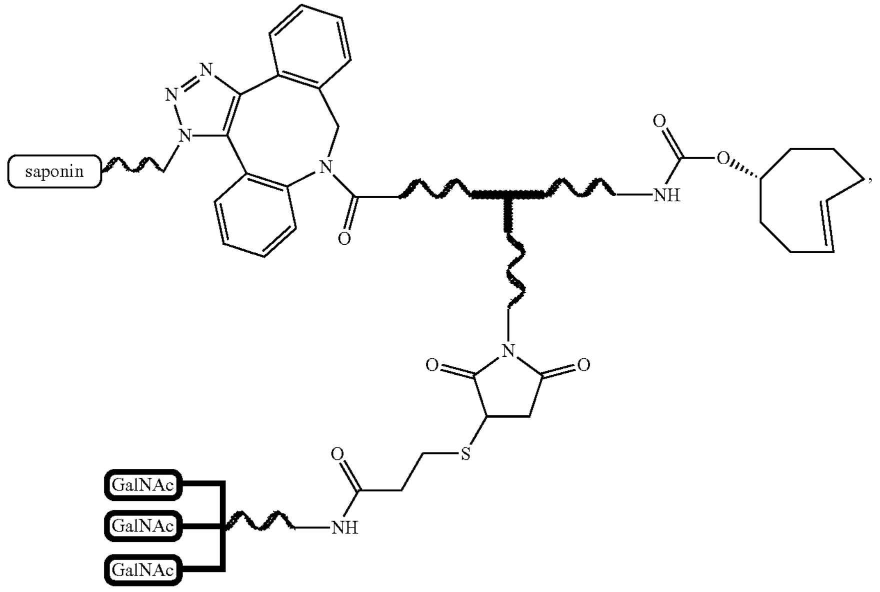

which molecule (CC) is the covalent conjugation product obtained by the covalent conjugation of the tri-functional linker according to formula (XXI) with the saponin derivative according to molecule (AA) and with GalNAc conjugate according to molecule (FF):
(FF)
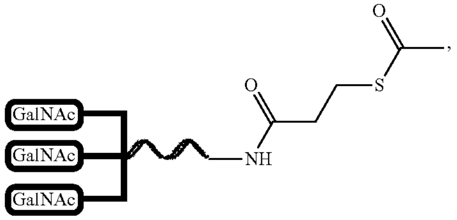
wherein
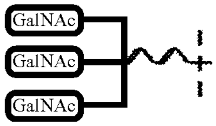
represents the tri-GalNAc conjugate according to molecule (DD):
(DD)
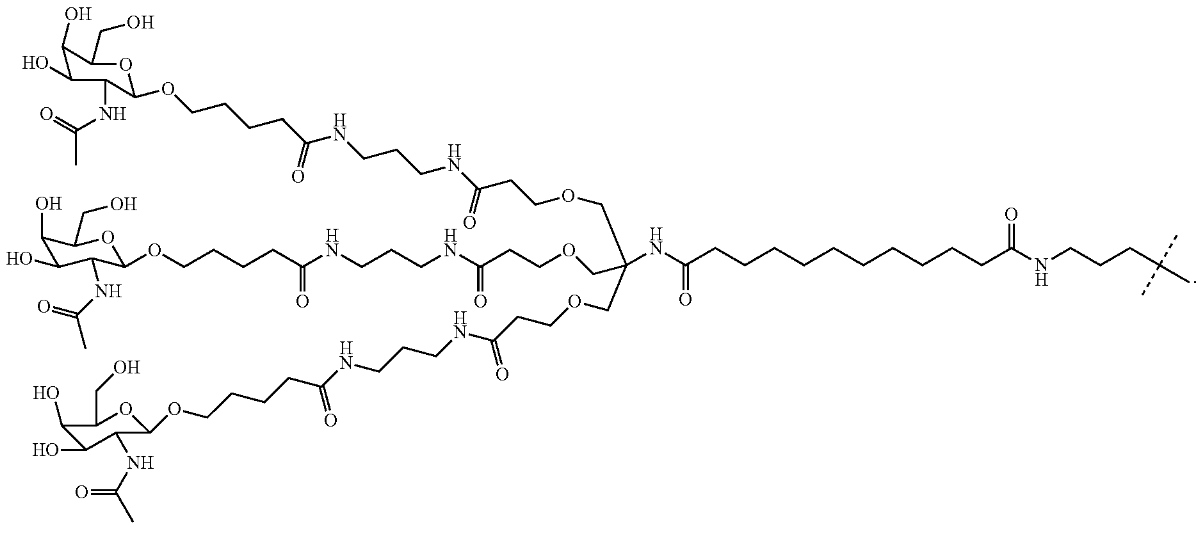

Preferably, the saponin conjugate of molecule (CC) is based on saponin SO1861, SO1832 or QS-21, more preferably SO1861 or SO1832, most preferably SO1861.

A saponin conjugate according to the invention is the saponin conjugate according to molecule (EE):

(EE)

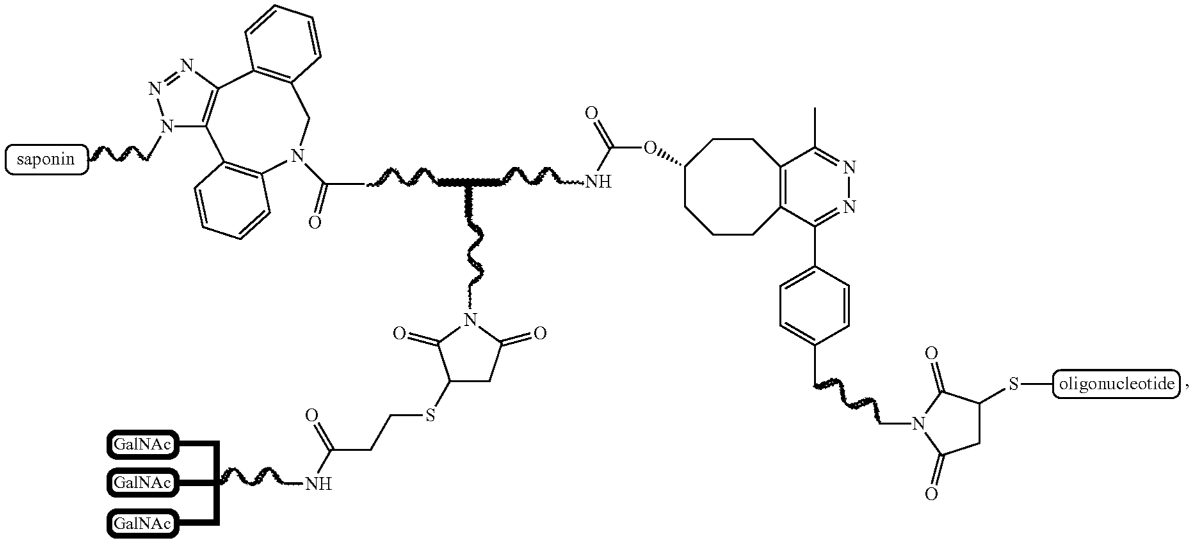

which molecule (EE) is the covalent conjugation product obtained by the covalent conjugation of the tri-functional linker according to formula (XXI) with the saponin derivative according to molecule (AA) and with GalNAc conjugate according to molecule (FF) and with the oligonucleotide provided with a linker according to molecule (GG):

(GG)

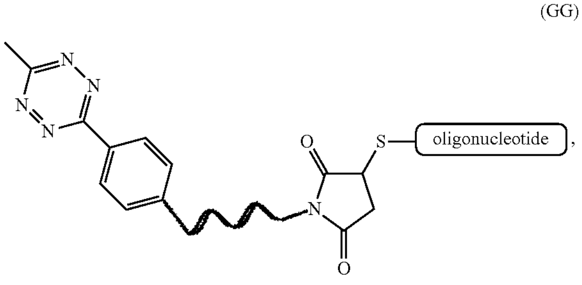

wherein the molecule (GG) represents the conjugation product of the conjugation reaction between the linker (E)-1-(4-((2-(6-(2,5-dioxo-2,5-dihydro-1H-pyrrol-1-yl)hexanoyl)hydrazineylidene)methyl)benzamido)-N-(4-(6-methyl-1,2,4,5-tetrazin-3-yl)benzyl)-3,6,9,12-tetraoxapentadecan-15-amide and the oligonucleotide-linker molecule according to molecule (HH):

(HH)

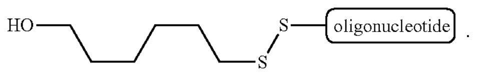

Preferably, the saponin conjugate of molecule (EE) is based on saponin SO1861, SO1832 or QS-21, more preferably SO1861 or SO1832, most preferably SO1861. Typically the oligonucleotide of molecule (EE) is an AON such as a BNA or an siRNA. For example, the oligonucleotide of molecule (EE) is a BNA, for example a BNA for silencing HSP27 expression or apoB expression, preferably in a human cell.

A saponin derivative according to the invention is the saponin derivative according to molecule (JJ):

(JJ)

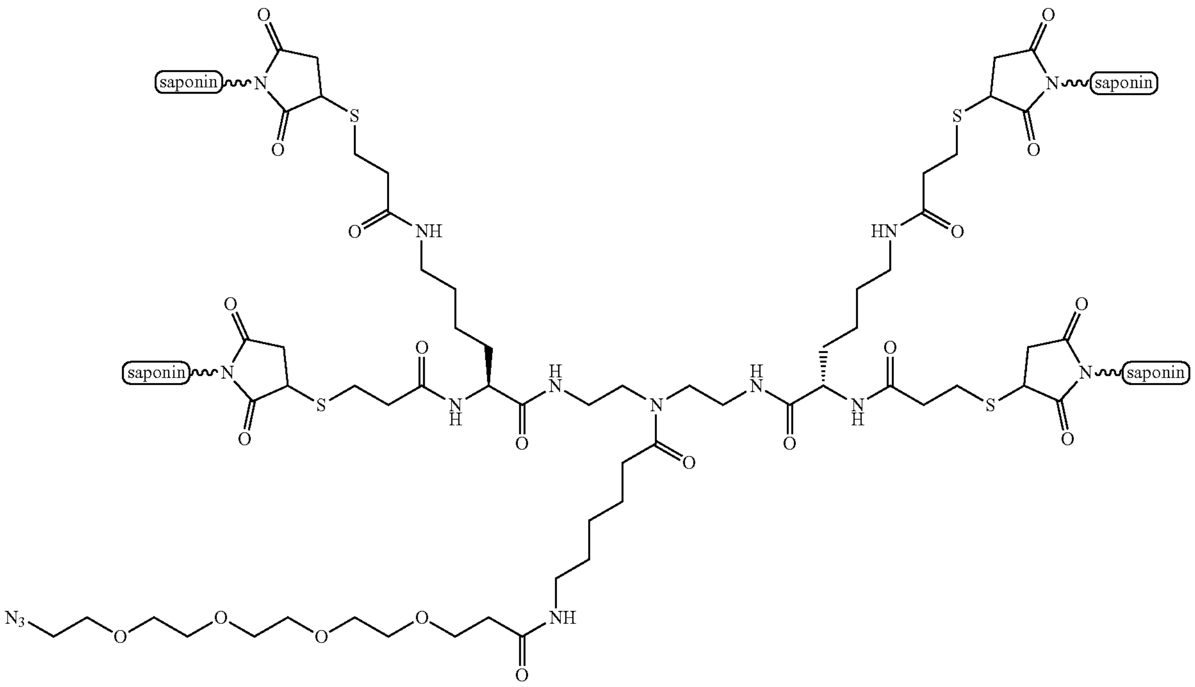

which molecule (JJ) is the conjugate product of conjugation of N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide first with saponin derivative according to molecule (KK):

(KK)

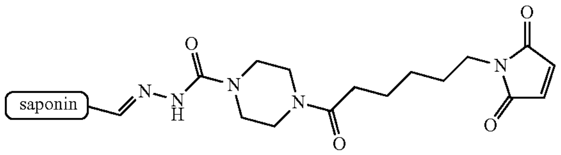

and subsequently with 2,5-dioxopyrrolidin-1-yl 1-azido-3,6,9,12-tetraoxapentadecan-15-oate, wherein

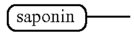

represents a saponin moiety according to formula (SM).

Preferably, the saponin derivative of molecule (JJ) is based on SO1861, SO1832 or QS-21, more preferably SO1861 or SO1832, most preferably SO1861.

A saponin conjugate according to the invention is the saponin conjugate according to molecule (LL):
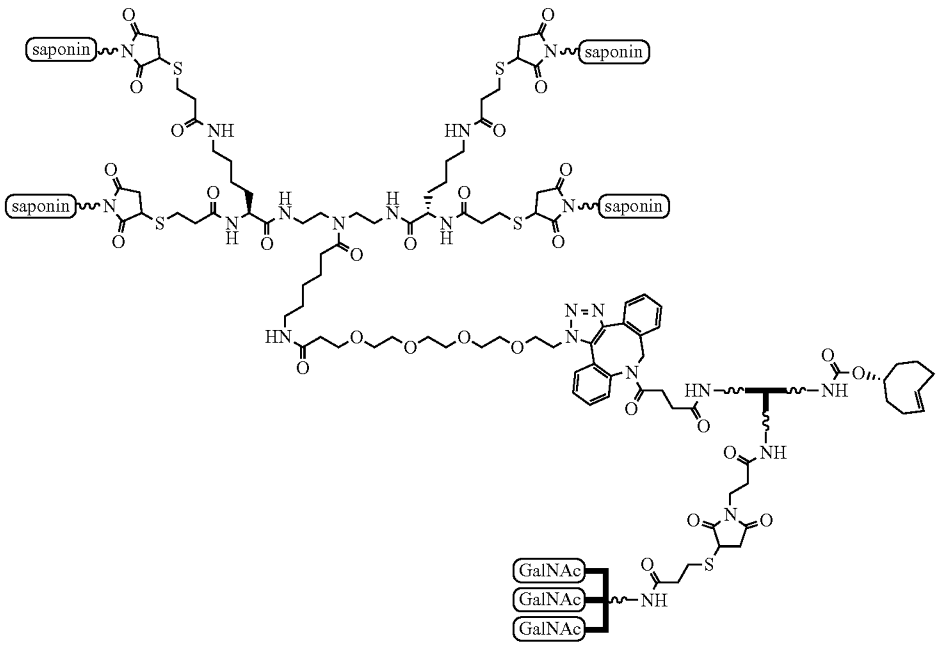
(LL)
,
which molecule (LL) is the covalent conjugation product obtained by the covalent conjugation of the molecule (JJ) with the conjugate of the tri-functional linker and GalNAc according to molecule (MM):
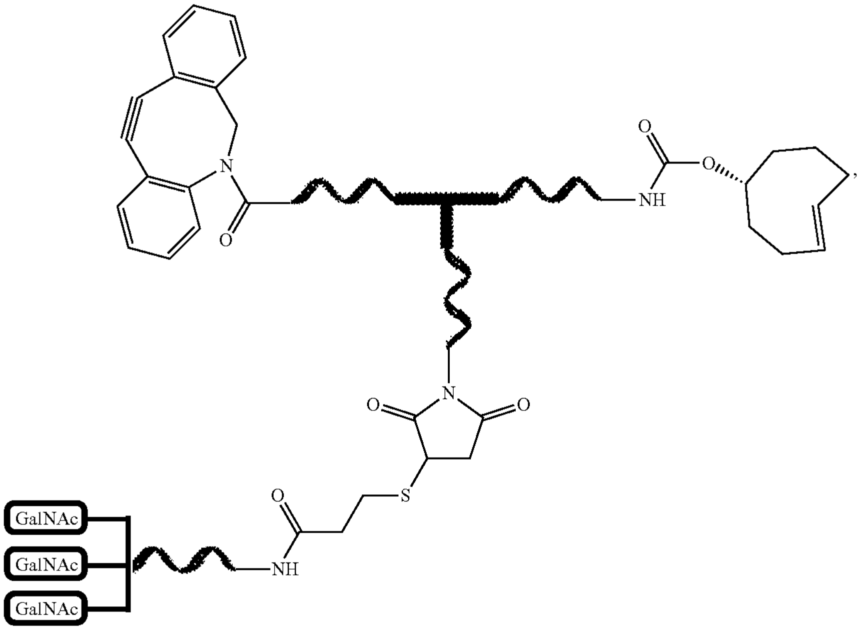
(MM)
, wherein molecule (MM) is the conjugate of the tri-functional linker according to formula (XXI) and the GalNAc conjugate according to molecule (NN):
(NN)
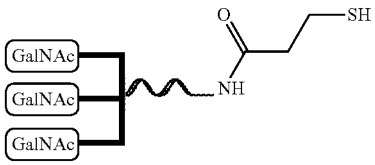
wherein
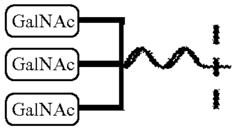
represents the tri-GalNAc conjugate according to molecule (DD).
A saponin conjugate according to the invention is the saponin conjugate according to molecule (PP):
(PP)
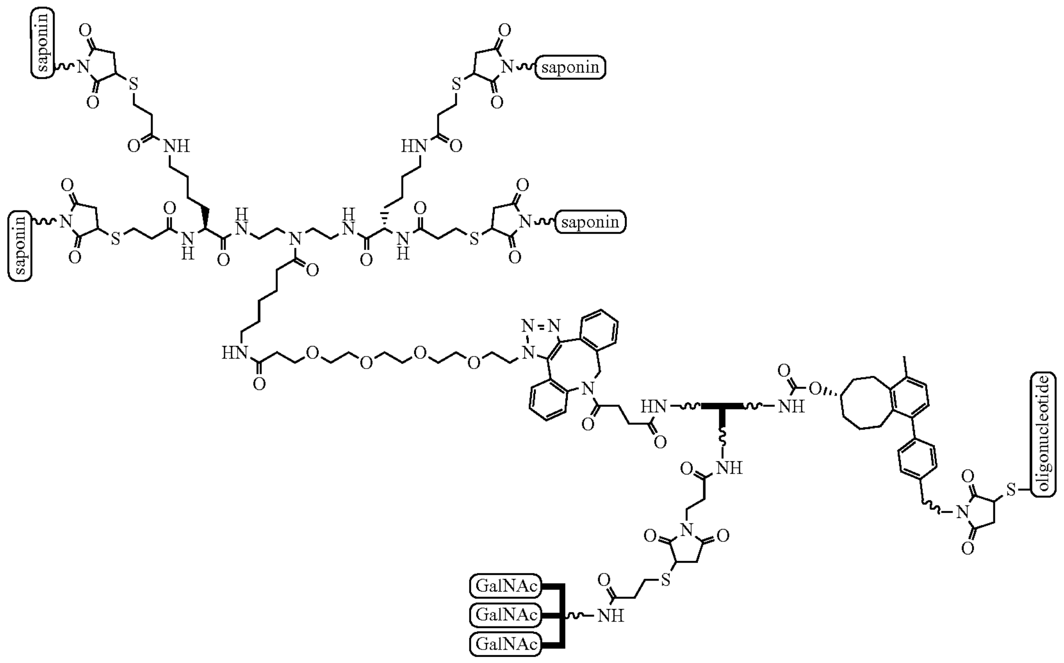
, which molecule (PP) is the covalent conjugation product obtained by the covalent conjugation of the molecule (LL) with the oligonucleotide provided with a linker according to molecule (GG).

A saponin derivative according to the invention is the saponin derivative according to molecule (QQ):

(QQ)

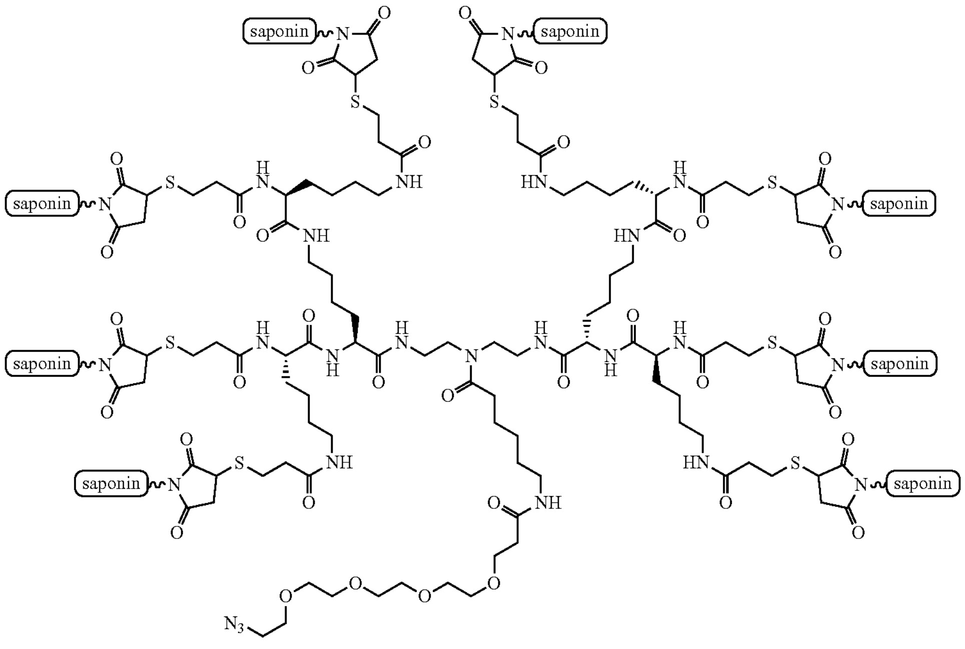

, which molecule (QQ) is the conjugate product of conjugation of (2S)—N-[(1 S)-1-{[2-(6-amino-N-{2-[(2S)-2,6-bis[(2S)-2,6-bis(3-sulfanylpropanamido)hexanamido]hexanamido]ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate first with saponin derivative according to molecule (KK) and subsequently with 2,5-dioxopyrrolidin-1-yl 1-azido-3,6,9,12-tetraoxapentadecan-15-oate. Preferably, the saponin derivative of molecule (QQ) is based on SO1861, SO1832 or QS-21, more preferably SO1861 or SO1832, most preferably SO1861.

A saponin conjugate according to the invention is the saponin conjugate according to molecule (RR):
(RR)
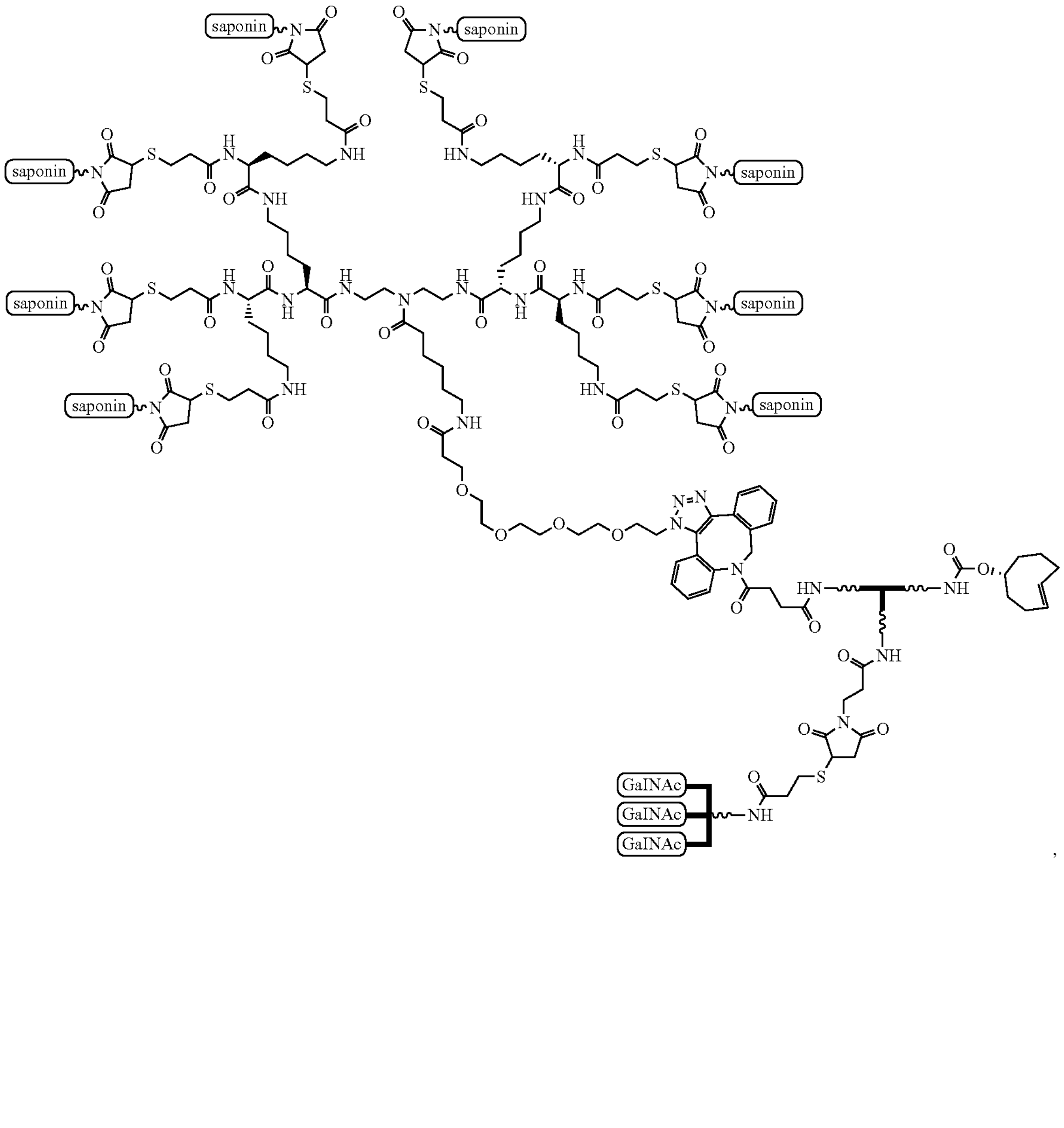
,
which molecule (RR) is the covalent conjugation product obtained by the covalent conjugation of the molecule (QQ) with the conjugate of the tri-functional linker and GalNAc according to molecule (MM).

A saponin conjugate according to the invention is the saponin conjugate according to molecule (SS):

(SS)

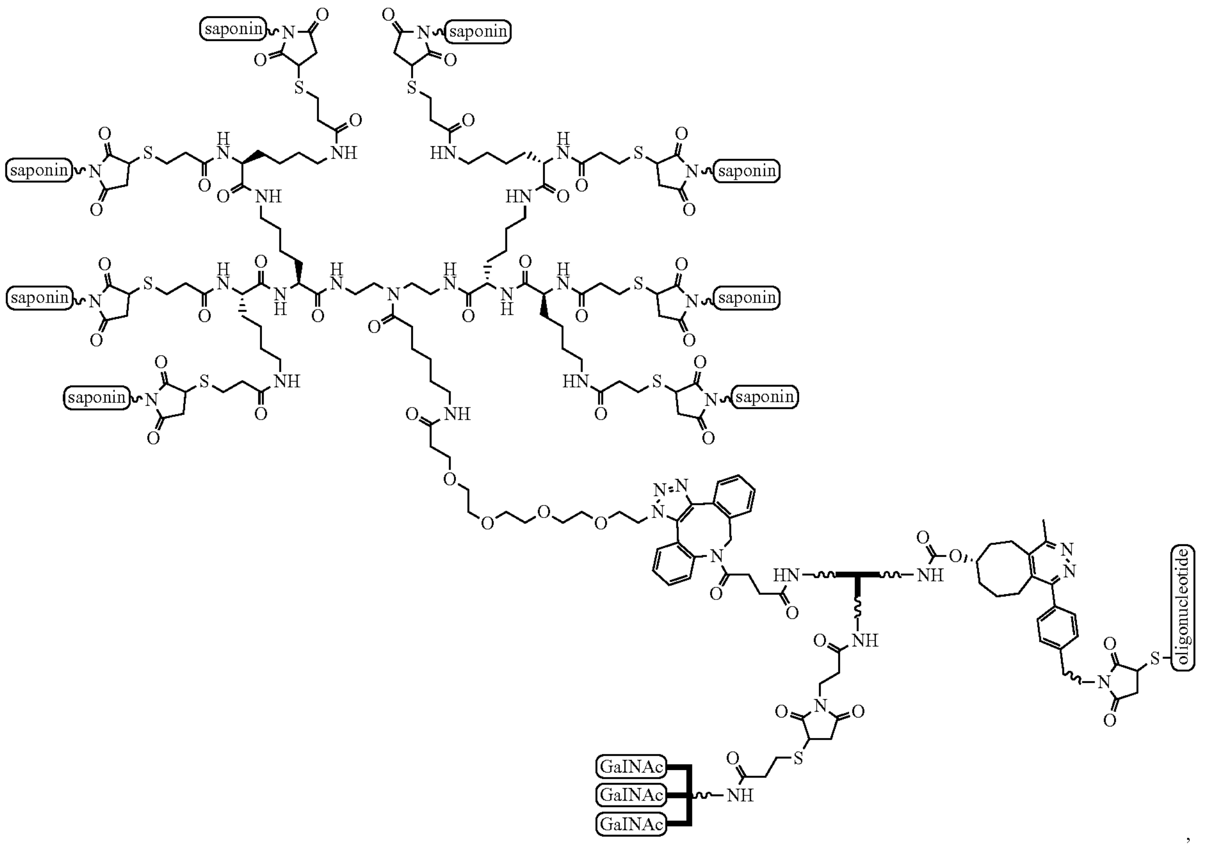

, which molecule (SS) is the covalent conjugation product obtained by the covalent conjugation of the molecule (RR) with the oligonucleotide provided with a linker according to molecule (GG).

Preferably, the saponin derivatives of molecule (JJ) and molecule (QQ) and/or the saponin conjugates of molecules (LL), (PP), (RR) and/or (SS) is/are based on saponin SO1861, SO1832 or QS-21, more preferably SO1861 or SO1832, most preferably SO1861. Typically the oligonucleotide of molecule (PP) and/or of molecule (SS) is/are an AON such as a BNA or an siRNA. For example, the oligonucleotide of molecule (SS) is a BNA, for example a BNA for silencing HSP27 expression or apoB expression, preferably in a human cell.

An aspect of the invention relates to a ninth pharmaceutical composition comprising any one of the conjugates according to molecules (LL), (PP), (RR) and (SS).

An aspect of the invention relates to the ninth pharmaceutical composition comprising any one of the conjugates according to molecules (LL), (PP), (RR) and (SS) or to any one of the conjugates according to molecules (LL), (PP), (RR) and (SS), for use as a medicament.

An aspect of the invention relates to the ninth pharmaceutical composition comprising any one of the conjugates according molecules (LL), (PP), (RR) and (SS) or to anyone of the conjugates according to molecules (LL), (PP), (RR) and (SS), for use in the treatment or prophylaxis of a cancer, an infectious disease, a viral infection, hypercholesterolemia, cardiovascular disease, primary hyperoxaluria, haemophilia A, haemophilia B, AAT related liver disease, acute hepatic porphyria, TTR-mediated amyloidosis, hereditary TTR amyloidosis (hATTR), complement-mediated disease, hepatitis B infection, hepatitis C infection, α1-antitrypsin deficiency, β-thalassaemia, or an auto-immune disease.

An aspect of the invention relates to the ninth pharmaceutical composition comprising any one of the conjugates according to molecules (LL), (PP), (RR) and (SS) or to any one of the conjugates according to molecules (LL), (PP), (RR) and (SS), for use in the lowering of LDL-cholesterol in a subject.

In preferred saponin derivatives according to the invention $R^1$ is selected from:

H,

GlcA-,

Glc-,

Gal-,

Rha-(1→2)-Ara-,

Gal-(1→2)-[Xyl-(1→3)]-GlcA-,

Glc-(1→2)-[Glc-(1→4)]-GlcA-,

Glc-(1→2)-Ara-(1→3)-[Gal-(1→2)]-GlcA-,

Xyl-(1→2)-Ara-(1→3)-[Gal-(1→2)]-GlcA-,

Glc-(1→3)-Gal-(1→2)-[Xyl-(1→3)]-Glc-(1→4)-Gal-,

Rha-(1→2)-Gal-(1→3)-[Glc-(1→2)]-GlcA-,

Ara-(1→4)-Rha-(1→2)-Glc-(1→2)-Rha-(1→2)-GlcA-,

Ara-(1→4)-Fuc-(1→2)-Glc-(1→2)-Rha-(1→2)-GlcA-,

Ara-(1→4)-Rha-(1→2)-Gal-(1→2)-Rha-(1→2)-GlcA-,
Ara-(1→4)-Fuc-(1→2)-Gal-(1→2)-Rha-(1→2)-GlcA-,
Ara-(1→4)-Rha-(1→2)-Glc-(1→2)-Fuc-(1→2)-GlcA-,
Ara-(1→4)-Fuc-(1→2)-Glc-(1→2)-Fuc-(1→2)-GlcA-,
Ara-(1→4)-Rha-(1→2)-Gal-(1→2)-Fuc-(1→2)-GlcA-,
Ara-(1→4)-Fuc-(1→2)-Gal-(1→2)-Fuc-(1→2)-GlcA-,
Xyl-(1→4)-Rha-(1→2)-Glc-(1→2)-Rha-(1→2)-GlcA-,
Xyl-(1→4)-Fuc-(1→2)-Glc-(1→2)-Rha-(1→2)-GlcA-,
Xyl-(1→4)-Rha-(1→2)-Gal-(1→2)-Rha-(1→2)-GlcA-,
Xyl-(1→4)-Fuc-(1→2)-Gal-(1→2)-Rha-(1→2)-GlcA-,
Xyl-(1→4)-Rha-(1→2)-Glc-(1→2)-Fuc-(1→2)-GlcA-,
Xyl-(1→4)-Fuc-(1→2)-Glc-(1→2)-Fuc-(1→2)-GlcA-,
Xyl-(1→4)-Rha-(1→2)-Gal-(1→2)-Fuc-(1→2)-GlcA-,
Xyl-(1→4)-Fuc-(1→2)-Gal-(1→2)-Fuc-(1→2)-GlcA-, and derivatives thereof, and $R^2$ is selected from:

H,
Glc-,
Gal-,
Rha-(1→2)-[Xyl-(1→4)]-Rha-,
Rha-(1→2)-[Ara-(1→3)-Xyl-(1→4)]-Rha-,
Ara-,
Xyl-,
Xyl-(1→4)-Rha-(1→2)-[$R^1$-(→4)]-Fuc- wherein $R^1$ is 4E-Methoxycinnamic acid,
Xyl-(1→4)-Rha-(1→2)-[$R^2$-(→4)]-Fuc- wherein $R^2$ is 4Z-Methoxycinnamic acid,
Xyl-(1→4)-[Gal-(1→3)]-Rha-(1→2)-4-OAc-Fuc-,
Xyl-(1→4)-[Glc-(1→3)]-Rha-(1→2)-3,4-di-OAc-Fuc-,
Xyl-(1→4)-[Glc-(1→3)]-Rha-(1→2)-[$R^6$-(→4)]-3-OAc-Fuc- wherein $R^6$ is 4E-Methoxycinnamic acid,
Glc-(1→3)-Xyl-(1→4)-[Glc-(1→3)]-Rha-(1→2)-4-OAc-Fuc-,
Glc-(1→3)-Xyl-(1→4)-Rha-(1→2)-4-OAc-Fuc-,
(Ara- or Xyl-)(1→3)-(Ara- or Xyl-)(1→4)-(Rha- or Fuc-)(1→2)-[4-OAc-(Rha- or Fuc-)(1→4)]-(Rha- or Fuc-),
Xyl-(1→3)-Xyl-(1→4)-Rha-(1→2)-[Qui-(1→4)]-Fuc-,
Api-(1→3)-Xyl-(1→4)-[Glc-(1→3)]-Rha-(1→2)-Fuc-,
Xyl-(1→4)-[Gal-(1→3)]-Rha-(1→2)-Fuc-,
Xyl-(1→4)-[Glc-(1→3)]-Rha-(1→2)-Fuc-,
Ara/Xyl-(1→4)-Rha/Fuc-(1→4)-[Glc/Gal-(1→2)]-Fuc-,
Api-(1→3)-Xyl-(1→4)-[Glc-(1→3)]-Rha-(1→2)-[$R^7$-(→4)]-Fuc- wherein $R^7$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^8$-(→4)]-Fuc- wherein $R^8$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[Rha-(1→3)]-4-OAc-Fuc-,
Api-(1→3)-Xyl-(1→4)-[Glc-(1→3)]-Rha-(1→2)-[Rha-(1→3)]-4-OAc-Fuc-,
6-OAc-Glc-(1→3)-Xyl-(1→4)-Rha-(1→2)-[3-OAc-Rha-(1→3)]-Fuc-,
Glc-(1→3)-Xyl-(1→4)-Rha-(1→2)-[3-OAc-Rha-(1→3)]-Fuc-,
Xyl-(1→3)-Xyl-(1→4)-Rha-(1→2)-[Qui-(1→4)]-Fuc-,
Glc-(1→3)-[Xyl-(1→4)]-Rha-(1→2)-[Qui-(1→4)]-Fuc-,
Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Glc-(1→3)-[Xyl-(1→4)]-Rha-(1→2)-Fuc-,
6-OAc-Glc-(1→3)-[Xyl-(1→4)]-Rha-(1→2)-Fuc-,
Glc-(1→3)-[Xyl-(1→3)-Xyl-(1→4)]-Rha-(1→2)-Fuc-,
Xyl-(1→3)-Xyl-(1→4)-Rha-(1→2)-[Xyl-(1→3)-4-OAc-Qui-(1→4)]-Fuc-,
Api/Xyl-(1→3)-Xyl-(1→4)-[Glc-(1→3)]-Rha-(1→2)-[Rha-(1→3)]-4OAc-Fuc-,
Api-(1→3)-Xyl-(1→4)-[Glc-(1→3)]-Rha-(1→2)-[Rha-(1→3)]-4OAc-Fuc-,
Api/Xyl-(1→3)-Xyl-(1→4)-[Glc-(1→3)]-Rha-(1→2)-[$R^9$-(→4)]-Fuc- wherein $R^9$ is 5-O-[5-O-Rha-(1→2)-Ara/Api-3,5-dihydroxy-6-methyl-octanoyl]-3,5-dihydroxy-6-methyl-octanoic acid),
Api/Xyl-(1→3)-Xyl-(1→4)-[Glc-(1→3)]-Rha-(1→2)-[$R^{10}$-(→4)]-Fuc- wherein $R^{10}$ is 5-O-[5-O-Ara/Api-3,5-dihydroxy-6-methyl-octanoyl]-3,5-dihydroxy-6-methyl-octanoic acid),
Api/Xyl-(1→3)-Xyl-(1→4)-[Glc-(1→3)]-Rha-(1→2)-[$R^{11}$-(→4)]-Fuc- wherein $R^{11}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid)
Glc-(1→3)-[Glc-(1→6)]-Gal-, and derivatives thereof.

In preferred saponin derivatives according to the invention, $R^1$ is Gal-(1→2)-[Xyl-(1→3)]-GlcA-; and $R^2$ is selected from:

Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid,
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid,
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid, and
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid, preferably, $R^1$ is Gal-(1→2)-[Xyl-(1→3)]-GlcA- and $R^2$ is Glc-(1→3)-Xyl-(1→4)-Rha-(1→2)-[Xyl-(1→3)-4-OAc-Qui-(1→4)]-Fuc-.

Typically, for the saponin derivative according to the invention, the saponin derivative is a derivative of a saponin selected from the group of saponins consisting of: *Quillaja* bark saponin, dipsacoside B, saikosaponin A, saikosaponin D, macranthoidin A, esculentoside A, phytolaccagenin, aescinate, AS6.2, NP-005236, AMA-1, AMR, alpha-Hederin, NP-012672, NP-017777, NP-017778, NP-017774, NP-018110, NP-017772, NP-018109, NP-017888, NP-017889, NP-018108, SA1641, AE X55, NP-017674, NP-017810, AG1, NP-003881, NP-017676, NP-017677, NP-017706, NP-017705, NP-017773, NP-017775, SA1657, AG2, SO1861, GE1741, SO1542, SO1584, SO1658, SO1674, SO1832, SO1904, SO1862, QS-7, QS1861, QS-7 api, QS1862, QS-17, QS-18, QS-21 A-apio, QS-21 A-xylo, QS-21 B-apio, QS-21 B-xylo, beta-Aescin, Aescin Ia, Teaseed saponin I, Teaseedsaponin J, Assamsaponin F, Digitonin, Primula acid 1 and AS64R, preferably the saponin derivative is selected from the group consisting of a QS-21 derivative, an SO1861 derivative, an SA1641 derivative and a GE1741 derivative, more preferably the saponin derivative is selected from the group consisting of a QS-21 derivative and an SO1861 derivative, most preferably the saponin derivative is an SO1861 derivative. Also preferred is the saponin derivative according to the invention, which is a derivative of SO1861, SO1832 or QS-21, preferably SO1861 and SO1832.

Particularly preferred is a saponin derivative of the invention, wherein the saponin derivative is according to formula (V), formula (VI), formula (VII) or formula (VIII):

(V)

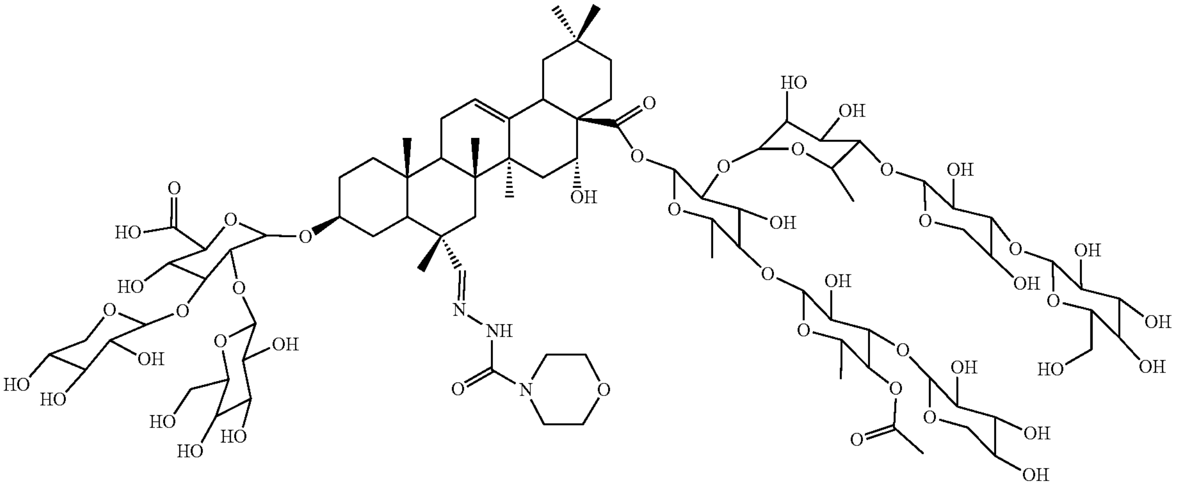

(VI)

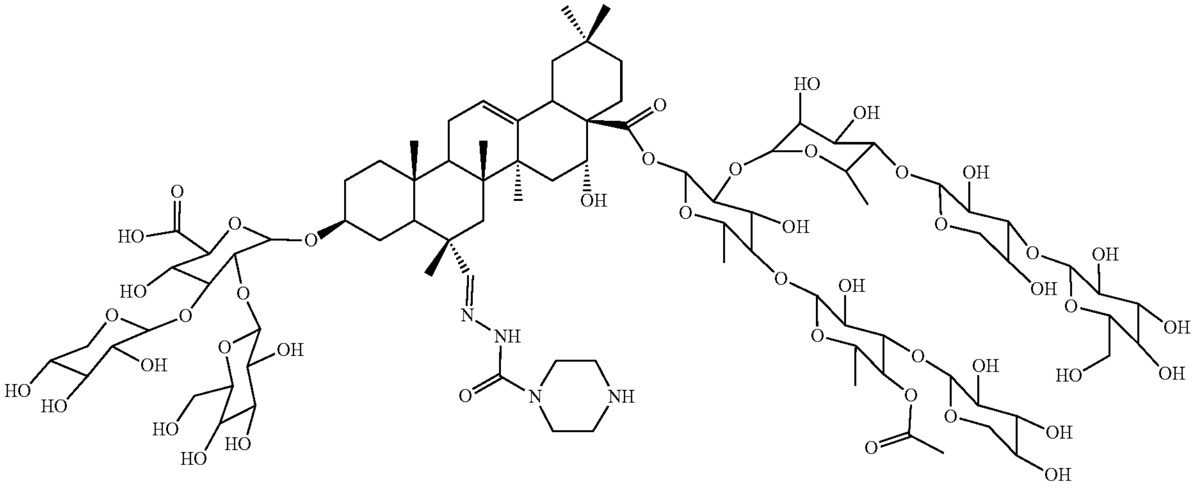

-continued (VII)

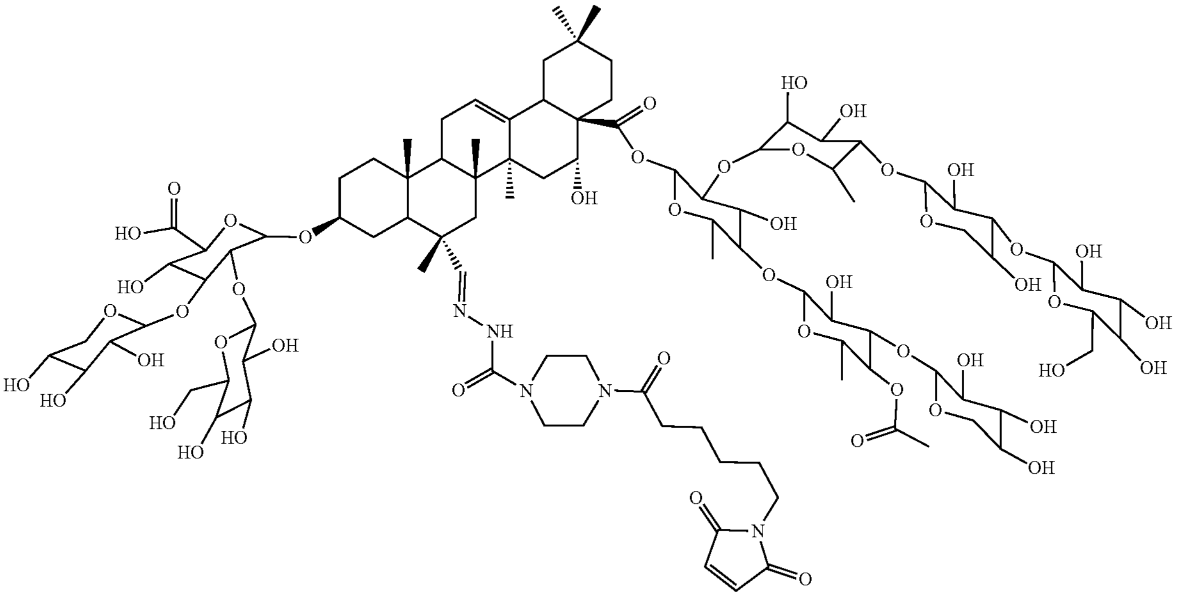

(VIII)

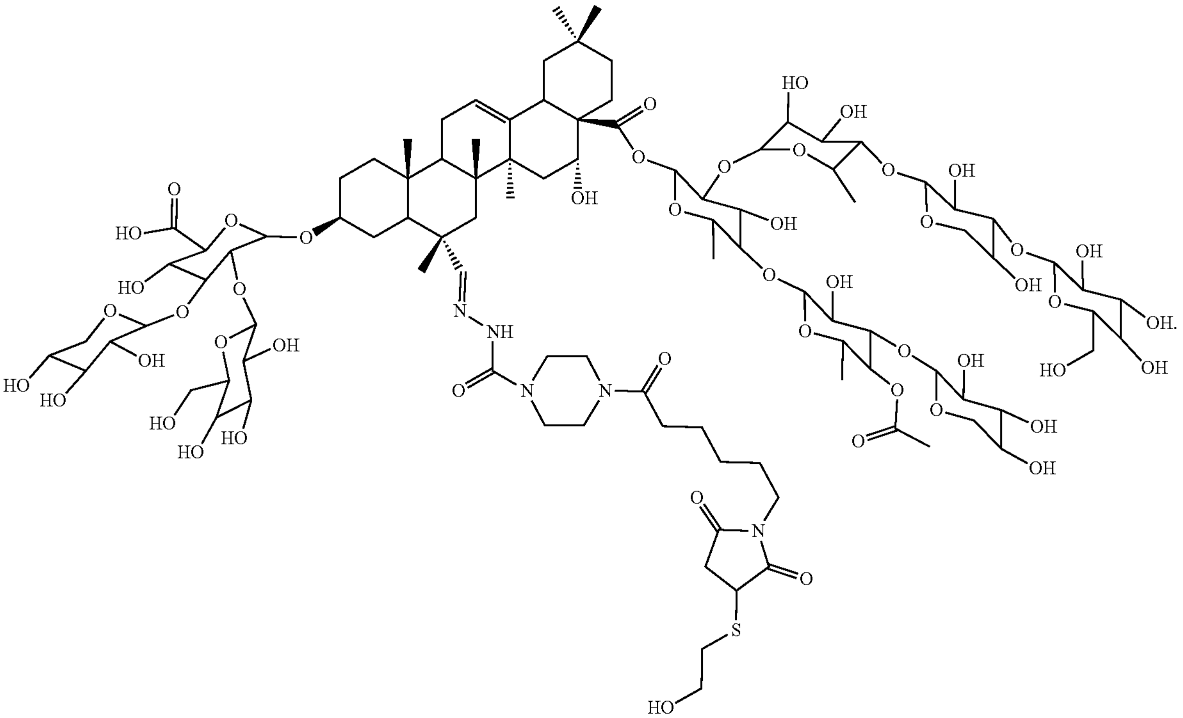

An aspect of the invention relates to a first pharmaceutical composition comprising the saponin derivative according to the invention and optionally a pharmaceutically acceptable excipient and/or diluent.

An aspect of the invention relates to a first pharmaceutical combination comprising:

(a) the first pharmaceutical composition of the invention; and (b) a second pharmaceutical composition comprising a conjugate of a cell-surface molecule binding-molecule and an effector moiety, wherein the cell-surface molecule binding-molecule is a proteinaceous molecule such as an antibody, and optionally comprising a pharmaceutically acceptable excipient and/or diluent.

An aspect of the invention relates to a first pharmaceutical combination comprising:

(a) the first pharmaceutical composition of the invention; and (b) a second pharmaceutical composition comprising any one or more of: a conjugate of a cell-surface molecule binding-molecule and an effector moiety, an antibody-effector moiety conjugate, a receptor-ligand-effector moiety conjugate, an antibody-toxin conjugate, a receptor-ligand-toxin conjugate, an antibody-drug conjugate, a receptor-ligand-drug conjugate, an antibody-oligonucleotide conjugate and a receptor-ligand-oligonucleotide conjugate, and optionally comprising a pharmaceutically acceptable excipient and/or diluent.

An aspect of the invention relates to a third pharmaceutical composition comprising the saponin derivative of the invention and further comprising a conjugate of a cell-surface molecule binding-molecule and an effector moiety, wherein the cell-surface molecule binding-molecule is a proteinaceous molecule such as an antibody, and optionally comprising a pharmaceutically acceptable excipient and/or diluent.

An aspect of the invention relates to a third pharmaceutical composition comprising the saponin derivative of the invention and further comprising any one or more of: a conjugate of a cell-surface molecule binding-molecule and an effector moiety, an antibody-effector moiety conjugate, a receptor-ligand-effector moiety conjugate, an antibody-toxin conjugate, a receptor-ligand-toxin conjugate, an antibody-drug conjugate, a receptor-ligand-drug conjugate, an antibody-oligonucleotide conjugate and a receptor-ligand-oligonucleotide conjugate, and optionally comprising a pharmaceutically acceptable excipient and/or diluent.

An embodiment is the first pharmaceutical combination comprising the second pharmaceutical composition of the invention, or the third pharmaceutical composition of the invention, wherein the second pharmaceutical composition or the third pharmaceutical composition comprises any one or more of an antibody-toxin conjugate, a receptor-ligand-toxin conjugate, an antibody-oligonucleotide conjugate or a receptor-ligand-oligonucleotide conjugate, wherein preferably the toxin is a protein toxin.

Preferred is the first pharmaceutical combination comprising the first pharmaceutical composition of the invention, or the third pharmaceutical composition of the invention, wherein the saponin derivative is any one or more of the saponin derivatives according to the invention.

An aspect of the invention relates to the first pharmaceutical composition of the invention, the first pharmaceutical combination of the invention or the third pharmaceutical composition of the invention, for use as a medicament.

An aspect of the invention relates to the first pharmaceutical combination of the invention or the third pharmaceutical composition of the invention, for use as a medicament.

An aspect of the invention relates to the first pharmaceutical composition of the invention, the first pharmaceutical combination of the invention or the third pharmaceutical composition of the invention, for use in the treatment or prophylaxis of a cancer or an auto-immune disease.

An aspect of the invention relates to the first pharmaceutical combination of the invention or the third pharmaceutical composition of the invention, for use in the treatment or prophylaxis of a cancer or an auto-immune disease. An aspect of the invention relates to the first pharmaceutical combination of the invention or the third pharmaceutical composition of the invention, for use in the treatment or prophylaxis of a cardiovascular disease or of hypercholesterolemia, or for use in a method for lowering LDL-cholesterol in the blood of a subject, preferably a human subject.

An aspect of the invention relates to an in vitro or ex vivo method for transferring a molecule from outside a cell to inside said cell, preferably into the cytosol of said cell, comprising the steps of:

a) providing a cell;

b) providing the molecule for transferring from outside the cell into the cell provided in step a);

c) providing a saponin derivative according to the invention;

d) contacting the cell of step a) in vitro or ex vivo with the molecule of step b) and the saponin derivative of step c), therewith establishing the transfer of the molecule from outside the cell into said cell.

An aspect of the invention relates to a saponin conjugate based on a saponin derivative according to the invention, wherein the aldehyde group is transformed into a semicarbazone functional group according to formula (IX)

(IX)

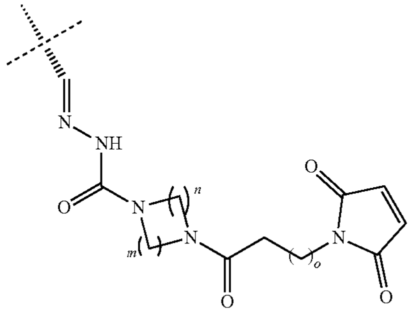

wherein n and m each are an integer independently selected from 1, 2, or 3;

o is an integer selected from 0-10, preferably 2-7, more preferably 4-6;

and wherein the maleimide functional group is further transformed into a thioether bond through reaction with a first proteinaceous molecule ('proteinaceous molecule 1') comprising a thiol functional group according to formula (X)

(X)

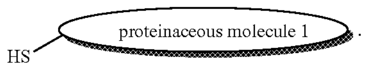

A preferred saponin conjugate according to the invention is the saponin conjugate according to formula (XI)

(XI)

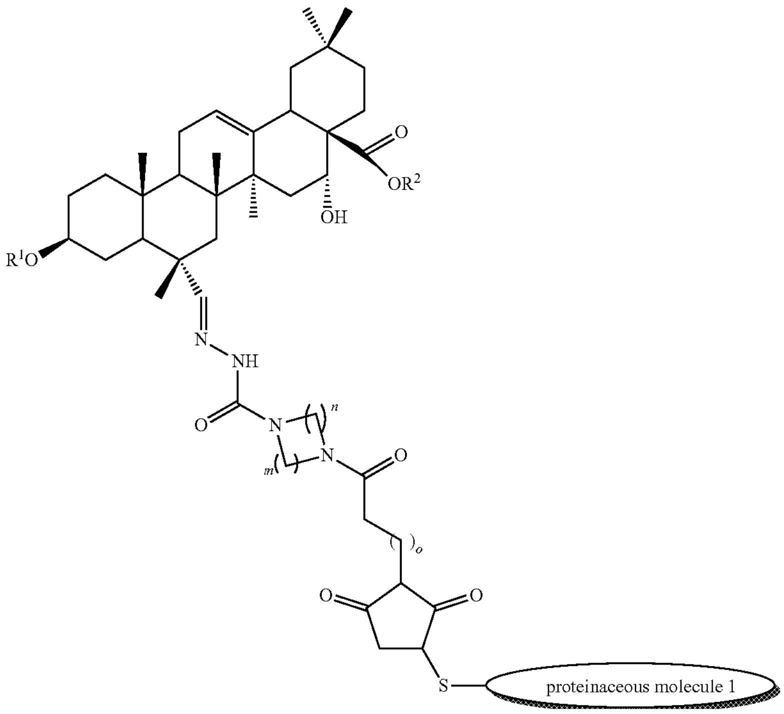, wherein $R^1$ and $R^2$ are as defined in any one of claims 1-10;

n and m each are an integer independently selected from 1, 2 or 3; and is an integer selected from 0-10, preferably 2-7, more preferably 4-6.

A typical saponin conjugate according to the invention is a saponin conjugate, wherein n=1 and m=1, or n=2 and m=1, or n=2 and m=2, or n=3 and m=2, or n=3 and m=3;

preferably wherein n=2 and m=2.

Preferred is the saponin conjugate according to the invention, wherein the saponin conjugate is according to formula (XII)

(XII)

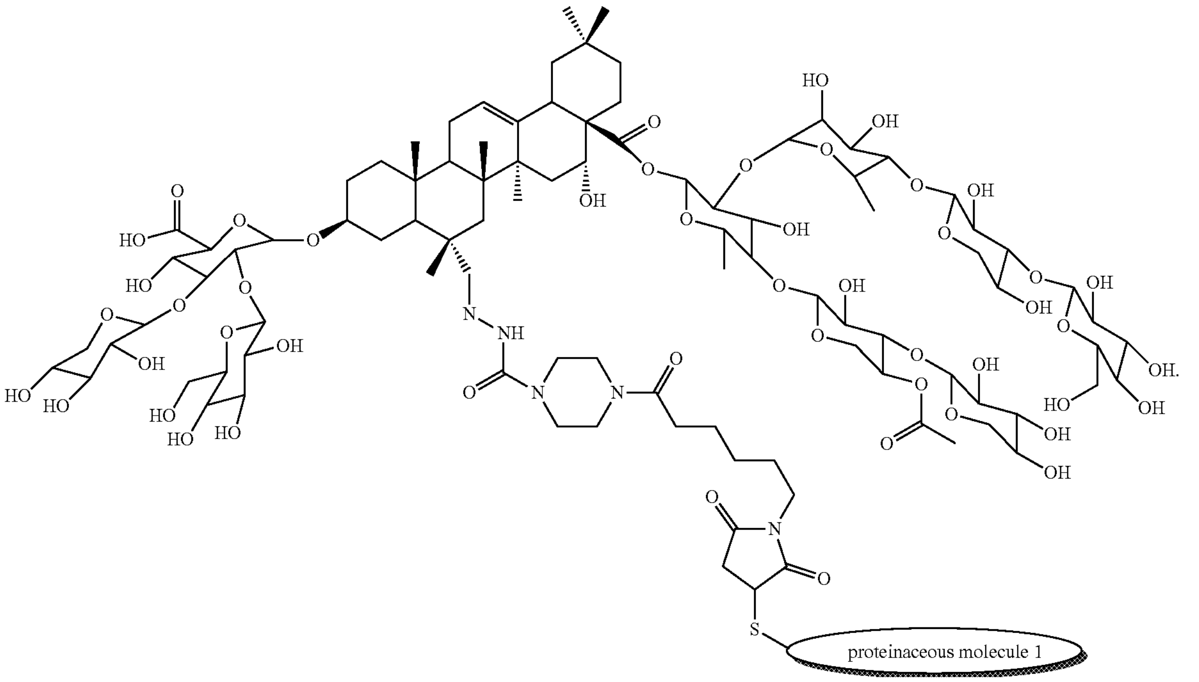

Also part of the invention is the saponin conjugate according to the invention, wherein the proteinaceous molecule 1 comprises a covalently bound effector moiety.

Preferred is the saponin conjugate according to the invention, wherein the effector moiety is an oligonucleotide.

An aspect of the invention relates to an eighth pharmaceutical composition comprising the saponin conjugate which comprises the proteinaceous molecule 1 comprising a covalently bound effector moiety, preferably an oligonucleotide, and optionally a pharmaceutically acceptable excipient and/or diluent.

An aspect of the invention relates to the eighth pharmaceutical composition for use as a medicament.

Preferably, in the saponin conjugate according to the invention, the proteinaceous molecule 1 comprises a cell-surface molecule binding-molecule comprising a first binding site for binding to a first epitope of a first cell-surface molecule.

A typical saponin conjugate of the invention is the saponin conjugate, wherein the proteinaceous molecule 1 comprises a cell-surface molecule binding-molecule comprising a first binding site for binding to a first epitope of a first cell-surface molecule, wherein said first binding site is or comprises any one or more of: an amino acid, a peptide, a protein, an antibody or a binding derivative or binding fragment or binding domain thereof such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, a ligand for a cell-surface molecule such as a receptor such as EGF and a cytokine.

The antibodies (immunoglobulins) of the present invention may be bi- or multifunctional. For example, a bifunctional antibody has one arm having a specificity for one receptor or antigen, while the other arm recognizes a different receptor or antigen. Alternatively, each arm of the bifunctional antibody may have specificity for a different epitope of the same receptor or antigen of the target cell.

The antibodies (immunoglobulins) of the present invention may be, but are not limited to, polyclonal antibodies, monoclonal antibodies, human antibodies, humanized antibodies, chimeric antibodies, resurfaced antibodies, anti-idiotypic antibodies, mouse antibodies, rat antibodies, rat/mouse hybrid antibodies, llama antibodies, llama heavy-chain only antibodies, heavy-chain only antibodies, and veterinary antibodies. Preferably, the antibody (immunoglobulin) of the present invention is a monoclonal antibody. The resurfaced, chimeric, humanized and fully human antibodies are also more preferred because they are less likely to cause immunogenicity in humans. The antibodies of the ADC of the present invention preferably specifically binds to an antigen expressed on the surface of a cancer cell, an autoimmune cell, a diseased cell, an aberrant cell, while leaving any healthy cell essentially unaltered (e.g. by not binding to such normal cell, or by binding to a lesser extent in number and/or affinity to such healthy cell).

A preferred embodiment is the saponin conjugate according to the invention, wherein the proteinaceous molecule 1 comprises a cell-surface molecule binding-molecule comprising a first binding site for binding to a first epitope of a first cell-surface molecule, wherein said first binding site is or comprises any one or more of: a single-domain antibody (sdAb), preferably a $V_H$ domain derived from a heavy chain of an antibody, preferably of immunoglobulin G origin, preferably of human origin, a $V_L$ domain derived from a light chain of an antibody, preferably of immunoglobulin G origin, preferably of human origin, a $V_{HH}$ domain such as derived from a heavy-chain only antibody (HCAb) such as from Camelidae origin or/g-NARorigin such as a variable heavy chain new antigen receptor (VNAR) domain, preferably the HCAb is from Camelidae origin, preferably the sdAb is a $V_{HH}$ domain derived from an HCAb from Camelidae origin (camelid $V_H$) such as derived from an HCAb from camel, lama, alpaca, dromedary, vicuna, guanaco and Bactrian camel.

Preferably, in the saponin conjugate according to the invention, the first epitope of the first cell-surface molecule, to which the proteinaceous molecule 1 can preferably bind, is a tumor-cell specific first epitope of a first tumor-cell surface molecule, more preferably a tumor-cell specific first epitope of a first tumor-cell surface receptor specifically present on a tumor cell.

It is specifically preferred that for the saponin derivative according to the invention and/or the saponin conjugate according to the invention, the semicarbazone functional group

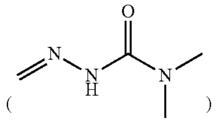

is hydrolysable (cleavable) under acidic conditions, preferably at pH 4.0-6.5, wherein hydrolysis of said semicarbazone functional group provides the aldehyde group on the aglycone core structure of the saponin on which the saponin derivative is based.

Thus, a specifically preferred embodiment is the saponin derivative according to the invention and/or the saponin conjugate according to the invention, wherein the semicarbazone functional group is subject to hydrolysis in vivo under acidic conditions as present in endosomes and/or lysosomes of mammalian cells, preferably human cells, preferably at pH 4.0-6.5, and more preferably at pH≤5.5.

Surprisingly, the inventors have found that the saponin derivatives according to the invention which are used as a component for potentiating the intracellular effect of an effector molecule or effector moiety when the effector molecule is provided as a conjugate comprising a cell-surface molecule binding-molecule such as an antibody, e.g. as an ADC or AOC, are now also suitably for (covalent) coupling to a cell-surface molecule binding-molecule such as a cell-surface molecule targeting antibody, such as an sdAb, such that by such coupling the saponin conjugate of the invention is provided, endowed with, for example, anti-tumor activity potentiating activity when used in combination with for example an ADC or an AOC.

An aspect of the invention relates to a second pharmaceutical combination comprising:

(a) a fourth pharmaceutical composition comprising the saponin conjugate of the invention and optionally a pharmaceutically acceptable excipient and/or diluent; and (b) a fifth pharmaceutical composition comprising a conjugate comprising a cell-surface molecule binding-molecule, such as a second proteinaceous molecule ('proteinaceous molecule 2'), and an effector moiety, wherein the proteinaceous molecule 2 is the same or different from the proteinaceous molecule 1 present in the saponin conjugate, and if the proteinaceous molecule 2 is different from the proteinaceous molecule 1, the proteinaceous molecule 2 comprising a second binding site for binding to a second epitope of a second cell-surface molecule, wherein the second cell-surface molecule is the same as or different from the first cell surface molecule, and if the second cell-surface molecule is different from the first cell surface molecule, the second cell-surface molecule and the first cell surface molecule are preferably present on the same cell, the fifth pharmaceutical composition optionally further comprising a pharmaceutically acceptable excipient and/or diluent. The effector moiety is not a saponin on which the saponin derivative or the saponin conjugate of the invention are based. The effector moiety is not the saponin derivative or the saponin conjugate of the invention.

An embodiment is the second pharmaceutical combination of the invention, comprising:

(a) the fourth pharmaceutical composition of the invention comprising the saponin conjugate of the invention, wherein the first epitope on the first cell-surface molecule is a tumor-cell specific first epitope on a first tumor cell-specific surface molecule, preferably a tumor-cell specific first epitope on a first cell-surface receptor specifically present at a tumor cell; and (b) the fifth pharmaceutical composition of the invention, wherein the second cell-surface molecule is a second tumor cell-specific surface molecule which is the same or different from the first tumor cell-specific surface molecule, preferably a second cell-surface receptor specifically present at a tumor cell which is the same or different from the first cell-surface receptor specifically present at said tumor cell, and wherein the second epitope is a tumor-cell specific second epitope, wherein the first epitope and the second epitope, which is the same as or different from the first epitope, are exposed at the same cell.

An aspect of the invention relates to a third pharmaceutical combination, comprising:

(a) the fourth pharmaceutical composition of the invention comprising the saponin conjugate according to the invention, comprising the first binding site for binding to the first epitope on the first cell-surface molecule, the fourth pharmaceutical composition optionally further comprising a pharmaceutically acceptable excipient and/or diluent; and (b) a sixth pharmaceutical composition comprising a conjugate comprising a cell-surface molecule binding-molecule, such as a third proteinaceous molecule ('proteinaceous molecule 3'), and an effector moiety, wherein the proteinaceous molecule 3 comprises the first binding site for binding to the first epitope on the cell-surface molecule of (a), the sixth pharmaceutical composition optionally further comprising a pharmaceutically acceptable excipient and/or diluent, wherein the first binding site of the proteinaceous molecule 1 and the first binding site of the proteinaceous molecule 3 are the same, and wherein the first cell-surface molecule and the first epitope on the first cell-surface molecule, to which the proteinaceous molecule 1 can bind, and the first cell-surface molecule and the first epitope on the first cell-surface molecule, to which the proteinaceous molecule 3 can bind, are the same. The effector moiety is not a saponin on which the saponin derivative or the saponin conjugate of the invention are based. The effector moiety is not the saponin derivative or the saponin conjugate of the invention.

An aspect of the invention relates to a third pharmaceutical combination, comprising:

(a) the fourth pharmaceutical composition of the invention and (b) the sixth pharmaceutical composition of the invention, wherein the first cell-surface molecule is expressed on a tumor cell surface, and preferably the first cell-surface molecule is a tumor cell-specific surface molecule, and wherein preferably the first epitope is a first tumor-cell specific epitope.

Preferred are the second pharmaceutical combination or third pharmaceutical combination according to the invention, wherein the second binding site of the proteinaceous molecule 2 and/or the third binding site of the proteinaceous molecule 3 comprises or consists of an antibody or a binding derivative or binding fragment or binding domain thereof such as a F(ab')2 fragment, Fab' fragment, Fab fragment, scFv, dsFv, single-domain antibody (sdAb), scFv-Fc, reduced IgG (rIgG), minibody, diabody, triabody, tetrabody, Fc fusion protein, nanobody, variable V domain, a ligand for a cell-surface molecule such as a receptor such as EGF and a cytokine, a single-domain antibody (sdAb), preferably $V_H$ domain derived from a heavy chain of an antibody, preferably of immunoglobulin G origin, preferably of human origin, a $V_L$ domain derived from a light chain of an antibody, preferably of immunoglobulin G origin, preferably of human origin, a $V_{HH}$ domain such as derived from a heavy-chain only antibody (HCAb) such as from Camelidae origin or Ig-NAR origin such as a variable heavy chain new antigen receptor (VNAR) domain, preferably the HCAb is from Camelidae origin, preferably the sdAb is a $V_{HH}$ domain derived from an HCAb from Camelidae origin (camelid $V_H$) such as derived from an HCAb from camel, lama, alpaca, dromedary, vicuna, guanaco and Bactrian camel.

An aspect of the invention relates to a seventh pharmaceutical composition comprising:

(a) the saponin conjugate of the invention; and (b) the conjugate comprising proteinaceous molecule 2 and an effector moiety of the invention, or the conjugate comprising proteinaceous molecule 3 and an effector moiety of the invention, and optionally further comprising a pharmaceutically acceptable excipient and/or diluent. The effector moiety is not a saponin on which the saponin derivative or the saponin conjugate of the invention are based. The effector moiety is not the saponin derivative or the saponin conjugate of the invention.

An aspect of the invention relates to the second pharmaceutical combination or third pharmaceutical combination of the invention, or the seventh pharmaceutical composition of the invention, for use as a medicament.

An aspect of the invention relates to the second pharmaceutical combination or third pharmaceutical combination of the invention, or the seventh pharmaceutical composition of the invention, for use in the treatment or prevention of a cancer or of an autoimmune disease such as rheumatoid arthritis.

Definitions

The term "saponin" has its regular scientific meaning and here refers to a group of amphipatic glycosides which comprise one or more hydrophilic glycone moieties combined with a lipophilic aglycone core which is a sapogenin. The saponin may be naturally occurring or synthetic (i.e. non-naturally occurring). The term "saponin" includes naturally-occurring saponins, derivatives of naturally-occurring saponins as well as saponins synthesized de novo through chemical and/or biotechnological synthesis routes.

The term "cell-surface molecule" has its regular scientific meaning and here refers to a molecule that is present and exposed at the outside surface of a cell such as a blood cell or an organ cell, such as a mammalian cell, such as a human cell.

The term "saponin derivative" has its regular scientific meaning and here refers to a saponin, i.e. a modified saponin, which has a chemical modification at a position where previously an aldehyde group was present in the non-derivatised saponin before being subjected to chemical modification for provision of the saponin derivative. For example, the saponin derivative is provided by chemical modification of an aldehyde group, in a saponin upon which the saponin derivative is based, i.e. the saponin is provided and an aldehyde group is chemically modified therewith providing the saponin derivative. For example, the saponin that is derivatised for provision of the saponin derivative is a naturally occurring saponin. Typically, the saponin derivative is a synthetic saponin, typically the saponin derivative is a derivatisation of a natural saponin, and is thus derived from a natural saponin, although a saponin derivative can also be derived from a synthetic saponin which may or may not have a natural counterpart. Typically, the saponin derivative has not a natural counterpart, i.e. the saponin derivative is not produced naturally by e.g. plants or trees. Optionally, the saponin derivative further has one or more chemical modifications at positions where previously any of a carboxyl group, an acetate group and/or an acetyl group was present in the non-derivatised or derivatised saponin before being subjected to chemical modification for provision of the saponin derivative. For example, the saponin derivative is provided by chemical modification of any one or more of an a carboxyl group, an acetate group and/or an acetyl group in a saponin upon which the saponin derivative is based, i.e. the saponin is provided and an aldehyde group, a carboxyl group, an acetate group and/or an acetyl group is chemically modified therewith providing the saponin derivative.

The term "mono-desmosidic saponin" has its regular scientific meaning and here refers to a triterpenoid saponin containing a single saccharide chain bound to the aglycone core, wherein the saccharide chain consists of one or more saccharide moieties.

The term "bi-desmosidic saponin" has its regular scientific meaning and here refers to a triterpenoid saponin containing two saccharide chains bound to the aglycone core, wherein each of the two saccharide chains consists of one or more saccharide moieties.

The term "triterpenoid saponin" has its regular scientific meaning and here refers to a saponin having a triterpenoid-type of aglycone core structure. The triterpenoid saponin differs from a saponin based on a steroid glycoside such as sapogenol in that such saponin comprising steroid glycoside has a steroid core structure, and the triterpenoid saponin differs from a saponin based on an alkaloid glycoside such as tomatidine in that such saponin comprising alkaloid glycoside has a alkaloid core structure.

The term "conjugate" has its regular scientific meaning and here refers to at least a first molecule that is covalently bound through chemical bonds to at least a second molecule, therewith forming a covalently coupled assembly comprising or consisting of the first molecule and the second molecule. Typical conjugates are an ADC, an AOC, and SO1861-EMCH (EMCH linked to the aldehyde group of the aglycone core structure of the saponin).

The term "tumor cell-specific surface molecule" and the term "tumor cell-specific receptor" have their regular scientific meaning and here refer to a molecule or a receptor that is expressed and exposed at the surface of a tumor cell and not at the surface of a healthy, non-cancerous cell, or is expressed at the surface of a healthy, non-cancerous cell to a lower extent than the level of expression (number of molecules/receptors) at the surface of the tumor cell.

The term "oligonucleotide" has its regular scientific meaning and here refers to a string of two or more nucleotides, i.e. an oligonucleotides is a short oligomer composed of ribonucleotides or deoxyribonucleotides. Examples are RNA and DNA, and any modified RNA or DNA, such as a string of nucleic acids comprising a nucleotide analogue such as a bridged nucleic acid (BNA), also known as locked nucleic acid (LNA) or a 2'-O,4'-C-aminoethylene or a 2'-O, 4'-C-aminomethylene bridged nucleic acid ($BNA^{NC}$), wherein the nucleotide is a ribonucleotide or a deoxyribonucleotide.

The term "BNA" refers to $BNA^{NC}$ or 2',4'-$BNA^{NC}$ (2'-O, 4'-aminoethylene bridged nucleic acid) and has its regular scientific meaning and here refers to an oligonucleotide that contains one or more nucleotide building blocks with a six-member bridged structure with an N—O linkage, and with an (N—H) or (N-Me) residue.

The term "payload" has its regular scientific meaning and here refers to a biologically active molecule such as for example a cytotoxic (anti-cancer) drug molecule.

The term "proteinaceous" has its regular scientific meaning and here refers to a molecule comprising at least two amino acid residues linked via a peptide bond with each other so that the molecule is of, relates to, resembles, or is a polypeptide or a protein, meaning that the molecule possesses, to some degree, the physicochemical properties characteristic of a protein, is of protein, relating to protein, containing protein, pertaining to protein, consisting of protein, resembling protein, or being a protein. The term "proteinaceous" as used in for example 'proteinaceous molecule' refers to the presence of at least two amino acid residues linked via a peptide bond with each other so that at least a part of the molecule that resembles or is a protein, wherein 'protein' is to be understood to include a chain of amino-acid residues at least two residues long, thus including a peptide, a polypeptide and a protein and an assembly of proteins or protein domains. In the proteinaceous molecule, the at least two amino-acid residues are for example linked via (an) amide bond(s), such as (a) peptide bond(s). In the proteinaceous molecule, the amino-acid residues are natural amino-acid residues and/or artificial amino-acid residues such as modified natural amino-acid residues. It is preferred that a proteinaceous molecule is a molecule comprising at least two amino-acid residues, preferably between 2 and about 2.000 amino-acid residues. Also preferred is a proteinaceous molecule that is a molecule comprising from 2 to 20 (typical for a peptide) amino acids. Also preferred is a proteinaceous molecule that is a molecule comprising from 21 to 1.000 amino acid residues (typical for a polypeptide, a protein, a protein domain, such as an antibody, a Fab, an scFv, a ligand for a receptor such as EGF). Preferably, the amino-acid residues are (typically) linked via (a) peptide bond(s). According to the invention, said amino-acid residues are or comprise (modified) (non-)natural amino acid residues.

The term "binding molecule" has its regular scientific meaning and here refers to a molecule capable of specifically binding to another molecule such as a cell-surface molecule, e.g. a cell-surface receptor. Typical binding molecules are peptides, proteins, non-protein molecules, cell-surface receptor ligands, protein ligands, that can bind to e.g. a protein, a lipid, a (poly)saccharide, such as a cell-surface receptor or a cell-surface molecule. "Specifically binding" here refers to specific and selective binding with higher affinity than non-specific background binding.

The term "moiety" has its regular scientific meaning and here refers to an molecule that is bound, linked, conjugated to a further molecule, linker, assembly of molecules, etc., and therewith forming part of a larger molecule, conjugate, assembly of molecules. Typically, an moiety is an molecule that is covalently bound to another molecules, involving one or more chemical groups initially present on the effector molecule. For example, saporin is a typical effector molecule. As part of an antibody-drug conjugate, the saporin is a typical effector moiety in the ADC. As part of an antibody-oligonucleotide conjugate, an AON such as a BNA or an siRNA is a typical effector moiety in the AOC.

The term "aglycone core structure" has its regular scientific meaning and here refers to the aglycone core of a saponin without the one or two carbohydrate antenna or saccharide chains (glycans) bound thereto. For example, quillaic acid is the aglycone core structure for SO1861, QS-7 and QS-21. Typically, the glycans of a saponin are mono-saccharides or oligo-saccharides, such as linear or branched glycans.

The term "QS-21" (also referred to as "QS21"), unless further specified, refers to any one of the isomers of QS-21. As will be understood by the skilled person, a typical natural extract comprising QS-21 will comprise a mixture of the different isomers of QS-21. However, through purification or (semi-)synthetic routes, a single isomer can be isolated.

The term "Saponinum album" has its normal meaning and here refers to a mixture of saponins produced by Merck KGaA (Darmstadt, Germany) containing saponins from *Gypsophila paniculata* and *Gypsophila arostii*, containing SA1657 and mainly SA1641.

The term "*Quillaja* saponin" has its normal meaning and here refers to the saponin fraction of *Quillaja saponaria* and thus the source for all other QS saponins, mainly containing QS-18 and QS-21.

"QS-21" or "QS21" has its regular scientific meaning and here refers to a mixture of QS-21 A-apio (~63%), QS-21 A-xylo (~32%), QS-21 B-apio (~3.3%), and QS-21 B-xylo (~1.7%).

Similarly, "QS-21A" has its regular scientific meaning and here refers to a mixture of QS-21 A-apio (~65%) and QS-21 A-xylo (~35%).

Similarly, "QS-21 B" has its regular scientific meaning and here refers to a mixture of QS-21 B-apio (~65%) and QS-21 B-xylo (~35%).

The term "Quil-A" refers to a commercially available semi-purified extract from *Quillaja saponaria* and contains variable quantities of more than 50 distinct saponins, many of which incorporate the triterpene-trisaccharide substructure Gal-(1→2)-[Xyl-(1→3)]-GlcA- at the C-3beta-OH group found in QS-7, QS-17, QS18, and QS-21. The saponins found in Quil-A are listed in van Setten (1995), Table 2 [Dirk C. van Setten, Gerrit van de Werken, Gijsbert Zomer and Gideon F. A. Kersten, *Glycosyl Compositions and Structural Characteristics of the Potential Immuno-adjuvant Active Saponins in the Quillaja saponaria Molina Extract Quil A, RAPID COMMUNICATIONS IN MASS SPECTROMETRY*, VOL. 9,660-666 (1995)]. Quil-A and also *Quillaja* saponin are fractions of saponins from *Quillaja saponaria* and both contain a large variety of different saponins with largely overlapping content. The two fractions differ in their specific composition as the two fractions are gained by different purification procedures.

The term "QS1861" and the term "QS1862" refer to QS-7 and QS-7 api. QS1861 has a molecular mass of 1861 Dalton, QS1862 has a molecular mass of 1862 Dalton. QS1862 is described in Fleck et al. (2019) in Table 1, row no. 28 [Juliane Deise Fleck, Andresa Heemann Betti, Francini Pereira da Silva, Eduardo Artur Troian, Cristina Olivaro, Fernando Ferreira and Simone Gasparin Verza, *Saponins from Quillaja saponaria and Quillaja brasiliensis: Particular Chemical Characteristics and Biological Activities, Molecules* 2019, 24, 171; doi:10.3390/molecules24010171]. The described structure is the api-variant QS1862 of QS-7. The molecular mass is 1862 Dalton as this mass is the formal mass including proton at the glucuronic acid. At neutral pH, the molecule is deprotonated. When measuring in mass spectrometry in negative ion mode, the measured mass is 1861 Dalton.

The term "saccharide chain" has its regular scientific meaning and here refers to any of a glycan, a carbohydrate antenna, a single saccharide moiety (mono-saccharide) or a chain comprising multiple saccharide moieties (oligosaccharide, polysaccharide). The saccharide chain can consist of only saccharide moieties or may also comprise further moieties such as any one of 4E-Methoxycinnamic acid, 4Z-Methoxycinnamic acid, and 5-O-[5-O-Ara/Api-3,5-dihydroxy-6-methyl-octanoyl]-3,5-dihydroxy-6-methyl-octanoic acid), such as for example present in QS-21.

The term "transformation" has its regular scientific meaning and here refers to the chemical transformation of modification of a first functional group or first chemical group or first chemical moiety such that a second functional group or second chemical group or second chemical moiety is provided. An example is the transformation of an aldehyde group carbonyl group into a semicarbazone functional group through reaction with a semicarbazide.

The term "Api/Xyl-" or "Api- or Xyl-" in the context of the name of a saccharide chain has its regular scientific meaning and here refers to the saccharide chain either comprising an apiose (Api) moiety, or comprising a xylose (Xyl) moiety.

The term "oligonucleotide" has its regular scientific meaning and here refers to amongst others any natural or synthetic string of nucleic acids encompassing DNA, modified DNA, RNA, mRNA, modified RNA, synthetic nucleic acids, presented as a single-stranded molecule or a double-stranded molecule, such as a BNA, an antisense oligonucleotide (ASO), a short or small interfering RNA (siRNA; silencing RNA), an anti-sense DNA, anti-sense RNA, etc.

The term "antibody" as used herein is used in the broadest sense, which may refer to an immunoglobulin (Ig) defined as a protein belonging to the class IgG, IgM, IgE, IgA, or IgD (or any subclass thereof), or a functional binding fragment or binding domain of an immunoglobulin. In the context of the present invention, a "binding fragment" or a "binding domain" of an immunoglobulin or of an antibody is defined as antigen-binding fragment or -domain or other derivative of a parental immunoglobulin that essentially maintains the antigen binding activity of such parental immunoglobulin. Functional fragments and functional domains are antibodies in the sense of the present invention even if their affinity to the antigen is lower than that of the parental immunoglobulin. "Functional fragments and -domains" in accordance with the invention include, but are not limited to, F(ab')2 fragments, Fab' fragments, Fab fragments, scFv, dsFv, single-domain antibody (sdAb), monovalent IgG, scFv-Fc, reduced IgG (rIgG), minibody, diabodies, triabodies, tetrabodies, Fc fusion proteins, nanobodies, variable V domains such as $V_{HH}$, Vh, and other types of antigen recognizing immunoglobulin fragments and domains. The fragments and domains may be engineered to minimize or completely remove the intermolecular disulphide interactions that occur between the CH1 and CL domains. Functional fragment and -domains offer the advantage of greater tumor penetration because of their smaller size. In addition, the functional fragment or -domain can be more evenly distributed throughout the tumor mass as compared to whole immunoglobulin.

The term "antibody-drug conjugate" or "ADC" has its regular scientific meaning and here refers to any conjugate of an antibody such as an IgG, an immunoglobulin, an immunoglobulin binding fragment, a binding derivative or binding fragment or binding domain of an antibody such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, a ligand for a cell-surface molecule such as a receptor such as EGF and a cytokine, multiple $V_H$ domains, single-domain antibodies, $V_{HH}$, or camelid $V_H$, etc., and any molecule that can exert a therapeutic effect when contacted with cells of a subject such as a human patient, such as an active pharmaceutical ingredient, a toxin, an oligonucleotide, an enzyme, a small molecule drug compound, etc.

The term "antibody-oligonucleotide conjugate" or "AOC" has its regular scientific meaning and here refers to any conjugate of an antibody such as an IgG, an immunoglobulin, an immunoglobulin binding fragment, a binding derivative or binding fragment or binding domain of an antibody such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, a ligand for a cell-surface molecule such as a receptor such as EGF and a cytokine, multiple $V_H$ domains, single-domain antibodies, $V_{HH}$, or camelid $V_H$, etc., and any oligonucleotide molecule that can exert a therapeutic effect when contacted with cells of a subject such as a human patient, such as an oligonucleotide selected from a natural or synthetic string of nucleic acids encompassing DNA, modified DNA, RNA, mRNA, modified RNA, synthetic nucleic acids, presented as a single-stranded molecule or a double-stranded molecule, such as a BNA, an antisense oligonucleotide (ASO), a short or small interfering RNA (siRNA; silencing RNA), an anti-sense DNA, anti-sense RNA, etc.

The term "linker" has its regular scientific meaning, and linkers are commonly known in the art of bioconjugation. Common linkers are for example described in G. T. Hermanson (*Bioconjugation Techniques*, Third edition, Elsevier, 2013, ISBN: 978-0-12-382239-0). Here, the term linker refers to a chemical moiety or a linear stretch of amino-acid residues complexed through peptide bonds, which is suitable for covalently attaching (binding) a first molecule, such as a saponin, to another molecule, e.g. to a (proteinaceous) ligand or to an effector molecule or to a scaffold, for example composed of or comprising amino-acid residues, nucleic acids, etc. Typically, the linker comprises a chain of atoms linked by chemical bonds. Any linker molecule or linker technology known in the art can be used in the present disclosure. Where indicated, the linker is a linker for covalently binding of molecules through a chemical group on such a molecule suitable for forming a covalent linkage or bond with the linker. The linker may be a non-cleavable linker, e.g., the linker is stable in physiological conditions. The linker may be a cleavable linker, e.g. a linker that is cleavable, in the presence of an enzyme or at a particular pH range or value, or under physiological conditions such as intracellular conditions in the endosomes such as the late endosomes and the lysosomes of mammalian cells such as human cells. Exemplary linkers that can be used in the context of the present disclosure include, but is not limited to, N-ε-maleimidocaproic acid hydrazide (EMCH), succinimidyl 3-(2-pyridyldithio)propionate or 3-(2-Pyridyldithio) propionic acid N-hydroxysuccinimide ester (SPDP), a linker represented by a maleimide moiety according to formula (II)a or formula (II)b, (II)a

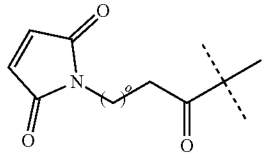

(II)b

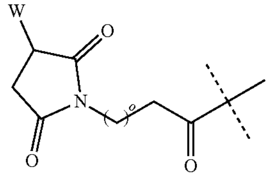

or an azide moiety according to formula (II)c (II)c

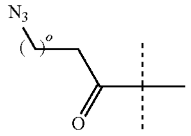

wherein o is an integer selected from 0-10, preferably 2-7, more preferably 4-6, and W is a thiol functional group according to formula (III), (III)

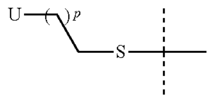

wherein U=SH, $NH_2$ or OH and p is an integer selected from 0-4, preferably 1-3, more preferably 1 or 2, and 1-[Bis(dimethylamino)methylene]-1H-1,2,3-triazolo[4,5-b]pyridinium 3-oxid hexafluorophosphate (HATU).

The term "effector molecule", or "effector moiety" when referring to the effector molecule as part of e.g. a covalent conjugate, has its regular scientific meaning and here refers to a molecule or moiety that has an effect on any one or more of a target molecule and/or proximally to any one or more of a target molecule and/or that can selectively bind to any one or more of a target molecule, wherein the target molecules are for example: a protein, a peptide, a carbohydrate, a saccharide such as a glycan, a (phospho)lipid, a nucleic acid such as DNA, RNA, an enzyme, and regulates the biological activity of such one or more target molecule(s). The effector molecule is for example a molecule selected from any one or more of a small molecule such as a drug molecule, a toxin such as a protein toxin, an oligonucleotide such as an AON such as a BNA, a xeno nucleic acid or an siRNA, an enzyme, a peptide, a protein, or any combination thereof. Thus, for example, an effector molecule or an effector moiety is a molecule or moiety selected from any one or more of a small molecule such as a drug molecule, a toxin such as a protein toxin, an oligonucleotide such as an AON such as a BNA, a xeno nucleic acid or an siRNA, an enzyme, a peptide, a protein, or any combination thereof, that can selectively bind to any one or more of the target molecules: a protein, a peptide, a carbohydrate, a saccharide such as a glycan, a (phospho)lipid, a nucleic acid such as DNA, RNA, an enzyme, and that upon binding to the target molecule regulates the biological activity of such one or more target molecule(s). An effect can include, but is not limited to, biological effect, a therapeutic effect, an imaging effect, and/or a cytotoxic effect. Typically, an effector molecule or moiety can exert a biological effect inside a cell such as a mammalian cell such as a human cell, such as in the cytosol of said cell. At a molecular or cellular level, an effect can include, but is not limited to, promotion or inhibition of the target's activity, labelling of the target, and/or cell death. Typical effector molecules and effector moieties are thus protein toxins, drug molecules, plasmid DNA, toxins such as toxins comprised by antibody-drug conjugates (ADCs), oligonucleotides such as an AON such as an siRNA, BNA, nucleic acids comprised by an antibody-oligonucleotide conjugate (AOC), enzymes. For example, an effector molecule or moiety is a molecule which can act as a ligand that can increase or decrease (intracellular) enzyme activity, gene expression, or cell signalling. The effector moiety is not a saponin on which the saponin derivative or the saponin conjugate of the invention are based. The effector moiety is not the saponin derivative or the saponin conjugate of the invention.

The term "HSP27" relates to a BNA oligonucleotide molecule which silences the expression of HSP27 in the cells. The term "ApoB", or "ApoBBNA", or "ApoB #02" relates to a BNA oligonucleotide molecule which silences the expression of apoB in the cells.

The term "bridged nucleic acid", or "BNA" in short, or "locked nucleic acid" or "LNA" in short or 2'-O,4'-C-aminoethylene or 2'-O,4'-C-aminomethylene bridged nucleic acid ($BNA^{NC}$), has its regular scientific meaning and here refers to a modified RNA nucleotide. The term "BNA-based antisense oligonucleotide", or in short "BNA-AON", has its regular scientific meaning and here refers to a string of antisense nucleotides wherein at least one of said nucleotides is a BNA. A BNA is also referred to as 'constrained RNA molecule' or 'inaccessible RNA molecule'. A BNA monomer can contain a five-membered, six-membered or even a seven-membered bridged structure with a "fixed" C3'-endo sugar puckering. The bridge is synthetically incorporated at the 2',4'-position of the ribose to afford a 2',4'-BNA monomer. A BNA monomer can be incorporated into an oligonucleotide polymeric structure using standard phosphoramidite chemistry known in the art. A BNA is a structurally rigid oligonucleotide with increased binding affinity and stability.

The terms first, second, third and the like in the description and in the claims, are used for distinguishing between for example similar elements, compositions, constituents in a composition, or separate method steps, and not necessarily for describing a sequential or chronological order. The terms are interchangeable under appropriate circumstances and the embodiments of the invention can operate in other sequences than described or illustrated herein, unless specified otherwise.

The term 'L' as used such as in an saponin derivative or an antibody-saponin conjugate or construct comprising a linker, represents 'labile linker' which is cleaved under slightly acid conditions (pH<6.6, such as pH 4.0-5.5) in the endosome, endolysosome and in the lysosome of mammalian cells, such as human cells, such as a human tumor cell.

The term "GalNAc" has its regular scientific meaning and here refers to N-acetylgalactosamine and to the IUPAC name thereof: 2-(acetylamino)-2-deoxy-D-galactose.

The term "$(GalNAc)_3$Tris" has its regular scientific meaning in for example the field of siRNA-based therapy, and here refers to a moiety comprising three GalNAc units each separately covalently bound to the hydroxyl groups of tris(hydroxymethyl)aminomethane (Tris) (IUPAC name: 2-amino-2-(hydroxymethyl) propane-1,3-diol), preferably via at least one linker. $(GalNAc)_3$Tris can exist as a free amine comprising molecule or may be further functionalized via the remaining amine binding site, for example to form the $(GalNAc)_3$Tris-moiety comprising conjugates described herein.

The embodiments of the invention described herein can operate in combination and cooperation, unless specified otherwise.

Furthermore, the various embodiments, although referred to as "preferred" or "e.g." or "for example" or "in particular" and the like are to be construed as exemplary manners in which the invention may be implemented rather than as limiting the scope of the invention.

The term "comprising", used in the claims, should not be interpreted as being restricted to for example the elements or the method steps or the constituents of a compositions listed thereafter; it does not exclude other elements or method steps or constituents in a certain composition. It needs to be interpreted as specifying the presence of the stated features, integers, (method) steps or components as referred to, but does not preclude the presence or addition of one or more other features, integers, steps or components, or groups thereof. Thus, the scope of the expression "a method comprising steps A and B" should not be limited to a method consisting only of steps A and B, rather with respect to the present invention, the only enumerated steps of the method are A and B, and further the claim should be interpreted as including equivalents of those method steps. Thus, the scope of the expression "a composition comprising components A and B" should not be limited to a composition consisting only of components A and B, rather with respect to the present invention, the only enumerated components of the composition are A and B, and further the claim should be interpreted as including equivalents of those components.

The term "DAR" normally stands for Drug Antibody Ratio and refers to the average drug to antibody ratio for a given preparation of antibody drug conjugate (ADC) and here refers to a ratio of the amount of bound SO1861 moieties, or SPT001, or bound payload, e.g. an AON such as ApoB BNA with respect to the conjugate molecule.

In addition, reference to an element or a component by the indefinite article "a" or "an" does not exclude the possibility that more than one of the element or component are present, unless the context clearly requires that there is one and only one of the elements or components. The indefinite article "a" or "an" thus usually means "at least one".

BRIEF DESCRIPTION OF THE DRAWINGS

The present invention will be discussed in more detail below, with reference to the attached drawings, in which

FIG. 5B is the same and is displayed next to the graphs in FIG. 5A.

FIG. 6B is the same and is displayed next to the graphs in FIG. 6A.

FIG. 7B is the same and is displayed next to the graphs in FIG. 7A.

FIG. 9B is the same and is displayed next to the graphs in FIG. 9A. 'SC' is 'semicarbazone'

FIG. 12B is the same and is displayed next to the graphs in FIG. 12B.

FIG. 13B is the same and is displayed next to the graphs in FIG. 13B.

FIG. 15B is the same and is displayed next to the graphs in FIG. 15B.

DETAILED DESCRIPTION

Figure 1:
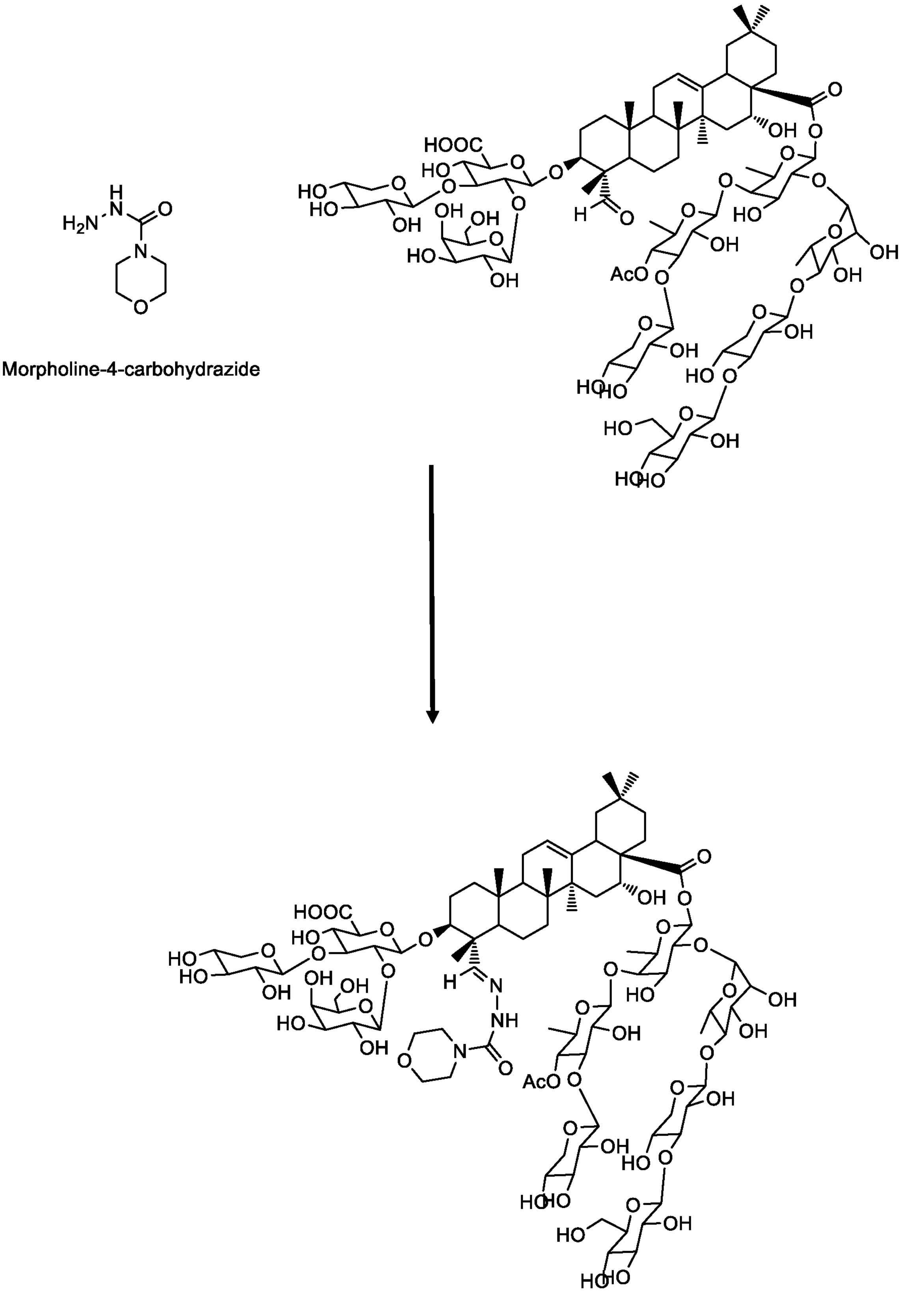
FIG. 1: Synthesis and chemical structure of SO1861-semicarbazone (Molecule V)

The present invention will be described with respect to particular embodiments but the invention is not limited thereto but only by the claims.

Surprisingly, the inventors have found that a saponin derivative based on a saponin comprising a triterpene aglycone core structure and at least one of a first saccharide chain '$R^1$' and a second saccharide chain '$R^2$' linked to the aglycone core structure, wherein the saponin derivative comprises an aglycone core structure comprising an aldehyde group, wherein the aldehyde group is transformed into a semicarbazone functional group according to formula (I)

(I)

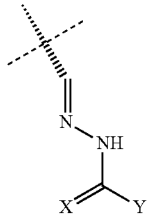

wherein $R^1$ and $R^2$ are independently selected from hydrogen, a monosaccharide, a linear oligosaccharide and a branched oligosaccharide, X=O, P or S, and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H; or

Y=

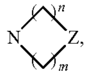

wherein n and m each are an integer independently selected from 1, 2, or 3,

Z=$CH_2$, O, S, P or $NR^5$, and wherein $R^5$ represent H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b, (II)a

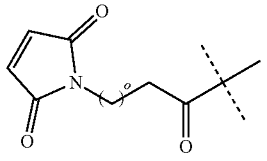

(II)b

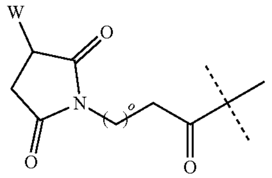

or an azide moiety according to formula (II)c (II)c

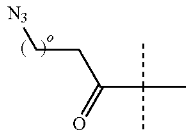

wherein o is an integer selected from 0-10, preferably 2-7, more preferably 4-6, and W is a thiol functional group according to formula (III), (III)

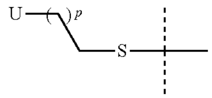

wherein U=SH, $NH_2$ or OH and p is an integer selected from 0-4, preferably 1-3, more preferably 1 or 2, has a reduced toxicity when cell viability is considered of cells contacted with the saponin derivatives; has activity when potentiation of e.g. toxin cytotoxicity or AON-, such as BNA, mediated gene silencing is considered (without wishing to be bound by any theory: relating to similar or improved endosomal escape enhancing activity of the modified saponin), if the aldehyde functional group is transformed to a semicarbazone functional group according to formula (I); and/or has reduced hemolytic activity, when compared with the toxicity, activity and haemolytic activity of unmodified saponin. That is to say, the saponin derivative of the invention has at least one, preferably to, more preferably all three of:

(i) a reduced toxicity when cell viability is considered of cells contacted with the saponin derivatives;

(ii) enhanced activity when potentiation of e.g. toxin cytotoxicity or AON-mediated gene silencing such as BNA-mediated gene silencing is considered (without wishing to be bound by any theory: relating to similar or improved endosomal escape enhancing activity of the modified saponin), if the aldehyde functional group is transformed to a semicarbazone functional group according to formula (I); and/or (iii) reduced hemolytic activity, when compared with the toxicity, activity and haemolytic activity of unmodified saponin on which the saponin derivative is based. Therewith, the inventors provide saponin derivatives with an improved therapeutic window, since for the saponin derivatives, the cytotoxicity is lower than cytotoxicity determined for their naturally occurring counterparts, the haemolytic activity is lower than haemolytic activity determined for the naturally occurring counterparts of the saponin derivatives, the ratio between IC50 values for cell toxicity and e.g. IC50 values for toxin potentiation or IC50 values for gene silencing is similar or increased, and/or since the ratio between IC50 values for saponin haemolytic activity and e.g. IC50 values for toxin potentiation or IC50 values for gene silencing is similar or increased. Reference is made to Table 3 and Table 4 of the examples for an overview of exemplified saponin derivatives for an overview of the cytotoxicity, haemolytic activity and endosomal escape enhancing activity ('activity'), as well as an overview of the ratio between IC50 for cytotoxicity and IC50 for activity, and the ratio between IC50 for haemolytic activity and IC50 for activity.

In addition, the inventors surprisingly established (tumor) cell killing by contacting such cells with a saponin conjugate of the current invention based on a saponin derivative of the current invention, together with an ADC such as an antibody-protein toxin conjugate, despite the medium to low expression of the cell-surface receptor targeted by the cell-surface molecule binding-molecule (e.g. antibody) comprised by the saponin conjugate and/or despite the medium to low expression of the cell-surface receptor targeted by the ADC. The saponin derivative and the saponin conjugate of the invention comprise the semicarbazone functional group. For example, in a comparative example, such cell killing could not be established or only to a lower extent, when a saponin conjugate comprising the same cell-surface molecule binding-molecule (e.g. antibody) but comprising a hydrazone functional group (=N—N(H)—C(O)—) instead of the semicarbazone functional group, was contacted with the cells. Therewith, the inventors now provide for a more potent saponin derivative and saponin conjugate, when the activation or potentiating of an effector moiety such as an effector moiety comprised by an ADC or AOC, is considered.

Furthermore, the inventors have found that the saponin derivatives according to the invention comprising the semicarbazone functional group hydrolyses more rapidly and in an higher amount towards the corresponding native saponin comprising a "free" aldehyde functional group, as compared to saponin derivatives comprising a hydrazone functional group (=N—N(H)—C(O)—) known in the art, under acidic conditions which are the conditions present in endosomes and/or lysosomes of mammalian cells. This has the benefit that a lower amount of the saponin derivatives according to the invention should be administered to a patient in need of potentiation of e.g. an ADC or an AOC a gene-silencing oligonucleotide such as an AON such as a BNA, e.g. coupled to one or more GalNAc moieties, to obtain the same amount of native saponin comprising the "free" aldehyde to act as endosomal escape enhancers for targeted toxins or targeted oligonucleotides, compared to the required amount of saponin derivative comprising e.g. the hydrazone functional group (=N—N(H)—C(O)—). Without wishing to be bound by any theory, faster and more efficacious release of the saponin comprising the aldehyde functional group from the saponin derivative that comprises the semicarbazone functional group according to the invention, when compared to release of the saponin comprising the aldehyde functional group from the saponin derivative that comprises e.g. the hydrazone functional group, is at the basis for the improved activity of the saponin conjugate of the invention comprising a saponin derivative of the invention, such as a conjugate comprising the saponin, an oligonucleotide and a cell-surface receptor ligand such as one to three GalNAc moieties (for targeting (liver) cells expressing ASGPR), wherein the activity is the potentiation of the effector moiety activity such as a gene-silencing oligonucleotide, inside the cytosol or nucleus of the targeted cell by endosomal escape enhancement.

Surprisingly, transformation (derivatisation) of the aldehyde group at C-23 of the aglycone of the saponin into a semicarbazone functional group according to formula (I), results in a decrease in cytotoxicity when such saponin derivatives are contacted with cells, i.e. various types of cells. It is thus part of the invention that these series of saponin derivatives with decreased cytotoxicity are provided, wherein the decrease in cytotoxicity is relative to the cytotoxicity as determined for the unmodified naturally occurring saponin counterparts. The saponin derivatives can be formed from such naturally occurring saponins, such as SO1861, equally active SO1832 and QS-21 (isoforms), preferably from SO1861 or SO1832. When the decrease in cytotoxicity is considered, saponin derivatives according to the invention, are equally suitable, when saponins with decreased cytotoxicity are to be provided.

The saponin SO1832 consists of the quillaic acid aglycone core with the carbohydrate substituent Gal-(1→2)-[Xyl-(1→3)]-GlcA- at the C-3beta-OH group and with the carbohydrate substituent Xyl-(1→3)-Xyl-(1→4)-Rha-(1→2)-[Xyl-(1→3)-4-OAc-Qui-(1→4)]-Fuc- at the C-28-OH group (See also Table A1). The chemical formula is $C_{82}H_{128}O_{45}$ and the exact mass is 1832.77 Dalton. The saponin structure of SO1832 is according to molecule (SO1832):

(SO1832)

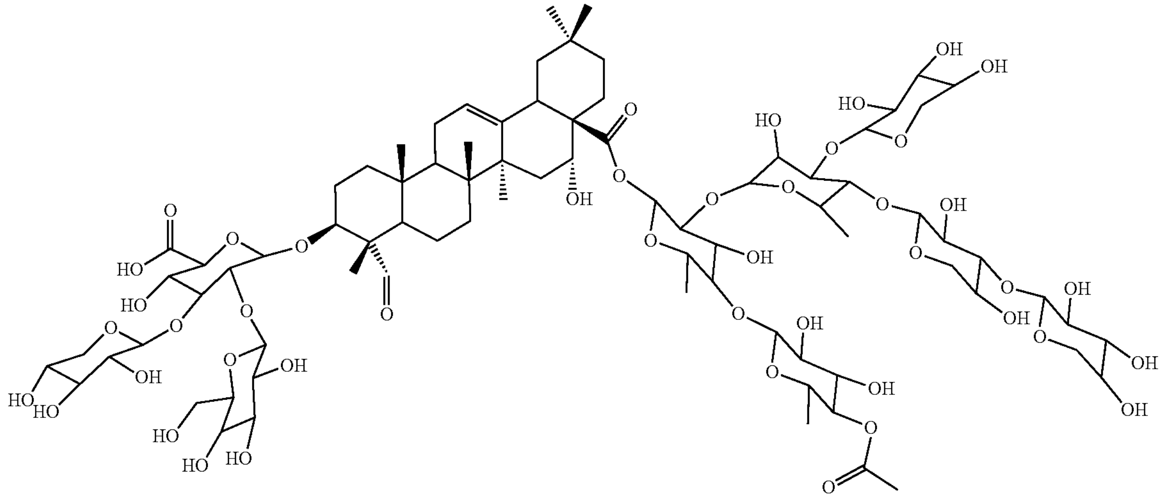

The inventors have also found that the modifications lead to an increased critical micelle concentration (CMC) when compared with the corresponding unmodified saponin. For example, the saponin derivative according to formula (VIII) has an increased CMC when compared to their corresponding underivatised saponin and are hence explicitly envisaged embodiments of the invention. Without wishing to be bound by any theory, it is believed that an increased CMC is advantageous for several reasons. For example, an increased CMC may facilitate the use of the modified saponins in subsequent conjugation reactions since free molecules are generally more susceptible to conjugation reactions than molecules ordered in a micellar structure. Furthermore, in case the saponin derivatives need to exert a biological function (e.g. in an in vivo treatment or ex vivo method or in vitro method), for example in case the saponin derivatives are used as such or even in case they are released in-situ after cleavage from a carrier or another entity, an increased CMC when compared to unmodified saponin is advantageous since the free saponin molecules will be more readily available to interact with their biological target than in case these saponin derivatives are ordered in a micellar structure. An increased CMC may also be useful to facilitate the large scale production and concentration of the saponin derivatives since at concentrations beyond (above) the critical micellar concentration, saponins form micelles which hinder isolation (e.g. using preparative HPLC). Surprisingly, for the saponin derivatives according to the invention the observed increased CMC was not associated with increased cytotoxicity or haemolytic activity. The relationship between CMC and cytotoxicity is not predictable and complex, as can for example be seen from the data in Table 2 of de Groot et al. ("Saponin interactions with model membrane systems-Langmuir monolayer studies, hemolysis and formation of ISCOMs", Planta medica 82.18 (2016): 1496-1512.), which shows that, taking α-Hederin as the reference point, an increase in CMC may be associated with an increase in general cytotoxicity (as is the case for Digitonin) but may just as well be associated with a decrease in cytotoxicity (as is the case for Glycyrrhizin and Hederacoside C). Furthermore, for the saponin derivative according to formula (VIII) the increased CMC is also associated with an increased ratio: IC50 hemolysis/IC50 activity, compared to the corresponding free saponin, such that this saponin derivative is a particularly preferred embodiment of the invention. The inventors thus provide saponin derivatives with an improved therapeutic window when cytotoxicity is considered and/or when haemolytic activity is considered, and when the potentiation of e.g. toxins is considered and/or when an increased CMC compared to the corresponding underivatised saponin is considered. Such saponin derivatives of the invention are in particular suitable for application in a therapeutic regimen involving e.g. an ADC or an AOC for the prophylaxis or treatment of e.g. a cancer, or a GalNAc-oligonucleotide conjugate for the prophylaxis or treatment of e.g. a cancer, hypercholesterolemia, cardiovascular disease or enhanced level of LDL-cholesterol above normal levels for healthy subjects in a (human) subject in need thereof. The safety of such saponin derivatives is improved when cytotoxicity and/or haemolytic activity is considered, especially when such saponin derivatives are administered to a patient in need of e.g. treatment with an ADC or with and AOC or with a conjugate comprising at least one GalNAc moiety and comprising an oligonucleotide, e.g. an AON such as a BNA for silencing a gene such as HSP27 and apoB.

An aspect of the invention relates to a saponin derivative based on a saponin comprising a triterpene aglycone core structure and at least one of a first saccharide chain 'R¹' and a second saccharide chain 'R²' linked to the aglycone core structure, wherein the saponin derivative comprises an aglycone core structure comprising an aldehyde group, wherein the aldehyde group is transformed into a semicarbazone functional group according to formula (I)

(I)

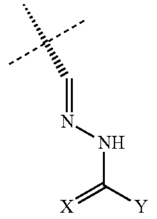

wherein $R^1$ and $R^2$ are independently selected from hydrogen, a monosaccharide, a linear oligosaccharide and a branched oligosaccharide, X=O, P or S, and Y=$NR^3R^4$, wherein $R^3$ and $R^4$ independently represent H or a covalently bound linker, preferably one of $R^3$ and $R^4$ is H; or

Y=

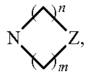

wherein n and m each are an integer independently selected from 1, 2, or 3,

Z=$CH_2$, O, S, P or $NR^5$, and wherein $R^5$ represents H or a covalently bound linker, or a maleimide moiety according to formula (II)a or formula (II)b (II)a

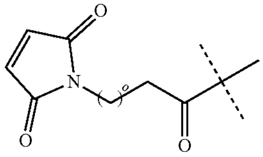

(II)b

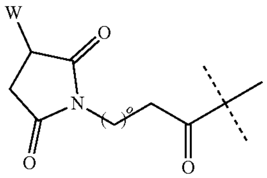

or an azide moiety according to formula (II)c (II)c

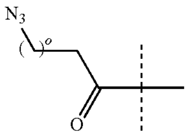

wherein o is an integer selected from 0-10, preferably 2-7, more preferably 4-6, and W is a thiol functional group according to formula (III)

(III)

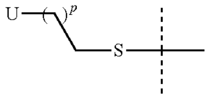

wherein U=SH, $NH_2$ or OH and p is an integer selected from 0-4, preferably 1-3, more preferably 1 or 2.

An aspect of the invention relates to a saponin derivative based on a saponin comprising a triterpene aglycone core structure and at least one of a first saccharide chain '$R^1$' and a second saccharide chain '$R^2$' linked to the aglycone core structure, wherein the saponin derivative comprises an aglycone core structure comprising an aldehyde group, wherein the aldehyde group is transformed into a semicarbazone functional group according to formula (I)

(I)

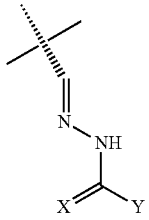

wherein $R^1$ and $R^2$ are independently selected from hydrogen, a monosaccharide, a linear oligosaccharide and a branched oligosaccharide, X=O, P or S, and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, preferably one of $R^3$ and $R^4$ is H; or

Y=

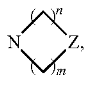

wherein n and m each are an integer independently selected from 1, 2, or 3,

Z=$CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a maleimide moiety according to formula (II)a or formula (II)b (II)a

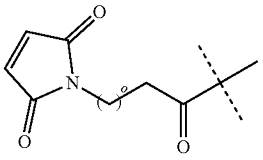

(II)b

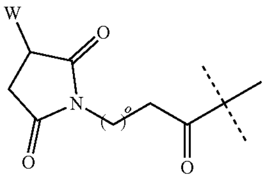

or an azide moiety according to formula (II)c (II)c

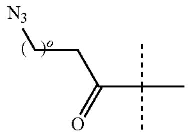

wherein o is an integer selected from 0-10, preferably 2-7, more preferably 4-6, and W is a thiol functional group according to formula (III)

(III)

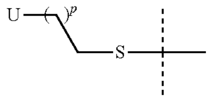

wherein U=SH, $NH_2$ or OH and p is an integer selected from 0-4, preferably 1-3, more preferably 1 or 2.

An aspect of the invention relates to a saponin derivative based on a saponin comprising a triterpene aglycone core structure and at least one of a first saccharide chain '$R^1$' and a second saccharide chain '$R^2$' linked to the aglycone core structure, wherein the saponin derivative comprises an aglycone core structure comprising an aldehyde group, wherein the aldehyde group is transformed into a semicarbazone functional group according to formula (I)

(I)

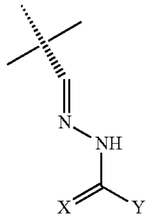

wherein $R^1$ and $R^2$ are independently selected from hydrogen, a monosaccharide, a linear oligosaccharide and a branched oligosaccharide, X=O, P or S, and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H; or

Y=

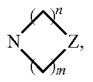

wherein n and m each are an integer independently selected from 1, 2, or 3, $Z=CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b (II)a

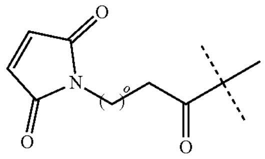

(II)b

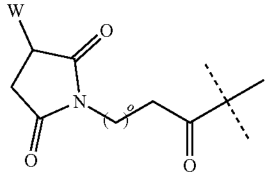

or an azide moiety according to formula (II)c (II)c

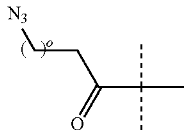

wherein o is an integer selected from 0-10, preferably 2-7, more preferably 4-6, and W is a thiol functional group according to formula (III)

(III)

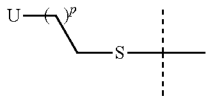

wherein U=SH, $NH_2$ or OH and p is an integer selected from 0-4, preferably 1-3, more preferably 1 or 2.

Worded differently, the saponin derivative according to the invention is a saponin comprising a triterpene aglycone core structure and at least one of a first saccharide chain '$R^1$' and a second saccharide chain '$R^2$' linked to the aglycone core structure, wherein $R^1$ and $R^2$ are independently selected from hydrogen, a monosaccharide, a linear oligosaccharide and a branched oligosaccharide and the aglycone core structure comprises an aldehyde group which has been derivatised by reacting with a semicarbazide according to formula (3)

(3)

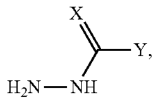

wherein X=O, P or S, $Y=NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H, or

Y=

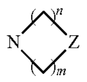

wherein n and m each are an integer independently selected from 1, 2, or 3, $Z=CH_2$, O, S, P or $NR^5$, and wherein $R^5$ represent H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b, (II)a

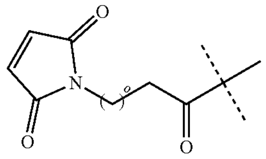

(II)b

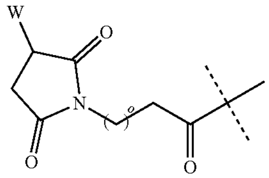

or an azide moiety according to formula (II)c (II)c

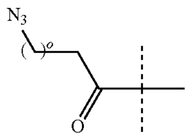

wherein o is an integer selected from 0-10, preferably 2-7, more preferably 4-6, and W is a thiol functional group according to formula (III), (III)

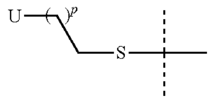

wherein U=SH, $NH_2$ or OH and p is an integer selected from 0-4, preferably 1-3, more preferably 1 or 2.

An embodiment is the saponin derivative according to the invention, wherein the saponin derivative is a monodesmosidic triterpene glycoside or a bidesmosidic triterpene glycoside, more preferably a bidesmosidic triterpene glycoside. A series of saponins known in the art have shown to enhance endosomal escape of molecules, which are most often bidesmosidic triterpene glycosides, although also a series of monodesmosidic triterpene glycosides have shown such enhancing activity. Table A1 summarizes the series of saponins for which endosomal escape enhancing activity has been established. Such saponins are good starting points for synthesising the saponin derivatives of the invention. In particular, SO1861 has proven to be a suitable natural saponin for derivatisation according to the invention. Since SO1832 has similar activity when compared to SO1861, as has been established by the inventors, also SO1832 is a suitable natural saponin for derivatisation according to the invention. Similarly, QS-21 can be a suitable natural saponin for derivatisation according to the invention, although the inventors established that the cytotoxicity and haemolytic activity of QS-21 is relatively higher than cytotoxicity and haemolytic activity of e.g. SO1861.

An embodiment is the saponin derivative according to the invention, wherein the saponin derivative comprises an aglycone core structure selected from the group consisting of:

2alpha-hydroxy oleanolic acid;
16alpha-hydroxy oleanolic acid;
hederagenin (23-hydroxy oleanolic acid);
16alpha,23-dihydroxy oleanolic acid;
gypsogenin;
quillaic acid;
protoaescigenin-21(2-methylbut-2-enoate)-22-acetate;
23-oxo-barringtogenol C-21,22-bis(2-methylbut-2-enoate);
23-oxo-barringtogenol C-21(2-methylbut-2-enoate)-16,22-diacetate;
digitogenin;
3,16,28-trihydroxy oleanan-12-en;
gypsogenic acid,
and
derivatives thereof, preferably the saponin derivative comprises an aglycone core structure selected from quillaic acid and gypsogenin or derivatives thereof, more preferably the saponin derivative aglycone core structure is quillaic acid or a derivative thereof. Since the inventors now found that improved saponin derivatives can be provided with regard to decreased cytotoxicity and lower haemolysis of cells contacted with such derivatives, based on saponins of the triterpene glycoside type, basically any saponin with such endosomal escape enhancing activity as tested by the inventors, such as saponins having the aglycone of the afore embodiment and listed in Table A1, can be improved accordingly. Lowering toxicity and lowering haemolytic activity while preserving activity to a sufficiently high extent when potentiation of toxins and for example an AON such as BNAs is considered, is an important achievement by the inventors, when the widening of the therapeutic window of the saponin derivatives alone or in combination with e.g. an ADC or an AOC is considered. A sufficiently high dose of derivatised saponin can be applied in e.g. tumor therapy for a cancer patient in need thereof, while the (risk for) cytotoxic side-effects and the (risk for) undesired haemolytic activity exerted or induced by the saponin derivative is decreased when compared with the application of the natural saponin counterpart. Improvements of the therapeutic window of the saponin derivatives of the invention are for example apparent for the exemplified saponin derivatives in Table 3 and Table 4: the ratio between the IC50 for either cytotoxicity, or haemolytic activity and the IC50 for endosomal escape enhancing activity are listed, as well as the haemolytic activity, cytotoxicity and the activity, and the CMC.

An embodiment is the saponin derivative according to the invention, wherein the saponin derivative comprises an aglycone core structure selected from the group consisting of quillaic acid, gypsogenin, and derivatives thereof, preferably the saponin derivative comprises an aglycone core structure selected from the group consisting of quillaic acid and derivatives thereof, wherein the first saccharide chain $R^1$, when present, is linked to the C3 atom (also denoted as 'C-3' atom) or the C28 atom (also denoted as 'C-28' atom) of the aglycone core structure, preferably to the C3 atom, and/or wherein the second saccharide chain $R^2$, when present, is linked to the C28 atom of the aglycone core structure. Preferred are those saponin derivatives which are based on a saponin having both saccharide chains bound to the aglycone, but in general any saponin that displays endosomal escape enhancing activity is suitable for derivatisation according to the invention, for the purpose to provide single, double, or triple, preferably single or double derivatised saponins with lower cytotoxicity, lower haemolytic activity and sufficiently high endosomal escape enhancing activity.

An embodiment is the saponin derivative according to the invention, wherein the saponin on which the saponin derivative is based is a penta-cyclic triterpene saponin of the 12,13-dehydrooleanane type, preferably the saponin is a monodesmosidic or bidesmosidic penta-cyclic triterpene saponin of the 12,13-dehydrooleanane type.

An embodiment is the saponin derivative according to the invention, wherein the saponin on which the saponin derivative is based is a mono-desmosidic or bi-desmosidic triterpene saponin belonging to the type of a 12,13-dehydrooleanane with the aldehyde group in position C-23 and optionally comprising a glucuronic acid group in a carbohydrate substituent at the C-3beta-OH group of the saponin, preferably a bi-desmosidic triterpene saponin belonging to the type of a 12,13-dehydrooleanane with the aldehyde group in position C-23 and comprising a glucuronic acid group in a carbohydrate substituent at the C-3beta-OH group of the saponin.

A preferred embodiment is the saponin derivative according to the invention, wherein the saponin derivative is according to formula (IV):

(IV)

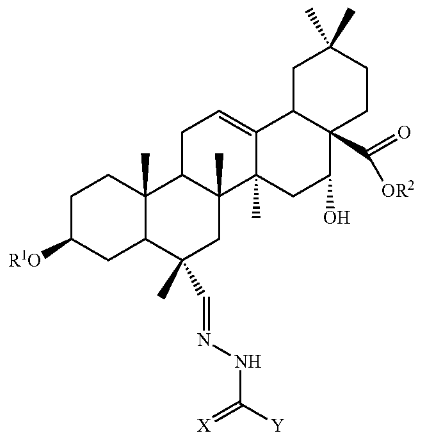

wherein $R^1$ and $R^2$ are independently selected from hydrogen, a monosaccharide, a linear oligosaccharide and a branched oligosaccharide, X=O, P or S, preferably O; and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, preferably one of $R^3$ and $R^4$ is H; or

Y=

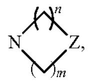

wherein n and m each are an integer independently selected from 1, 2 or 3;

Z=$CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, or a maleimide moiety according to formula (II)a or formula (II)b, (II)a

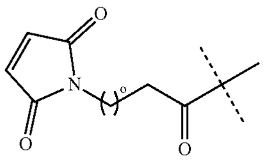

(II)b

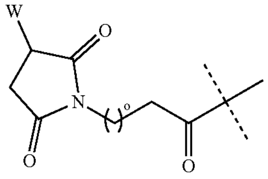

or an azide moiety according to formula (II)c (II)c

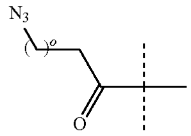

wherein o is an integer selected from 0-10, preferably 2-7, more preferably 4-6 and W is thiol functional group according to formula (III)

(III)

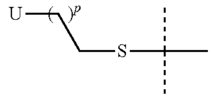

wherein U=SH, $NH_2$ or OH, preferably OH, and p is an integer selected from 0-4, preferably 1-3, more preferably 1 or 2.

A preferred embodiment is the saponin derivative according to the invention, wherein the saponin derivative is according to formula (IV):

(IV)

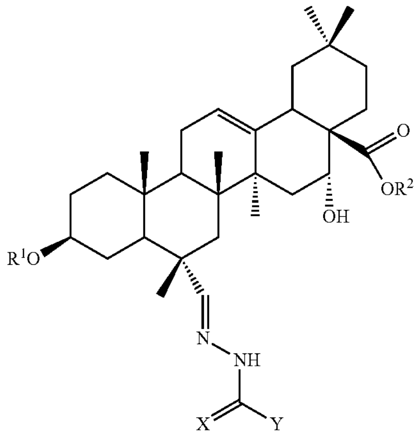

wherein $R^1$ and $R^2$ are independently selected from hydrogen, a monosaccharide, a linear oligosaccharide and a branched oligosaccharide, X=O, P or S, preferably O; and

Y=

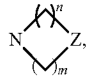

wherein n and m each are an integer independently selected from 1, 2 or 3;

Z=$CH_2$, O, S, P or $NR^5$, preferably O or $NR^5$, and wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or a branched alkynyl, or a covalently bound linker, or a maleimide moiety according to formula (II)a or formula (II)b, preferably H or a covalently bound linker or the branched alkynyl or a maleimide moiety according to formula (II)a or formula (II)b, (II)a

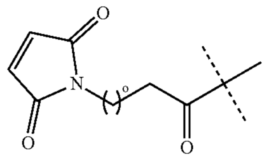

(II)b

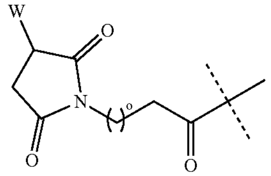

or an azide moiety according to formula (II)c (II)c

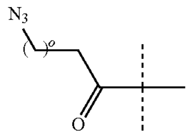

wherein o is an integer selected from 0-10, preferably 2-7, more preferably 4-6 and W is thiol functional group according to formula (III)

(III)

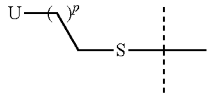

wherein U=SH, $NH_2$ or OH, preferably OH, and p is an integer selected from 0-4, preferably 1-3, more preferably 1 or 2.

An embodiment is the saponin derivative according to the invention, wherein the semicarbazone functional group according to formula (I), the linear semicarbazide is according formula (3) or saponin derivative is according to formula (IV), wherein Y=

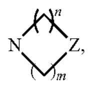

wherein n=1 and m=1, n=2 and m=1, n=2 and m=2, n=3 and m=2 or n=3 and m=3; preferably wherein n=1 and m=2, n=2 and m=2, or n=2 and m=3, more preferably n=2 and m=3 and Z is defined according to the previous embodiments. Particular saponin derivatives according to the invention are thus saponin derivatives, wherein n=1 and m=1, or n=2 and m=1, or n=2 and m=2, or n=3 and m=2, or n=3 and m=3; preferably wherein n=2 and m=2.

An embodiment is the saponin derivative according to the invention, wherein $R^1$ is selected from
H,
GlcA-,
Glc-,
Gal-,
Rha-(1→2)-Ara-,
Gal-(1→2)-[Xyl-(1→3)]-GlcA-,
Glc-(1→2)-[Glc-(1→4)]-GlcA-,
Glc-(1→2)-Ara-(1→3)-[Gal-(1→2)]-GlcA-,
Xyl-(1→2)-Ara-(1→3)-[Gal-(1→2)]-GlcA-,
Glc-(1→3)-Gal-(1→2)-[Xyl-(1→3)]-Glc-(1→4)-Gal-,
Rha-(1→2)-Gal-(1→3)-[Glc-(1→2)]-GlcA-,
Ara-(1→4)-Rha-(1→2)-Glc-(1→2)-Rha-(1→2)-GlcA-,
Ara-(1→4)-Fuc-(1→2)-Glc-(1→2)-Rha-(1→2)-GlcA-,
Ara-(1→4)-Rha-(1→2)-Gal-(1→2)-Rha-(1→2)-GlcA-,
Ara-(1→4)-Fuc-(1→2)-Gal-(1→2)-Rha-(1→2)-GlcA-,
Ara-(1→4)-Rha-(1→2)-Glc-(1→2)-Fuc-(1→2)-GlcA-,
Ara-(1→4)-Fuc-(1→2)-Glc-(1→2)-Fuc-(1→2)-GlcA-,
Ara-(1→4)-Rha-(1→2)-Gal-(1→2)-Fuc-(1→2)-GlcA-,
Ara-(1→4)-Fuc-(1→2)-Gal-(1→2)-Fuc-(1→2)-GlcA-,
Xyl-(1→4)-Rha-(1→2)-Glc-(1→2)-Rha-(1→2)-GlcA-,
Xyl-(1→4)-Fuc-(1→2)-Glc-(1→2)-Rha-(1→2)-GlcA-,
Xyl-(1→4)-Rha-(1→2)-Gal-(1→2)-Rha-(1→2)-GlcA-,
Xyl-(1→4)-Fuc-(1→2)-Gal-(1→2)-Rha-(1→2)-GlcA-,
Xyl-(1→4)-Rha-(1→2)-Glc-(1→2)-Fuc-(1→2)-GlcA-,
Xyl-(1→4)-Fuc-(1→2)-Glc-(1→2)-Fuc-(1→2)-GlcA-,
Xyl-(1→4)-Rha-(1→2)-Gal-(1→2)-Fuc-(1→2)-GlcA-,
Xyl-(1→4)-Fuc-(1→2)-Gal-(1→2)-Fuc-(1→2)-GlcA-, and
derivatives thereof, preferably $R^1$ is Gal-(1→2)-[Xyl-(1→3)]-GlcA-; and $R^2$ is selected from:
H,
Glc-,
Gal-,
Rha-(1→2)-[Xyl-(1→4)]-Rha-,
Rha-(1→2)-[Ara-(1→3)-Xyl-(1→4)]-Rha-,
Ara-,
Xyl-,
Xyl-(1→4)-Rha-(1→2)-[R1-(→4)]-Fuc- wherein R1 is 4E-Methoxycinnamic acid,
Xyl-(1→4)-Rha-(1→2)-[R2-(→4)]-Fuc- wherein R2 is 4Z-Methoxycinnamic acid,
Xyl-(1→4)-[Gal-(1→3)]-Rha-(1→2)-4-OAc-Fuc-,
Xyl-(1→4)-[Glc-(1→3)]-Rha-(1→2)-3,4-di-OAc-Fuc-,
Xyl-(1→4)-[Glc-(1→3)]-Rha-(1→2)-[$R^6$-(→4)]-3-OAc-Fuc- wherein $R^6$ is 4E-Methoxycinnamic acid,
Glc-(1→3)-Xyl-(1→4)-[Glc-(1→3)]-Rha-(1→2)-4-OAc-Fuc-,
Glc-(1→3)-Xyl-(1→4)-Rha-(1→2)-4-OAc-Fuc-,
(Ara- or Xyl-)(1→3)-(Ara- or Xyl-)(1→4)-(Rha- or Fuc-)(1→2)-[4-OAc-(Rha- or Fuc-)(1→4)]-(Rha- or Fuc-),
Xyl-(1→3)-Xyl-(1→4)-Rha-(1→2)-[Qui-(1→4)]-Fuc-,
Api-(1→3)-Xyl-(1→4)-[Glc-(1→3)]-Rha-(1→2)-Fuc-,
Xyl-(1→4)-[Gal-(1→3)]-Rha-(1→2)-Fuc-,
Xyl-(1→4)-[Glc-(1→3)]-Rha-(1→2)-Fuc-,
Ara/Xyl-(1→4)-Rha/Fuc-(1→4)-[Glc/Gal-(1→2)]-Fuc-,
Api-(1→3)-Xyl-(1→4)-[Glc-(1→3)]-Rha-(1→2)-[$R^7$-(→4)]-Fuc- wherein $R^7$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^8$-(→4)]-Fuc- wherein $R^8$ is 5-O-[5-O-Ara/Api-3,5-dihydroxy-6-methyl-octanoyl]-3,5-dihydroxy-6-methyl-octanoic acid), Api-(1→3)-Xyl-(1→4)-Rha-(1→2)-[Rha-(1→3)]-4-OAc-Fuc-,
Api-(1→3)-Xyl-(1→4)-[Glc-(1→3)]-Rha-(1→2)-[Rha-(1→3)]-4-OAc-Fuc-,
6-OAc-Glc-(1→3)-Xyl-(1→4)-Rha-(1→2)-[3-OAc-Rha-(1→3)]-Fuc-,
Glc-(1→3)-Xyl-(1→4)-Rha-(1→2)-[3-OAc-Rha-(1→3)]-Fuc-,
Xyl-(1→3)-Xyl-(1→4)-Rha-(1→2)-[Qui-(1→4)]-Fuc-,
Glc-(1→3)-[Xyl-(1→4)]-Rha-(1→2)-[Qui-(1→4)]-Fuc-,
Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Glc-(1→3)-[Xyl-(1→4)]-Rha-(1→2)-Fuc-,
6-OAc-Glc-(1→3)-[Xyl-(1→4)]-Rha-(1→2)-Fuc-,
Glc-(1→3)-[Xyl-(1→3)-Xyl-(1→4)]-Rha-(1→2)-Fuc-,
Xyl-(1→3)-Xyl-(1→4)-Rha-(1→2)-[Xyl-(1→3)-4-OAc-Qui-(1→4)]-Fuc-,
Api/Xyl-(1→3)-Xyl-(1→4)-[Glc-(1→3)]-Rha-(1→2)-[Rha-(1→3)]-4OAc-Fuc-,
Api-(1→3)-Xyl-(1→4)-[Glc-(1→3)]-Rha-(1→2)-[Rha-(1→3)]-4OAc-Fuc-,
Api/Xyl-(1→3)-Xyl-(1→4)-[Glc-(1→3)]-Rha-(1→2)-[$R^9$-(→4)]-Fuc- wherein $R^9$ is 5-O-[5-O-Rha-(1→2)-Ara/Api-3,5-dihydroxy-6-methyl-octanoyl]-3,5-dihydroxy-6-methyl-octanoic acid),
Api/Xyl-(1→3)-Xyl-(1→4)-[Glc-(1→3)]-Rha-(1→2)-[$R^{10}$-(→4)]-Fuc- wherein $R^{10}$ is 5-O-[5-O-Ara/Api-3,5-dihydroxy-6-methyl-octanoyl]-3,5-dihydroxy-6-methyl-octanoic acid),
Api/Xyl-(1→3)-Xyl-(1→4)-[Glc-(1→3)]-Rha-(1→2)-[$R^{11}$-(→4)]-Fuc- wherein $R^{11}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid)
Glc-(1→3)-[Glc-(1→6)]-Gal-, and
derivatives thereof;
preferably $R^2$ is selected from:
Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid,
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid,
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid, and
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid,
more preferably $R^2$ is Glc-(1→3)-Xyl-(1→4)-Rha-(1→2)-[Xyl-(1→3)-4-OAc-Qui-(1→4)]-Fuc-,
most preferably $R^1$ is Gal-(1→2)-[Xyl-(1→3)]-GlcA- and $R^2$ is Glc-(1→3)-Xyl-(1→4)-Rha-(1→2)-[Xyl-(1→3)-4-OAc-Qui-(1→4)]-Fuc-.

In preferred saponin derivatives according to the invention,
$R^1$ is Gal-(1→2)-[Xyl-(1→3)]-GlcA-; and
$R^2$ is selected from:
Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid,
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid,
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid, and
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid,
preferably, $R^1$ is Gal-(1→2)-[Xyl-(1→3)]-GlcA- and $R^2$ is Glc-(1→3)-Xyl-(1→4)-Rha-(1→2)-[Xyl-(1→3)-4-OAc-Qui-(1→4)]-Fuc-.

Saponin derivatives comprising such a $R^1$ group and such an $R^2$ group are preferably saponin derivatives based on a saponin listed in Table A1, for which endosomal escape enhancing activity has been established and/or predicted based on similarity or analogy.

An embodiment is the saponin derivative according to the invention, wherein the saponin derivative is a derivative of a saponin selected from the group of saponins consisting of: *Quillaja* bark saponin, dipsacoside B, saikosaponin A, saikosaponin D, macranthoidin A, esculentoside A, phytolaccagenin, aescinate, AS6.2, NP-005236, AMA-1, AMR, alpha-Hederin, NP-012672, NP-017777, NP-017778, NP-017774, NP-018110, NP-017772, NP-018109, NP-017888, NP-017889, NP-018108, SA1641, AE X55, NP-017674, NP-017810, AG1, NP-003881, NP-017676, NP-017677, NP-017706, NP-017705, NP-017773, NP-017775, SA1657, AG2, SO1861, GE1741, SO1542, SO1584, SO1658, SO1674, SO1832, SO1904, SO1862, QS-7, QS1861, QS-7 api, QS1862, QS-17, QS-18, QS-21 A-apio, QS-21 A-xylo, QS-21 B-apio, QS-21 B-xylo, beta-Aescin, Aescin Ia, Teaseed saponin I, Teaseedsaponin J, Assamsaponin F, Digitonin, Primula acid 1 and AS64R, preferably the saponin derivative is selected from the group consisting of a QS-21 derivative, an SO1861 derivative, an SA1641 derivative and an GE1741 derivative, more preferably the saponin derivative is selected from the group consisting of a QS-21 derivative and an SO1861 derivative, most preferably the saponin derivative is an SO1861 derivative. These saponins are essentially saponins displaying endosomal escape enhancing activity as established by the inventors, or that are structurally highly similar to saponins for which the endosomal escape enhancing activity has been established. Structural outline of these saponins is summarized in Table A1. Since SO1861 and SO1832 are about equally active (when endosomal escape enhancing effects are assessed), application of SO1861 and SO1832 in the saponin derivatives and in the saponin conjugates of the invention is equally preferred.

Thus, typically, for the saponin derivative according to the invention, the saponin derivative is a derivative of a saponin selected from the group of saponins consisting of: *Quillaja* bark saponin, dipsacoside B, saikosaponin A, saikosaponin D, macranthoidin A, esculentoside A, phytolaccagenin, aescinate, AS6.2, NP-005236, AMA-1, AMR, alpha-Hederin, NP-012672, NP-017777, NP-017778, NP-017774, NP-018110, NP-017772, NP-018109, NP-017888, NP-017889, NP-018108, SA1641, AE X55, NP-017674, NP-017810, AG1, NP-003881, NP-017676, NP-017677, NP-017706, NP-017705, NP-017773, NP-017775, SA1657, AG2, SO1861, GE1741, SO1542, SO1584, SO1658, SO1674, SO1832, SO1904, SO1862, QS-7, QS1861, QS-7 api, QS1862, QS-17, QS-18, QS-21 A-apio, QS-21 A-xylo, QS-21 B-apio, QS-21 B-xylo, beta-Aescin, Aescin Ia, Teaseed saponin I, Teaseedsaponin J, Assamsaponin F, Digitonin, Primula acid 1 and AS64R, preferably the saponin derivative is selected from the group consisting of a QS-21 derivative, an SO1861 derivative, an SA1641 derivative and a GE1741 derivative, more preferably the saponin derivative is selected from the group consisting of a QS-21 derivative and an SO1861 derivative, most preferably the saponin derivative is an SO1861 derivative. As said before, a derivative based on SO1861 and SO1832 is equally preferred.

An embodiment is the saponin derivative according to the invention, wherein the saponin derivative is selected from the group consisting of derivatives of: SO1861, SA1657, GE1741, SA1641, QS-21, QS-21A, QS-21 A-api, QS-21 A-xyl, QS-21B, QS-21 B-api, QS-21 B-xyl, QS-7-xyl, QS-7-api, QS-17-api, QS-17-xyl, QS1861, QS1862, *Quillaja saponin*, Saponinum album, QS-18, Quil-A, Gyp1, gypsoside A, AG1, AG2, SO1542, SO1584, SO1658, SO1674, SO1832, SO1862, SO1904, stereoisomers thereof and combinations thereof, preferably the saponin derivative is selected from the group consisting of a SO1861 derivative, a GE1741 derivative, a SA1641 derivative, a QS-21 derivative, and a combination thereof, more preferably the saponin derivative is a SO1861 derivative or a QS-21 derivative, most preferably, the saponin derivative is a SO1861 derivative.

Particularly preferred is a saponin derivative of the invention, wherein the saponin derivative is according to formula (V), formula (VI), formula (VII) (See FIG. 2) or formula (VIII)

(V)

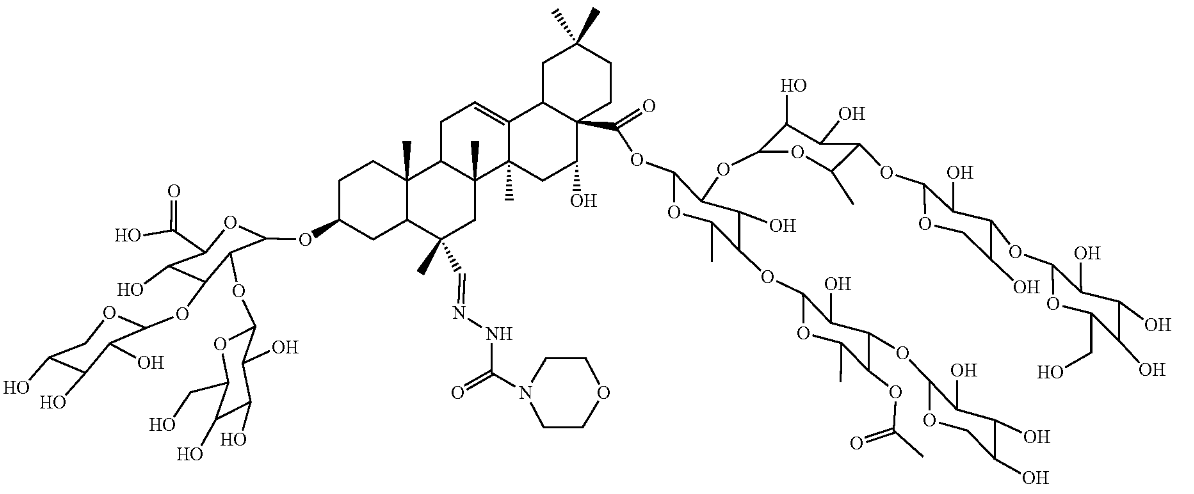

-continued
(VI)
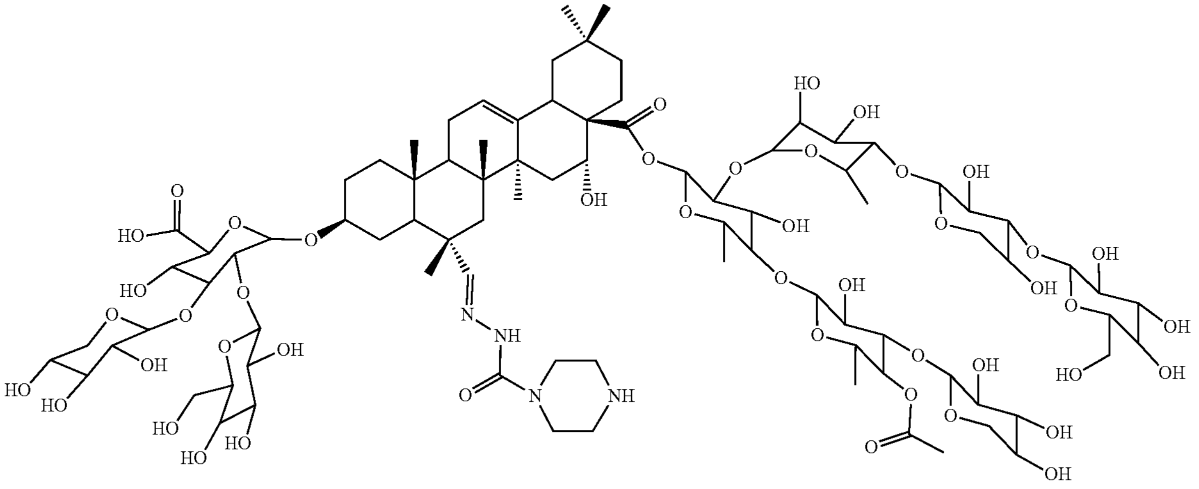
(VII)
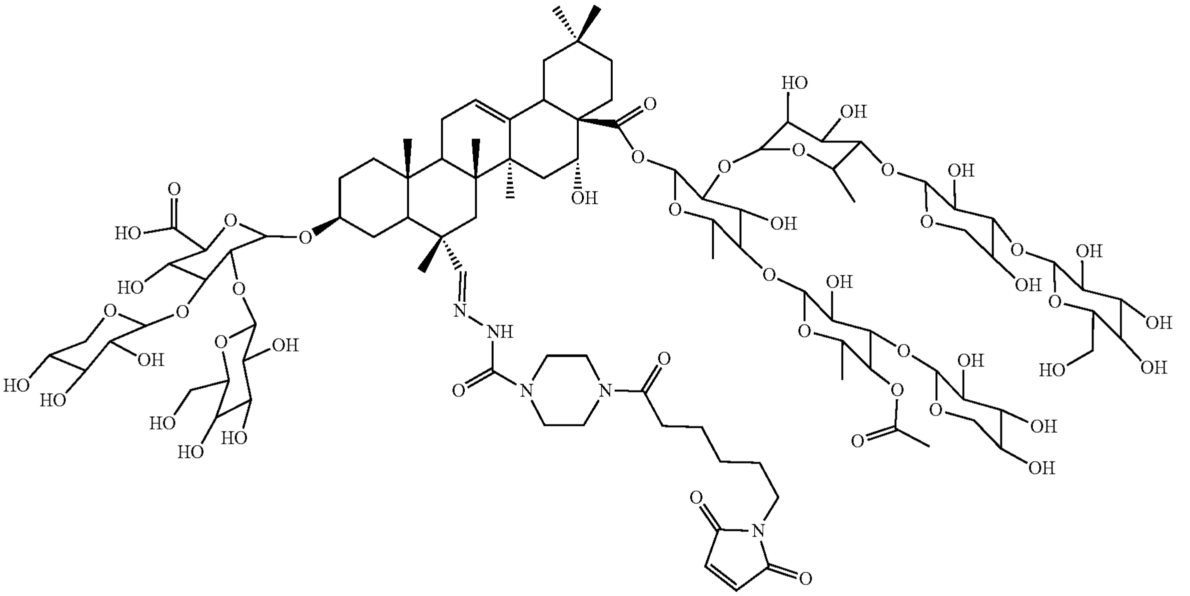

-continued (VIII)

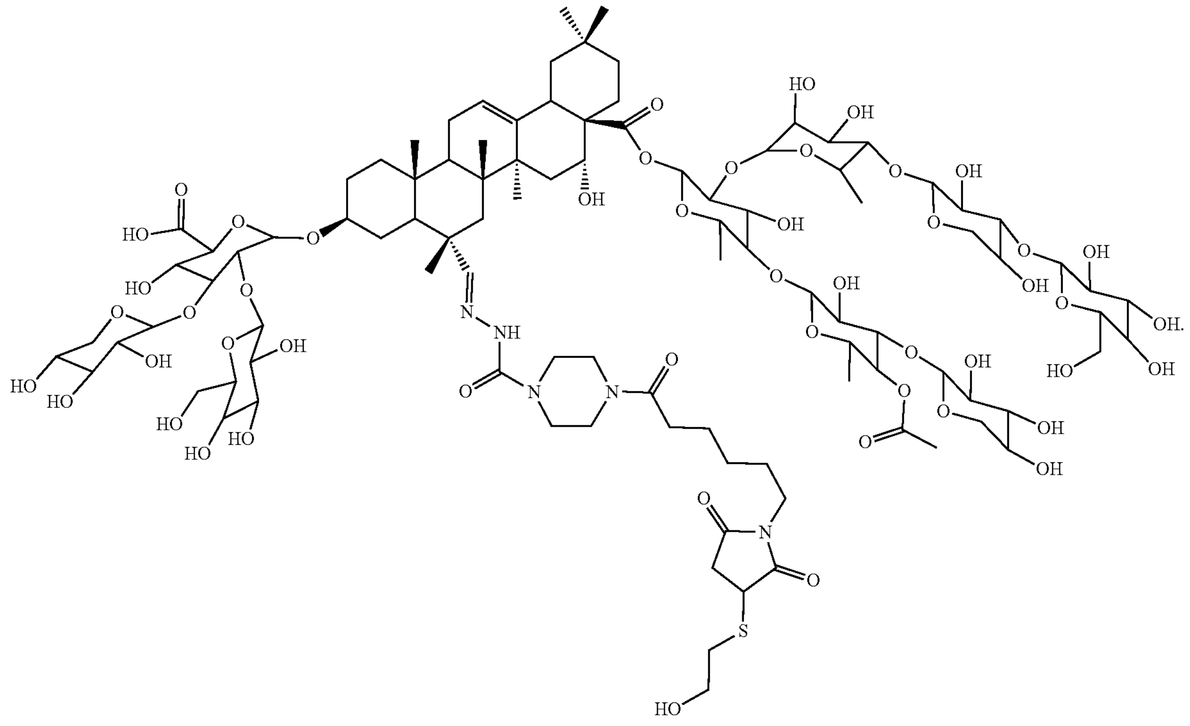

Particularly preferred is a saponin derivative of the invention, wherein the saponin derivative is according to molecule (AA):

(AA)

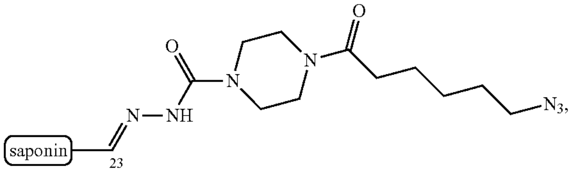

wherein

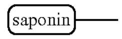

represents a saponin moiety according to formula (SM):

(SM)

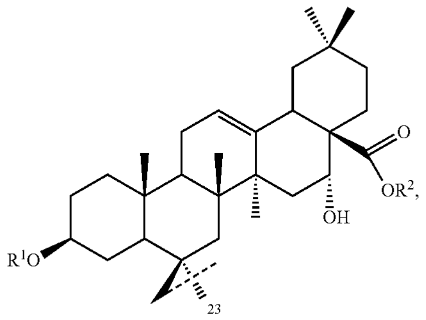

wherein $R^1$ and $R^2$ are independently selected from hydrogen, a monosaccharide, a linear oligosaccharide and a branched oligosaccharide, and wherein the saponin moiety according to formula (SM) is based on a saponin comprising an aldehyde group in position C-23. The saponin moiety is for example based on any one of the saponins listed here above or in Table A1, and SO1861, SO1832 and QS-21 are preferred, although SO1861 and SO1832 are most preferred.

Preferred is a saponin derivative of the invention, wherein the saponin derivative is according to molecule (BB):
(BB)
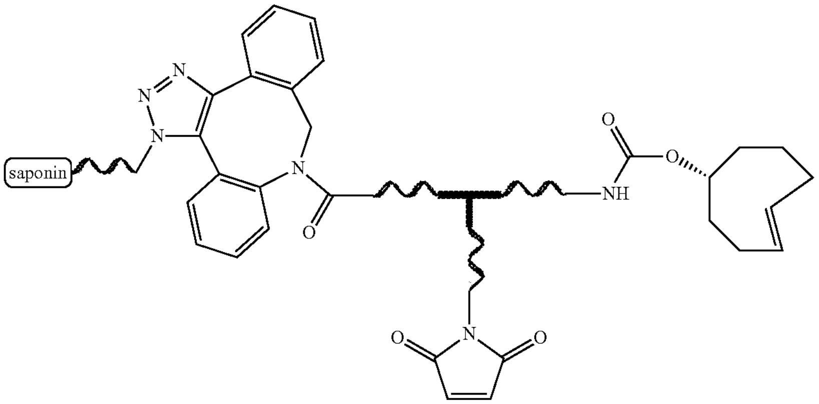
which molecule (BB) is the covalent conjugation product obtained by the covalent conjugation of the saponin derivative according to molecule (AA) outlined here above with the tri-functional linker according to formula (XXI):
(XXI)
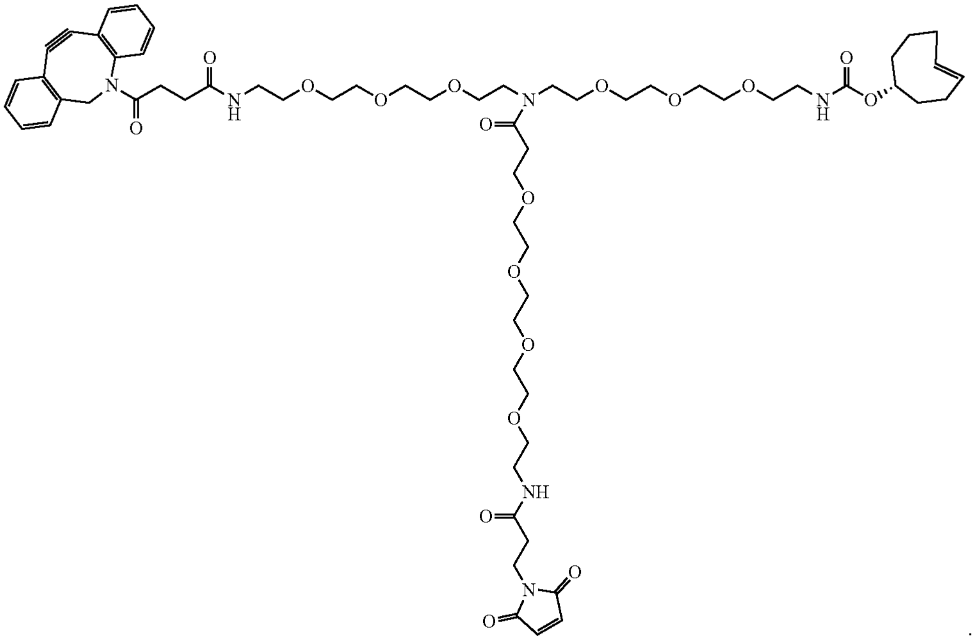
.

Also preferred is the saponin derivative according to the invention wherein the saponin derivative is according to molecule (KK):

(KK)

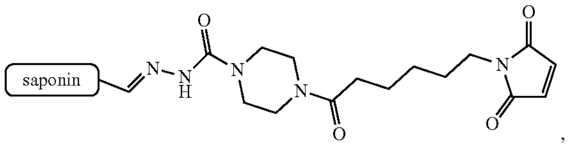

wherein

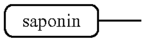

represents a saponin moiety according to formula (SM):

(SM)

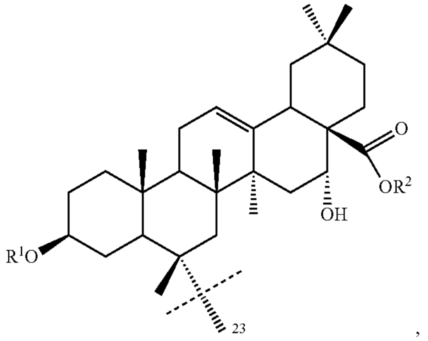

wherein $R^1$ and $R^2$ are independently selected from hydrogen, a monosaccharide, a linear oligosaccharide and a branched oligosaccharide according to the invention and as outlined here above, and wherein the saponin moiety according to formula (SM) is based on a saponin comprising an aldehyde group in position C-23 according to the invention. Suitable saponins are for example outlined in Table A1. SO1861, SO1832 and QS-21 are preferred, although SO1861 and SO1832 are more preferred.

A preferred embodiment is the saponin derivative according to the invention, characterized in that the saponin derivative comprises a single saponin moiety. A preferred embodiment is the saponin derivative according to the invention, characterized in that the saponin derivative comprises more than one saponin moiety, such as 2-64 moieties, preferably 4-32 moieties, more preferably 4-16 moieties, most preferably 4-8 moieties such as 4 or 8 moieties. Saponin derivatives comprising more than a single saponin moiety, such as a saponin derivative based on a G2 dendron or G3 dendron, comprising four or eight saponin moieties respectively, which are provided with the semicarbazone functional group, provide the advantage of providing higher extent of endosomal escape enhancing activity by a single saponin derivative molecule compared to a saponin derivative comprising a single saponin moiety.

Part of the invention is the saponin derivative according to molecule (JJ):

(JJ)

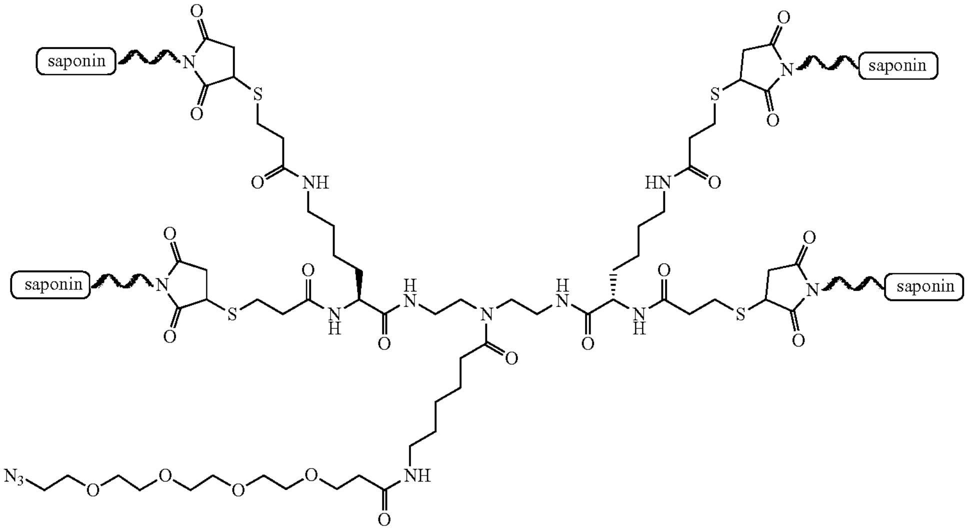

which molecule (JJ) is the conjugate product of conjugation of N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide first with the saponin derivative according to molecule (KK), as displayed here above, and subsequently with 2,5-dioxopyrrolidin-1-yl 1-azido-3,6,9,12-tetraoxapentadecan-15-oate.

Also part of the invention is the saponin derivative according to molecule (QQ):

(QQ)

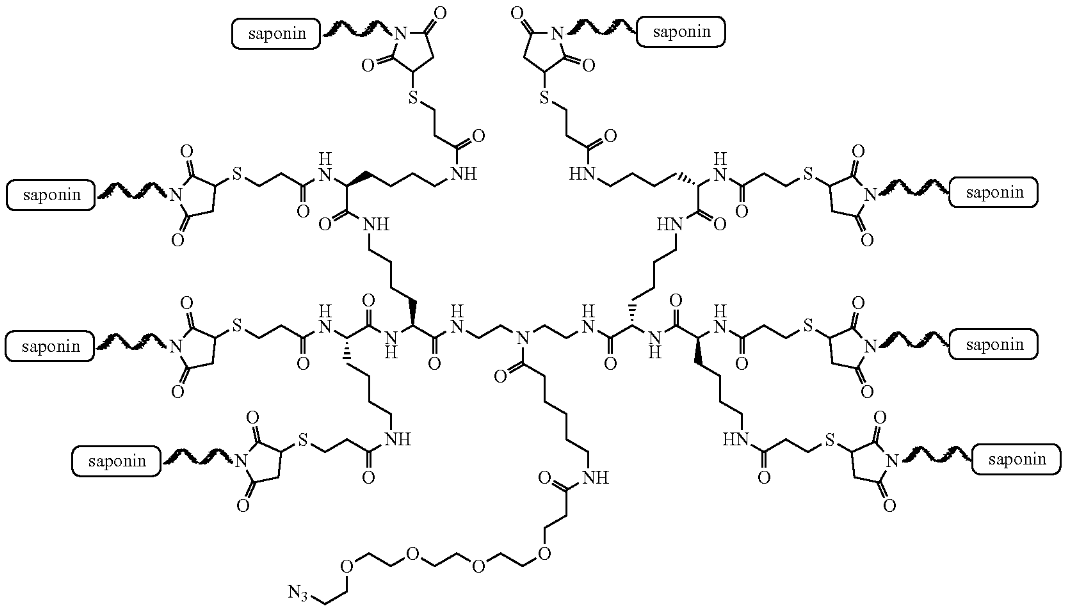

which molecule (QQ) is the conjugate product of conjugation of (2S)—N-[(1S)-1-{[2-(6-amino-N-{2-[(2S)-2,6-bis[(2S)-2,6-bis(3-sulfanylpropanamido)hexanamido]hexanamido]ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate first with saponin derivative according to the invention and according to molecule (KK) as displayed and described here above, and subsequently with 2,5-dioxopyrrolidin-1-yl 1-azido-3,6,9,12-tetraoxapentadecan-15-oate.

An embodiment is the saponin derivative according to the invention, characterized in that the saponin derivative has a molecular weight of less than 2500 g/mol, preferably less than 2300 g/mol, more preferably less than 2150 g/mol.

An embodiment is the saponin derivative according to the invention, characterized in that the saponin derivatisation has a molecular weight of less than 400 g/mol, preferably less than 300 g/mol, more preferably less than 270 g/mol. The molecular weight of the saponin derivative corresponds to the molecular weight of the saponin derivative exclusive of the aglycone core and the one (for monodesmosidic saponins) or two (for bidesmosidic saponins) glycon (sugar) chains.

Pharmaceutical Compositions and Combinations Comprising a Saponin Derivative

An aspect of the invention relates to a first pharmaceutical composition comprising the saponin derivative according to the invention and optionally a pharmaceutically acceptable excipient and/or diluent.

An embodiment is the first pharmaceutical composition according to the invention comprising the saponin derivative according to the invention, preferably a pharmaceutically acceptable diluent, and further comprising:

- a pharmaceutically acceptable salt, preferably a pharmaceutically acceptable inorganic salt, such as an ammonium, calcium, copper, iron, magnesium, manganese, potassium, sodium, strontium, or zinc salt, preferably NaCl; and/or
- a pharmaceutically acceptable buffer system, such as a phosphate, a borate, a citrate, a carbonate, a histidine, a lactate, a tromethamine, a gluconate, an aspartate, a glutamate, a tartarate, a succinate, a malate, a fumarate, an acetate and/or a ketoglutarate containing buffer system.

An embodiment is the first pharmaceutical composition according to the invention comprising the saponin derivative according to the invention and a pharmaceutically acceptable diluent, preferably water, wherein the composition is liquid at a temperature of 25° C. and has a pH within the range of 2-11, preferably within the range of 4-9, more preferably within the range of 6-8.

An embodiment is the first pharmaceutical composition according to the invention comprising a saponin derivative according to the invention and a pharmaceutically acceptable diluent, preferably water, wherein the composition is liquid at a temperature of 25° C. and wherein the concentration of the saponin derivative is within the range of $10^{-12}$ to 1 mol/l, preferably within the range of $10^{-9}$ to 0.1 mol/l, more preferably within the range of $10^{-6}$ to 0.1 mol/l.

Typically, such a first pharmaceutical composition is suitable for use in combination with e.g. an ADC or an AOC. For example, the first pharmaceutical composition is administered to a patient in need of administration of the ADC or AOC, before the ADC or AOC is administered, together with the ADC or AOC, or (shortly) after administration of the ADC or the AOC to the patient in need of such ADC or AOC therapy. For example, the first pharmaceutical composition is mixed with a pharmaceutical composition comprising the ADC or the AOC, and a suitable dose of the mixture obtained is administered to a patient in need of ADC or AOC therapy. According to the invention, the saponin derivative comprised by the first pharmaceutical composition enhances the efficacy and potency of the effector molecule comprised by such an ADC or AOC, when the saponin derivative and the ADC or AOC co-localize inside a target cell such as a tumor cell. Under influence of the saponin derivative, the effector molecule is released into the cytosol of the target cell to a higher extent, compared to contacting the same cells with the same dose of ADC or AOC in the absence of the saponin derivative. Thus, similar efficacy can be obtained at lower ADC or AOC dose when the effector molecule co-localizes inside a target cell together with the saponin derivative of the first pharmaceutical composition, compared to the dose required to achieve the same efficacy in the absence of the saponin derivative inside the cell where the ADC or the AOC comprising the effector molecule is delivered.

An embodiment is the first pharmaceutical composition of the invention, wherein the saponin derivative is the saponin derivative according to formula (V), the saponin derivative according to formula (VI), the saponin derivative according to formula (VII) (depicted in FIG. 2), the saponin derivative according to formula (VIII) or any combination thereof.

An aspect of the invention relates to a first pharmaceutical combination comprising:

(a) the first pharmaceutical composition of the invention; and (b) a second pharmaceutical composition comprising a conjugate of a cell-surface molecule binding-molecule and an effector moiety, wherein the cell-surface molecule binding-molecule is a proteinaceous molecule such as an antibody, and optionally comprising a pharmaceutically acceptable excipient and/or diluent.

An aspect of the invention relates to a first pharmaceutical combination comprising:

(a) the first pharmaceutical composition of the invention; and (b) a second pharmaceutical composition comprising any one or more of: a conjugate of a cell-surface molecule binding-molecule and an effector moiety, an antibody-effector moiety conjugate, a receptor-ligand-effector moiety conjugate, an antibody-toxin conjugate, a receptor-ligand-toxin conjugate, an antibody-drug conjugate, a receptor-ligand-drug conjugate, an antibody-oligonucleotide conjugate and a receptor-ligand-oligonucleotide conjugate, and optionally comprising a pharmaceutically acceptable excipient and/or diluent.

Such a receptor ligand can be a receptor ligand known in the art of cell-targeting therapy, such as EGF. Typically, such a receptor ligand targets a receptor on a diseased cell such as a tumor cell or an auto-immune cell such as in rheumatoid arthritis. Typically, such a receptor ligand is a proteinaceous molecule such as a peptide or a protein, although non-proteinaceous receptor ligands known in the art are equally suitable. Such receptor ligands can also be selected from molecules such as adnectins, anticalins, affibodies, etc., etc. The common denominator for the receptor ligands is their specificity for an epitope on a target cell, for targeted delivery of an effector moiety bound to the receptor ligand, reminiscent to the targeted delivery of effector moieties such as toxins, enzymes, oligonucleotides, drug molecules, etc., linked to e.g. an antibody or a single domain antibody, etc. Suitable cell-surface molecule binding-molecules are proteinaceous molecules such as antibodies, sdAb, etc., and non-proteinaceous molecules, suitable for targeting a selected cell (type) and therewith suitable for bringing a saponin derivative of the invention and/or a payload, effector molecule, effector moiety such as a drug, toxin, oligonucleotide, enzyme, in close proximity of the target cell surface to which the cell-surface molecule binding-molecule can bind. Typically, the cell-surface molecule is a receptor. The binding of the cell-surface molecule binding-molecule to the target cell is followed by transfer of the saponin derivate and/or the payload, effector molecule, effector moiety, to the endosome of the cell to which the cell-surface molecule binding-molecule is bound.

An aspect of the invention relates to a therapeutic combination comprising:

the first pharmaceutical composition of the invention; and a second pharmaceutical composition comprising any one or more of an antibody-toxin conjugate, a receptor-ligand-toxin conjugate, an antibody-drug conjugate, a receptor-ligand-drug conjugate, an antibody-oligonucleotide conjugate or a receptor-ligand-oligonucleotide conjugate, and optionally comprising a pharmaceutically acceptable excipient and/or diluent.

An aspect of the invention relates to a third pharmaceutical composition comprising the saponin derivative of the invention and further comprising a conjugate of a cell-surface molecule binding-molecule and an effector moiety, wherein the cell-surface molecule binding-molecule is a proteinaceous molecule such as an antibody, and optionally comprising a pharmaceutically acceptable excipient and/or diluent.

An aspect of the invention relates to a third pharmaceutical composition comprising the saponin derivative of the invention and further comprising any one or more of: a conjugate of a cell-surface molecule binding-molecule and an effector moiety, an antibody-effector moiety conjugate, a receptor-ligand-effector moiety conjugate, an antibody-toxin conjugate, a receptor-ligand-toxin conjugate, an antibody-drug conjugate, a receptor-ligand-drug conjugate, an antibody-oligonucleotide conjugate and a receptor-ligand-oligonucleotide conjugate, and optionally comprising a pharmaceutically acceptable excipient and/or diluent.

An aspect of the invention relates to a third pharmaceutical composition comprising the saponin derivative of the invention and further comprising any one or more of: an antibody-toxin conjugate, a receptor-ligand-toxin conjugate, an antibody-drug conjugate, a receptor-ligand-drug conjugate, an antibody-nucleic acid conjugate or a receptor-ligand-nucleic acid conjugate, and optionally comprising a pharmaceutically acceptable excipient and/or diluent.

An embodiment is the first pharmaceutical combination of the invention or the third pharmaceutical composition of the invention, wherein the second pharmaceutical composition or the third pharmaceutical composition comprises any one or more of an antibody-drug conjugate, a receptor-ligand-drug conjugate, an antibody-oligonucleotide conjugate or a receptor-ligand-oligonucleotide conjugate, wherein the drug is for example a toxin such as saporin and dianthin, and wherein the oligonucleotide is for example an AON such as an siRNA or a BNA, for example for gene silencing of apolipoprotein B (apoB) or HSP27.

An embodiment is the first pharmaceutical combination comprising the second pharmaceutical composition of the invention, or the third pharmaceutical composition of the invention, wherein the second pharmaceutical composition or the third pharmaceutical composition comprises any one or more of an antibody-toxin conjugate, a receptor-ligand-toxin conjugate, an antibody-oligonucleotide conjugate or a receptor-ligand-oligonucleotide conjugate, wherein preferably the toxin is a protein toxin.

An embodiment is the first pharmaceutical combination of the invention or the third pharmaceutical composition of the invention, wherein the saponin derivative is a saponin derivative selected from the group consisting of derivatives of: SO1861, SA1657, GE1741, SA1641, QS-21, QS-21A, QS-21 A-api, QS-21 A-xyl, QS-21 B, QS-21 B-api, QS-21 B-xyl, QS-7-xyl, QS-7-api, QS-17-api, QS-17-xyl, QS1861, QS1862, *Quillaja saponin*, Saponinum album, QS-18, Quil-A, Gyp1, gypsoside A, AG1, AG2, SO1542, SO1584, SO1658, SO1674, SO1832, SO1862, SO1904, stereoisomers thereof and combinations thereof, preferably the saponin derivative is selected from the group consisting of an SO1861 derivative, a GE1741 derivative, an SA1641 derivative, a QS-21 derivative, and a combination thereof, more preferably the saponin derivative is an SO1861 derivative or a QS21 derivative, more preferably, the saponin derivative is an SO1861 derivative, even more preferably the saponin derivative is the saponin derivative according to formula (V), the saponin derivative according to formula (VI), the saponin derivative according to formula (VII), the saponin derivative according to formula (VIII) or any combination thereof. Also preferred is the saponin derivate according to molecule (AA), molecule (BB), molecule (KK), molecule (JJ) and molecule (QQ).

An embodiment is the third pharmaceutical composition according to the invention comprising a saponin derivative according to the invention, and further comprising preferably a pharmaceutically acceptable diluent, and further comprising:

a pharmaceutically acceptable salt, preferably a pharmaceutically acceptable inorganic salt, such as an ammonium, calcium, copper, iron, magnesium, manganese, potassium, sodium, strontium, or zinc salt, preferably NaCl; and/or a pharmaceutically acceptable buffer system, such as a phosphate, a borate, a citrate, a carbonate, a histidine, a lactate, a tromethamine, a gluconate, an aspartate, a glutamate, a tartarate, a succinate, a malate, a fumarate, an acetate and/or a ketoglutarate containing buffer system.

An embodiment is the third pharmaceutical composition according to the invention comprising a saponin derivative according to the invention and a pharmaceutically acceptable diluent, preferably water, wherein the composition is liquid at a temperature of 25° C. and has a pH within the range of 2-11, preferably within the range of 4-9, more preferably within the range of 6-8.

An embodiment is the third pharmaceutical composition according to the invention comprising a saponin derivative according to the invention and a pharmaceutically acceptable diluent, preferably water, wherein the composition is liquid at a temperature of 25° C. and wherein the concentration of the saponin derivative is within the range of $10^{-12}$ to 1 mol/l, preferably within the range of $10^{-9}$ to 0.1 mol/l, more preferably within the range of $10^{-6}$ to 0.1 mol/l.

Preferred is the first pharmaceutical combination comprising the second pharmaceutical composition or the third pharmaceutical composition according to the invention, wherein the second pharmaceutical composition or the third pharmaceutical composition comprise an antibody-toxin conjugate, an antibody-drug conjugate, or an antibody-oligonucleotide conjugate, wherein the antibody is a cell-surface molecule targeting molecule which can bind to a tumor-cell surface molecule, preferably to a tumor-cell receptor such as a tumor-cell specific receptor, more preferably to a receptor selected from CD71, CD63, CA125, EpCAM(17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably selected from CD71, HER2 and EGFR, more preferably wherein the antibody is a whole antibody or at least a cell-surface molecule binding fragment or -domain thereof, and preferably wherein the antibody comprises or consists of any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2, preferably cetuximab or trastuzumab or OKT-9, or at least one cell-surface molecule binding fragment or -domain thereof. Such an antibody can also be a binding derivative or binding fragment or binding domain thereof such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, a string of single-domain antibodies, a binding molecule comprising $V_{HH}$, a binding molecule comprising $V_H$, etc.

Preferred is the first pharmaceutical combination comprising the second pharmaceutical composition or the third pharmaceutical composition according to the invention wherein the effector moiety is an oligonucleotide comprising or consisting of any one or more of a nucleic acid and a xeno nucleic acid, preferably selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-O,4'-aminoethylene bridged nucleic acid, 3'-fluoro hexitol nucleic acid (FHNA), a plasmid, glycol nucleic acid (GNA) and threose nucleic acid (TNA), or a derivative thereof, more preferably a BNA or an siRNA, for example a BNA for silencing HSP27 protein expression or apoB protein expression.

Also preferred is the first pharmaceutical combination comprising the second pharmaceutical composition or the third pharmaceutical composition according to the invention wherein the effector moiety comprises or consists of at least one proteinaceous molecule, preferably selected from any one or more of a peptide, a protein, an enzyme such as urease and Cre-recombinase, a ribosome-inactivating protein, a proteinaceous toxin selected from any one or more of a viral toxin such as apoptin; a bacterial toxin such as Shiga toxin, Shiga-like toxin, *Pseudomonas aeruginosa* exotoxin (PE) or exotoxin A of PE, full-length or truncated diphtheria toxin (DT), cholera toxin; a fungal toxin such as alpha-sarcin; a plant toxin including ribosome-inactivating proteins and the A chain of type 2 ribosome-inactivating proteins such as dianthin e.g. dianthin-30 or dianthin-32, saporin e.g. saporin-S3 or saporin-S6, bouganin or de-immunized derivative debouganin of bouganin, shiga-like toxin A, pokeweed antiviral protein, ricin, ricin A chain, modeccin, modeccin A chain, abrin, abrin A chain, volkensin, volkensin A chain, viscumin, viscumin A chain; or an animal or human toxin such as frog RNase, or granzyme B or angiogenin from humans, or any fragment or derivative thereof; preferably the protein toxin is dianthin and/or saporin.

An embodiment is the first pharmaceutical combination comprising the second pharmaceutical composition of the invention or the third pharmaceutical composition of the invention, wherein the second pharmaceutical composition or the third pharmaceutical composition comprises any one or more of an antibody-effector moiety conjugate, a receptor-ligand-effector moiety conjugate, an antibody-drug conjugate, a receptor-ligand-drug conjugate, an antibody-oligonucleotide conjugate or a receptor-ligand-oligonucleotide conjugate, wherein the drug is for example a toxin such as saporin and dianthin, and wherein the oligonucleotide is for example an AON such as an siRNA or a BNA, for example for gene silencing of apolipoprotein B (apoB) or HSP27.

Preferred is the first pharmaceutical combination comprising the first pharmaceutical composition of the invention, or the third pharmaceutical composition of the invention, wherein the saponin derivative is any one or more of the saponin derivatives according to the invention.

An aspect of the invention relates to the first pharmaceutical composition of the invention, the first pharmaceutical combination of the invention or the third pharmaceutical composition of the invention, for use as a medicament.

An aspect of the invention relates to the first pharmaceutical combination of the invention or the third pharmaceutical composition of the invention, for use as a medicament.

An aspect of the invention relates to the first pharmaceutical composition of the invention, the first pharmaceutical combination comprising the first pharmaceutical composition of the invention, or the third pharmaceutical composition of the invention, for use as a medicament. In preferred embodiments there is provided the first pharmaceutical composition of the invention wherein the saponin derivative comprises, preferably consists of the saponin derivative according to formula (V), the saponin derivative according to formula (VI), the saponin derivative according to formula (VII), the saponin derivative according to formula (VIII) or any combination thereof; the first pharmaceutical combination of the invention wherein the saponin derivative comprises, preferably consists of the saponin derivative according to formula (V), the saponin derivative according to formula (VI), the saponin derivative according to formula (VII), the saponin derivative according to formula (VIII) or any combination thereof, or the third pharmaceutical composition of the invention wherein the saponin derivative comprises, preferably consists the saponin derivative according to formula (V), the saponin derivative according to formula (VI), the saponin derivative according to formula (VII), the saponin derivative according to formula (VIII) or any combination thereof, for use as a medicament.

An aspect of the invention is the provision of the saponin derivative as described herein, preferably the saponin derivative according to formula (V), the saponin derivative according to formula (VI), the saponin derivative according to formula (VII), the saponin derivative according to formula (VIII) or any combination thereof, for use as a medicament.

An aspect of the invention relates to the first pharmaceutical composition of the invention, the first pharmaceutical combination of the invention or the third pharmaceutical composition of the invention, for use in the treatment or prophylaxis of a cancer or an auto-immune disease.

An aspect of the invention relates to the first pharmaceutical combination of the invention or the third pharmaceutical composition of the invention, for use in the treatment or prophylaxis of a cancer or an auto-immune disease.

An aspect of the invention relates to the first pharmaceutical composition of the invention, the first pharmaceutical combination of the invention, or the third pharmaceutical composition of the invention, for use in the treatment or prophylaxis of a cancer or an auto-immune disease. In preferred embodiments there is provided the first pharmaceutical composition of the invention wherein the saponin derivative comprises, preferably consists of the saponin derivative according to formula (V), the saponin derivative according to formula (VI), the saponin derivative according to formula (VII), the saponin derivative according to formula (VIII) or any combination thereof; the first pharmaceutical combination of the invention wherein the saponin derivative comprises, preferably consists of the saponin derivative according to formula (V), the saponin derivative according to formula (VI), the saponin derivative according to formula (VII), the saponin derivative according to formula (VIII) or any combination thereof; or the third pharmaceutical composition of the invention wherein the saponin derivative comprises, preferably consists of the saponin derivative according to formula (V), the saponin derivative according to formula (VI), the saponin derivative according to formula (VII), the saponin derivative according to formula (VIII) or any combination thereof, for use in the treatment or prophylaxis of a cancer or an auto-immune disease.

Method for Delivering an Effector Molecule Inside a Cell, Using a Saponin Derivative An aspect of the invention relates to an in vitro or ex vivo method for transferring a molecule from outside a cell to inside said cell, preferably into the cytosol of said cell, comprising the steps of:

a) providing a cell;
b) providing the molecule for transferring from outside the cell into the cell provided in step a);
c) providing a saponin derivative according to the invention;
d) contacting the cell of step a) in vitro or ex vivo with the molecule of step b) and the saponin derivative of step c), therewith establishing the transfer of the molecule from outside the cell into said cell.

An embodiment is the method of the invention, wherein the cell is a human cell such as a T-cell, an NK-cell, a tumor cell, and/or wherein the molecule of step b) is any one of: an antibody-drug conjugate, a receptor-ligand-drug conjugate, an antibody-oligonucleotide conjugate or a receptor-ligand-oligonucleotide conjugate, wherein the drug is for example a toxin and wherein the oligonucleotide is for example an AON such as an siRNA or a BNA, and/or wherein the saponin derivative is selected from the group consisting of derivatives of: SO1861, SA1657, GE1741, SA1641, QS-21, QS-21A, QS-21 A-api, QS-21 A-xyl, QS-211B, QS-21 B-api, QS-21 B-xyl, QS-7-xyl, QS-7-api, QS-17-api, QS-17-xyl, QS1861, QS1862, *Quillaja saponin*, Saponinum album, QS-18, Quil-A, Gyp1, gypsoside A, AG1, AG2, SO1542, SO1584, SO1658, SO1674, SO1832, SO1862, SO1904, stereoisomers thereof and combinations thereof, preferably the saponin derivative is selected from the group consisting of an SO1861 derivative, a GE1741 derivative, an SA1641 derivative, a QS-21 derivative, and a combination thereof, more preferably the saponin derivative is an SO1861 derivative or a QS-21 derivative, most preferably, the saponin derivative is an SO1861 derivative; or wherein the saponin derivative is according to any one of formula (V), formula (VI), formula (VII) and formula (VIII), preferably the saponin derivative is according to formula (V) or formula (VIII).

In particular embodiments the in vitro or ex vivo method for transferring a molecule from outside a cell to inside said cell, preferably into the cytosol of said cell as described herein is provided wherein the saponin derivative comprises, preferably consists of the saponin derivative according to formula (V), the saponin derivative according to formula (VI), the saponin derivative according to formula (VII), the saponin derivative according to formula (VIII) or any combination thereof.

Saponin Conjugate Based on the Saponin Derivatives

An aspect of the invention relates to a saponin conjugate comprising a cell-surface molecule binding-molecule such as a first proteinaceous molecule ('proteinaceous molecule 1') that is covalently bound to the saponin derivative according to the invention, i.e. covalently linked to the saponin derivative. The cell-surface molecule binding-molecule is covalently bound to the derivatisation in the saponin derivative, i.e. the derivatised aldehyde functional group of the saponin on which the saponin derivative is based, i.e. through (via) a linker. The cell-surface molecule binding-molecule typically is a protein, such as an antibody or a binding fragment thereof, or a single-domain antibody (sdAb) or a binding molecule comprising a sdAb.

An aspect of the invention relates to a saponin conjugate based on a saponin derivative according to the invention, wherein the aldehyde group is transformed into a semicarbazone functional group according to formula (IX)

(IX)

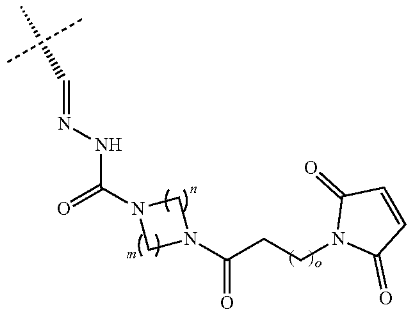

wherein n and m each are an integer independently selected from 1, 2, or 3;

o is an integer selected from 0-10, preferably 2-7, more preferably 4-6;

and wherein the maleimide functional group is further transformed into a thioether bond through reaction with a first proteinaceous molecule ('proteinaceous molecule 1') comprising a thiol functional group according to formula (X)

(X)

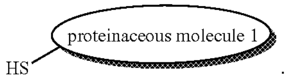

The saponin derivatives, wherein the aldehyde group is transformed into a semicarbazone functional group according to formula (IX)

(IX)

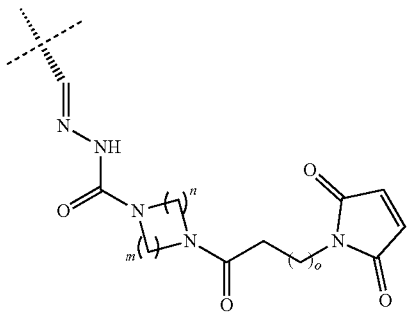

wherein n and m each are an integer independently selected from 1, 2, or 3; and o is an integer selected from 0-10, preferably 2-7, more preferably 4-6;

are suitable for application as a precursor for a conjugation reaction with a further molecule comprising a free sulfhydryl group. The maleimide functional group of the saponin derivative according to formula (IX) can form a thio-ether bond with such a free sulfhydryl group. For example, the saponin derivative according to formula (IX) can be covalently coupled to a peptide or a protein which comprises a free sulfhydryl group such as a cysteine with a free sulfhydryl group. Such a protein is for example an antibody or a binding derivative or binding fragment or binding domain thereof such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, for example camelid $V_H$, or a ligand for a cell-surface molecule such as a receptor such as EGF and a cytokine. Application of the saponin derivative according to formula (IX) in a coupling reaction with e.g. an antibody that comprises a free sulfhydryl group, provides a conjugate for targeted delivery of the saponin to and inside a cell, when the antibody (or the binding domain or fragment thereof) is an antibody for specific binding to a target cell surface molecule such as a receptor, e.g. as present on a tumor cell. Preferably, the saponin derivative is coupled to an antibody or $V_{HH}$ capable of binding to a tumor-cell specific surface molecule such as a receptor, e.g. HER2, EGFR, CD71.

It will be appreciated by the skilled person that since the saponin conjugate of the invention comprises (is based on) the saponin derivative according to the invention, all embodiments referring to the saponin derivative applies mutatis mutandis to the saponin conjugate. That is to say, the saponin conjugates of the invention are based on the saponin derivatives according to the invention, detailed here above.

A preferred embodiment is the saponin conjugate according to the invention, wherein the saponin conjugate is according to formula (XI)

(XI)

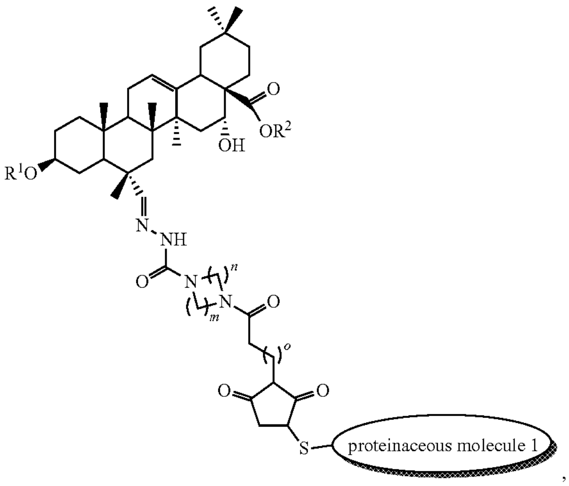

wherein $R^1$ and $R^2$ are as defined in any one of claims 1-10;

n and m each are an integer independently selected from 1, 2 or 3; and o is an integer selected from 0-10, preferably 2-7, more preferably 4-6.

A preferred embodiment is the saponin conjugate according to the invention, wherein the semicarbazone functional group according to formula (IX) or the saponin conjugate is according to formula (XI), wherein n=1 and m=1, n=2 and m=1, n=2 and m=2, n=3 and m=2, n=3 and m=3; preferably wherein n=1 and m=2, n=2 and m=2, or n=2 and m=3; more preferably wherein n=2 and m=2.

A highly preferred embodiment is the saponin conjugate according to formula (XII)

(XII)

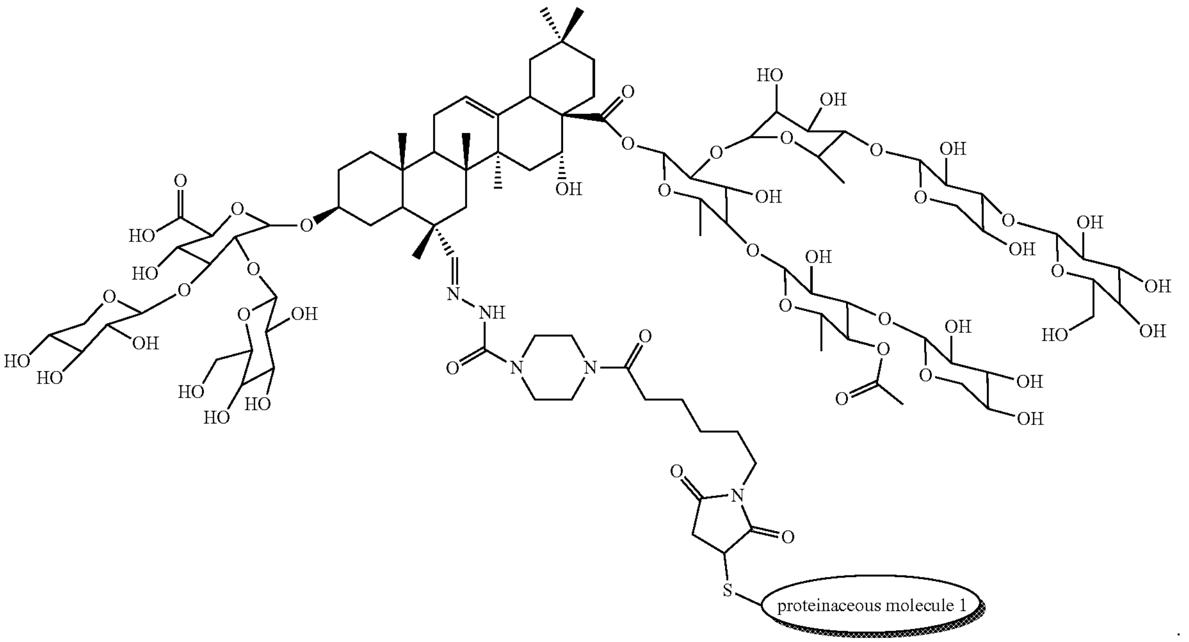

An embodiment is the saponin conjugate according to the invention, wherein the proteinaceous molecule 1 comprises a same first binding site for binding to a first epitope of a first cell-surface molecule. Preferably, in the saponin conjugate according to the invention, the proteinaceous molecule 1 comprises a cell-surface molecule binding-molecule comprising a first binding site for binding to a first epitope of a first cell-surface molecule.

An embodiment is the saponin conjugate according to the invention, wherein the first binding site of the proteinaceous molecule 1 is selected from any one or more of cell-surface molecule binding-molecules: an amino acid, a peptide, a protein, an antibody or a binding derivative or binding fragment or binding domain thereof such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, for example camelid $V_H$, or a ligand for a cell-surface molecule such as a receptor such as EGF and a cytokine, an adnectin, an affibody, an anticalin, or binding molecules comprising one or more of any of these cell-surface molecule binding-molecules.

An embodiment is the saponin conjugate according to the invention, wherein the first binding site of the proteinaceous molecule 1 is or comprises a single-domain antibody (sdAb), preferably $V_H$ domain derived from a heavy chain of an antibody, preferably of immunoglobulin G origin, preferably of human origin, a $V_L$ domain derived from a light chain of an antibody, preferably of immunoglobulin G origin, preferably of human origin, a $V_{HH}$ domain such as derived from a heavy-chain only antibody (HCAb) such as from Camelidae origin or Ig-NAR origin such as a variable heavy chain new antigen receptor (VNAR) domain, preferably the HCAb is from Camelidae origin, preferably the sdAb is a $V_{HH}$ domain derived from an HCAb from Camelidae origin (camelid $V_H$) such as derived from an HCAb from camel, lama, alpaca, dromedary, vicuna, guanaco and Bactrian camel.

An embodiment is the saponin conjugate according to the invention, wherein the first epitope of the first cell-surface molecule to which the first binding site can bind is a tumor-cell specific first epitope of a first tumor-cell surface molecule, more preferably a tumor-cell specific first epitope of a first tumor-cell surface receptor specifically present on a tumor cell. Thus, preferably, in the saponin conjugate according to the invention, the first epitope of the first cell-surface molecule, to which the proteinaceous molecule 1 can preferably bind, is a tumor-cell specific first epitope of a first tumor-cell surface molecule, more preferably a tumor-cell specific first epitope of a first tumor-cell surface receptor specifically present on a tumor cell.

Preferred is the saponin conjugate according to the invention, wherein the proteinaceous molecule 1 comprises a covalently bound effector moiety, and preferably, said effector moiety is an oligonucleotide.

An aspect of the invention relates to an eighth pharmaceutical composition comprising the saponin conjugate, wherein the proteinaceous molecule 1 comprised by said conjugate comprises a covalently bound effector moiety, and preferably, said effector moiety is an oligonucleotide, and the eighth pharmaceutical composition optionally comprising a pharmaceutically acceptable excipient and/or diluent.

According to the invention is the eighth pharmaceutical composition or the saponin conjugate comprised by said eighth pharmaceutical composition, for use as a medicament.

According to the invention is the eighth pharmaceutical composition or the saponin conjugate comprised by said eighth pharmaceutical composition, for use in the treatment of a cardiovascular disease or hypercholesterolemia or for use in a method for lowering LDL-cholesterol in the blood of a subject, wherein the effector moiety is an oligonucleotide capable of, for example when present inside a mammalian cell and preferably when present inside a human cell, silencing gene apolipoprotein B (apoB), wherein preferably the oligonucleotide is any one of an AON such as a BNA, a xeno nucleic acid, an siRNA, an antisense oligonucleotide.

The inventors established that combining in a single conjugate at least one saponin provided with a semicarbazone functional group according to the invention, a binding partner for a cell receptor such as an antibody or a binding domain or fragment thereof or such as one or more such as three GalNAc moieties for binding ASGPR, and an effector moiety such as an oligonucleotide e.g. an AON such as a BNA for silencing the HSP27 gene or the apoB gene, provides a conjugate with a higher potency when the activity and effect of the effector moiety in the target cell is considered and compared with the potency and activity achieved with a similar conjugate, though comprising at least one saponin provided with a hydrazone functional group. Without wishing to be bound by any theory, the improved potency is related to more efficacious release of the saponin moiety from the conjugate due to higher susceptibility for bond cleavage under the slightly acidic pH condition in the endosome of the target cell, when the at least one saponin is provided with the semicarbazone functional group. Examples with an antibody-oligonucleotide conjugate (AOC) comprising at least one saponin provided with the semicarbazone functional group covalently bound to the AOC indeed show the improved gene-silencing effect of this conjugate, compared to the similar conjugate though comprising at least one saponin provided with the hydrazone functional group covalently bound to the AOC. Similar improved potency is achieved when the antibody is replaced by at least one GalNAc moiety, preferably three GalNAc moieties, for binding to the cellular asialoglycoprotein receptor (ASGPR).

An embodiment is the saponin conjugate according to the invention, wherein the cell-surface molecule targeting (binding) molecule can bind to a tumor-cell surface molecule, preferably a tumor-cell receptor such as a tumor-cell specific receptor, more preferably a receptor selected from CD71, CD63, CA125, EpCAM(17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably selected from CD71, HER2 and EGFR; more preferably wherein the cell-surface molecule targeting (binding) molecule is or comprises a monoclonal antibody or at least one cell-surface molecule binding fragment or -domain thereof, and preferably comprises or consists of any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2, preferably cetuximab or trastuzumab or OKT-9, or at least one cell-surface molecule binding fragment or -domain thereof.

An embodiment is the saponin conjugate or the saponin derivative according to the invention, wherein the semicarbazone functional group

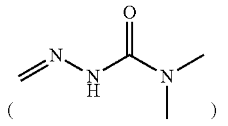

is cleavable or hydrolysable under acidic conditions, preferably at pH 4.0-6.5, such that the aldehyde group of the saponin on which the saponin derivative is based is formed upon cleavage of the semicarbazone functional group. It is specifically preferred that for the saponin derivative according to the invention and/or the saponin conjugate according to the invention, the semicarbazone functional group

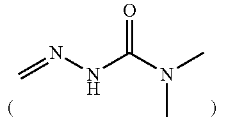

is hydrolysable (cleavable) under acidic conditions, preferably at pH 4.0-6.5, wherein hydrolysis of said semicarbazone functional group provides the aldehyde group on the aglycone core structure of the saponin on which the saponin derivative is based.

Since the semicarbazone functional group is not hydrolysed at physiological pH as apparent in e.g. the circulation and in tissue of mammals, e.g. human subjects, the saponin in the saponin conjugate is not split off from the conjugate while in the circulation or in tissue. Once the cell-surface molecule binding-molecule of the saponin conjugate, e.g. an antibody, bound to the cell-surface molecule on the target cell, the saponin conjugate is endocytosed by the cell and the saponin conjugate is transferred to and delivered into the cell endosome. In the endosome, the pH is suitable for hydrolysis (cleavage) of the semicarbazone functional group, such that the aldehyde functional group of the saponin on which the saponin conjugate is based, is again formed and the free saponin is provided. The free saponin in the endosome facilitates endosomal escape of any effector molecule or effector moiety into the cytosol, when such effector molecule or effector moiety is co-localized in the endosome. Without wishing to be bound by any theory, conjugating the saponin to a binding molecule through the semicarbazone functional group (e.g. via a maleimide linker) efficiently and sufficiently masks the cytotoxic activity of the free saponin on which the conjugate is based, by altering the initial aldehyde functional group of the saponin into the semicarbazone functional group. Once in the endosome, the semicarbazone functional group is susceptible to hydrolysis at the endosomal acidic pH, stimulating formation of the aldehyde functional group in the saponin, therewith providing the 'active' form of the saponin, when endosomal escape enhancing activity is concerned. Once inside the endosome of e.g. an auto-immune cell or a tumor cell, any cytotoxicity of the free saponin comprising the aldehyde functional group is not anymore hampering the benefits of the improved delivery of any effector moiety or molecule in the cytosol. That is to say, in the saponin conjugate, cytotoxicity of the saponin is efficiently blocked, inhibited or diminished, when the conjugate circulates or is present in the body extracellularly, and once inside the endosome, the formed free saponin comprising the aldehyde functional group is an efficient molecule for potentiating a desired effect of an effector molecule or moiety (that is for example co-administered to a subject in the form of for example an ADC, AOC, and capable of binding to the same cell as to which the saponin-conjugate of the invention can bind).

An embodiment is the saponin conjugate or the saponin derivative according to the invention, wherein the semicarbazone functional group is cleavable or hydrolysable in vivo under acidic conditions as present in endosomes and/or lysosomes of mammalian cells, preferably human cells, preferably at pH 4.0-6.5, and more preferably at pH 5.5, such that the aldehyde group of the saponin on which the saponin derivative is based is formed upon hydrolysis of the semicarbazone functional group. Thus, a specifically preferred embodiment is the saponin derivative according to the invention and/or the saponin conjugate according to the invention, wherein the semicarbazone functional group is subject to hydrolysis in vivo under acidic conditions as present in endosomes and/or lysosomes of mammalian cells, preferably human cells, preferably at pH 4.0-6.5, and more preferably at pH 5.5.

Surprisingly, the inventors have found that the saponin derivative according to the invention, in particular the saponin derivative according to formula (XII), comprising the semicarbazone functional group hydrolyses more rapidly and in an higher amount towards the corresponding saponin comprising a "free" aldehyde functional group, i.e. native saponin, such as SO1861, as compared to saponin derivatives comprising a hydrazone functional group (=N—N(H)—C(O)—), such as the saponin derivative SO1861-EMCH-blocked according to formula (4) (see formula (4) here below), under acidic conditions, such as at pH 4.0-6.5 which are the conditions present in endosomes and/or lysosomes of mammalian cells, such as human cells (see FIGS. 4A and 4B). This has the benefit that a lower amount of the saponin derivatives according to the invention should be administered to obtain the same amount of saponin comprising the "free" aldehyde to act as endosomal escape enhancers for targeted toxins.

(4)

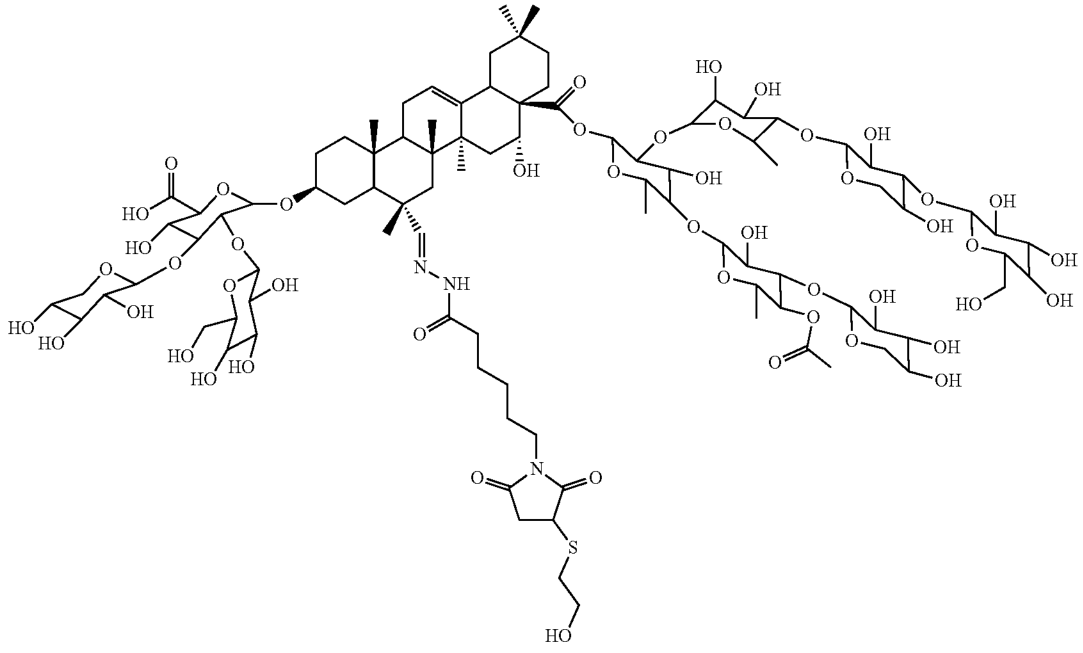

An embodiment is the saponin derivative according to the invention, wherein the saponin derivative is according to molecule (AA):

(AA)

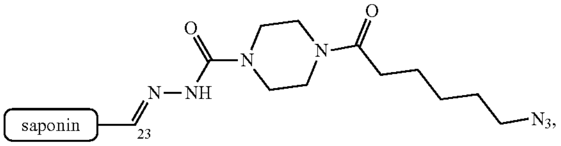

wherein

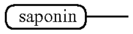

represents a saponin moiety according to formula (SM):

(SM)

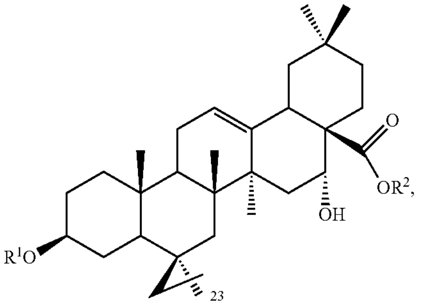

wherein $R^1$ and $R^2$ are independently selected from hydrogen, a monosaccharide, a linear oligosaccharide and a branched oligosaccharide, and wherein the saponin moiety according to formula (SM) is based on a saponin comprising an aldehyde group in position C-23.

The inventors established that the saponin derivative according to molecule (AA) is particularly suitable for synthesizing saponin conjugates of the invention, comprising either at least one GalNAc moiety, preferably three GalNAc moieties, or an oligonucleotide such as a gene-silencing siRNA or BNA, preferably BNA, or both. Therewith, the inventors now provide the saponin derivative according to molecule (AA) as a semi-product for preparing saponin conjugates of the invention, which display enhanced potency with regard to the endosomal escape enhancing activity of the saponin comprised by the conjugate, and which display improved efficacy when the (gene-silencing) effect of an oligonucleotide is considered, when comprised by such a conjugate.

Preferred is the saponin derivative according to molecule (BB):

(BB)

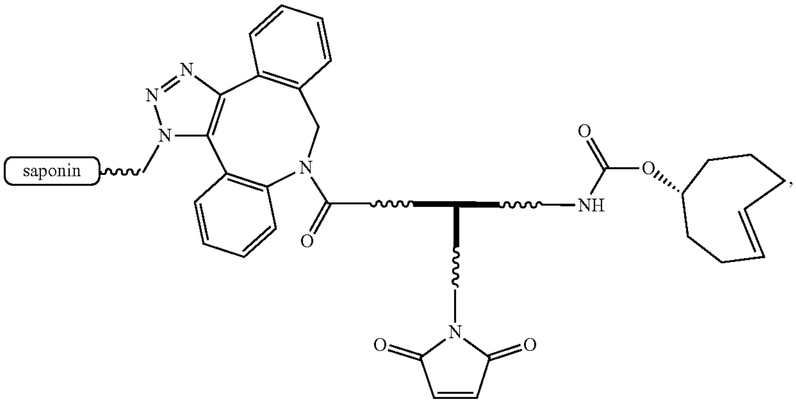, which molecule (BB) is the covalent conjugation product obtained by the covalent conjugation of the saponin derivative according to molecule (AA) as here above described with the tri-functional linker according to formula (XXI):

(XXI)

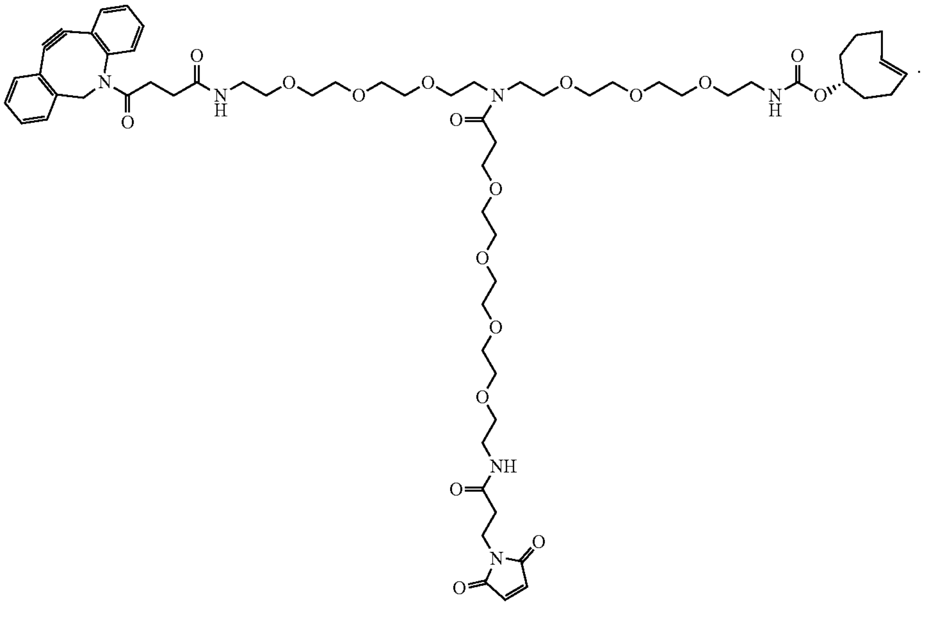

Such saponin derivative according to molecule (BB) is a semi-product suitable for providing a conjugate comprising the saponin with a semicarbazone functional group, and for example comprising a cell-surface receptor ligand such as one-three GalNAc moieties, and/or an oligonucleotide such as an AON such as an siRNA or a BNA. As said, such as conjugate displays improved potency when the activity of the oligonucleotide is considered, when also when the endosomal escape enhancing activity of the saponin is considered.

An aspect of the invention relates to saponin conjugate according to molecule (CC):

(CC)

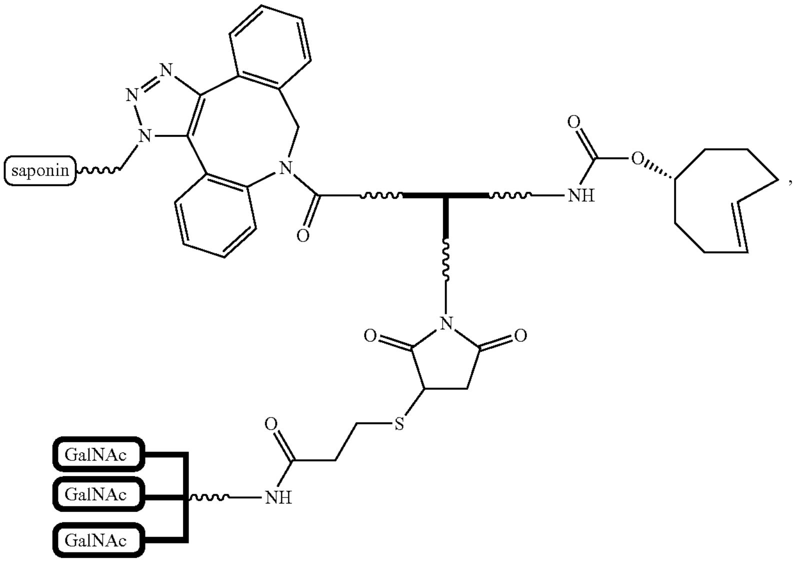

which molecule (CC) is the covalent conjugation product obtained by the covalent conjugation of the tri-functional linker according to formula (XXI) (as here above displayed) with the saponin derivative according to molecule (AA) as provided here above and with GalNAc conjugate according to molecule (FF):

(FF)

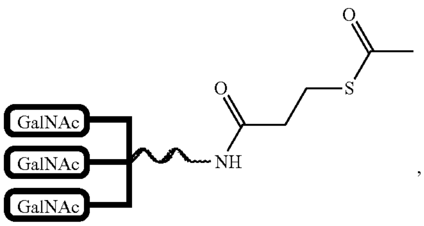

, wherein

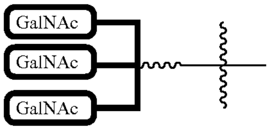

represents the tri-GalNAc conjugate according to molecule (DD):

(DD)

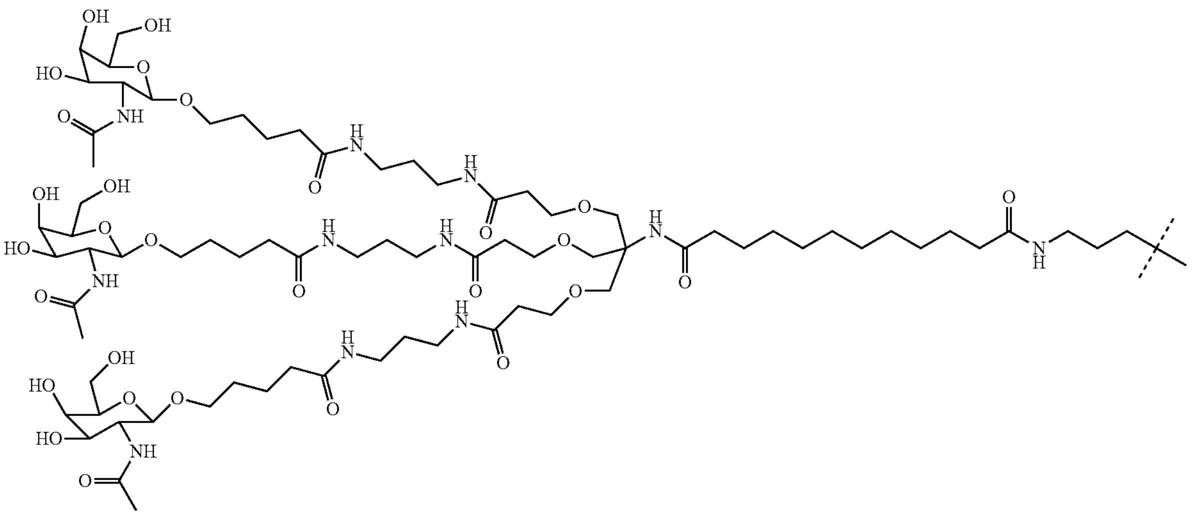

.

Such a saponin conjugate according to molecule (CC) is for example a semi-product for preparation of a conjugate further comprising an oligonucleotide such as a gene-silencing BNA or siRNA. In addition, the saponin conjugate according to molecule (CC) is suitable for enhancing the effect and potency of for example a gene-silencing oligonucleotide for example provided with (liver) cell-targeting ligand such as an antibody or one or more GalNAc moieties, preferably three, when cells are contacted with both the saponin conjugate according to molecule (CC) and such an AOC or oligonucleotide-GalNAc conjugate. Such a targeted cell should thus typically expose ASGPR and the binding partner for the antibody (or a binding domain or fragment thereof).

An aspect of the invention relates to saponin conjugate according to molecule (EE):

(EE)

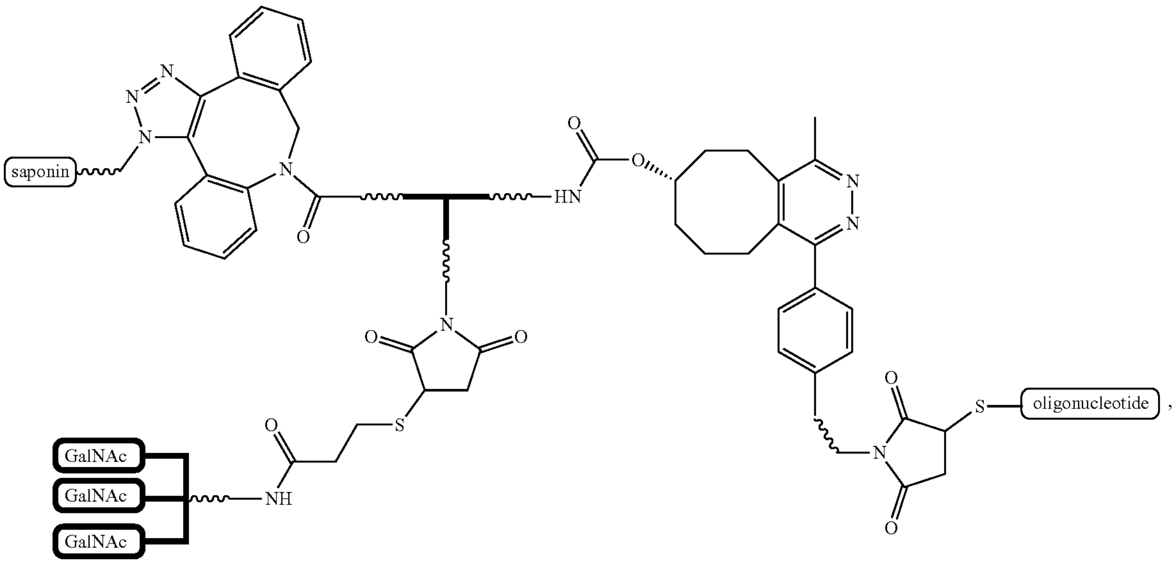

which molecule (EE) is the covalent conjugation product obtained by the covalent conjugation of the tri-functional linker according to formula (XXI) (displayed here above) with the saponin derivative according to molecule (AA) as shown here above and with GalNAc conjugate according to molecule (FF) as shown here above and with the oligonucleotide provided with a linker according to molecule (GG):

(GG)

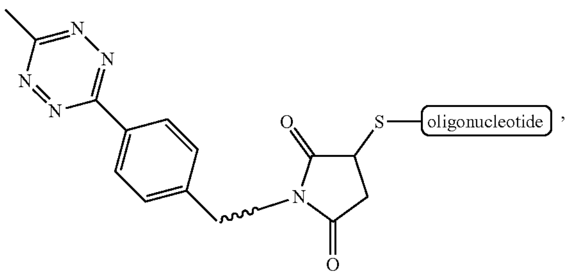

wherein the molecule (GG) represents the conjugation product of the conjugation reaction between the linker (E)-1-(4-((2-(6-(2,5-dioxo-2,5-dihydro-1H-pyrrol-1-yl)hexanoyl)hydrazineylidene)methyl)benzamido)-N-(4-(6-methyl-1,2,4,5-tetrazin-3-yl)benzyl)-3,6,9,12-tetraoxapentadecan-15-amide and the oligonucleotide-linker molecule according to molecule (HH):

(HH)

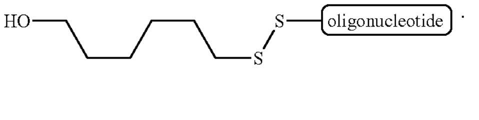

Such a saponin conjugate according to molecule (EE) of the invention displays a surprisingly improved potency when the endosomal escape enhancing activity of the saponin moiety is considered. It is thought that improved efficacy relates to improved de-coupling (release) of the saponin from the conjugate by cleavage of the semicarbazone functional group under influence of the slightly acidic pH in the endosome of cells which have taken up the conjugate mediated by binding of the conjugate to the ASGPR. Therewith, endosomal escape of the oligonucleotide is enhanced and (gene-silencing) activity of the oligonucleotide in the cytosol and/or in the nucleus is enhanced, compared to applying the similar conjugate though with a hydrazone functional group instead of the semicarbazone functional group of the saponin conjugate according to molecule (EE).

An embodiment is the saponin derivative according to the invention wherein the saponin derivative is according to molecule (KK):

(KK)

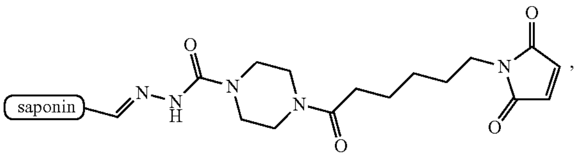

wherein

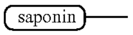

represents a saponin moiety according to formula (SM):

(SM)

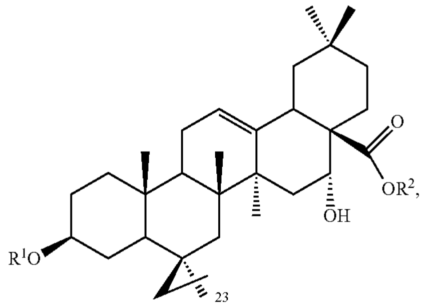

wherein $R^1$ and $R^2$ are independently selected from hydrogen, a monosaccharide, a linear oligosaccharide and a branched oligosaccharide according to any one of the oligosaccharides as listed here above, and wherein the saponin moiety according to formula (SM) is based on a saponin comprising an aldehyde group in position C-23 according to any one of the saponins listed here above, and in Table A1.

The saponin derivative according to molecule (KK) is for example a derivative suitable for conjugation with e.g. a cell-targeting antibody, e.g. in the context of an ADC or AOC. Molecule (KK) is applicable as a semi-product for synthesizing such an ADC or AOC, providing a single conjugate comprising the cell-targeting moiety (e.g. an antibody or a binding domain thereof), an effector moiety such as a toxin or a (gene-silencing) oligonucleotide (e.g. an AON) such as a BNA or siRNA, and the saponin moiety with improved activity due to enhanced release from the conjugate under influence of slightly acidic pH in the endosome of a targeted cell, by virtue of the presence of the semicarbazone functional group, and as compared with a similar conjugate though comprising the hydrazone functional group instead of the semicarbazone functional group. The saponin derivative according to molecule (KK) is for example also a semi-product for producing a conjugate comprising more than one copies of the saponin moiety comprising the semicarbazone functional group. Examples are the synthesis of a conjugate comprising for example a G2 dendron or G3 dendron and four or eight covalently bound saponin derivatives comprising the semicarbazone functional group. As such, such a dendron-based conjugate with four or eight saponin moieties, is a semi-product for providing a conjugate comprising an effector moiety such as a (gene-silencing) oligonucleotide, such as a BNA or an siRNA, and/or comprising a ligand for a cell-surface molecule such as a cell-receptor binding antibody or binding fragment or domain thereof or a cell-surface receptor ligand such as 1-3 GalNAc moieties for binding to ASGPR, preferably three GalNAc moieties. Providing such conjugates of the invention with a single saponin derivative or multiple saponin derivatives provides the opportunity to fine-tune and select the optimal number of saponin moieties most suitable for optimal enhancement of the intracellular potency of the effector molecule such as a gene-silencing oligonucleotide (an AON), e.g. a BNA. That is to say, for certain applications involving a combination of a certain target cell, a certain selected cell-surface molecule such as a receptor, a certain cell-surface molecule binding ligand such as an antibody or 1-3 GalNAc moieties, and a certain effector molecule such as a (gene-silencing) oligonucleotide (e.g. an AON) such as a BNA, presence of a single saponin derivative comprising the semicarbazone functional group in a conjugate of the saponin derivative, the effector molecule and the cell-surface molecule binding ligand may suffice to obtain optimal potency of the effector molecule, whereas for other combinations more than one saponin derivative moieties in the conjugate may be applied to achieve optimal potency, such as 2-32 saponin derivative moieties, preferably 2-16 moieties, more preferably 4-8 moieties, such as 4 or 8 moieties. The saponin derivatives of the invention provide for a flexible platform when adapting the number of saponin derivative moieties in a saponin conjugate of the invention such that optimal efficacy of the effector molecule is achieved, is considered. Indeed, the inventors established that gene silencing was enhanced when the number of saponin derivative moieties comprising the semicarbazone functional group was increased from 1 to 4 to 8 for a conjugate of the invention comprising three GalNAc moieties and a BNA for silencing the apoB gene (see also the Examples section).

An aspect of the invention relates to saponin derivative according to molecule (JJ):

(JJ)

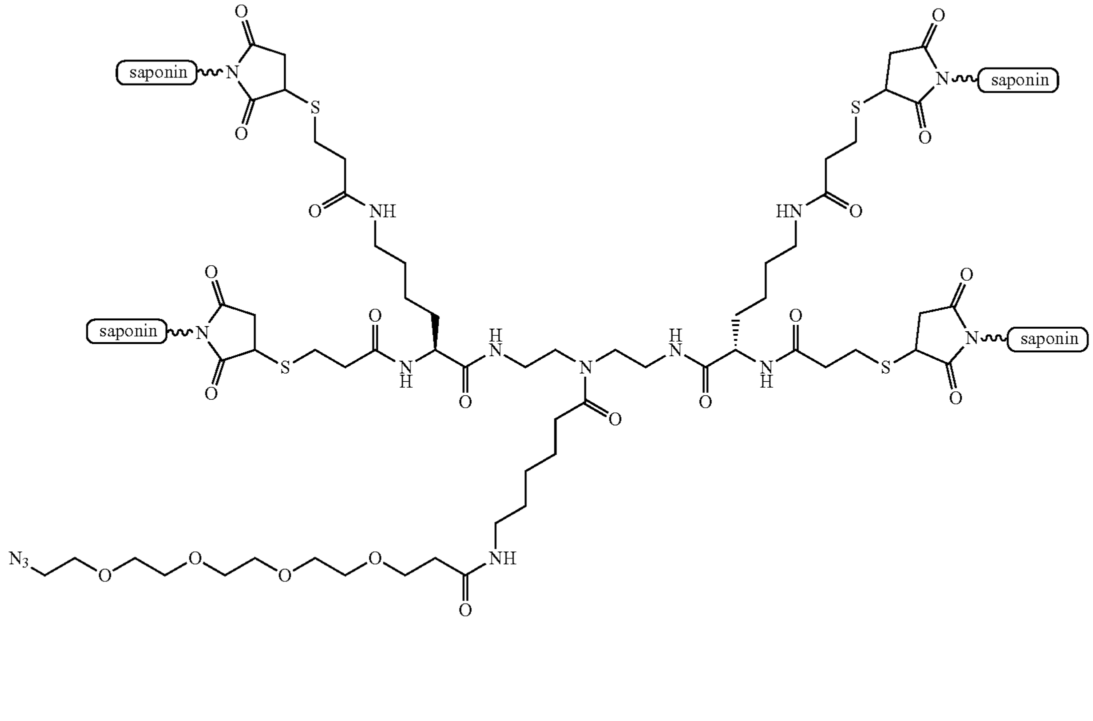

which molecule (JJ) is the conjugate product of conjugation of N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide first with the saponin derivative according to molecule (KK), as outlined here above, and subsequently with 2,5-dioxopyrrolidin-1-yl 1-azido-3,6,9,12-tetraoxapentadecan-15-oate.

Part of the invention is saponin conjugate according to molecule (LL):

(LL)

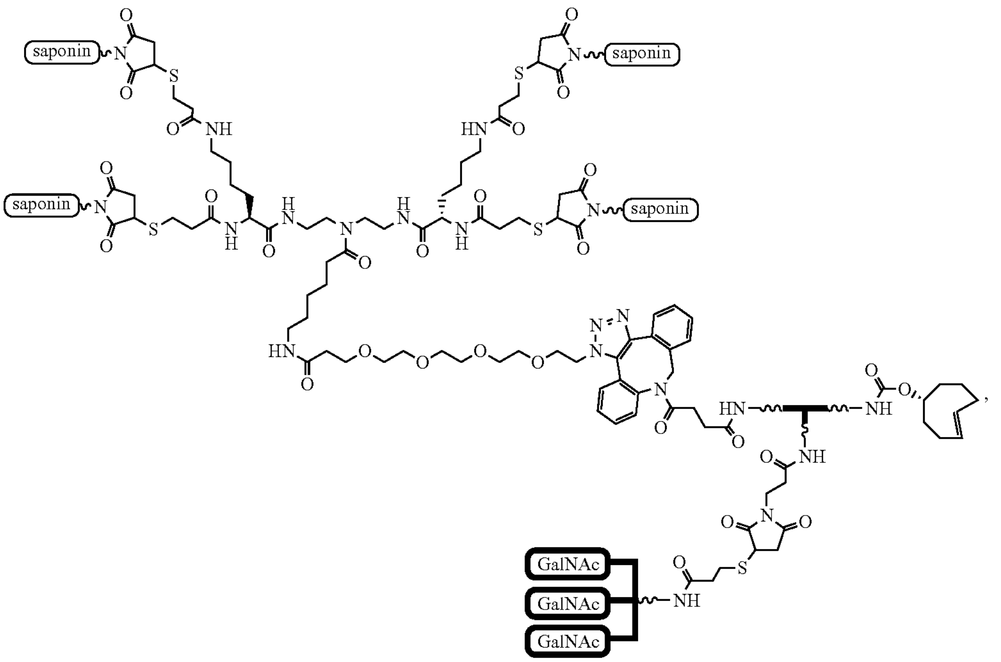

which molecule (LL) is the covalent conjugation product obtained by the covalent conjugation of the molecule (JJ) as detailed here above with the conjugate of the tri-functional linker and GalNAc according to molecule (MM):

(MM)

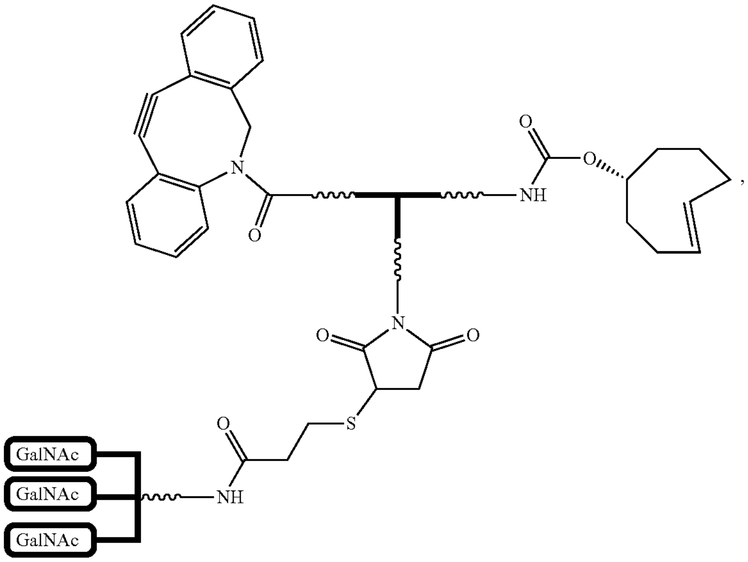

wherein molecule (MM) is the conjugate of the tri-functional linker according to formula (XXI) as displayed here above and the GalNAc conjugate according to molecule (NN):
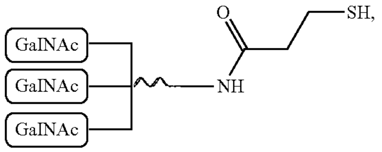
wherein
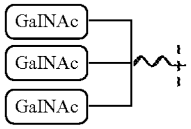
represents the tri-GalNAc conjugate according to molecule (DD) as detailed here above.
An aspect of the invention relates to saponin conjugate according to molecule (PP):

(PP)
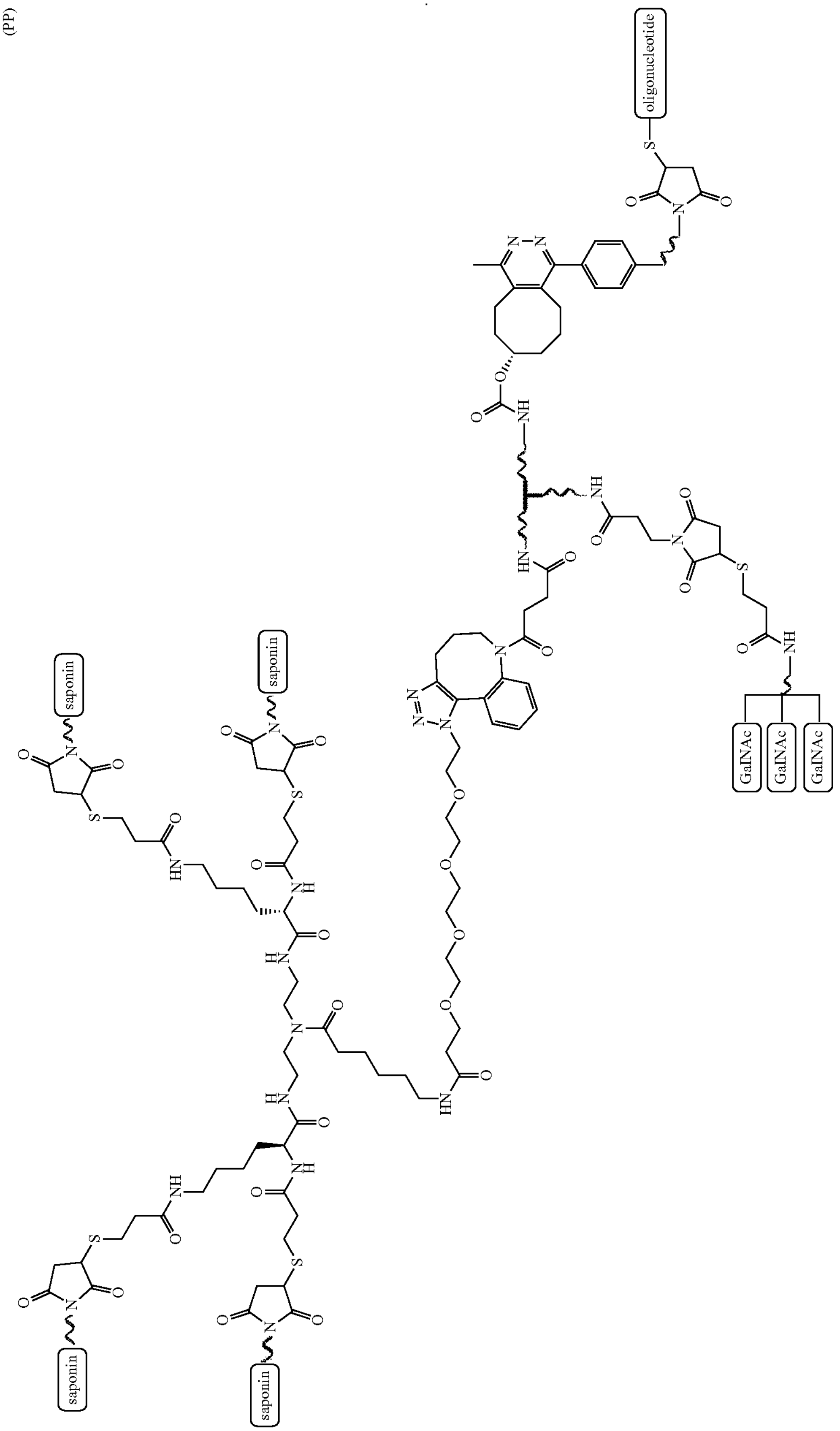

which molecule (PP) is the covalent conjugation product obtained by the covalent conjugation of the molecule (LL) as given here above with the oligonucleotide provided with a linker according to molecule (GG) as detailed here above.

An aspect of the invention relates to saponin derivative according to molecule (QQ):

(QQ)

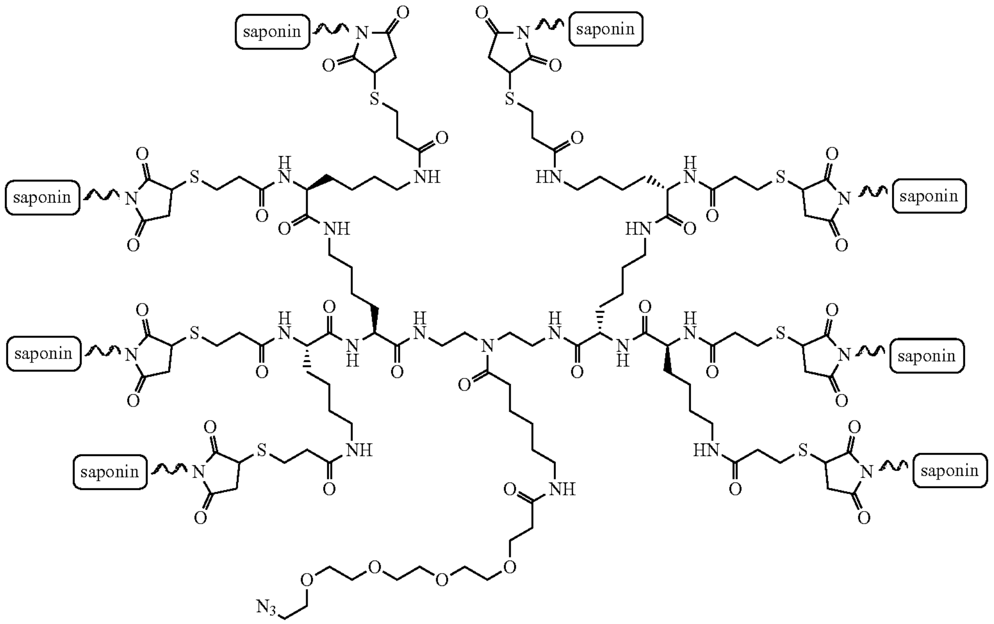

which molecule (QQ) is the conjugate product of conjugation of (2S)—N-[(1S)-1-{[2-(6-amino-N-{2-[(2S)-2,6-bis[(2S)-2,6-bis(3-sulfanylpropanamido)hexanamido]hexanamido]ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate first with saponin derivative according to molecule (KK) as detailed here above and subsequently with 2,5-dioxopyrrolidin-1-yl 1-azido-3,6,9,12-tetraoxapentadecan-15-oate.

An aspect of the invention relates to saponin conjugate according to molecule (RR):
(RR)
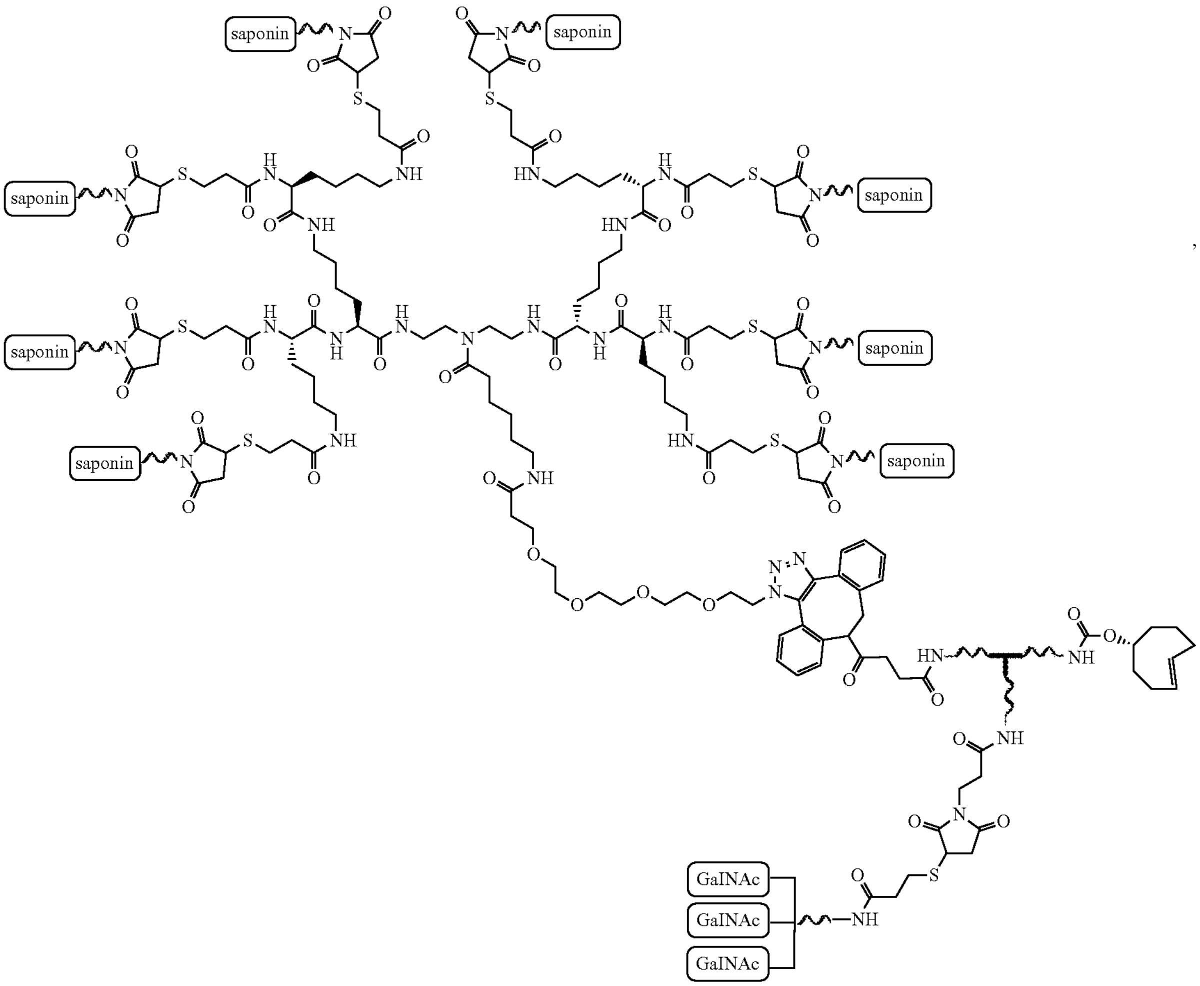
,
which molecule (RR) is the covalent conjugation product obtained by the covalent conjugation of the molecule (QQ) as outlined here above with the conjugate of the tri-functional linker and GalNAc according to molecule (MM) as outlined here above.

Part of the invention is saponin conjugate according to molecule (SS):
(SS)
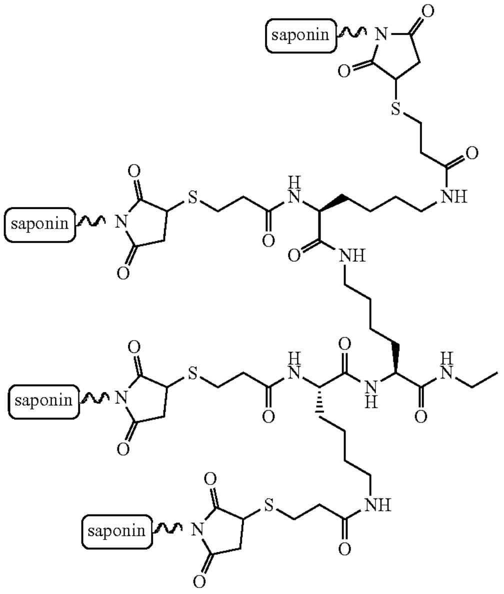
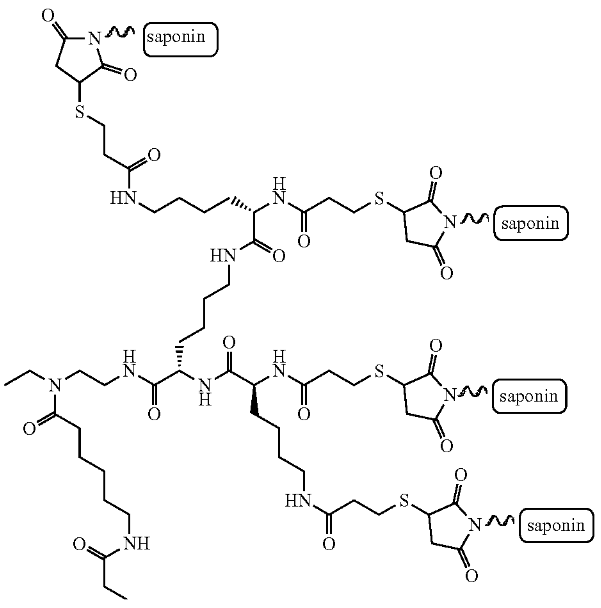
, -continued

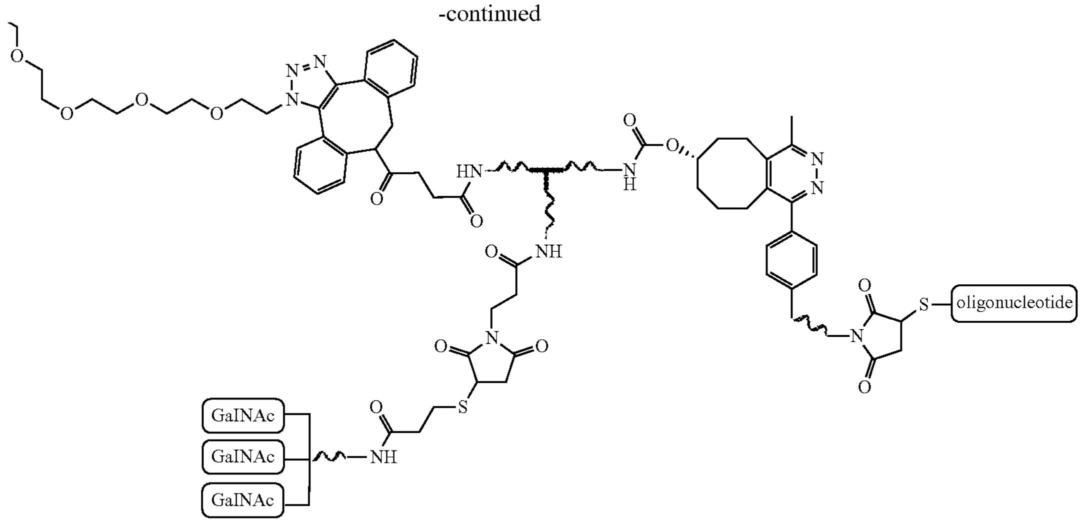

which molecule (SS) is the covalent conjugation product obtained by the covalent conjugation of the molecule (RR) as detailed here above with the oligonucleotide provided with a linker according to molecule (GG) as detailed here above.

An embodiment is the saponin derivative according to the invention, and according to any one of the molecules (AA), (BB), (KK), (JJ) and (QQ) or saponin conjugate according to the invention and according to any one of the molecules (CC), (EE), (LL), (PP), (RR) and (SS), wherein the saponin derivative or the saponin conjugate is based on a saponin according to any one of the saponins listed here above and in Table A1.

Preferred is the saponin derivative according to the invention, and according to any one of the molecules (AA), (BB), (KK), (JJ) and (QQ) or the saponin conjugate according to the invention and according to any one of the molecules (CC), (EE), (LL), (PP), (RR) and (SS), wherein the saponin derivative or the saponin conjugate is based on a saponin selected from SO1861, SO1832 and QS-21, preferably SO1861 and SO1832, more preferably SO1861.

Also preferred is the saponin derivative according to the invention, and according to any one of the molecules (AA), (BB), (KK), (JJ) and (QQ) or the saponin conjugate according to the invention and according to any one of the molecules (CC), (EE), (LL), (PP), (RR) and (SS), wherein the semicarbazone functional group is subject to hydrolysis in vivo under acidic conditions as present in endosomes and/or lysosomes of mammalian cells, preferably human cells, preferably at pH 4.0-6.5, and more preferably at pH 5.5.

An embodiment is the saponin conjugate according to the invention and according to any one of the molecules (EE), (PP) and (SS), comprising an oligonucleotide, wherein the oligonucleotide is any one of an AON, a BNA, a xeno nucleic acid, an siRNA, an antisense oligonucleotide.

An embodiment is the saponin conjugate according to the invention and according to any one of the molecules (EE), (PP) and (SS), comprising an oligonucleotide, wherein the oligonucleotide is selected from any one or more of a(n): short interfering RNA (siRNA), short hairpin RNA (shRNA), anti-hairpin-shaped microRNA (miRNA), single-stranded RNA, aptamer RNA, double-stranded RNA (dsRNA), anti-microRNA (anti-miRNA, anti-miR), antisense oligonucleotide (ASO), DNA, antisense DNA, locked nucleic acid (LNA), bridged nucleic acid (BNA), 2'-O,4'-aminoethylene bridged nucleic acid ($BNA^{NC}$), BNA-based siRNA, and BNA-based antisense oligonucleotide (BNA-AON).

An embodiment is the saponin conjugate according to the invention and according to any one of the molecules (EE), (PP) and (SS), comprising an oligonucleotide, wherein the oligonucleotide is selected from any one or more of a(n): anti-miRNA, a BNA-AON or an siRNA, such as BNA-based siRNA, selected from chemically modified siRNA, metabolically stable siRNA and chemically modified, metabolically stable siRNA.

An embodiment is the saponin conjugate according to the invention and according to any one of the molecules (EE), (PP) and (SS), comprising an oligonucleotide, wherein the oligonucleotide is an oligonucleotide capable of, for example when present inside a mammalian cell and preferably when present inside a human cell, silencing any one of genes: apolipoprotein B (apoB), HSP27, transthyretin (TTR), proprotein convertase subtilisin/kexin type 9 (PCSK9), TMPRSS6, delta-aminolevulinate synthase 1 (ALAS1), anti-thrombin 3 (AT3), glycolate oxidase (GO), complement component C5 (CC5), X gene of hepatitis B virus (HBV), S gene of HBV, alpha-1 antitrypsin (AAT), miR-122, hepatitis B virus HbsAg, LDHA, CEBPA and lactate dehydrogenase (LDH), and/or is an oligonucleotide capable of, for example when present inside a mammalian cell, targeting an aberrant miRNA.

An embodiment is the saponin conjugate according to the invention and according to any one of the molecules (EE), (PP) and (SS), comprising an oligonucleotide, wherein the oligonucleotide is an oligonucleotide capable of, for example when present inside a mammalian cell and preferably when present inside a human cell, silencing any one of genes: apolipoprotein B (apoB) and HSP27.

An embodiment is the saponin conjugate according to the invention and according to any one of the molecules (EE), (PP) and (SS), comprising an oligonucleotide, wherein the oligonucleotide is an oligonucleotide capable of, for example when present inside a mammalian cell and preferably when present inside a human cell, targeting an mRNA involved in expression of any one of proteins: apoB, HSP27, TTR, PCSK9, TMPRSS6, ALAS1, AT3, GO, CC5, expression product of X gene of HBV, expression product of S gene of HBV, AAT, miR-122, hepatitis B virus HbsAg, LDHA, CEBPA and LDH, or is capable of, for example when present inside a mammalian cell and preferably when present inside a human cell, antagonizing or restoring an miRNA function such as inhibiting an oncogenic miRNA (onco-miR) or suppression of expression of an onco-miR.

An embodiment is the saponin conjugate according to the invention and according to any one of the molecules (EE), (PP) and (SS), comprising an oligonucleotide, wherein the oligonucleotide is an oligonucleotide capable of, for example when present inside a mammalian cell and preferably when present inside a human cell, targeting an mRNA involved in expression of any one of proteins: HSP27, apoB, TTR, PCSK9, TMPRSS6, ALAS1, AAT, miR-122, hepatitis B virus HbsAg, LDHA and CEBPA.

An embodiment is the saponin conjugate according to the invention and according to any one of the molecules (EE), (PP) and (SS), comprising an oligonucleotide, wherein the oligonucleotide is an oligonucleotide capable of, for example when present inside a mammalian cell and preferably when present inside a human cell, targeting an mRNA involved in expression of any one of proteins: apoB and HSP27.

Pharmaceutical Combination and Pharmaceutical Composition Comprising a Saponin Conjugate An aspect of the invention relates to a second pharmaceutical combination comprising:

(a) a fourth pharmaceutical composition comprising the saponin conjugate of the invention and optionally a pharmaceutically acceptable excipient and/or diluent; and (b) a fifth pharmaceutical composition comprising a conjugate comprising a cell-surface molecule binding-molecule, such as a second proteinaceous molecule ('proteinaceous molecule 2'), and an effector moiety, wherein the proteinaceous molecule 2 is the same or different from the proteinaceous molecule 1 present in the saponin conjugate, and if the proteinaceous molecule 2 is different from the proteinaceous molecule 1, the proteinaceous molecule 2 comprising a second binding site for binding to a second epitope of a second cell-surface molecule, wherein the second cell-surface molecule is the same as or different from the first cell surface molecule, and if the second cell-surface molecule is different from the first cell surface molecule, the second cell-surface molecule and the first cell surface molecule are preferably present on the same cell, the fifth pharmaceutical composition optionally further comprising a pharmaceutically acceptable excipient and/or diluent. The effector moiety is not a saponin on which the saponin derivative or the saponin conjugate of the invention are based. The effector moiety is not the saponin derivative or the saponin conjugate of the invention.

Surprisingly, the inventors have found that the saponin derivatives according to the invention which are used as a component for potentiating the intracellular effect of an effector molecule or effector moiety when the effector molecule is provided as a conjugate comprising a cell-surface molecule binding-molecule such as an antibody, e.g. as an ADC or AOC, are now also suitably for (covalent) coupling to a cell-surface molecule binding-molecule such as a cell-surface molecule targeting antibody, such as an sdAb, such that by such coupling the saponin conjugate of the invention is provided, endowed with, for example, anti-tumor activity potentiating activity when used in combination with for example an ADC or an AOC.

An embodiment is the fourth pharmaceutical composition according to the invention comprising the saponin conjugate according to the invention, preferably a pharmaceutically acceptable diluent, and further comprising:

a pharmaceutically acceptable salt, preferably a pharmaceutically acceptable inorganic salt, such as an ammonium, calcium, copper, iron, magnesium, manganese, potassium, sodium, strontium, or zinc salt, preferably NaCl; and/or a pharmaceutically acceptable buffer system, such as a phosphate, a borate, a citrate, a carbonate, a histidine, a lactate, a tromethamine, a gluconate, an aspartate, a glutamate, a tartarate, a succinate, a malate, a fumarate, an acetate and/or a ketoglutarate containing buffer system.

An embodiment is the fourth pharmaceutical composition according to the invention comprising the saponin conjugate according to the invention and a pharmaceutically acceptable diluent, preferably water, wherein the composition is liquid at a temperature of 25° C. and has a pH within the range of 2-11, preferably within the range of 4-9, more preferably within the range of 6-8.

An embodiment is the first pharmaceutical composition of the invention, wherein the saponin conjugate is the saponin conjugate according to formula (XII).

An embodiment is the second pharmaceutical combination of the invention, comprising:

(a) the fourth pharmaceutical composition of the invention comprising the saponin conjugate of the invention, wherein the first epitope on the first cell-surface molecule is a tumor-cell specific first epitope on a first tumor cell-specific surface molecule, preferably a tumor-cell specific first epitope on a first cell-surface receptor specifically present at a tumor cell; and (b) the fifth pharmaceutical composition of the invention, wherein the second cell-surface molecule is a second tumor cell-specific surface molecule which is the same or different from the first tumor cell-specific surface molecule, preferably a second cell-surface receptor specifically present at a tumor cell which is the same or different from the first cell-surface receptor specifically present at said tumor cell, and wherein the second epitope is a tumor-cell specific second epitope, wherein the first epitope and the second epitope, which is the same as or different from the first epitope, are exposed at the same cell.

An aspect of the invention relates to a third pharmaceutical combination, comprising:

(a) the fourth pharmaceutical composition of the invention comprising the saponin conjugate according to the invention, comprising the first binding site for binding to the first epitope on the first cell-surface molecule, the fourth pharmaceutical composition optionally further comprising a pharmaceutically acceptable excipient and/or diluent; and (b) a sixth pharmaceutical composition comprising a conjugate comprising a cell-surface molecule binding-molecule, such as a third proteinaceous molecule ('proteinaceous molecule 3'), and an effector moiety, wherein the proteinaceous molecule 3 comprises the first binding site for binding to the first epitope on the cell-surface molecule of (a), the sixth pharmaceutical composition optionally further comprising a pharmaceutically acceptable excipient and/or diluent, wherein the first binding site of the proteinaceous molecule 1 and the first binding site of the proteinaceous molecule 3 are the same, and wherein the first cell-surface molecule and the first epitope on the first cell-surface molecule, to which the proteinaceous molecule 1 can bind, and the first cell-surface molecule and the first epitope on the first cell-surface molecule, to which the proteinaceous molecule 3 can bind, are the same. The effector moiety is not a saponin on which the saponin derivative or the saponin conjugate of the invention are based. The effector moiety is not the saponin derivative or the saponin conjugate of the invention.

An embodiment is the sixth pharmaceutical composition according to the invention, further comprising:

a pharmaceutically acceptable salt, preferably a pharmaceutically acceptable inorganic salt, such as an ammonium, calcium, copper, iron, magnesium, manganese, potassium, sodium, strontium, or zinc salt, preferably NaCl; and/or a pharmaceutically acceptable buffer system, such as a phosphate, a borate, a citrate, a carbonate, a histidine, a lactate, a tromethamine, a gluconate, an aspartate, a glutamate, a tartrate, a succinate, a malate, a fumarate, an acetate and/or a ketoglutarate containing buffer system.

An embodiment is the sixth pharmaceutical composition according to the invention comprising the saponin conjugate according to the invention and a pharmaceutically acceptable diluent, preferably water, wherein the composition is liquid at a temperature of 25° C. and has a pH within the range of 2-11, preferably within the range of 4-9, more preferably within the range of 6-8.

An embodiment is the second pharmaceutical combination or the third pharmaceutical combination according to the invention, wherein the proteinaceous molecule 2 and the proteinaceous molecule 3 is of a type as detailed or the proteinaceous molecule 1, e.g. an antibody or an antigen binding fragment or antigen binding domain thereof, a ligand for a cell-surface molecule or cell-surface receptor such as EGF or a cytokine, an scFv, a Fab, a binding molecule comprising an sdAb, such as a $V_{HH}$, a binding molecule comprising any of an adnectin, an anticalin, an affibody. The skilled person will appreciate that for the proteinaceous molecule 1 and proteinaceous molecule 2 and proteinaceous molecule 3 any cell-surface molecule binding-molecule can be selected and is suitable for application in the saponin conjugates of the invention and for application in the pharmaceutical compositions and combinations of the invention, that is known today in the technological field of (specifically) targeting a mammalian (aberrant, tumor, auto-immune, etc.) cell with a binding molecule, e.g. for (targeted and specific) delivery of an effector molecule or effector moiety conjugated to the cell-surface molecule binding-molecule. Typical examples of such suitable cell-surface molecule binding-molecules are the antibodies and binding fragments, binding domains and binding derivatives thereof and ligands such as EGF or cytokines used today to deliver drug molecules, payloads, effector moieties, protein toxins, small-molecule toxins, enzymes, oligonucleotides, etc., etc., e.g. in ADCs and AOCs. Any cell-surface molecule binding-molecule applicable for e.g. designing and providing ADCs and AOCs is typically also applicable for providing the saponin conjugate of the invention (e.g. proteinaceous molecule 1). Any cell-surface molecule binding-molecule applicable for e.g. designing and providing ADCs and AOCs is typically also applicable for providing the cell-surface molecule binding-molecule conjugated with an effector moiety, e.g. the proteinaceous molecule 3 and proteinaceous molecule 2 conjugated to an effector moiety. The skilled person will also appreciate that it is within the scope of the invention that for the proteinaceous molecule 1 and proteinaceous molecule 2 and proteinaceous molecule 3 any cell-surface molecule binding-molecule can be selected and is suitable for application in the saponin conjugates of the invention and for application in the pharmaceutical compositions and combinations of the invention, that is known today in the technological field of (specifically) targeting a mammalian (aberrant, tumor, auto-immune, etc.) cell with a binding molecule, e.g. for (targeted and specific) delivery of an effector molecule or effector moiety conjugated to the cell-surface molecule binding-molecule, wherein the cell-surface molecule binding-molecule is either a proteinaceous molecule or a non-proteinaceous molecule. That is to say, according to the invention, any of the cell-surface molecule binding-molecules proteinaceous molecule 1, proteinaceous molecule 2, proteinaceous molecule 3 can be replaced by a non-proteinaceous cell-surface molecule binding-molecule suitable for targeting (binding to) a selected and desired cell such as a mammalian cell, e.g. a tumor cell or an auto-immune cell. According to the invention, it is preferred that the cell-surface molecules to which combinations of the proteinaceous molecule 1, proteinaceous molecule 2, proteinaceous molecule 3 bind, are present at the surface of the same target cell, when combinations of proteinaceous molecule 1, proteinaceous molecule 2 and proteinaceous molecule 3 bind to different cell-surface molecules. For example, according to the invention, if in pharmaceutical combinations and compositions proteinaceous molecule 1 binds to HER2 and proteinaceous molecule 2 binds to CD71 or EGFR, HER2 and CD71 or HER2 and EGFR are typically present at the same cell.

An embodiment is the second pharmaceutical combination or the third pharmaceutical combination according to the invention, wherein the second binding site of the proteinaceous molecule 2 and the first binding site of the proteinaceous molecule 3 is/are or comprise(s) a single-domain antibody (sdAb), preferably $V_H$ domain derived from a heavy chain of an antibody, preferably of immunoglobulin G origin, preferably of human origin, a $V_L$ domain derived from a light chain of an antibody, preferably of immunoglobulin G origin, preferably of human origin, a $V_{HH}$ domain such as derived from a heavy-chain only antibody (HCAb) such as from Camelidae origin or Ig-NAR origin such as a variable heavy chain new antigen receptor (VNAR) domain, preferably the HCAb is from Camelidae origin, preferably the sdAb is a $V_{HH}$ domain derived from an HCAb from Camelidae origin (camelid $V_H$) such as derived from an HCAb from camel, lama, alpaca, dromedary, vicuna, guanaco and Bactrian camel.

An embodiment is the second pharmaceutical combination or the third pharmaceutical combination according to the invention, wherein the second epitope of the second cell-surface molecule to which the second binding site can bind is a tumor-cell specific second epitope of a second tumor-cell surface molecule, more preferably a tumor-cell specific second epitope of a second tumor-cell surface receptor specifically present on a tumor cell, and wherein the first epitope of the first cell-surface molecule is a tumor-cell specific first epitope of a first tumor-cell surface molecule, more preferably a tumor-cell specific first epitope of a first tumor-cell surface receptor specifically present on a tumor cell, wherein the second cell-surface molecule and the first cell-surface molecule are present on the same cell.

An embodiment is the second pharmaceutical combination or the third pharmaceutical combination according to the invention, wherein the second and third cell-surface molecule binding (targeting) molecule can bind to a tumor-cell surface molecule, preferably a tumor-cell receptor such as a tumor-cell specific receptor, more preferably a receptor selected from CD71, CD63, CA125, EpCAM(17-1A), CD52, CEA, CD44v6, FAP, EGF-IR, integrin, syndecan-1, vascular integrin alpha-V beta-3, HER2, EGFR, CD20, CD22, Folate receptor 1, CD146, CD56, CD19, CD138, CD27L receptor, PSMA, CanAg, integrin-alphaV, CA6, CD33, mesothelin, Cripto, CD3, CD30, CD239, CD70, CD123, CD352, DLL3, CD25, ephrinA4, MUC1, Trop2, CEACAM5, CEACAM6, HER3, CD74, PTK7, Notch3, FGF2, C4.4A, FLT3, CD38, FGFR3, CD7, PD-L1, CTLA4, CD52, PDGFRA, VEGFR1, VEGFR2, preferably selected from CD71, HER2 and EGFR, more preferably wherein the second and third cell-surface molecule binding molecule is or comprises a monoclonal antibody or at least one cell-surface molecule binding fragment or -domain thereof, and preferably comprises or consists of any one of cetuximab, daratumumab, gemtuzumab, trastuzumab, panitumumab, brentuximab, inotuzumab, moxetumomab, polatuzumab, obinutuzumab, OKT-9 anti-CD71 monoclonal antibody of the IgG type, pertuzumab, rituximab, ofatumumab, Herceptin, alemtuzumab, pinatuzumab, OKT-10 anti-CD38 monoclonal antibody, an antibody of Table A2, preferably cetuximab or trastuzumab or OKT-9, or at least one cell-surface molecule binding fragment or -domain thereof.

An aspect of the invention relates to a third pharmaceutical combination, comprising:

(a) the fourth pharmaceutical composition of the invention and (b) the sixth pharmaceutical composition of the invention, wherein the first cell-surface molecule is expressed on a tumor cell surface, and preferably the first cell-surface molecule is a tumor cell-specific surface molecule, and wherein preferably the first epitope is a first tumor-cell specific epitope.

Preferred are the second pharmaceutical combination or third pharmaceutical combination according to the invention, wherein the second binding site of the proteinaceous molecule 2 and/or the first binding site of the proteinaceous molecule 3 comprises or consists of an antibody or a binding derivative or binding fragment or binding domain thereof such as a F(ab')2 fragment, Fab' fragment, Fab fragment, scFv, dsFv, scFv-Fc, reduced IgG (rIgG), minibody, diabody, triabody, tetrabody, Fc fusion protein, nanobody, variable V domain, a single-domain antibody (sdAb), preferably a $V_{HH}$, for example camelid $V_H$, or a ligand for a cell-surface molecule such as a receptor such as EGF and a cytokine, preferably $V_H$ domain derived from a heavy chain of an antibody, preferably of immunoglobulin G origin, preferably of human origin, a $V_L$ domain derived from a light chain of an antibody, preferably of immunoglobulin G origin, preferably of human origin, a $V_{HH}$ domain such as derived from a heavy-chain only antibody (HCAb) such as from Camelidae origin or Ig-NAR origin such as a variable heavy chain new antigen receptor (VNAR) domain, preferably the HCAb is from Camelidae origin, preferably the sdAb is a $V_{HH}$ domain derived from an HCAb from Camelidae origin (camelid $V_H$) such as derived from an HCAb from camel, lama, alpaca, dromedary, vicuna, guanaco and Bactrian camel.

An aspect of the invention relates to a seventh pharmaceutical composition comprising:

(a) the saponin conjugate of the invention; and (b) the conjugate comprising proteinaceous molecule 2 and an effector moiety of the invention, or the conjugate comprising proteinaceous molecule 3 and an effector moiety of the invention, and optionally further comprising a pharmaceutically acceptable excipient and/or diluent. The effector moiety is not a saponin on which the saponin derivative or the saponin conjugate of the invention are based. The effector moiety is not the saponin derivative or the saponin conjugate of the invention.

An embodiment is the second pharmaceutical combination or third pharmaceutical combination of the invention, or the seventh pharmaceutical composition of the invention, wherein the effector moiety that is comprised by the conjugate comprising a cell-surface molecule binding-molecule, such as a third proteinaceous molecule (‘proteinaceous molecule 2’), and an effector moiety or that is comprised by the conjugate comprising a cell-surface molecule binding-molecule, such as a third proteinaceous molecule (‘proteinaceous molecule 3’), and an effector moiety, comprises or consists of any one or more of: an oligonucleotide, a nucleic acid and a xeno nucleic acid, preferably selected from any one or more of a vector, a gene, a cell suicide inducing transgene, deoxyribonucleic acid (DNA), ribonucleic acid (RNA), anti-sense oligonucleotide (ASO, AON), short interfering RNA (siRNA), microRNA (miRNA), DNA aptamer, RNA aptamer, mRNA, mini-circle DNA, peptide nucleic acid (PNA), phosphoramidate morpholino oligomer (PMO), locked nucleic acid (LNA), bridged nucleic acid (BNA), 2'-deoxy-2'-fluoroarabino nucleic acid (FANA), 2'-O-methoxyethyl-RNA (MOE), 2'-O,4'-aminoethylene bridged nucleic acid, 3'-fluoro hexitol nucleic acid (FHNA), a plasmid, glycol nucleic acid (GNA) and threose nucleic acid (TNA), or a derivative thereof, more preferably a BNA, for example a BNA for silencing HSP27 or apoB protein expression.

An embodiment is the second pharmaceutical combination or third pharmaceutical combination of the invention, or the seventh pharmaceutical composition of the invention, wherein the effector moiety that is comprised by the conjugate comprising a cell-surface molecule binding-molecule, such as a third proteinaceous molecule (‘proteinaceous molecule 2’), and an effector moiety or that is comprised by the conjugate comprising a cell-surface molecule binding-molecule, such as a third proteinaceous molecule (‘proteinaceous molecule 3’), and an effector moiety, comprises or consists of any one or more of: at least one proteinaceous molecule, preferably selected from any one or more of a peptide, a protein, protein toxin, an enzyme such as urease and Cre-recombinase, a ribosome-inactivating protein, and more preferably selected from any one or more of a viral toxin such as apoptin; a bacterial toxin such as Shiga toxin, Shiga-like toxin, *Pseudomonas aeruginosa* exotoxin (PE) or exotoxin A of PE, full-length or truncated diphtheria toxin (DT), cholera toxin; a fungal toxin such as alpha-sarcin; a plant toxin including ribosome-inactivating proteins and the A chain of type 2 ribosome-inactivating proteins such as dianthin e.g. dianthin-30 or dianthin-32, saporin e.g. saporin-S3 or saporin-S6, bouganin or de-immunized derivative debouganin of bouganin, shiga-like toxin A, pokeweed antiviral protein, ricin, ricin A chain, modeccin, modeccin A chain, abrin, abrin A chain, volkensin, volkensin A chain, viscumin, viscumin A chain; or an animal or human toxin such as frog RNase, or granzyme B or angiogenin from humans, or any fragment or derivative thereof; preferably the protein toxin is dianthin and/or saporin.

An embodiment is the second pharmaceutical combination or third pharmaceutical combination of the invention, or the seventh pharmaceutical composition of the invention, wherein the effector moiety that is comprised by the conjugate comprising a cell-surface molecule binding-molecule, such as a third proteinaceous molecule (‘proteinaceous molecule 2’), and an effector moiety or that is comprised by the conjugate comprising a cell-surface molecule binding-molecule, such as a third proteinaceous molecule (‘proteinaceous molecule 3’), and an effector moiety, comprises or consists of any one or more of: at least one payload, preferably selected from any one or more of a toxin targeting ribosomes, a toxin targeting elongation factors, a toxin targeting tubulin, a toxin targeting DNA and a toxin targeting RNA, more preferably any one or more of emtansine, pasudotox, maytansinoid derivative DM1, maytansinoid derivative DM4, monomethyl auristatin E (MMAE, vedotin), monomethyl auristatin F (MMAF, mafodotin), a Calicheamicin, N-Acetyl-γ-calicheamicin, a pyrrolobenzodiazepine (PBD) dimer, a benzodiazepine, a CC-1065 analogue, a duocarmycin, Doxorubicin, paclitaxel, docetaxel, cisplatin, cyclophosphamide, etoposide, docetaxel, 5-fluorouracyl (5-FU), mitoxantrone, a tubulysin, an indolinobenzodiazepine, AZ13599185, a cryptophycin, rhizoxin, methotrexate, an anthracycline, a camptothecin analogue, SN-38, DX-8951f, exatecan mesylate, truncated form of *Pseudomonas aeruginosa* exotoxin (PE38), a Duocarmycin derivative, an amanitin, α-amanitin, a spliceostatin, a thailanstatin, ozogamicin, tesirine, Amberstatin269 and soravtansine, or a derivative thereof.

An aspect of the invention relates to the second pharmaceutical combination or third pharmaceutical combination of the invention, or the seventh pharmaceutical composition of the invention, for use as a medicament.

An aspect of the invention relates to the second pharmaceutical combination or third pharmaceutical combination of the invention, or the seventh pharmaceutical composition of the invention, for use in the treatment or prevention of a cancer or of an autoimmune disease such as rheumatoid arthritis.

An aspect of the invention relates to a ninth pharmaceutical composition comprising the saponin conjugate of the invention and according to any one of the molecules (EE), (PP) and (SS), and optionally a pharmaceutically acceptable excipient and/or optionally a pharmaceutically acceptable diluent.

An aspect of the invention relates to the ninth pharmaceutical composition of the invention or to the oligonucleotide conjugate of the invention and according to any one of the molecules (EE), (PP) and (SS), for use as a medicament.

An aspect of the invention relates to the ninth pharmaceutical composition of the invention or to the oligonucleotide conjugate of the invention and according to any one of the molecules (EE), (PP) and (SS), for use in the treatment or prophylaxis of a disease or health problem in which an expression product is involved of any one or more of genes: HSP27, apoB, TTR, PCSK9, TMPRSS6, ALAS1, AT3, GO, CC5, X gene of HBV, S gene of HBV, AAT, miR-122, hepatitis B virus HbsAg, LDHA, CEBPA and LDH, and/or for use in the treatment or prophylaxis of a disease or health problem which involves any one or more of genes: HSP27, apoB, TTR, PCSK9, TMPRSS6, ALAS1, AT3, GO, CC5, X gene of HBV, S gene of HBV, AAT, miR-122, hepatitis B virus HbsAg, LDHA, CEBPA and LDH.

An aspect of the invention relates to the ninth pharmaceutical composition of the invention or to the oligonucleotide conjugate of the invention and according to any one of the molecules (EE), (PP) and (SS), for use in the treatment or prophylaxis of a disease or health problem in which an expression product is involved of any one or more of genes: HSP27, apoB, TTR, PCSK9, TMPRSS6, ALAS1, AAT, miR-122, hepatitis B virus HbsAg, LDHA and CEBPA, and/or for use in the treatment or prophylaxis of a disease or health problem which involves any one or more of genes: HSP27, apoB, TTR, PCSK9, TMPRSS6, ALAS1, AAT, miR-122, hepatitis B virus HbsAg, LDHA and CEBPA.

An embodiment is the ninth pharmaceutical composition of the invention or the oligonucleotide conjugate of the invention and according to any one of the molecules (EE), (PP) and (SS), for use as here above outlined, wherein said use is in the treatment or prophylaxis of a disease or health problem in which an expression product is involved of any one or more of genes: HSP27 and apoB, preferably apoB, and/or for use in the treatment or prophylaxis of a disease or health problem which involves any one or more of genes: HSP27 and apoB, preferably apoB.

An embodiment is the ninth pharmaceutical composition of the invention or the oligonucleotide conjugate of the invention and according to any one of the molecules (EE), (PP) and (SS), for use as here above outlined, for use in the treatment or prophylaxis of a cancer, an infectious disease, a viral infection, hypercholesterolemia, cardiovascular disease, primary hyperoxaluria, haemophilia A, haemophilia B, AAT related liver disease, acute hepatic porphyria, TTR-mediated amyloidosis, hereditary TTR amyloidosis (hATTR), complement-mediated disease, hepatitis B infection, hepatitis C infection, α1-antitrypsin deficiency, β-thalassaemia, or an auto-immune disease.

An embodiment is the ninth pharmaceutical composition of the invention or the oligonucleotide conjugate of the invention and according to any one of the molecules (EE), (PP) and (SS), for use as here above outlined, wherein said use is in the treatment or prophylaxis of a cancer such as endometrial carcinoma, breast cancer, lung cancer or hepatocellular carcinoma, and/or a cardiovascular disease such as hypercholesterolemia, preferably hypercholesterolemia.

An aspect of the invention relates to the ninth pharmaceutical composition of the invention or to the oligonucleotide conjugate of the invention and according to any one of the molecules (EE), (PP) and (SS), for use in the lowering of LDL-cholesterol in a subject.

TABLE A1

Saponins displaying (late) endosomal/lysosomal escape enhancing activity, and saponins comprising a structure reminiscent to such saponins displaying (late) endosomal/lysosomal escape enhancing activity

| Saponin Name | Aglycone core | Carbohydrate substituent at the C-3beta-OH group | Carbohydrate substituent at the C-28-OH group |
|---|---|---|---|
| NP-005236 | 2alpha-Hydroxyoleanolic acid | GlcA- | Glc/Gal- |
| AMA-1 | 16alpha-Hydroxyoleanolic acid | Glc- | Rha-(1→2)-[Xyl-(1→4)]-Rha- |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycone core | Carbohydrate substituent at the C-3beta-OH group | Carbohydrate substituent at the C-28-OH group |
|---|---|---|---|
| AMR | 16alpha-Hydroxyoleanolic acid | Glc- | Rha-(1→2)-[Ara-(1→3)-Xyl-(1→4)]-Rha- |
| alpha-Hederin | Hederagenin (23-Hydroxyoleanolic acid) | Rha-(1→2)-Ara- | — |
| NP-012672 | 16alpha,23-Dihydroxyoleanolic acid | Ara/Xyl-(1→4)-Rha/Fuc-(1→2)-Glc/Gal-(1→2)-Rha/Fuc-(1→2)-GlcA- | Ara/Xyl- |
| NP-017777 | Gypsogenin | Gal-(1→2)-[Xyl-(1→3)]-GlcA- | Xyl-(1→4)-Rha-(1→2)-[R-(→4)]-Fuc- (R = 4E-Methoxycinnamic acid) |
| NP-017778 | Gypsogenin | Gal-(1→2)-[Xyl-(1→3)]-GlcA- | Xyl-(1→4)-Rha-(1→2)-[R-(→4)]-Fuc- (R = 4Z-Methoxycinnamic acid) |
| NP-017774 | Gypsogenin | Gal-(1→2)-[Xyl-(1→3)]-GlcA- | Xyl-(1→4)-[Gal-(1→3)]-Rha-(1→2)-4-OAc-Fuc- |
| NP-018110[c], NP-017772[d] | Gypsogenin | Gal-(1→2)-[Xyl-(1→3)]-GlcA- | Xyl-(1→4)-[Glc-(1→3)]-Rha-(1→2)-3,4-di-OAc-Fuc- |
| NP-018109 | Gypsogenin | Gal-(1→2)-[Xyl-(1→3)]-GlcA- | Xyl-(1→4)-[Glc-(1→3)]-Rha-(1→2)-[R-(→4)]-3-OAc-Fuc- (R = 4E-Methoxycinnamic acid) |
| NP-017888 | Gypsogenin | Gal-(1→2)-[Xyl-(1→3)]-GlcA- | Glc-(1→3)-Xyl-(1→4)-[Glc-(1→3)]-Rha-(1→2)-4-OAc-Fuc- |
| NP-017889 | Gypsogenin | Gal-(1→2)-[Xyl-(1→3)]-GlcA- | Glc-(1→3)-Xyl-(1→4)-Rha-(1→2)-4-OAc-Fuc- |
| NP-018108 | Gypsogenin | Gal-(1→2)-[Xyl-(1→3)]-GlcA- | Ara/Xyl-(1→3)-Ara/Xyl-(1→4)-Rha/Fuc-(1→2)-[4-OAc-Rha/Fuc-(1→4)]-Rha/Fuc- |
| SA1641[a], AE X55[b] | Gypsogenin | Gal-(1→2)-[Xyl-(1→3)]-GlcA- | Xyl-(1→3)-Xyl-(1→4)-Rha-(1→2)-[Qui-(1→4)]-Fuc- |
| NP-017674 | Quillaic acid | Gal-(1→2)-[Xyl-(1→3)]-GlcA- | Api-(1→3)-Xyl-(1→4)-[Glc-(1→3)]-Rha-(1-2)-Fuc- |
| NP-017810 | Quillaic acid | Gal-(1→2)-[Xyl-(1→3)]-GlcA- | Xyl-(1→4)-[Gal-(1→3)]-Rha-(1→2)-Fuc- |
| AG1 | Quillaic acid | Gal-(1→2)-[Xyl-(1→3)]-GlcA- | Xyl-(1→4)-[Glc-(1→3)]-Rha-(1→2)-Fuc- |
| NP-003881 | Quillaic acid | Gal-(1→2)-[Xyl-(1→3)]-GlcA- | Ara/Xyl-(1→4)-Rha/Fuc-(1→4)-[Glc/Gal-(1→2)]-Fuc- |
| NP-017676 | Quillaic acid | Gal-(1→2)-[Xyl-(1→3)]-GlcA- | Api-(1→3)-Xyl-(1→4)-[Glc-(1→3)]-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| NP-017677 | Quillaic acid | Gal-(1→2)-[Xyl-(1→3)]-GlcA- | Api-(1→3)-Xyl-(1→4)-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| NP-017706 | Quillaic acid | Gal-(1→2)-[Xyl-(1→3)]-GlcA- | Api-(1→3)-Xyl-(1→4)-Rha-(1→2)-[Rha-(1→3)]-4-OAc-Fuc- |
| NP-017705 | Quillaic acid | Gal-(1→2)-[Xyl-(1→3)]-GlcA- | Api-(1→3)-Xyl-(1→4)-[Glc-(1→3)]-Rha-(1→2)-[Rha-(1→3)]-4-OAc-Fuc- |
| NP-017773 | Quillaic acid | Gal-(1→2)-[Xyl-(1→3)]-GlcA- | 6-OAc-Glc-(1→3)-Xyl-(1→4)-Rha-(1→2)-[3-OAc-Rha-(1→3)]-Fuc- |
| NP-017775 | Quillaic acid | Gal-(1→2)-[Xyl-(1→3)]-GICA- | Glc-(1→3)-Xyl-(1→4)-Rha-(1→2)-[3-OAc --Rha-(1→3)]-Fuc- |
| SA1657 | Quillaic acid | Gal-(1→2)-[Xyl-(1→3)]-GlcA- | Xyl-(1→3)-Xyl-(1→4)-Rha-(1→2)-[Qui-(1→4)]-Fuc- |
| AG2 | Quillaic acid | Gal-(1→2)-[Xyl-(1→3)]-GlcA- | Glc-(1→3)-[Xyl-(1→4)]-Rha-(1→2)-[Qui-(1→4)]-Fuc- |
| SO1861 | Quillaic acid | Gal-(1→2)-[Xyl-(1→3)]-GlcA- | Glc-(1→3)-Xyl-(1→4)-Rha-(1→2)-[Xyl-(1→3)-4-OAc-Qui-(1→4)]-Fuc- |
| GE1741 | Quillaic acid | Gal-(1→2)-[Xyl-(1→3)]-GlcA- | Xyl-(1→3)-Xyl-(1→4)-Rha-(1→2)-[3,4-di-OAc-Qui-(1→4)]-Fuc- |
| SO1542 | Quillaic acid | Gal-(1→2)-[Xyl-(1→3)]-GlcA- | Glc-(1→3)-[Xyl-(1→4)]-Rha-(1→2)-Fuc- |
| SO1584 | Quillaic acid | Gal-(1→2)-[Xyl-(1→3)]-GlcA- | 6-OAc-Glc-(1→3)-[Xyl-(1→4)]-Rha-(1→2)-Fuc- |
| SO1658 | Gypsogenin | Gal-(1→2)-[Xyl-(1→3)]-GlcA- | Glc-(1→3)-[Xyl-(1→3)-Xyl-(1→4)]-Rha-(1→2)-Fuc- |
| SO1674 | Quillaic acid | Gal-(1→2)-[Xyl-(1→3)]-GlcA- | Glc-(1→3)-[Xyl-(1→3)-Xyl-(1→4)]-Rha-(1→2)-Fuc- |
| SO1832 | Quillaic acid | Gal-(1→2)-[Xyl-(1→3)]-GlcA- | Xyl-(1→3)-Xyl-(1→4)-Rha-(1→2)-[Xyl-(1→3)-4-OAc-Qui-(1→4)]-Fuc- |

TABLE A1-continued

Saponins displaying (late) endosomal/lysosomal escape enhancing activity, and saponins comprising a structure reminiscent to such saponins displaying (late) endosomal/lysosomal escape enhancing activity

| Saponin Name | Aglycone core | Carbohydrate substituent at the C-3beta-OH group | Carbohydrate substituent at the C-28-OH group |
|---|---|---|---|
| QS-7 (also referred to as QS1861) | Quillaic acid | Gal-(1→2)-[Xyl-(1→3)]-GlcA- | Api/Xyl-(1→3)-Xyl-(1→4)-[Glc-(1→3)]-Rha-(1→2)-[Rha-(1→3)]-40Ac-Fuc- |
| QS-7 api (also referred to as QS1862) | Quillaic acid | Gal-(1→2)-[Xyl-(1→3)]-GlcA- | Api-(1→3)-Xyl-(1→4)-[Glc-(1→3)]-Rha-(1→2)-[Rha-(1→3)]-40Ac-Fuc- |
| QS-17 | Quillaic acid | Gal-(1→2)-[Xyl-(1→3)]-GlcA- | Api/Xyl-(1→3)-Xyl-(1→4)-[Glc-(1→3)]-Rha-(1→2)-[R-(→4)]-Fuc- (R = 5-O-[5-O-Rha-(1→2)-Ara/Api-3,5-dihydroxy-6-methyl-octanoyl]-3,5-dihydroxy-6-methyl-octanoic acid) |
| QS-18 | Quillaic acid | Gal-(1→2)-[Xyl-(1→3)]-GlcA- | Api/Xyl-(1→3)-Xyl-(1→4)-[Glc-(1→3)]-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| QS-21 A-apio | Quillaic acid | Gal-(1→2)-[Xyl-(1→3)]-GlcA- | Api-(1→3)-Xyl-(1→4)-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| QS-21 A-xylo | Quillaic acid | Gal-(1→2)-[Xyl-(1→3)]-GlcA- | Xyl-(1→3)-Xyl-(1→4)-Rha-(1→2)-[R-(→4)]-Fuc- (R = 5-O-[5-O-Ara/Api-3,5-dihydroxy-6-methyl-octanoyl]-3,5-dihydroxy-6-methyl-octanoic acid) |
| QS-21 B-apio | Quillaic acid | Gal-(1→2)-[Xyl-(1→3)]-GlcA- | Api-(1→3)-Xyl-(1→4)-Rha-(1→2)-[R-(→3)]-Fuc- (R = 5-O-[5-O-Ara/Api-3,5-dihydroxy-6-methyl-octanoyl]-3,5-dihydroxy-6-methyl-octanoic acid) |
| QS-21 B-xylo | Quillaic acid | Gal-(1→2)-[Xyl-(1→3)]-GlcA- | Xyl-(1→3)-Xyl-(1→4)-Rha-(1→2)-[R-(→3)]-Fuc- (R = 5-O-[5-O-Ara/Api-3,5-dihydroxy-6-methyl-octanoyl]-3,5-dihydroxy-6-methyl-octanoic acid) |
| beta-Aescin (described: Aescin la) | Protoaescigenin-21(2-methylbut-2-enoate)-22-acetat | Glc-(1→2)-[Glc-(1→4)]-GlcA- | — |
| Teaseed saponin I | 23-Oxo-barringtogenol C - 21,22-bis(2-methylbut-2-enoate) | Glc-(1→2)-Ara-(1→3)-[Gal-(1→2)]-GlcA- | — |
| Teaseedsaponin J | 23-Oxo-barringtogenol C - 21,22-bis(2-methylbut-2-enoate) | Xyl-(1→2)-Ara-(1→3)-[Gal-(1→2)]-GlcA- | — |
| Assamsaponin F | 23-Oxo-barringtogenol C - 21(2-methylbut-2-enoate)-16,22-diacetat | Glc-(1→2)-Ara-(1→3)-[Gal-(1→2)]-GlcA- | — |
| Digitonin | Digitogenin | Glc-(1→3)-Gal-(1→2)-[Xyl-(1→3)]-Glc-(1→4)-Gal- | — |
| Primula acid 1 | 3,16,28-Trihydroxyoleanan-12-en | Rha-(1→2)-Gal-(1→3)-[Glc-(1→2)]-GlcA- | — |
| AS64R | Gypsogenic acid | — | Glc-(1→3)-[Glc-(1→6)]-Gal- |

55

| | | Carbohydrate substituent at the C-23-OH group | |
|---|---|---|---|
| AS6.2 | Gypsogenic acid | Gal- | Glc-(1→3)-[Glc-(1→6)]-Gal- |

a, b: Different names refer to different isolates of the same structure c, d: Different names refer to different isolates of the same structure

TABLE A2

Tumor-specific cell-surface receptor targets which can be targeted by a cell-surface molecule targeting (binding) molecule such as immunoglobulins, and antibodies that can be used for the saponin conjugates of the invention (not presented as a limitation; further immunoglobulins are equally suitable for the invention)

| Target cell-surface receptor | Example monoclonal antibodies |
|---|---|
| HER2 | anti-HER2 monoclonal antibody such as trastuzumab and pertuzumab |
| CD20 | anti-CD20 monoclonal antibody such as rituximab, ofatumumab, tositumomab and ibritumomab |
| CA125 | anti-CA125 monoclonal antibody such as oregovomab |
| EpCAM (17-1A) | anti-EpCAM (17-1A) monoclonal antibody such as edrecolomab |
| EGFR | anti-EGFR monoclonal antibody such as cetuximab, panitumumab and nimotuzumab |
| CD30 | anti-CD30 monoclonal antibody such brentuximab |
| CD33 | anti-CD33 monoclonal antibody such as gemtuzumab and huMy9-6 |
| vascular integrin alpha-v beta-3 | anti-vascular integrin alpha-v beta-3 monoclonal antibody such as etaracizumab |
| CD52 | anti-CD52 monoclonal antibody such as alemtuzumab |
| CD22 | anti-CD22 monoclonal antibody such as epratuzumab |
| CEA | anti-CEA monoclonal antibody such as labetuzumab |
| CD44v6 | anti-CD44v6 monoclonal antibody such as bivatuzumab |
| FAP | anti-FAP monoclonal antibody such as sibrotuzumab |
| CD19 | anti-CD19 monoclonal antibody such as huB4 |
| CanAg | anti-CanAg monoclonal antibody such as huC242 |
| CD56 | anti-CD56 monoclonal antibody such huN901 |
| CD38 | anti-CD38 monoclonal antibody such as daratumumab |
| CA6 | anti-CA6 monoclonal antibody such as DS6 |
| IGF-IR | anti-IGF-IR monoclonal antibody such as cixutumumab and 3B7 |
| integrin | anti-integrin monoclonal antibody such as CNTO 95 |
| syndecan-1 | anti-syndecan-1 monoclonal antibody such as B-B4 |

The invention is further illustrated by the following examples, which should not be interpreted as limiting the present invention in any way.

EXAMPLES

Example 1

Materials and Methods

Abbreviations

BOP (Benzotriazol-1-yloxy)tris(dimethylamino)phosphonium hexafluorophosphate
DIPEA N,N-diisopropylethylamine
DMF N,N-dimethylformamide
EDCI·HCl 3-((Ethylimino)methyleneamino)-N,N-dimethylpropan-1-aminium chloride
EMCH·TFA N-(ε-maleimidocaproic acid) hydrazide, trifluoroacetic acid salt
mab monoclonal antibody
SC semicarbazone
min minutes
NMM 4-methylmorpholine
r.t. retention time
TCEP tris(2-carboxyethyl)phosphine hydrochloride
Temp temperature
TFA trifluoroacetic acid Analytical Methods LC-MS Method 1,[1]

Apparatus: Waters IClass; Bin. Pump: UPIBSM, SM: UPISMFTN with SO; UPCMA, PDA: UPPDATC, 210-320 nm, SQD: ACQ-SQD2 ESI, pos/neg 100-800; ELSD: gas pressure 40 psi, drift tube temp: 50° C.; column: Acquity C18, 50×2.1 mm, 1.7 μm Temp: 60° C., Flow: 0.6 mL/min, Gradient: $t_0$=5% B, $t_{2.0\ min}$=98% B, $t_{2.7\ min}$=98% B, Post time: 0.3 min, Eluent A: 0.1% formic acid in water, Eluent B: 0.1% formic acid in acetonitrile.

LC-MS Method 1,[2]

Apparatus: Waters IClass; Bin. Pump: UPIBSM, SM: UPISMFTN with SO; UPCMA, PDA: UPPDATC, 210-320 nm, SQD: ACQ-SQD2 ESI, neg 2000-3000; ELSD: gas pressure 40 psi, drift tube temp: 50° C.; column: Acquity C18, 50×2.1 mm, 1.7 μm Temp: 60° C., Flow: 0.6 mL/min, Gradient: $t_0$=5% B, $t_{5.0\ min}$=98% B, $t_{6.0\ min}$=98% B, Post time: 1.0 min, Eluent A: 0.1% formic acid in water, Eluent B: 0.1% formic acid in acetonitrile.

LC-MS Method 1,[3]

Apparatus: Waters IClass; Bin. Pump: UPIBSM, SM: UPISMFTN with SO; UPCMA, PDA: UPPDATC, 210-320 nm, SQD: ACQ-SQD2 ESI, neg/pos 1500-2400; ELSD: gas pressure 40 psi, drift tube temp: 50° C.; column: Acquity C18, 50×2.1 mm, 1.7 μm Temp: 60° C., Flow: 0.6 mL/min, lin. Gradient depending on the polarity of the product: $t_0$=2% B, $t_{5.0\ min}$=98% B, $t_{6.0\ min}$=98% B, Post time: 1.0 min, Eluent A: 10 mM ammonium bicarbonate in water (pH=9.5), Eluent B: acetonitrile.

LC-MS Method 1,[4]

Apparatus: Waters IClass; Bin. Pump: UPIBSM, SM: UPISMFTN with SO; UPCMA, PDA: UPPDATC, 210-320 nm, SQD: ACQ-SQD2 ESI, neg/pos 1500-2400; ELSD: gas pressure 40 psi, drift tube temp: 50° C.; column: Acquity C18, 50×2.1 mm, 1.7 μm Temp: 60° C., Flow: 0.6 mL/min, lin. Gradient depending on the polarity of the product: $t_0$=2% B, $t_{5.0\ min}$=50% B, $t_{6.0\ min}$=98% B, Post time: 1.0 min, Eluent A: 10 mM ammonium bicarbonate in water (pH=9.5), Eluent B: acetonitrile.

Preparative Methods

Preparative MP-LC Method 1,[1]

Instrument type: Reveleris™ prep MPLC; Column: Phenomenex LUNA C18(3) (150×25 mm, 10 μm); Flow: 40 mL/min; Column temp: room temperature; Eluent A: 0.1% (v/v) Formic acid in water, Eluent B: 0.1% (v/v) Formic acid in acetonitrile; Gradient: $t_{0\ min}$=5% B, $t_{1\ min}$=5% B, $t_{2\ min}$=20% B, $t_{17\ min}$=60% B, $t_{18\ min}$=100% B, $t_{23\ min}$=100% B; Detection UV: 210, 235, 254 nm and ELSD.

Preparative MP-LC Method 2,[2]

Instrument type: Reveleris™ prep MPLC; column: Waters XSelect™ CSH C18 (145×25 mm, 10 μm); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient: $t_{0\ min}$=5% B, $t_{1\ min}$=5% B, $t_{2\ min}$=10% B, $t_{17\ min}$=50% B, $t_{18\ min}$=100% B, $t_{23\ min}$=100% B; Detection UV: 210, 235, 254 nm and ELSD.

Flash Chromatography

Grace Reveleris X2® C-815 Flash; Solvent delivery system: 3-piston pump with auto-priming, 4 independent channels with up to 4 solvents in a single run, auto-switches lines when solvent depletes; maximum pump flow rate 250 mL/min; maximum pressure 50 bar (725 psi); Detection: UV 200-400 nm, combination of up to 4 UV signals and scan of entire UV range, ELSD; Column sizes: 4-330 g on instrument, luer type, 750 g up to 3000 g with optional holder.

Materials

Trastuzumab (Herceptin®, Roche), cetuximab (Erbitux®, Merck KGaA) were purchased from the pharmacy (Charite, Berlin). CD71 monoclonal antibody was purchased from BioCell (Okt9, #BE0023). SO1861 was isolated and purified by Analyticon Discovery GmbH from raw plant extract obtained from *Saponaria officinalis* L. EGFdianthin was produced from *E. coli* according to standard procedures. HSP27BNA oligo and ApoB and ApoB #02 were produced by Bio-Synthesis Inc, (Lewisville). Tris(2-carboxyethyl) phosphine hydrochloride (TCEP, 98%, Sigma-Aldrich), 5,5-Dithiobis(2-nitrobenzoic acid) (DTNB, Ellman's reagent, 99%, Sigma-Aldrich), Zeba™ Spin Desalting Columns (2 mL, Thermo-Fisher), NuPAGE™ 4-12% Bis-Tris Protein Gels (Thermo-Fisher), NuPAGE™ MES SDS Running Buffer (Thermo-Fisher), Novex™ Sharp Pre-stained Protein Standard (Thermo-Fisher), PageBlue™ Protein Staining Solution (Thermo-Fischer), Pierce™ BCA Protein Assay Kit (Thermo-Fisher), N-Ethylmaleimide (NEM, 98%, Sigma-Aldrich), 1,4-Dithiothreitol (DTT, 98%, Sigma-Aldrich), Sephadex G25 (GE Healthcare), Sephadex G50 M (GE Healthcare), Superdex 200P (GE Healthcare), Isopropyl alcohol (IPA, 99.6%, VWR), Tris(hydroxymethyl)aminomethane (Tris, 99%, Sigma-Aldrich), Tris(hydroxymethyl)aminomethane hydrochloride (Tris·HCL, Sigma-Aldrich), L-Histidine (99%, Sigma-Aldrich), D-(+)-Trehalose dehydrate (99%, Sigma-Aldrich), Polyethylene glycol sorbitan monolaurate (TWEEN 20, Sigma-Aldrich), Dulbecco's Phosphate-Buffered Saline (DPBS, Thermo-Fisher), Guanidine hydrochloride (99%, Sigma-Aldrich), Ethylenediaminetetraacetic acid disodium salt dihydrate (EDTA-Naz, 99%, Sigma-Aldrich), sterile filters 0.2 μm and 0.45 μm (Sartorius), Succinimidyl 4-(N-maleimidomethyl)cyclohexane-1-carboxylate (SMCC, Thermo-Fisher), Vivaspin T4 and T15 concentrator (Sartorius), Superdex 200PG (GE Healthcare), Tetra(ethylene glycol) succinimidyl 3-(2-pyridyldithio)propionate ($PEG_4$-SPDP, Thermo-Fisher), [O-(7-Azabenzotriazol-1-yl)-N,N,N,N-tetramethyluronium-hexafluorphosphat] (HATU, 97%, Sigma-Aldrich), Dimethyl sulfoxide (DMSO, 99%, Sigma-Aldrich), N-(2-Aminoethyl)maleimide trifluoroacetate salt (AEM, 98%, Sigma-Aldrich), L-Cysteine (98.5%, Sigma-Aldrich), deionized water (DI) was freshly taken from Ultrapure Lab Water Systems (MilliQ, Merck), Nickel-nitrilotriacetic acid agarose (Ni-NTA agarose, Protino), Glycine (99.5%, VWR), 5,5-Dithiobis(2-nitrobenzoic acid (Ellman's reagent, DTNB, 98%, Sigma-Aldrich), S-Acetylmercaptosuccinic anhydride Fluorescein (SAMSA reagent, Invitrogen) Sodium bicarbonate (99.7%, Sigma-Aldrich), Sodium carbonate (99.9%, Sigma-Aldrich), PD MiniTrap desalting columns with Sephadex G-25 resin (GE Healthcare), PD10 G25 desalting column (GE Healthcare), Zeba Spin Desalting Columns in 0.5, 2, 5, and 10 mL (Thermo-Fisher), Vivaspin Centrifugal Filters T4 10 kDa MWCO, T4 100 kDa MWCO, and T15 (Sartorius), Biosep s3000 aSEC column (Phenomenex), Vivacell Ultrafiltration Units 10 and 30 kDa MWCO (Sartorius), Nalgene Rapid-Flow filter (Thermo-Fisher), SO1861-EMCH Synthesis To SO1861 (121 mg, 0.065 mmol) and EMCH·TFA (110 mg, 0.325 mmol) was added methanol (extra dry, 3.00 mL) and TFA (0.020 mL, 0.260 mmol). The reaction mixture stirred at room temperature. After 1.5 hours the reaction mixture was subjected to preparative MP-LC.[1] Fractions corresponding to the product were immediately pooled together, frozen and lyophilized overnight to give the title compound (120 mg, 90%) as a white fluffy solid. Purity based on LC-MS 96%.

LRMS (m/z): 2069 $[M-1]^{1-}$

LC-MS r.t. (min): 1.084

SO1861-SC-Mal

Intermediate 1 benzyl 4-(2-(tert-butoxycarbonyl)hydrazine-1-carbonyl)piperazine-1-carboxylate

To a stirring solution of phosgene in toluene (20%, w/w, 15.8 mL, 30.0 mmol) at 0° C. was added slowly (10 min) a solution of 1-Cbz-piperazine (1.93 mL, 10.0 mmol) in dichloromethane (25 mL) and DIPEA (3.83 mL, 22.0 mmol). The reaction mixture was stirred at room temperature. After 30 min the reaction mixture was evaporated in vacuo and co-evaporated with dichloromethane (2×50 mL). Next, the residue was dissolved in dichloromethane (100 mL) and resulting solution was stirred at 0° C. A solution of Boc hydrazine (2.33 mL, 15.0 mmol) in dichloromethane (20 mL) and DiPEA (3.83 mL, 22.0 mL) was added and the reaction mixture was stirred overnight at room temperature. The reaction mixture was diluted with dichloromethane (100 mL) and the resulting solution was washed with 0.5 N potassium bisulphate solution (2×100 mL) and brine (100 mL), dried over $Na_2SO_4$, filtered and evaporated in vacuo. The residue was purified by flash chromatography (first by an ethyl acetate-heptane gradient, 5:95 (v/v) rising to 100% ethyl acetate followed by a flush with 10% methanol in DCM (v/v)) to give the title compound (2.42 g, 64%) as a white solid. Purity based on LC-MS 100%.

LRMS (m/z): 279/323/401 $[M-99/M-55/M+23]^{1+}$

LC-MS r.t. (min): 1.271

Intermediate 2 tert-butyl 2-(piperazine-1-carbonyl)hydrazine-1-carboxylate

To benzyl 4-(2-(tert-butoxycarbonyl)hydrazine-1-carbonyl)piperazine-1-carboxylate (2.42 g, 6.39 mmol) was added methanol (50 mL). The mixture was heated to obtain a clear solution. Next, palladium (10% on activated carbon, 50% wet with water, 1.50 g) was added and the resulting mixture was stirred under a hydrogen atmosphere by using a balloon.

After 1 hour the reaction mixture was filtered over celite and the filtrate evaporated in vacuo to give the title product (1.56 g, quant.) as a white solid.

LRMS (m/z): 189/245 $[M-55/M+1]^{1+}$

Intermediate 3 tert-butyl 2-(4-(6-(2,5-dioxo-2,5-dihydro-1H-pyrrol-1-yl)hexanoyl)piperazine-1-carbonyl)hydrazine-1-carboxylate 6-maleimidocaproic acid (810 mg, 3.84 mmol), tert-butyl 2-(piperazine-1-carbonyl)hydrazine-1-carboxylate (781 mg, 3.20 mmol), EDCI·HCl (735 mg, 3.84 mmol) and Oxyma Pure (591 mg, 4.16 mmol) were dissolved in a mixture of dichloromethane (25 mL) and DIPEA (835 μL, 4.80 mmol) and the reaction mixture was stirred at room temperature. After 2 hours the reaction mixture was evaporated in vacuo and the residue was dissolved in ethyl acetate (50 mL). The resulting solution was washed with 0.5 N potassium bisulphate solution (50 mL), saturated sodium bicarbonate solution (2×50 mL) and brine (50 mL), dried over $Na_2SO_4$, filtered and evaporated in vacuo. The residue was purified by flash chromatography (DCM—10% methanol in DCM (v/v) gradient 100:0 rising to 40:60) to give the title compound (634 mg, 45%) as a white solid. Purity based on LC-MS 97%.

LRMS (m/z): 338/382/460 $[M-99/M-55/M+23]^{1+}$

LC-MS r.t. (min): 1.02[1]

SO1861-SC (Formula (V), Molecule V, see FIG. 1)

Chemical Formula: SO1861-SC: $C_{88}H_{139}N_3O_{47}$, Exact Mass: 1989.86

Morpholine-4-carbohydrazide (3.89 mg, 26.8 μmol) and SO1861 (5.00 mg, 2.68 μmol) were dissolved in methanol (extra dry, 250 μL). Next, TFA (1.03 μL) was added and the resulting mixture was shaken for 1 min and left standing at room temperature. After 1 hour the reaction mixture was subjected to preparative MP-LC.[2] Fractions corresponding to the product were immediately pooled together, frozen and lyophilized overnight to yield the title compound (3.29 mg, 62%) as a white fluffy solid. Purity based on LC-MS 95%.

LRMS (m/z): 1991 $[M-1]^{1-}$

LC-MS r.t. (min): 1.99[3]

Figure 2:
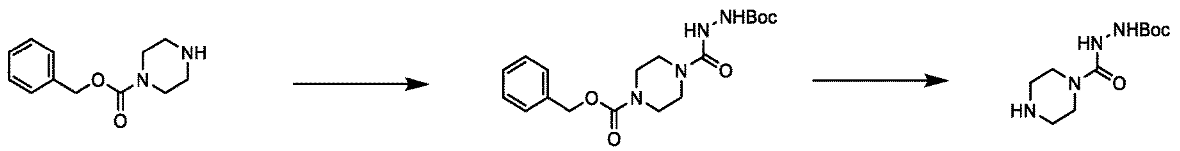
FIG. 2: Synthesis and chemical structure of SO1861-semicarbazone-Mal ('ready for conjugation') (Molecule VII)
Figure 2:
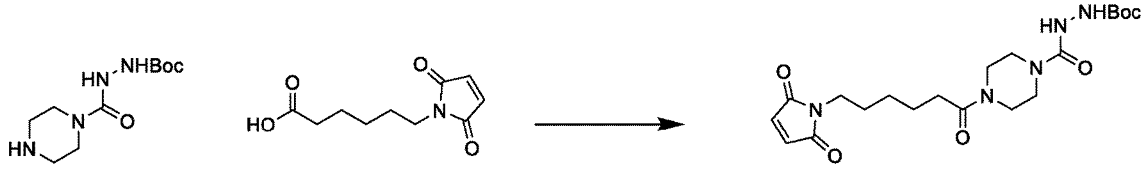
Figure 2:
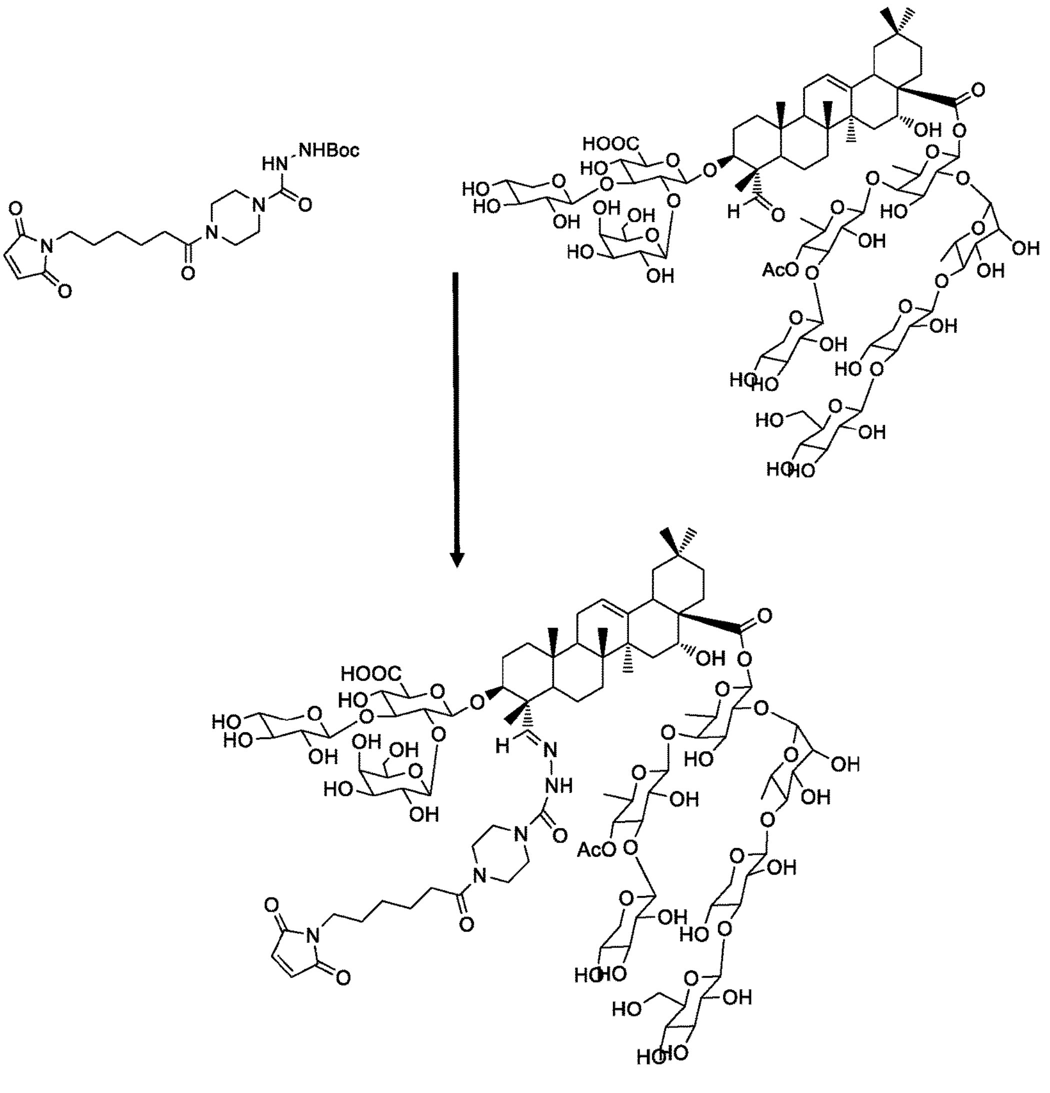

S01861-SC-Mal (Formula (VII), Molecule VII, See FIG. 2)

Chemical Formula: SO1861-SC-Mal: $C_{98}H_{151}N_5O_{49}$, Exact Mass: 2181.95 tert-butyl 2-(4-(6-(2,5-dioxo-2,5-dihydro-1H-pyrrol-1-yl)hexanoyl)piperazine-1-carbonyl)hydrazine-1-carboxylate (intermediate 3, 25.0 mg, 57.1 μmol) was dissolved in a mixture of dichloromethane (500 μL) and TFA (500 μL) and the reaction mixture was stirred at room temperature. After 30 min the reaction mixture was evaporated in vacuo and co-evaporated with dichloromethane (3×5 mL) and methanol (5 mL). The residue and SO1861 (21.3 mg, 11.4 μmol) were dissolved in methanol (extra dry, 1.00 mL) and the resulting mixture was shaken for 1 min and left standing at room temperature. After 4 hours the reaction mixture was subjected to preparative MP-LC.[2] Fractions corresponding to the product were immediately pooled together, frozen and lyophilized overnight to yield the title compound (13.7 mg, 55%) as a white fluffy solid. Purity based on LC-MS 97%.

LRMS (m/z): 2181 $[M-1]^{1-}$

LC-MS r.t. (min): 2.133

Figure 3:
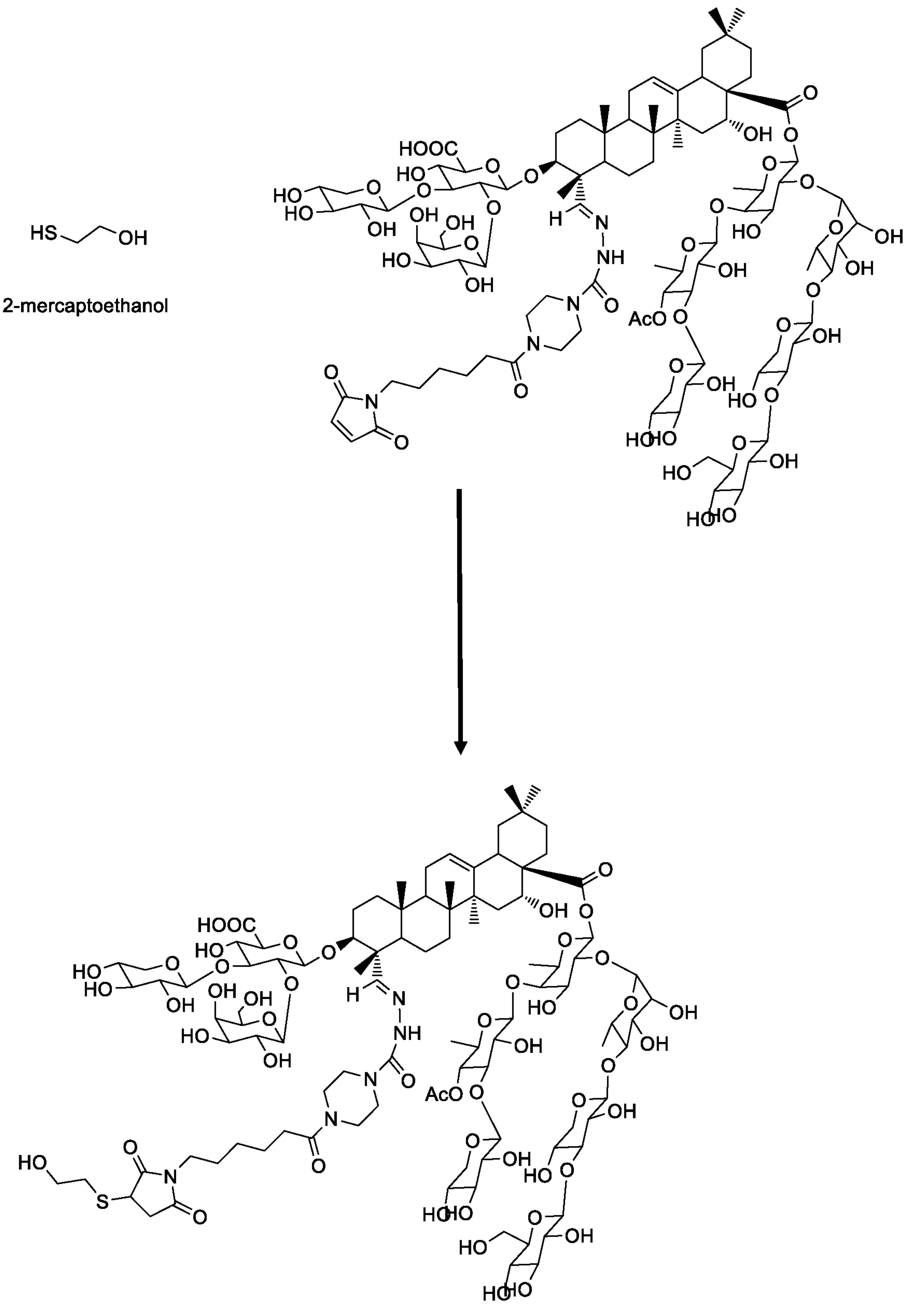
FIG. 3: Synthesis and chemical structure of SO1861-semicarbazone-Mal (Blocked) (Molecule VIII)

SO1861-SC-Mal (blocked) (Formula (VIII), Molecule VIII see FIG. 3)

SO1861-SC-Mal (3.63 mg, 1.66 μmol) was dissolved in a solution of 20 mM ammonium bicarbonate/acetonitrile (3:1, v/v, 500 μL). Directly afterwards 2-mercaptoethanol (0.466 μL, 6.65 μmol) was added. The reaction mixture was shaken for 1 min and left standing at room temperature. After 30 min the reaction mixture was subjected to preparative MP-LC.[2] Fractions corresponding to the product were immediately pooled together, frozen and lyophilized overnight to yield the title compound (2.35 mg, 63%) as a white fluffy solid. Purity based on LC-MS 96%.

LRMS (m/z): 2260 $[M-1]^{1-}$

LC-MS r.t. (min): 3.53[4]

Release Kinetics Assay

The S01861 conjugate of interest was dissolved in an acetate buffer (20 mM, pH 4.0 or pH 5.0), a phosphate buffer (20 mM) or in a PBS buffer (pH 7.4) with a final concentration of 10 μM at 20° C. or at 37° C. The release of SO1861 was followed over time by monitoring the decrease of the UPLC-UV[4] peak area of the SO1861 conjugate of interest at different time points.

Cell Viability Assay

Cell viability was determined by an MTS-assay, performed according to the manufacturer's instruction (CellTiter 96® AQueous One Solution Cell Proliferation Assay, Promega). Briefly, the MTS solution was diluted 20× in DMEM without phenol red (PAN-Biotech GmbH) supplemented with 10% FBS (PAN-Biotech GmbH). The cells were washed once with 200 μL PBS per well, after which 100 μL diluted MTS solution was added per well. The plate was incubated for approximately 20-30 minutes at 37° C. Subsequently, the optical density at 492 nm was measured on a Thermo Scientific Multiskan FC plate reader (Thermo Scientific). For quantification the background signal of 'medium only' wells was subtracted from all other wells, before the ratio of untreated/treated cells was calculated, by dividing the background corrected signal of untreated wells over the background corrected signal of the treated wells.

FACS Analysis

Cells were seeded in DMEM (PAN-Biotech GmbH) supplemented with 10% fetal calf serum (PAN-Biotech GmbH) and 1% penicillin/streptomycin (PAN-Biotech GmbH), at 500,000 c/plate in 10 cm dishes and incubated for 48 hrs (5% $CO_2$, 37° C.), until a confluency of 90% was reached. Next, the cells were trypsinized (TrypIE Express, Gibco Thermo Scientific) to single cells. $0.75\times10^6$ Cells were transferred to a 15 mL Falcon tube and centrifuged (1,400 rpm, 3 min). The supernatant was discarded while leaving the cell pellet submerged. The pellet was dissociated by gentle tapping the Falcon tube on a vortex shaker and the cells were washed with 4 mL cold PBS ($Mg^{2+}$ and $Ca^{2+}$ free, 2% FBS). After washing the cells were resuspended in 3 mL cold PBS ($Mg^{2+}$ and $Ca^{2+}$ free, 2% FBS) and divided equally over 3 round bottom FACS tubes (1 mL/tube). The cells were centrifuged again and resuspended in 200 μL cold PBS ($Mg^{2+}$ and $Ca^{2+}$ free, 2% FBS) or 200 μL antibody solution; containing 5 μL antibody in 195 μL cold PBS ($Mg^{2+}$ and $Ca^{2+}$ free, 2% FBS). APC Mouse IgG1, κ APC anti-human EGFR (#352906, Biolegend) was used to stain the EGFR receptor. PE anti-human HER2 APC anti-human CD340 (erbB2/HER-2) (#324408 Biolegend) was used to stain the HER2 receptor, PE Mouse IgG2a, κ Isotype Ctrl FC (#400212, Biolegend) was used as its matched isotype control. PE anti-human CD71 (#334106, Biolegend) was used to stain the CD71 receptor, PE Mouse IgG2a, κ Isotype Ctrl FC (#400212, Biolegend) was used as its matched isotype control. Samples were incubated for 30 min at 4° C. on a tube roller mixer. Afterwards, the cells were washed 3× with cold PBS ($Mg^{2+}$ and $Ca^{2+}$ free, 2% FBS) and fixated for 20 min at room temperature using a 2% PFA solution in PBS. Cells were washed 2× with cold PBS, and resuspended in 250-350 μL cold PBS for FACS analysis. Samples were analyzed with a BD FACSCanto II flow cytometry system (BD Biosciences) and FlowJo software.

TABLE 1

Expression levels of EGFR, HER2 and CD71 of various cells

| Cell line | EGFR expression level (MFI) | HER2 expression level (MFI) | CD71 expression level (MFI) |
|---|---|---|---|
| MDA-MB-468 | 1656 | 1 | 186 |
| A431 | 1593 | 10 | 322 |
| CaSki | 481 | 12 | 189 |
| SK-BR-3 | 28 | 1162 | 331 |
| JIMT-1 | 58 | 74 | 107 |
| HeLa | 91 | 7 | 312 |
| A2058 | 1 | 5 | 59 |

CMC Determination

The critical micellar concentration (CMC) of saponins derived from *Saponaria Officinalis* (SO) was determined by the method of DeVendittis et al. (www.sciencedirect.com/science/article/pii/0003269781900063, doi.org/10.1016/0003-2697(81)90006-3, Analytical Biochemistry, Volume 115, Issue 2, August 1981, Pages 278-286) as follows: The emission spectrum of 8-Anilinonaphthalene-1-sulfonic acid (ANS) in either purified water (MQ) or PBS (Dulbecco's PBS+/+) was determined at dry weight concentrations of saponins ranging from 1 to 1400 μM to cover the range below and above the CMC. Above the CMC, the fluorescence yield of ANS increases and the wavelength of maximum emission decreases due to portioning of the fluorescent dye into micelles. Fluorescence yields were recorded on a Fluoroskan Ascent FL (Thermo Scientific) at an excitation wavelength of 355 nm, and an emission wavelength of 460 nm. 6 μg at a concentration of 75.86 μM of ANS were used per sample and measurement.

Haemolysis Assay

Red blood cells (RBCs) were isolated from a buffy coat using a Ficoll gradient. The obtained RBC pellet (~4-5 ml) was washed 2× with 50 ml DPBS (without $Ca^{2+}/Mg^{2+}$, PAN-Biotech GmbH). Cells were pelleted by centrifugation for 10 min, 800×g at RT. RBC were counted and resuspended at 500.000.000 c/ml in DPBS (without $Ca^{2+}/Mg^{2+}$), based on total cell count. SO1861-linker dilutions were prepared in DPBS (with $Ca^{2+}/Mg^{2+}$, PAN-Biotech GmbH), at 1.11× final strength. For positive lysis control a 0.02% Triton-X100 solution was prepared in $DPBS^{+/+}$. Of all compound solutions 135 μl was dispensed/well in a 96 well V-bottom plate. To this 15 μl RBC suspension was added and mixed shortly (10 sec—600 rpm). The plate was incubated 30 min at RT, with gentle agitation. Afterwards the plate was spun for 10 min at 800×g to pellet the RBC and 100-120 μl supernatant was transferred to a standard 96 wp. Subsequently, the OD at 405 nm was measured on a Thermo Scientific Multiskan FC plate reader (Thermo Scientific). For quantification the background signal of '$DPBS^{+/+}$ only' wells was subtracted from all other wells before the percentage of hemolysis was calculated in comparison to 0.02% Triton-X100, by dividing the background corrected signal of treated wells over the background corrected signal of the 0.02% Triton-X100 wells (×100).

CD71mab-Saporin Conjugates

Custom CD71mab-saporin conjugates were produced and purchased from Advanced Targeting Systems (San Diego, CA).

Antibody-(SC-SO1861)$^n$ (FIG. 11), Antibody-(EMCH-SO1861)$^n$ Conjugates

Trastuzumab, Cetuximab, are referred hereafter as "Ab". Ab was conjugated to SO18161-EMCH or SO1861-semicarbazone-Mal (SO1861-SC-Mal) via Michael-type thiol-ene conjugation reaction at DAR 4. The SO1861-EMCH and SO1861-SC-Mal molecule obtains a labile (L) pH sensitive bond between its structure and its maleimide function generating a labile bond between the SO1861 and Ab. The procedure is exemplary described for Cetuximab-(SC-SO1861)$^4$: To a solution of Cetuximab (40 mg, 8.0 ml) was added 10 μl/ml each of Tris concentrate (127 mg/ml, 1.05 M), Tris·HCl concentrate (623 mg/ml, 3.95 M) and $EDTA\text{-}Na_2$ concentrate (95 mg/ml, 0.26 M) to give a 50 mM TBS, 2.5 mM EDTA buffer pH 7.5. To Cetuximab divided into four portions (each of 9.73 mg, 4.864 mg/ml, 65 nmol) was added an aliquot of freshly prepared TCEP solution (0.5-2.0 mg/ml, 1.15-7.02 mole equivalents, 75-455 nmol), the mixtures vortexed briefly then incubated for 300 minutes at 20° C. with roller-mixing. After incubation (prior to addition of SO1861-SC-Mal), a ca. 1 mg (0.210 ml) aliquot of Ab-SH was removed from each mixture and purified by gel filtration using a zeba spin desalting column into TBS pH 7.5. These aliquots were characterized by UV-vis analysis and Ellman's assay. To each of the bulk Ab-SH was added an aliquot of freshly prepared SO1861-SC-Mal solution (2 mg/ml, 1.3 mole equivalents per 'thiol', 0.15-0.61 μmol, 0.16-0.63 ml), the mixtures vortexed briefly then incubated for 120 minutes at 20° C. Besides each conjugation reaction, two aliquots of desalted Ab-SH (0.25 mg, 1.67 nmol) were reacted with NEM (1.3 mole equivalents per 'thiol', 4.3-17.4 nmol, 2.2-8.7 μl of a 0.25 mg/ml solution) or TBS pH 7.5 buffer (2.2-8.7 μl) for 120 minutes at 20° C., as positive and negative controls, respectively. After incubation (prior to addition of NEM), a 0.200 ml aliquot of Ab-SC-SO1861 mixture was removed and purified by gel filtration using zeba spin desalting column into TBS pH 7.5. This aliquot was characterized by UV-vis and alongside positive and negative controls were characterized by Ellman's assay to obtain SO1861-SC incorporations. To the bulk Ab-SC-SO1861 mixture was added an aliquot of freshly prepared NEM solution (2.5 mg/ml, 2.5-10 mole equivalents, 0.15-0.58 μmol) and the mixtures purified by zeba spin desalting columns eluting with DPBS pH 7.5 to give purified Cetuximab-(SC-SO1861) conjugates. The products were normalized to 2.5 mg/ml and filtered to 0.2 μm prior to dispensing for biological evaluation.

Antibody-(S-HSP27BNA)$^n$

To an aliquot of Trastuzumab (5.00 mg, $3.3\times10^{-5}$ mmol, 2.5 mg/ml) was added an aliquot of freshly prepared SMCC solution (2.00 mg/ml, 8.56 mole equivalents, $28.5\times10^{-5}$ mmol) in DMSO, the mixture vortexed briefly then incubated for 60 minutes at 20° C. with roller-mixing. After, the reaction was quenched by the addition of an aliquot of a freshly prepared glycine solution (10.0 mg/ml, 5.0 mole equivalents, $1.4\times10^{-3}$ mmol) in DPBS pH 7.5. Tras-SMCC (5.15 mg, $3.4\times10^{-5}$ mmol, 2.127 mg/ml, Tras:SMCC=4.4) was obtained after gel filtration using a zeba 10 ml spin column eluting with TBS pH 7.5, and characterised by UV-vis spectrophotometry and SAMSA colorimetric assay. BNA lyophilisate was reconstituted to 10 mg/ml using TBS pH 7.5 and analysed by UV-vis spectrophotometry. To (protected) BNA (9.5 mg, $1.6\times10^{-3}$ mmol, 9.59 mg/ml) was added an aliquot of freshly prepared TCEP solution (50.0 mg/ml, 10 mole equivalents, $16.3\times10^{-3}$ mmol) in TBS pH 7.5, the mixture briefly vortexed then incubated for 60 minutes at 37° C. with roller-mixing. After, the mixture was desalted using PD10 G25 desalting column eluting with TBS pH 7.5, followed by repeated washing via diafiltration using vivaspin T4 3K MWCO filters (3,000, 20° C., −15 minutes) and TBS pH 7.5 (seven cycles in total) to remove residual TCEP. BNA-SH (7.90 mg, $1.3\times10^{-3}$ mmol, 3.098 mg/ml, BNA:SH=1.2) was characterised by UV-vis spectrophotometry and Ellman's colorimetric assay. To Tras-SMCC (4.93 mg, $3.3\times10^{-5}$ mmol, 2.127 mg/ml) was added an aliquot of BNA-SH (8.0 mole equivalents, $26.3\times10^{-5}$ mmol, 3.098 mg/ml, 0.499 ml), the mixture vortexed briefly then incubated overnight at 20° C. After ca. 16 hours, the conjugate was purified by gel filtration using a 1.6×35 cm Sephadex G50M column eluting with DPBS pH 7.5. The conjugate was collected, pooled and concentrated to ca. 1 ml. The concentrate was analysed by BCA assay to ascertain antibody concentration and then by UV-vis spectrophotometry to ascertain a combined mass ε value for the conjugate and incorporation of BNA. The product was normalised to 2.0 mg/ml and spin-filtered to 0.2 μm. The result was Trastuzumab-BNA conjugate (2.0 mg/ml, 1.1 ml, 48%, Ab:BNA=2.2, purity=99.0%).

Figure 40:
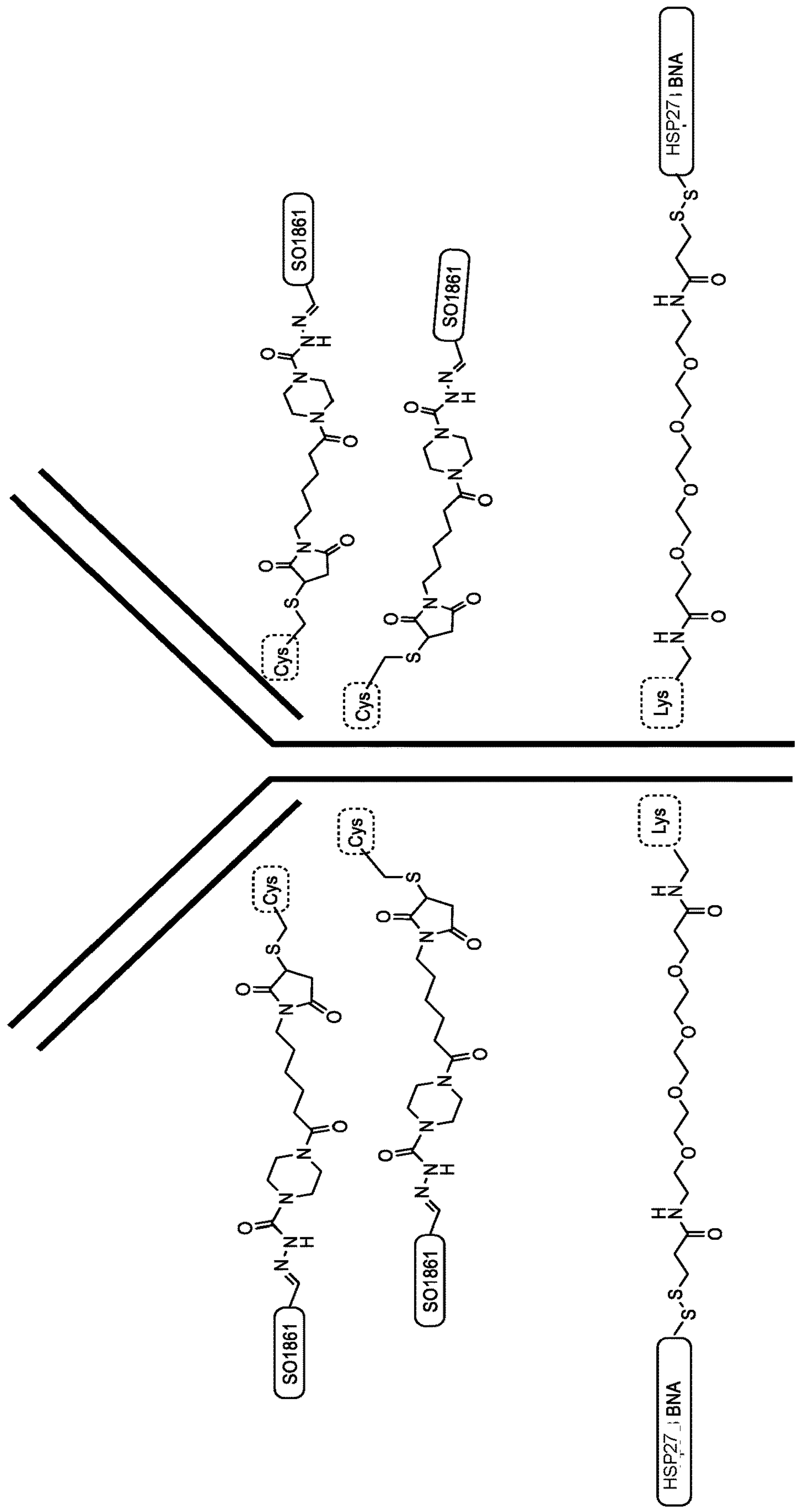
FIG. 40: Graphic of antibody(-L-SC-SO1861)4-(S-HSP27 BNA)2. The amino-acid residues labelled 'Cys' and 'Lys' are part of the amino-acid sequence of the antibody.

Synthesis of Antibody(-L-SC-SO1861)4-(S-HSP27BNA)2 (FIG. 40), Antibody(-L-EMCH-SO1861)4-(S-HSP27BNA)2 Conjugates Trastuzumab, Cetuximab, are referred hereafter as "Ab". Ab was conjugated to SO18161-EMCH or SO1861-semicarbazone-Mal (SO1861-SC-Mal) via Michael-type thiol-ene conjugation reaction at DAR 4. The SO1861-EMCH and SO1861-SC-Mal molecule obtains a labile (L) pH sensitive bond between its structure and its maleimide function generating a labile bond between the SO1861 and Ab. The procedure is exemplary described for conjugate Cetuximab-(SC-SO1861)4-(BNA)2 (Cetuximab-(SC-SO1861)-(BNA) (DAR4/DAR2) comprising four copies of the SO1861 and two copies of the BNA. This exemplary conjugate is tested for its influence on HSP27 expression in A431 cells (See FIG. 18).

To an aliquot of Cet-(SC-SO1861)4 (24.7 mg, $1.65\times10^{-4}$ mmol, 2.50 mg/ml) was added an aliquot of freshly prepared PEG4-SPDP solution (5.00 mg/ml, 3.31 mole equivalents, $5.45\times10^{-4}$ mmol), the mixture vortexed briefly then incubated for 60 minutes at 20° C. with roller-mixing. After incubation, the reaction was quenched by the addition of an aliquot of a freshly prepared glycine solution (10.0 mg/ml, 16 mole equivalents, $2.64\times10^{-3}$ mmol), the mixture vortexed briefly then incubated for >15 minutes at 20° C. with roller-mixing. The conjugate was purified by 2.6×26 cm Sephadex G50M eluting with TBS pH 7.5 and analysed by UV-vis to give purified Cet-(SC-SO1861)4-SPDP (23.7 mg, 96%, 1.32 mg/ml, Cet:SPDP=2.5). Cet-(SC-S SO1861)4-SPDP was stored at 2-8° C. in the dark until required.

Separately, an aliquot of Thiol HSP27BNA (4.16 mg, $7.08\times10^{-4}$ mmol, 10.80 mg/ml) reconstituted using TBS pH 7.5 was added an aliquot of freshly prepared THPP solution (50 mg/ml, 10 mole equivalents, $7.08\times10^{-3}$ mmol, 29.5 μl), the mixture vortexed briefly then incubated for 60 minutes at 37° C. with roller-mixing. After incubation, the BNA was purified by PD10 Sephadex G25M column eluting with TBS pH 7.5, to afford BNA-SH (3.15 mg, 76%, HSP27BNA: SH=0.88).

To an aliquot of Cet-(SC-SO1861)4-SPDP (10.01 mg, $6.67\times10^{-5}$ mmol, 1.32 mg/ml) was added an aliquot of BNA-SH (2.10 mg/ml, 4.0 mole equivalents, $2.67\times10^{-4}$ mmol, 0.747 ml), the mixture vortexed briefly then incubated for 3 hours at 20° C. then overnight at 5° C. with roller-mixing. Reaction progression was measured by PDT displacement. After ca. 18 hours, the conjugate mixture was again UV analysed to confirm PDT displacement by HSP27BNA and was then purified by 2.6×26 cm Sephadex G50M column eluting with DPBS pH 7.5 to give purified Cet-(SC-SO1861)4-HSP27BNA conjugate. The aliquot was analysed by BCA colorimetric assay and assigned a new molar absorptivity, then concentrated and normalised to 2.5 mg/ml, filtered to 0.2 μm and then dispensed into an aliquot for characterisation (retain) and two aliquots for product testing, one supplied refrigerated and the other frozen. The result was a Cet-(SC-SO1861)4-HSP27BNA conjugate (total yield=8.75 mg, 87%, Cet:HSP27BNA=1.4).

HSP27BNA, ApoB and ApoB #02 Oligonucleotide Sequences

HSP27 (5'-GGCacagccagtgGCG-3') [SEQ ID NO: 1], more specifically BNA$^{NC}$, modified from Zhang et al. (2011) [Y Zhang, Z Qu, S Kim, V Shi, B Liao1, P Kraft, R Bandaru, Y Wu, L M Greenberger and I D Horak, *Down-modulation of cancer targets using locked nucleic acid (LNA)-based antisense oligonucleotides without transfection, Gene Therapy* (2011) 18, 326-333]), ApoB (5'-GCCTCagtctgcttcGCACC-3') [SEQ ID NO: 8], and murine and human sequence-compatible ApoB #02 (5'-GCattggtat-TCA-3') [SEQ ID NO: 14] BNA$^{NC}$ oligos were ordered with 5'-Thiol C6 linker at Bio-Synthesis Inc (Lewisville, Texas), with BNA bases in capitals, and fully phosphorothioated backbones.

RNA Isolation and Gene Expression Analysis

RNA from cells was isolated and analysed according to standard protocols (Biorad). The qPCR primers that were used are indicated in Table 2.

TABLE 2

Primers used in qPCR are shown below:

| Gene | Primer | Sequence (5'-3') [SEQ ID No.] |
|---|---|---|
| HSP27 | Forward | GCAGTCCAACGAGATCACCA [SEQ ID NO. 2] |
| | Reverse | TAAGGCTTTACTTGGCGGCA [SEQ ID NO. 3] |
| HBMS (control) | Forward | CACCCACACACAGCCTACTT [SEQ ID NO. 4] |
| | Reverse | GTACCCACGCGAATCACTCT [SEQ ID NO. 5] |
| GUSB (control) | Forward | GAAAATACGTGGTTGGAGAGCT [SEQ ID NO. 6] |
| | Reverse | CCGAGTGAAGATCCCCTTTTTA [SEQ ID NO. 7] |

Results

Figure 4:
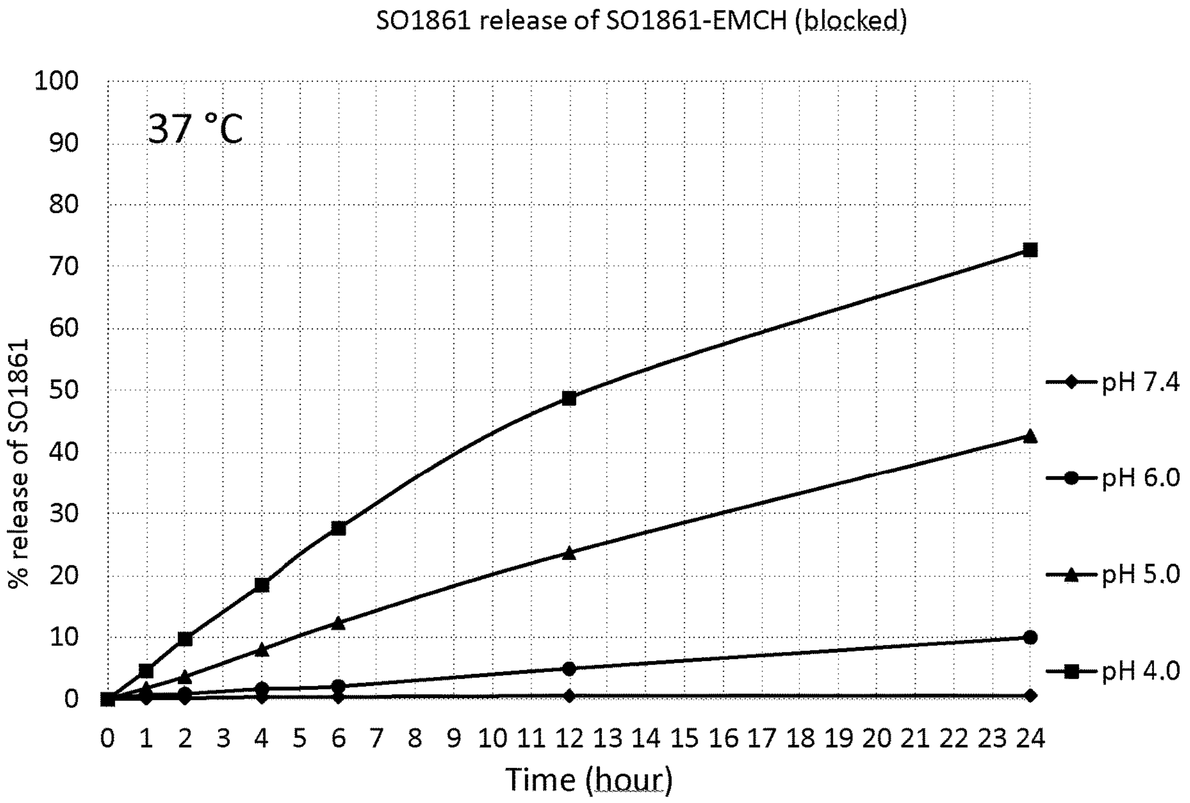
FIG. 4: Release kinetic assay of SO1861-EMCH (formula (4)) (A) and SO1861-SC-Mal (blocked) (Molecule VIII) (B) at various pH
Figure 4:
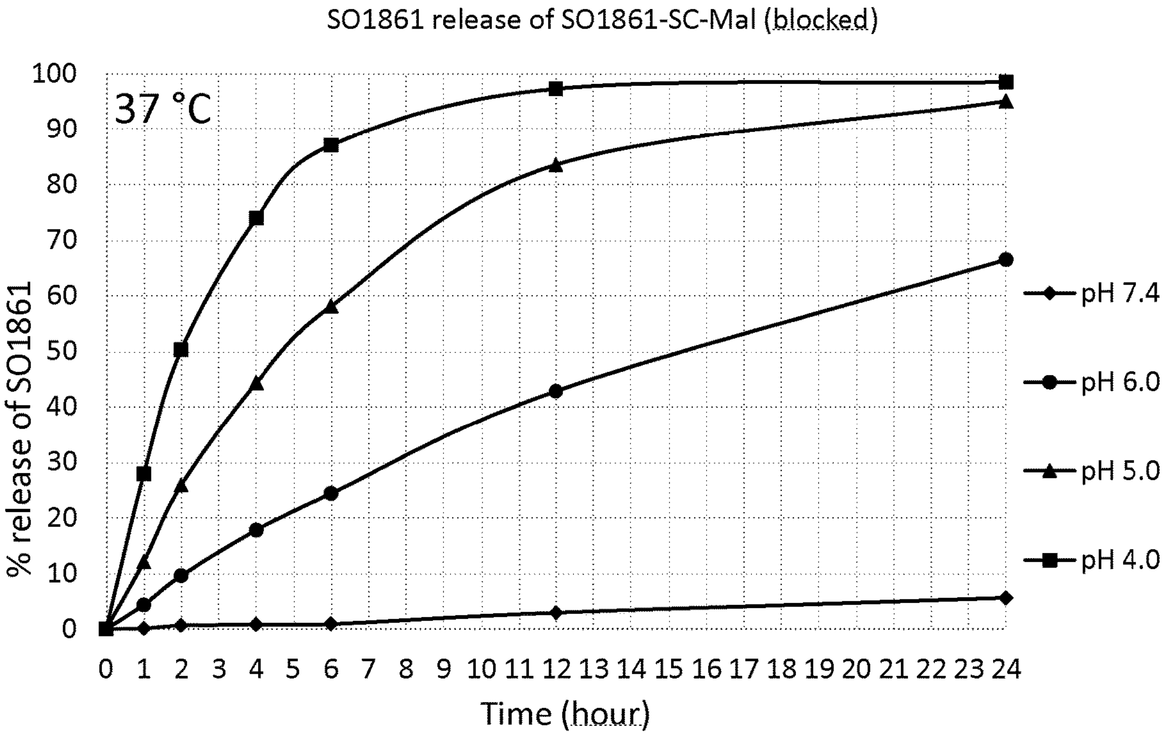

SO1861-SC-Mal (blocked) (FIG. 3; molecule VIII) was tested for efficient pH sensitive release with a release kinetic assay and compared with SO1861-EMCH (blocked). The assay was performed in buffers with pH 7.4, pH 6.0 pH, pH 5.0, pH 4.0 at 37 degrees for 24 hours. This revealed that SO1861-SC-Mal (blocked) shows a 6-fold faster release compared to SO1861-EMCH (blocked) (50% release at pH 4.0=2 hours (SO1861-SC-Mal (Blocked)) vs 50% release in 12 hours (SO1861-EMCH (Blocked)) (FIG. 4).

Figure 5:
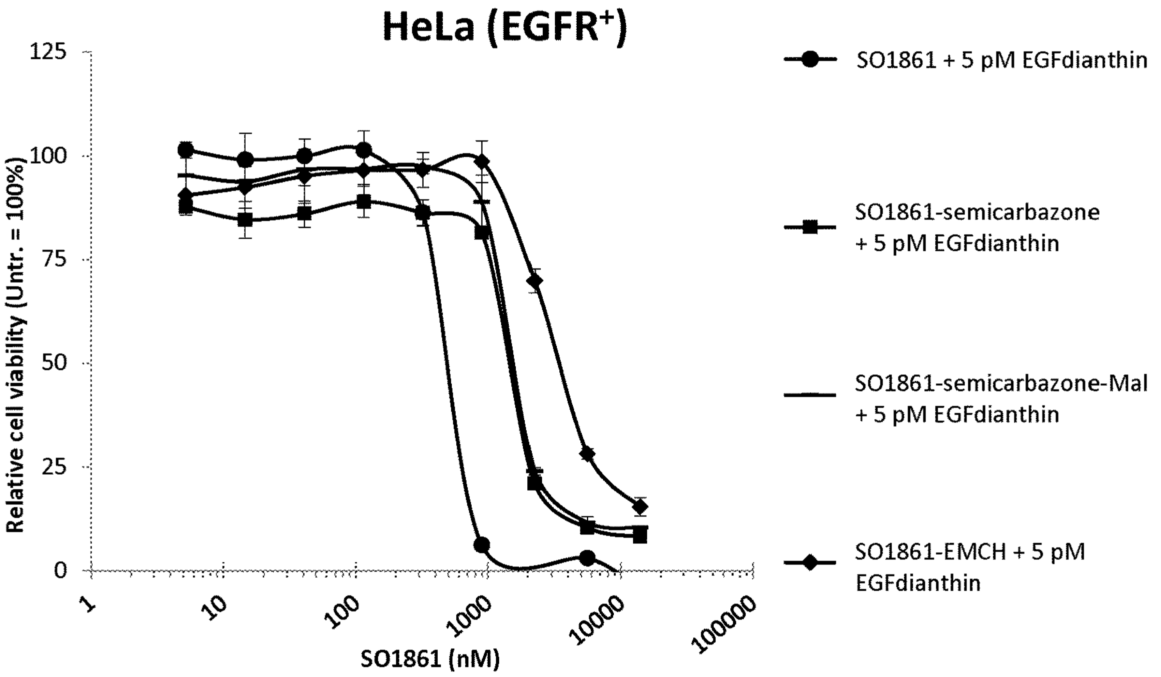
FIG. 5: Cell killing assay (MTS) of SO1861-SC-Mal+5 pM EGF-dianthin on HeLa (A) and A431 (B) cell lines. Note: the legend to FIG. 5A
Figure 5:
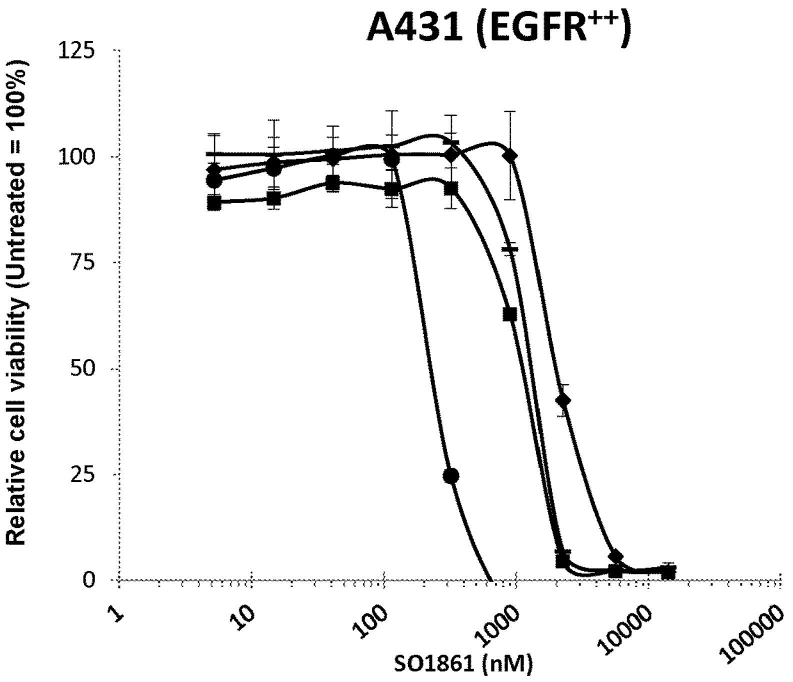
Figure 6:
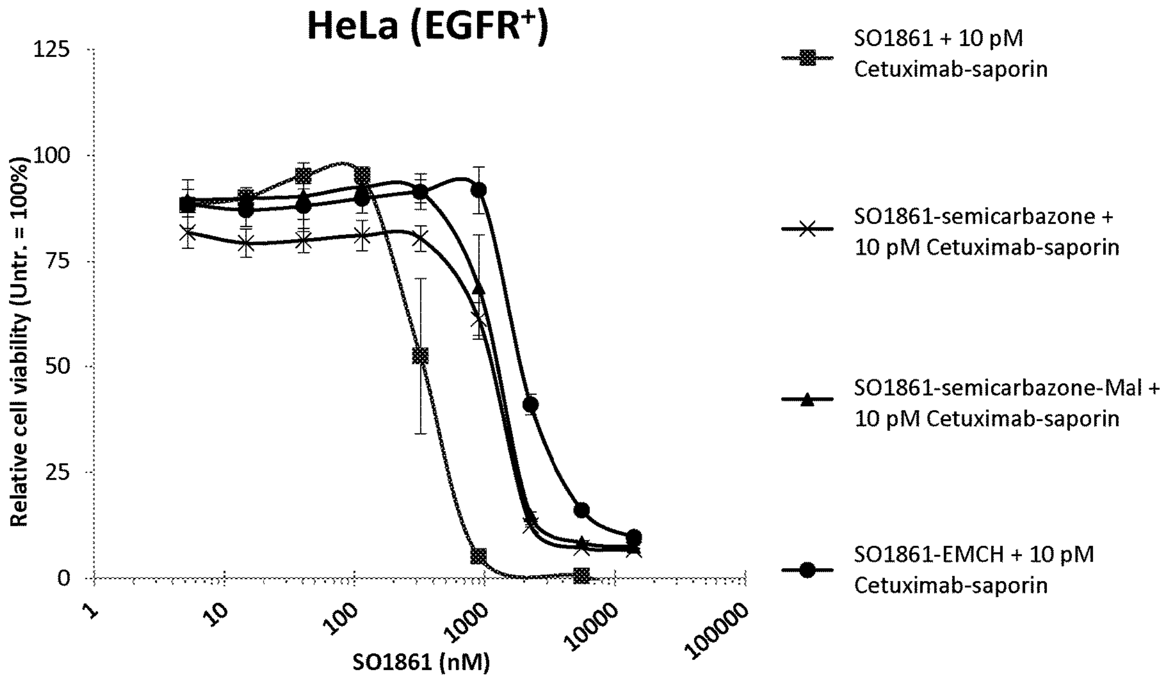
FIG. 6: Cell killing assay (MTS) of SO1861-SC-Mal+10 pM Cetuximab-saporin on HeLa (A) and A431 (B) cell lines. Note: the legend to FIG. 6A
Figure 6:
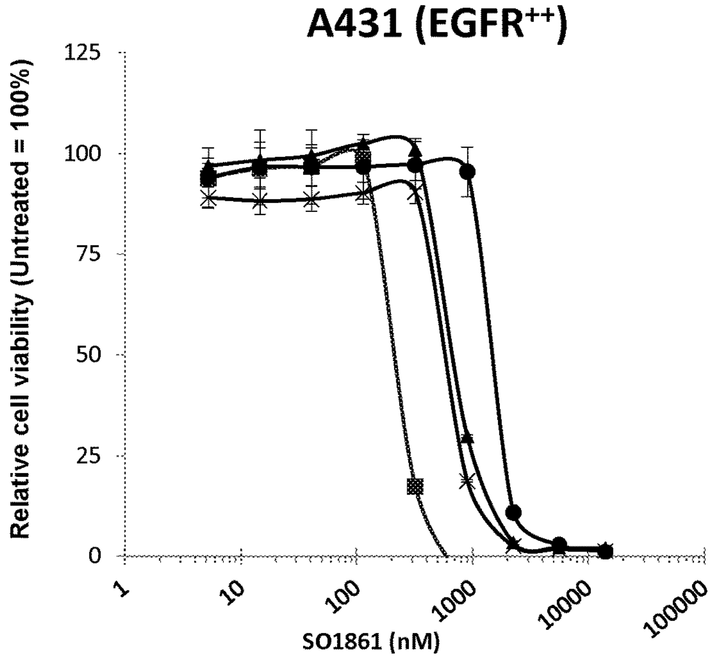
Figure 7:
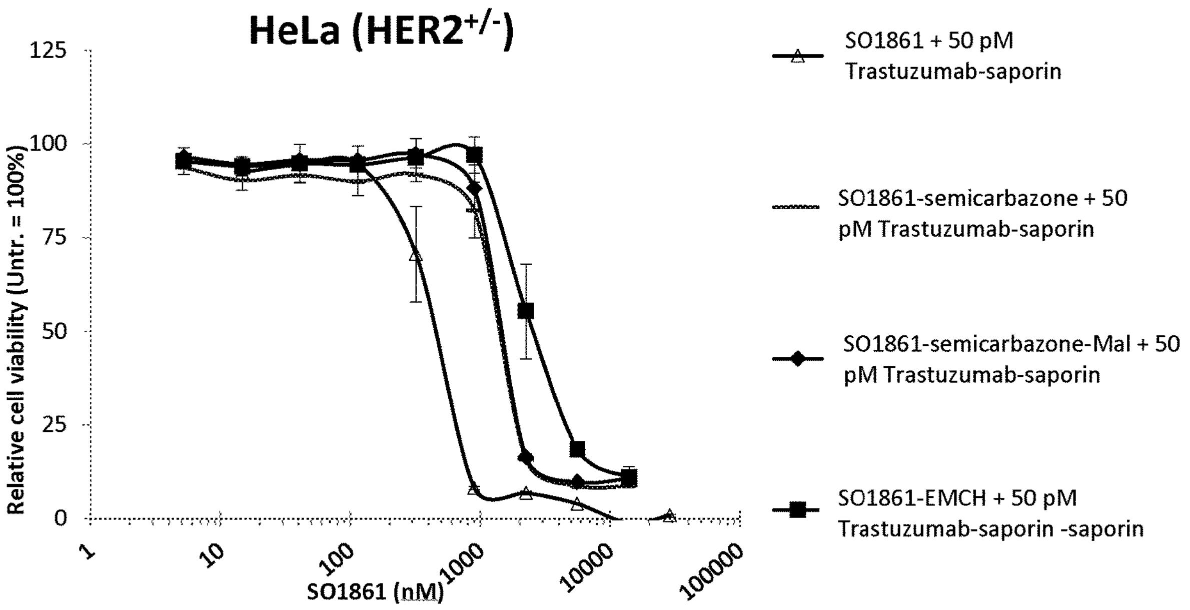
FIG. 7: Cell killing assay (MTS) of SO1861-SC-Mal+50 pM Trastuzumab-saporin on HeLa (A) and A431 (B) cell lines. Note: the legend to FIG. 7A
Figure 7:
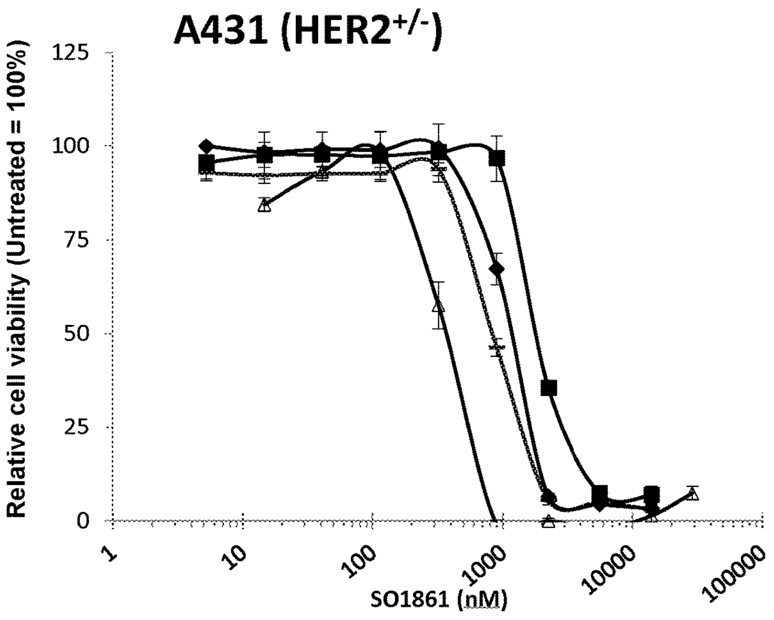

Next, SO1861-SC and SO1861-SC-Mal (FIG. 1, FIG. 2) were tested for endosomal escape enhancing activity. For this, SO1861, SO1861-EMCH, SO1861-SC and SO1861-SC-Mal were titrated in the presence of a non-effective, fixed concentration (FIG. 17) of 5 pM EGFdianthin (Dia-EGF), 50 pM Trastuzumab-saporin, 10 pM CD71-saporin or 10 pM Cetuximab-saporin on EGFR/HER2 expressing cells (HeLa and A431, Table 1, 3, 4). This revealed that both SO1861-SC or SO1861-SC-Mal combined with 5 pM EGF-dianthin (IC50=2000 nM (HeLa); IC50=1500 nM (A431)) (FIG. 5) or 10 pM Cetuximab-saporin (IC50=1500 nM (HeLa); IC50=1000 nM (A431) (FIG. 6) or 50 pM Trastuzumab-saporin (IC50=2000 nM (HeLa); IC50=1500 nM (A431)) (FIG. 7) was more effective compared to SO1861-EMCH combined with 5 pM EGFdianthin (IC50=4000 nM (HeLa); IC50=3000 nM (A431)) (FIG. 5) or 10 pM Cetuximab-saporin (IC50=3000 nM (HeLa); IC50=2000 nM (A431)) (FIG. 6) or 50 pM Trastuzumab-saporin (IC50=3000 nM (HeLa); IC50=2500 nM (A431)) (FIG. 7). Unmodified (non-derivatized) SO1861+5 pM EGFdianthin or 10 pM cetuximab-saporin or 50 pM Trastuzumab-saporin showed strongest activity (FIG. 5, FIG. 6, FIG. 7).

Figure 8:
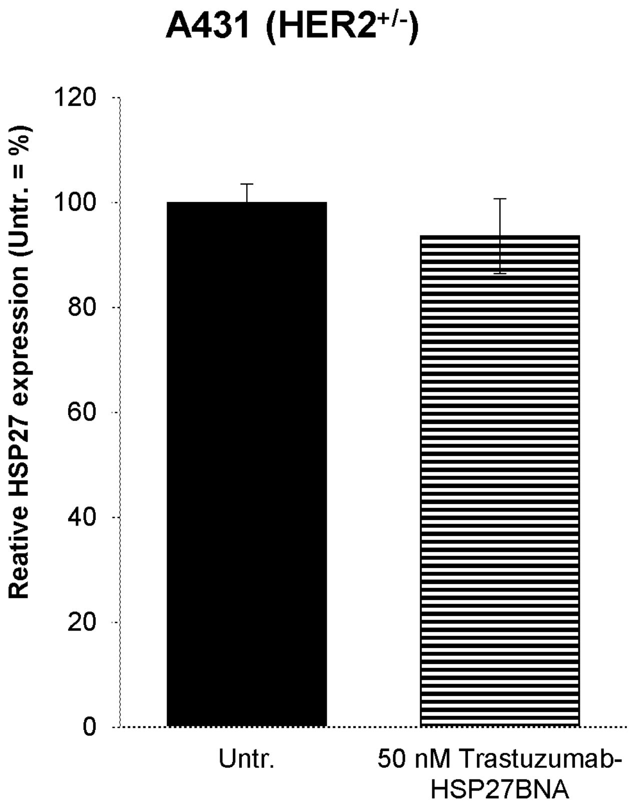
FIG. 8: HSP27 gene silencing of SO1861-SC-Mal+Tmab-HSP27BNA on A431 cell lines. (A) Relative HSP27 expression in the absence of saponin. (B) Relative HSP27 expression under influence of saponin analogues SO1861-EMCH and SO1861-SC-Mal and of wild type (non-modified, non-derivatised) saponin SO1861.
Figure 8:
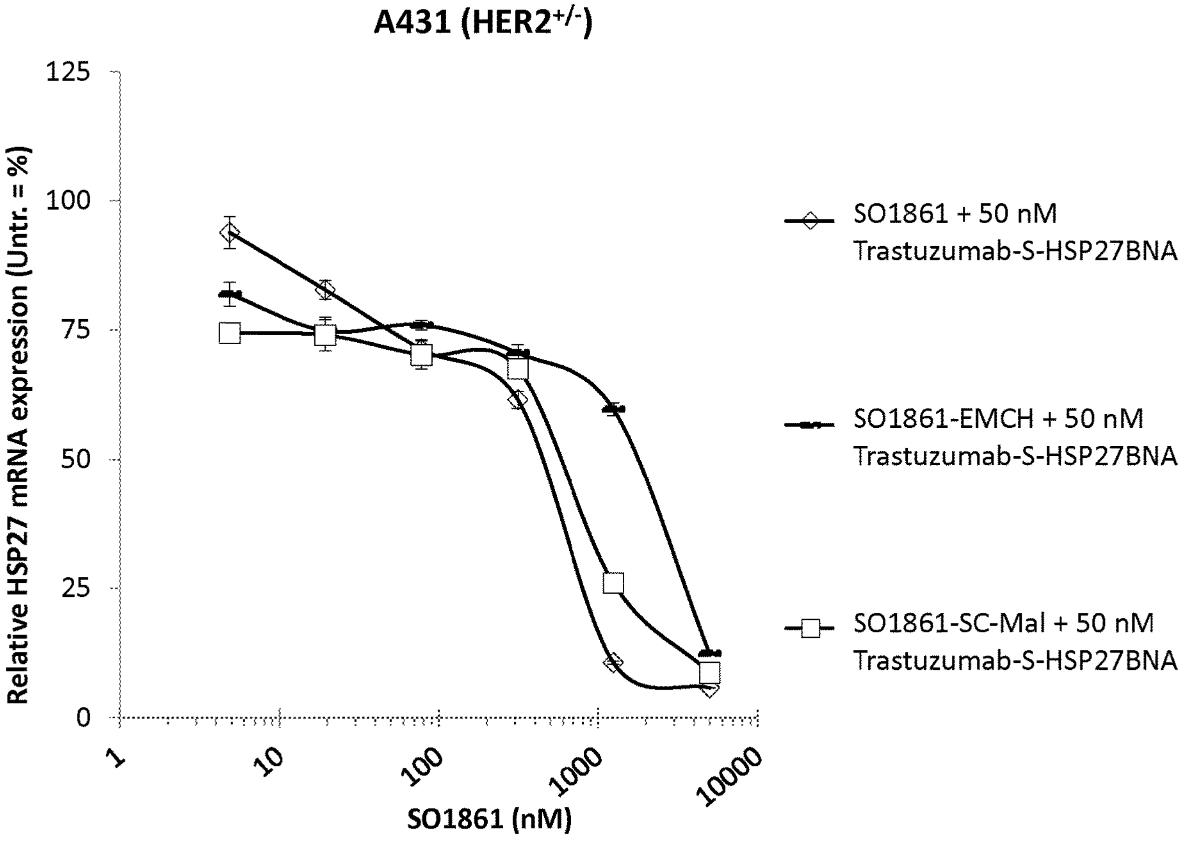

Next, the ability of SO1861-SC-Mal to induce enhanced cytoplasmic oligonucleotide delivery and targeted gene silencing was tested. For this, SO1861, SO1861-EMCH or SO1861-SC-Mal were titrated on a fixed (non-effective) concentration (determined in FIG. 8A) of 50 nM Trastuzumab-S-HSP27BNA, an antisense (BNA) oligonucleotide targeting heat-shock protein 27 (HSP27) conjugated to Trastuzumab with a DAR 2, in A431 cells ($HER2^{+/-}$) (FIG. 8B) and HSP27 mRNA gene silencing activity was determined. This revealed that SO1861-SC-Mal+50 nM Trastuzumab-HSP27BNA (IC50 of 600 nM (A431), FIG. 8B) is more effective in gene silencing activity compared to SO1861-EMCH+50 nM Trastuzumab-HSP27BNA (IC50 of 2000 nM (A431), FIG. 8B)

Figure 9:
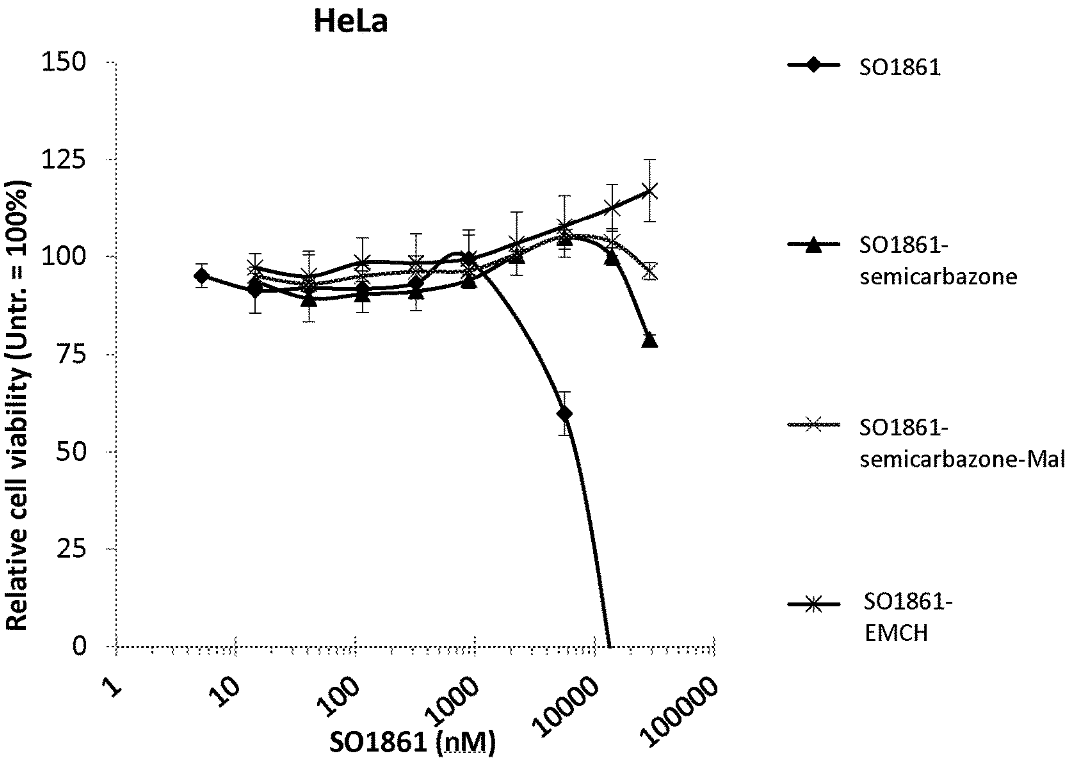
FIG. 9: Cell killing assay (MTS) of SO1861-SC-Mal, SO1861-SC, SO1861-EMCH and non-derivatised SO1861 on HeLa (A) and A431 (B) cell lines. Note: the legend to FIG. 9A
Figure 9:
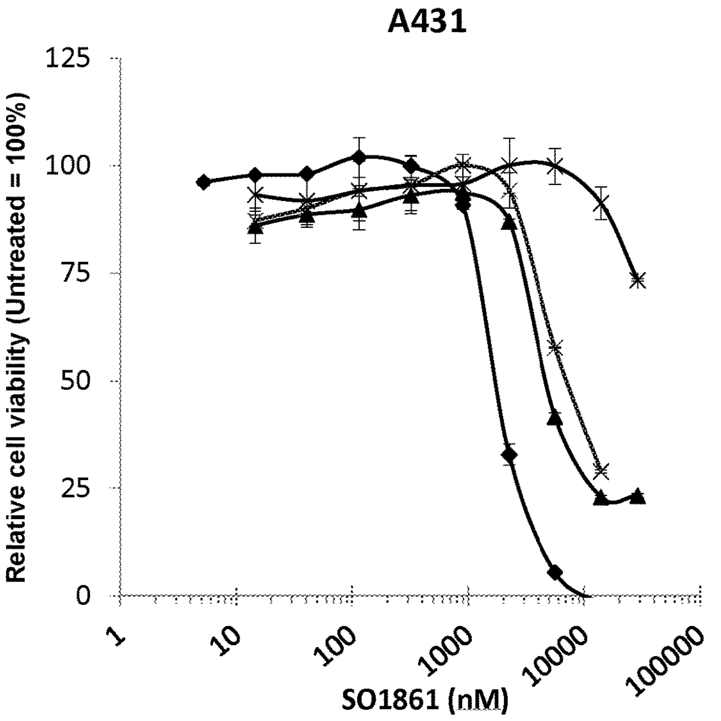

Next, cell toxicity was determined; for this, SO1861, SO1861-EMCH SO1861-SC and SO1861-SC-Mal were titrated on HeLa and A431 cells (Table 3, Table 4). This revealed that unmodified SO1861 showed toxicity at IC50=9000 nM (HeLa) and IC50=2000 nM (A431), whereas in Hela cells SO1861-EMCH or SO1861-SC-Mal showed toxicity at IC50>100000 nM and in A431 cells SO1861-EMCH showed toxicity at IC50>30000 nM, whereas SO1861-SC-Mal and SO1861-SC showed toxicity at IC50=6000 nM (FIG. 9; Table 3, Table 4).

TABLE 3

IC50 overview of modified SO1861 activity (HeLa cells)/toxicity (HeLa cells/hemolysis (red blood cells)/CMC.

| Conjugate Sample | modified group | IC50 nM (Activity; + 5 pM EGFdianthin) | IC50 (Toxicity) | IC50 (Haemolysis) | CMC | Ratio: IC50 toxicity/ IC50 activity | Ratio: IC50 haemolysis/ IC50 activity |
|---|---|---|---|---|---|---|---|
| SO1861 | none | 500 nM | 9000 nM | 10000 nM | 120 μM | 18 | 20 |
| SO1861-EMCH | aldehyde | 4000 nM | >100000 nM | >500000 nM | >800 μM | >25 | >125 |
| SO1861-Semicarbazone | aldehyde | 2000 nM | 30.000 nM | 100000 nM | n.d. | 15 | 50 |
| SO1861-semicarbazone Mal | aldehyde | 2000 nM | >100000 nM | 250000 nM | >800 μM | >50 | 125 |

Figure 10:
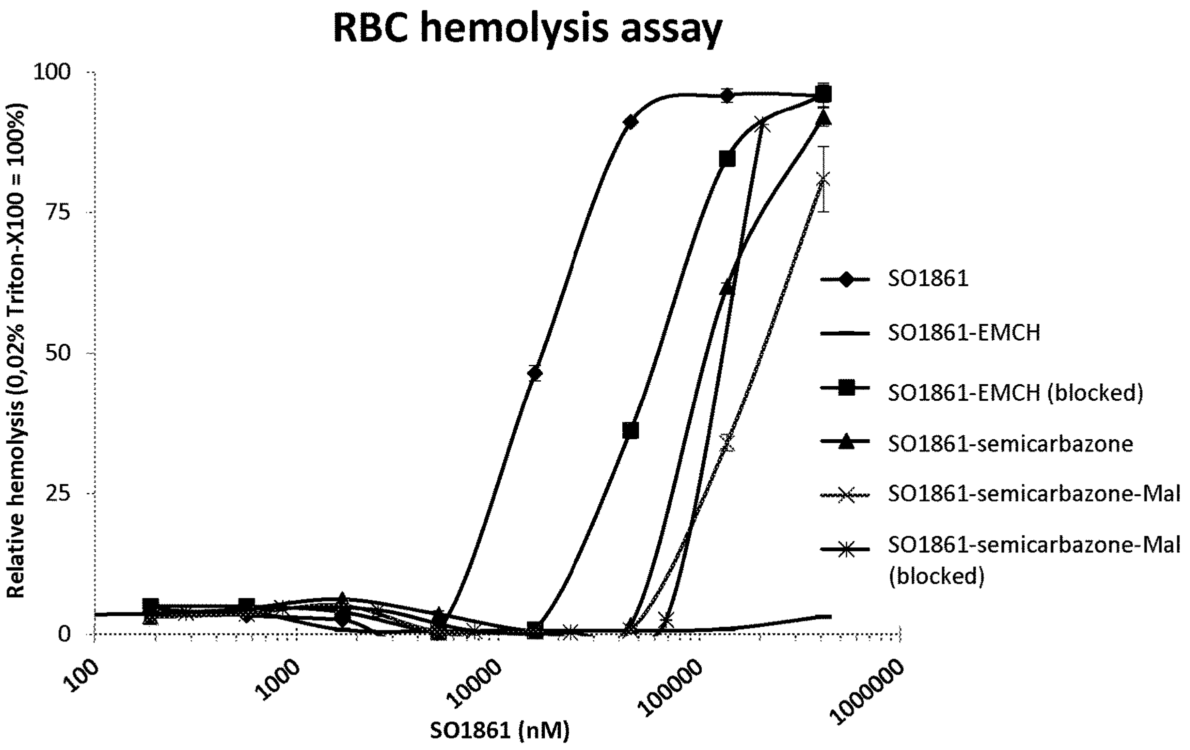
FIG. 10: Hemolytic activity of modified SO1861 (SO1861 derivatives) and non-derivatised SO1861 on human red blood cells (RBC).

Next, a haemolysis assay was performed; for this SO1861, SO1861-EMCH, SO1861-EMCH (blocked) SO1861-SC, SO1861-SC-Mal and SO1861-SC-Mal (blocked) were tested on fresh human red blood cells (RBC) and this revealed haemolytic activity of SO1861-SC at IC50=100000 nM, SO1861-SC-Mal at IC50=250000 nM and SO1861-SC-Mal (blocked) at IC50=100000 nM (FIG. 10; Table 3, Table 4), whereas no haemolytic activity was detected with SO1861-EMCH at the range of concentrations tested (IC50>500000 nM) and SO1861-EMCH (blocked) showed haemolytic activity at IC50=6000 nM.

Next, the critical micelle concentration (CMC) was determined for SO1861, SO1861-EMCH, SO1861-EMCH (blocked), SO1861-SC-Mal and SO1861-SC-Mal (blocked) (Table 3, Table 4). This revealed a CMC value of 129 μM for SO1861, whereas for SO1861-SC-Mal and SO1861-EMCH, a CMC could not be detected and determined within this range of concentrations, which indicates that the CMS for these two saponin derivatives is higher than 800 μM (Table 3, Table 4).

TABLE 4

IC50 overview of modified SO1861 activity (A431 cells)/toxicity (A431 cells/hemolysis (red blood cells)/CMC.

| Conjugate Sample | modified group | IC50 nM (Activity; + 5 pM EGFdianthin) | IC50 (Toxicity) | IC50 (Haemolysis) | CMC | Ratio: IC50 toxicity/ IC50 activity | Ratio: IC50 haemolysis/ IC50 activity |
|---|---|---|---|---|---|---|---|
| SO1861 | none | 300 nM | 2000 nM | 10000 nM | 120 μM | 7 | 33 |
| SO1861-EMCH | aldehyde | 2500 nM | >30000 nM | >500000 nM | >800 μM | >12 | >200 |
| SO1861-semicarbazone | aldehyde | 1500 nM | 6000 nM | 100000 nM | n.d. | 4 | 67 |
| SO1861-Semicarbazone Mal | aldehyde | 1500 nM | 6000 nM | 250000 nM | >800 μM | 4 | 166 |

Figure 11:
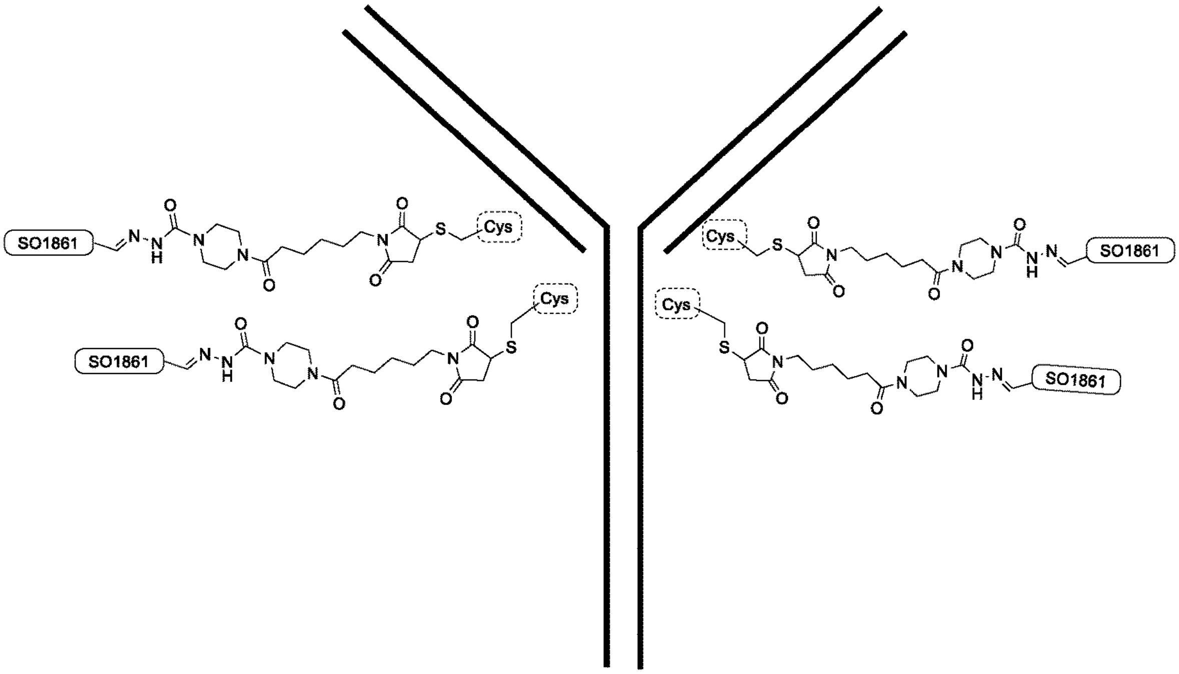
FIG. 11: graphical representation of mAb-semicarbazone-SO1861 (DAR4). The derivatised saponin SO1861-SC-Mal is covalently linked to the central monoclonal antibody (e.g. an IgG) via covalent bond formation between Cysteine residues of the antibody and the maleimide group of the derivatised SO1861. Four SO1861 moieties are bound to the antibody.
Figure 12:
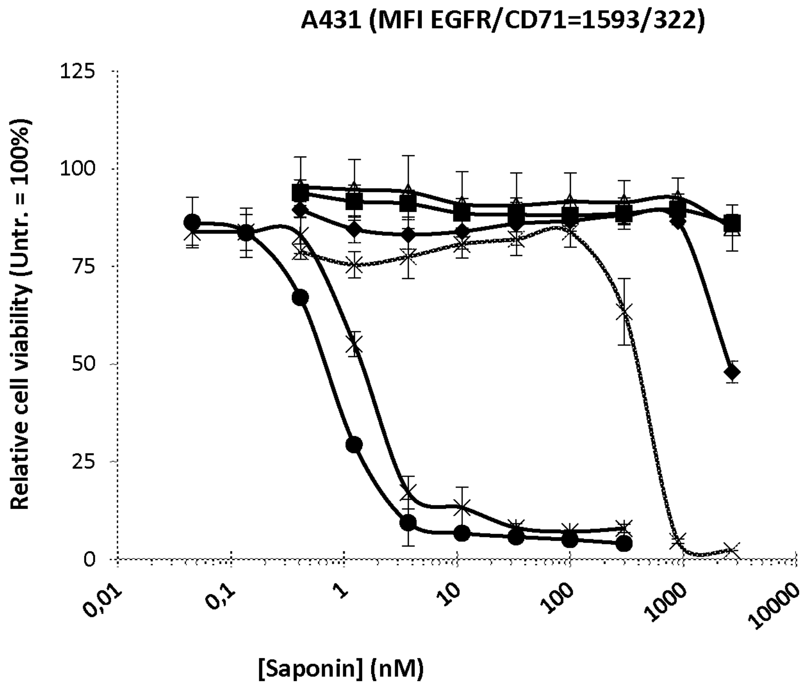
FIG. 12: EGFR/CD71 targeted cell killing in A431 cells (A) and CaSKi cells (B).) Cetuximab-$(SC\text{-}SO1861)^4$, also called Cetuximab-SC-SO1861 (DAR 4) and Cetuximab-$(EMCH\text{-}SO1861)^4$ titration+fixed concentration 10 pM CD71mab-saporin and controls on A431 cells ($EGFR^{++}$/$CD71^+$) and CaSKi cells ($EGFR^{++}$/$CD71^+$). Note: the legend to FIG. 12A
Figure 12:
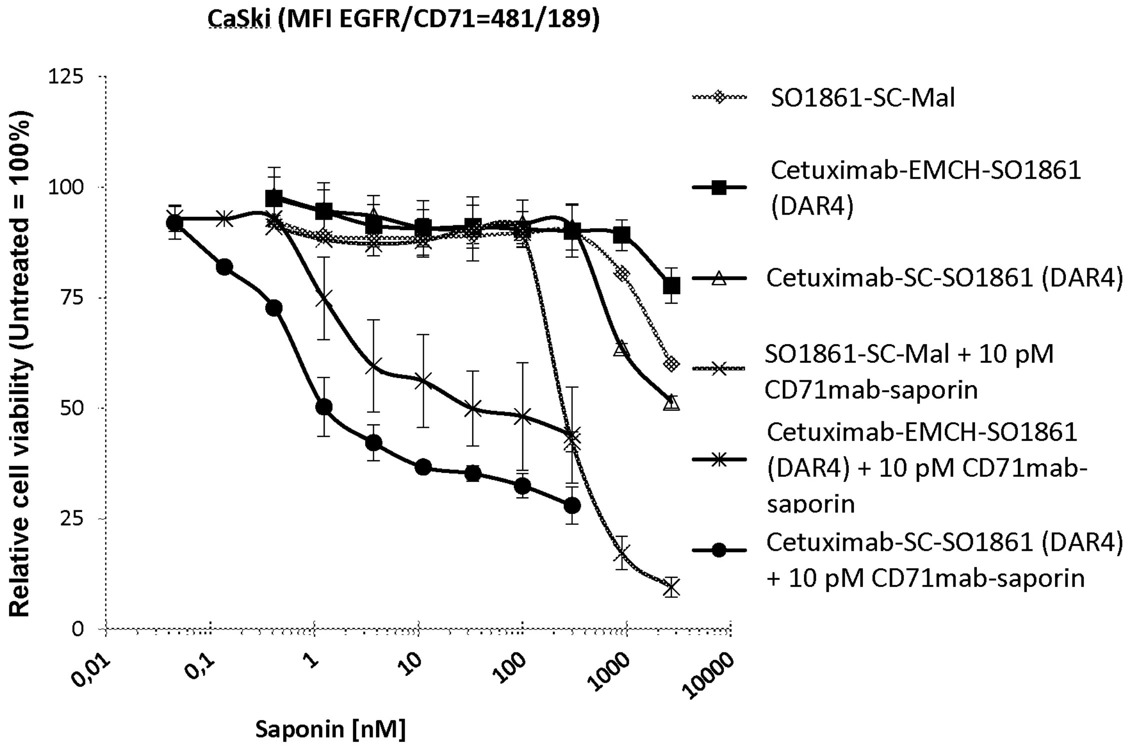

Next, SO1861-semicarbazone-Mal (SO1861-SC-Mal) was conjugated via cysteine residues (Cys) to Cetuximab (a monoclonal antibody recognizing and binding human EGFR), with a DAR 4, to yield Cetuximab-(SC-SO1861)$^4$ as depicted in FIG. 11. Cetuximab-(SC-SO1861)$^4$ was titrated on a fixed non-effective concentration (see FIG. 17) of 10 pM CD71 mab-saporin (monoclonal antibody recognizing human CD71; clone OKT-9), conjugated to the protein toxin, saporin and targeted protein toxin mediated cell killing on EGFR/CD71 expressing cells (A431, EGFR$^{++}$/CD71$^+$; CaSki, EGFR$^{++}$/CD71$^+$) was determined. This revealed strong cell killing at low concentrations of Cetuximab-(SC-SO1861)$^4$ (A431: IC50=0.6 nM and CaSki IC50=1 nM; FIG. 12A, 12B) and compared to Cetuximab-(EMCH-SO1861)$^4$ the activity was stronger (A431: IC50=2 nM and CaSki IC50=30 nM; FIG. 12A, 12B). Equivalent concentrations of Cetuximab-(SC-SO1861)$^4$ or Cetuximab-(EMCH-SO1861)$^4$ could not induce any cell killing activity in EGFR$^{++}$/CD71$^+$ expressing cells. This shows that compared to Cetuximab-(EMCH-SO1861)$^4$, Cetuximab-(SC-SO1861)$^4$ more potently enhances endosomal escape of the CD71 mab conjugated protein toxin (the same concentration of 10 pM the protein toxin is not effective in the absence of saponin; see FIG. 17), thereby inducing efficient cell killing of EGFR$^{++}$/CD71$^+$ expressing cells. Improved acid-sensitive linker release of SO1861 from an antibody at low pH in endosomes thus improves the efficacy of mAb-SO1861 conjugates for delivery of a protein toxin such as a ribosomal inactivating protein toxin in the cytoplasm.

Figure 13:
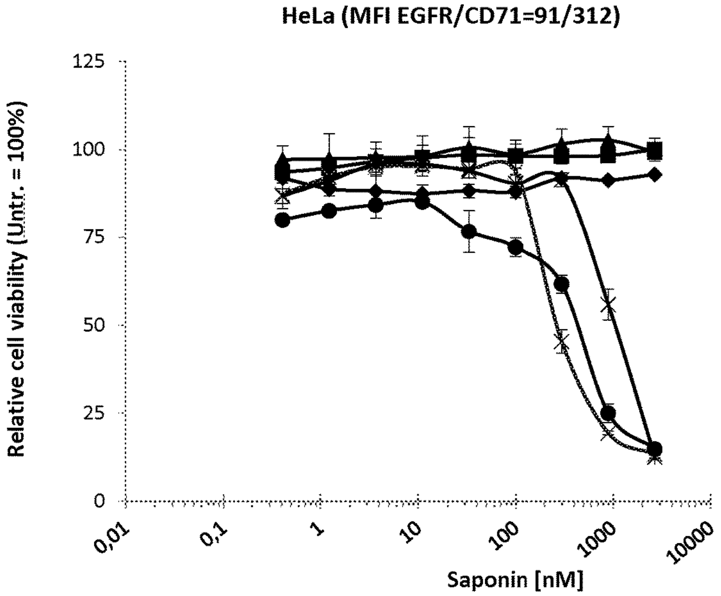
FIG. 13: EGFR/CD71 targeted cell killing in HeLa cells (A) and A2058 cells (B). Cetuximab-$(SC\text{-}SO1861)^4$ and Cetuximab-$(EMCH\text{-}SO1861)^4$ titration+fixed concentration 10 pM CD71mab-saporin and controls on HeLa cells ($EGFR^{+/-}$/$CD71^+$) and A2058 cells ($EGFR^-$/$CD71^+$). Note: the legend to FIG. 13A
Figure 13:
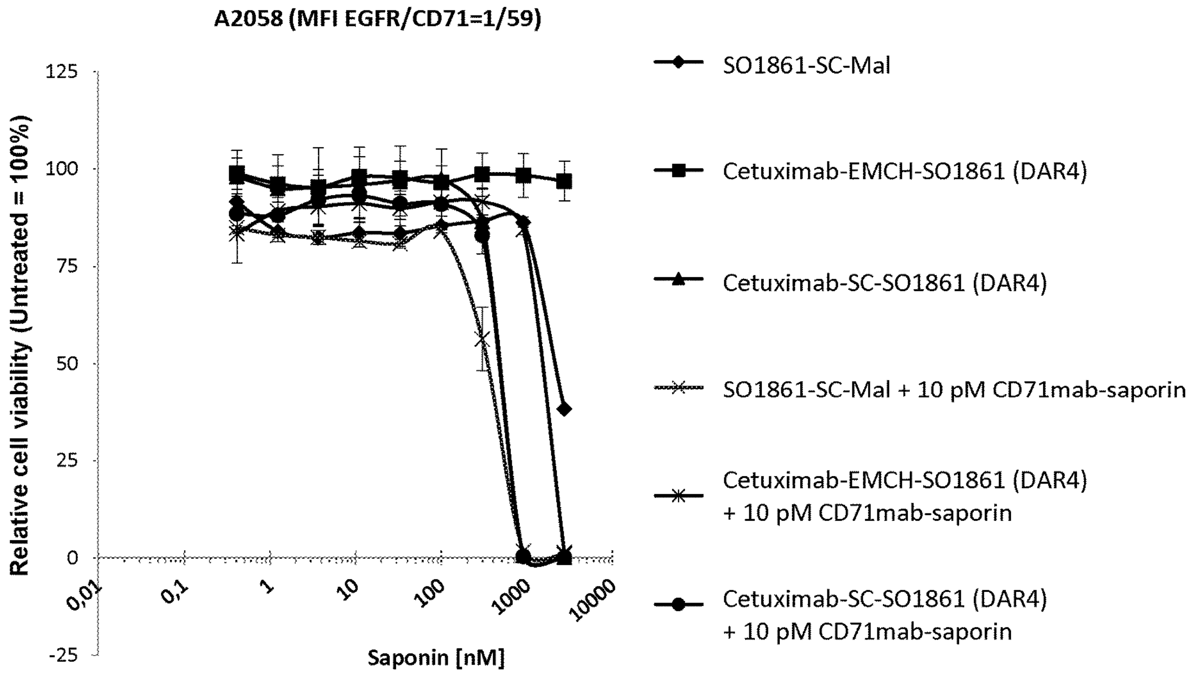

Next, Cetuximab-(SC-SO1861)$^4$ was titrated on a fixed concentration of 10 pM CD71 mab-saporin and targeted protein toxin-mediated cell killing on HeLa (EGFR$^{+/-}$/CD71$^+$) and A2058 (EGFR$^-$/CD71$^+$) was determined (FIG. 13). Cetuximab-(SC-SO1861)$^4$+10 pM CD71 mab-saporin in HeLa cells (EGFR$^{+/-}$/HER2$^{+/-}$) could already induce partial protein toxin-mediated cell killing at lower concentrations (between 50-100 nM) of Cetuximab-(SC-SO1861)$^4$ (compared to HeLa: IC50=500 nM, FIG. 13A), whereas this was not observed for Cetuximab-(EMCH-SO1861)$^4$+10 pM CD71mab-saporin (HeLa: IC50=1000 nM (FIG. 13 A)). In A2058 cells (that lack EGFR receptor expression), no improved activity was observed for Cetuximab-(SC-SO1861)$^4$+10 pM CD71 mab-saporin (A2058: IC50=1000 nM); FIG. 13B). This shows that improved release of SO1861 in acidified endosomes due to a more efficiently releasable semicarbazone linker also triggers cells with lower EGFR expression (where endosomal SO1861 threshold concentrations is reached) for the combination therapy. When EGFR expression is absent (in A2058 cells), effective SO1861 concentrations are not reached (i.e., below threshold) to induce endosomal escape and cytoplasmic delivery of the protein toxin.

Figure 14:
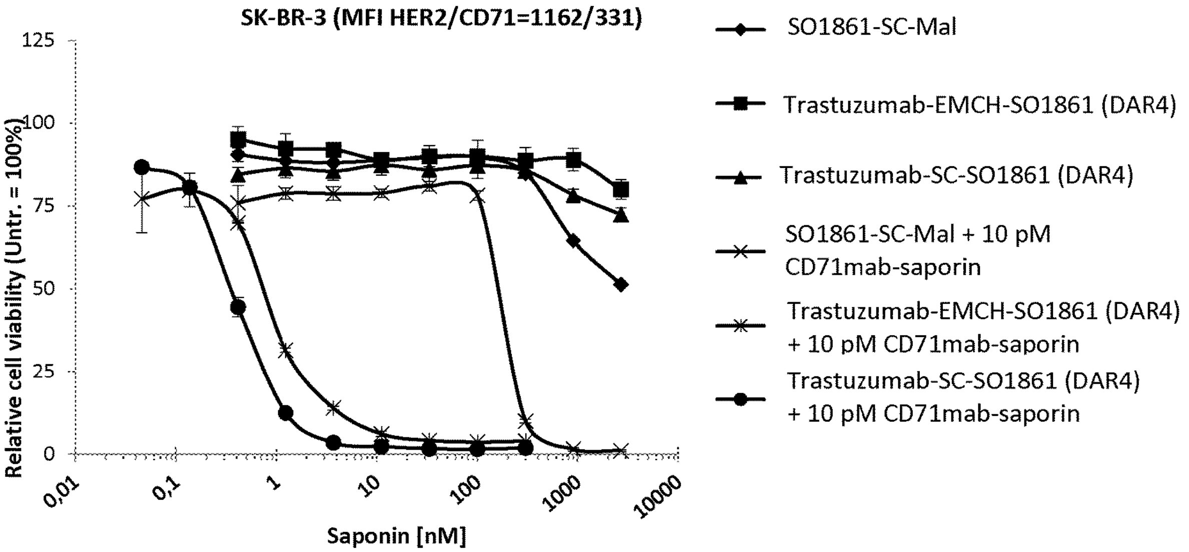
FIG. 14: HER2/CD71 targeted cell killing. Trastuzumab-$(SC\text{-}SO1861)^4$ or Trastuzumab-$(EMCH\text{-}SO1861)^4$ titration+fixed concentration 10 pM CD71mab-saporin and controls on SK-BR3 cells ($HER2^{++}$/$CD71^+$).
Figure 17:
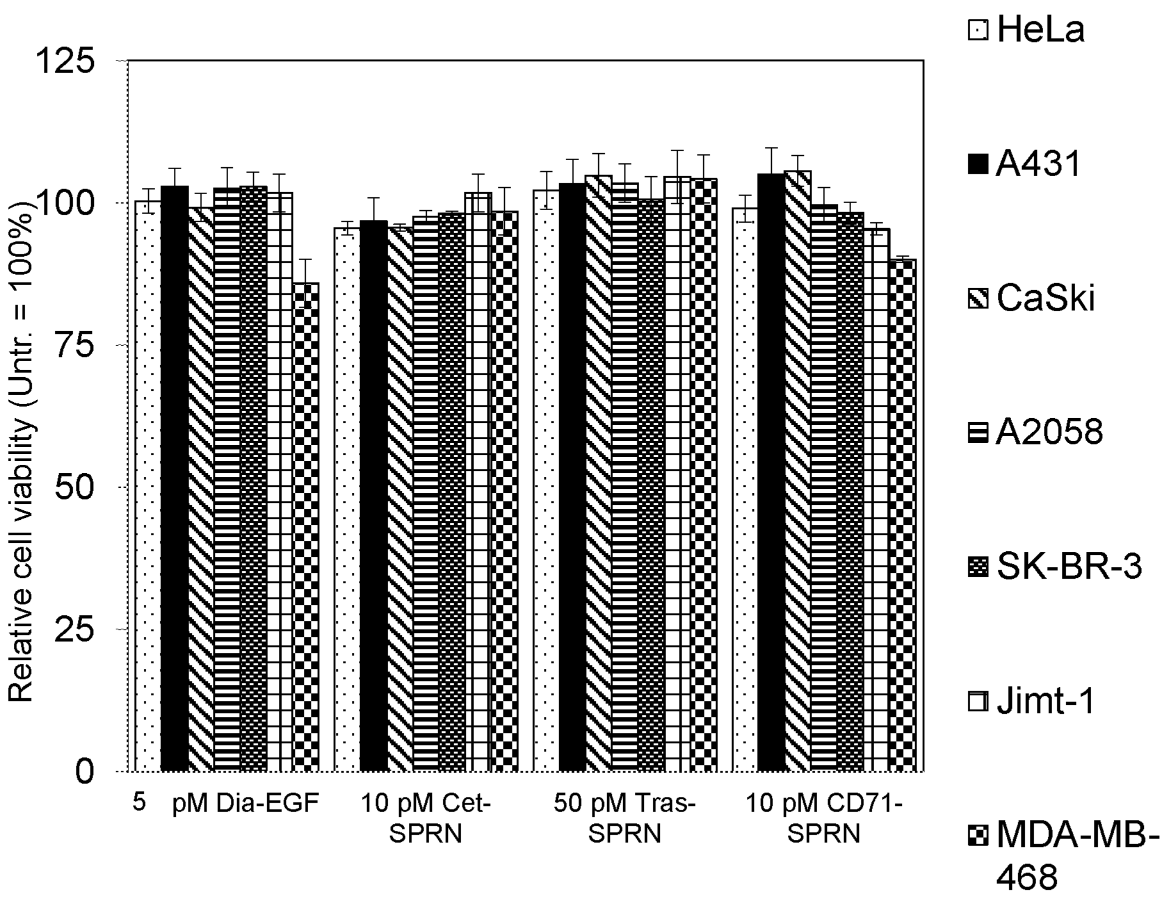
FIG. 17: Cell killing assay (MTS) of various cell lines treated with 5 pM EGFdianthin (Dia-EGF), pM Cetuximab-saporin (Cet-SPRN), 50 pM Trastuzumab-saporin (Tras-SPRN) or 10 pM CD71-saporin (CD71-SPRN).

Next, SO1861-SC-Mal was conjugated via cysteine residues (Cys) to Trastuzumab (monoclonal antibody recognizing and binding human HER2), with a DAR 4, to yield Trastuzumab-(SC-SO1861)$^4$. Trastuzumab-(SC-SO1861)$^4$ was titrated to a fixed concentration of 10 pM CD71 mab-saporin and targeted protein toxin mediated cell killing on HER2/CD71 expressing cells (SK-BR-3: HER2$^{++}$/CD71$^+$) was determined (FIG. 14). This revealed strong cell killing at low concentrations of Trastuzumab-(SC-SO1861)$^4$ (SK-BR-3: IC50=0.3 nM; FIG. 14) and compared to Trastuzumab-(EMCH-SO1861)$^4$, the activity was 5-fold improved (SK-BR-3: IC50=1 nM; FIG. 14). Equivalent concentrations of Cetuximab-(SC-SO1861)$^4$ or Cetuximab-(EMCH-SO1861)$^4$ alone could not induce any significant cell killing activity in SK-BR-3 cells (FIG. 14). This shows that compared to Trastuzumab-(EMCH-SO1861)$^4$, Trastuzumab-(SC-SO1861)$^4$ more potently enhances endosomal escape of the CD71 mab conjugated protein toxin (at otherwise non-effective concentrations; FIG. 17), thereby inducing efficient cell killing of HER2$^{++}$/CD71$^+$ expressing cells. Improved acid-sensitive linker release of SO1861 from an antibody at low pH in endosomes thus improves effectiveness of mAb-SO1861 conjugates for delivery of a ribosomal inactivating protein toxin in the cytoplasm.

Figure 15:
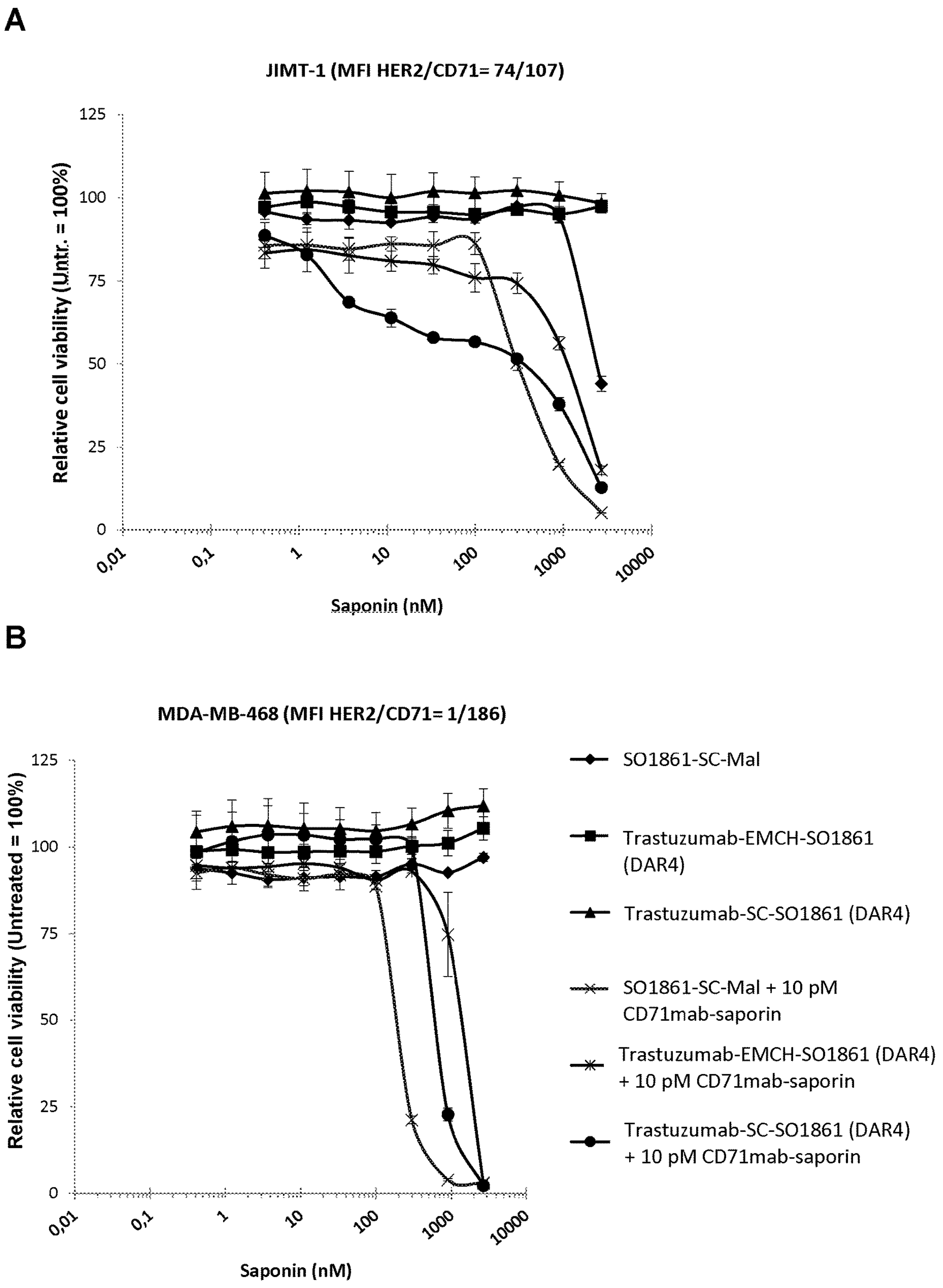
FIG. 15: HER2/CD71 targeted cell killing. (A,B) Trastuzumab-(SC-SO1861)$^4$ or Trastuzumab-(Cys-EMCH-SO1861)$^4$ titration+fixed concentration 10 pM CD71mab-saporin and controls on JIMT-1 cells (HER2+/−/CD71+) (A), and MDA-MB-468 (HER2−/CD71+) (B). Note: the legend to FIG. 15A

Next, Trastuzumab-(SC-SO1861)$^4$ was titrated to a fixed concentration of 10 pM CD71 mab-saporin and targeted protein toxin-mediated cell killing on JIMT-1 (HER2$^{+/-}$/CD71$^+$) and MDA-MB-468 (HER2$^-$/CD71$^+$) was determined. Trastuzumab-(SC-SO1861)$^4$+10 pM CD71 mab-saporin in JIMT-1 cells (HER2$^{+/-}$/CD71$^+$) could already induce toxin mediated cell killing at low conjugated SO1861 concentrations (JIMT-1: IC50=100 nM; FIG. 15A) whereas this was not observed for Trastuzumab-(EMCH-SO1861)$^4$+10 pM CD71 mab-saporin (JIMT-1: IC50=1000 nM; FIG. 15A). In MDA-MB-468 cells (that lack HER2 receptor expression), no improved activity was observed for Trastuzumab-(SC-SO1861)$^4$+10 pM CD71mab-saporin (A2058: IC50=1000 nM; FIG. 15B). This shows that improved release of SO1861 in acidified endosomes (due to a more efficient release of semicarbazone-conjugated SO1861) also triggers cells with lower HER2 expression (i.e., that endosomal SO1861 threshold concentrations are reached) for the combination therapy. When HER2 expression is absent (in A2058 cells), effective SO1861 concentrations are not reached (i.e. below threshold) to induce endosomal escape and cytoplasmic delivery of the protein toxin.

Figure 16:
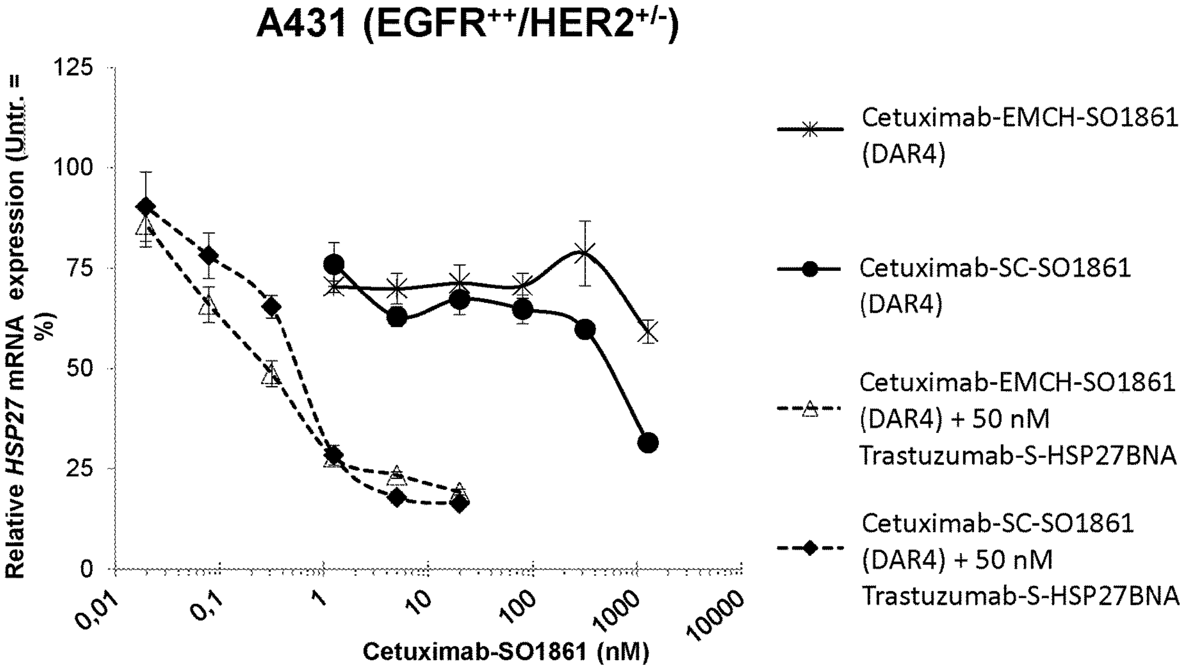
FIG. 16: EGFR/HER2 targeted gene silencing in A431 cells. Cetuximab-(SC-SO1861)$^4$ and Cetuximab-(EMCH-SO1861)$^4$ titration+fixed concentration 50 pM Trastuzumab-S-HSP27BNA and controls on A431 cells (EGFR++/HER2+/−). The term 'S' as used such as in an antibody-oligonucleotide conjugate, represents 'stable linker' which is a non-cleavable linker in the endosome, endolysosome and in the lysosome of mammalian cells, such as human cells, such as a human tumor cell, thus under slightly acidic conditions (pH<6.6, such as pH 4.0-5.5).

Next, Cetuximab-(SC-SO1861)[4] was titrated to a fixed concentration of 50 pM Trastuzumab-HSP27BNA and targeted HSP27 gene silencing on A431 cells ($EGFR^{++}$/$HER2^{+/-}$) was determined. This revealed strong HSP27 gene silencing at low concentrations of Cetuximab-(SC-SO1861)[4] (A431: IC50=0.5 nM; FIG. 16), comparable to the activity observed with Cetuximab-(EMCH-SO1861)[4]+50 pM Trastuzuzmab-HSP27BNA (A431: IC50=0.5 nM FIG. 16).

In Vitro Potency of Cetuximab-(SC-SO1861)-HSP27 BNA (DAR 4/DAR2)

Figure 18:
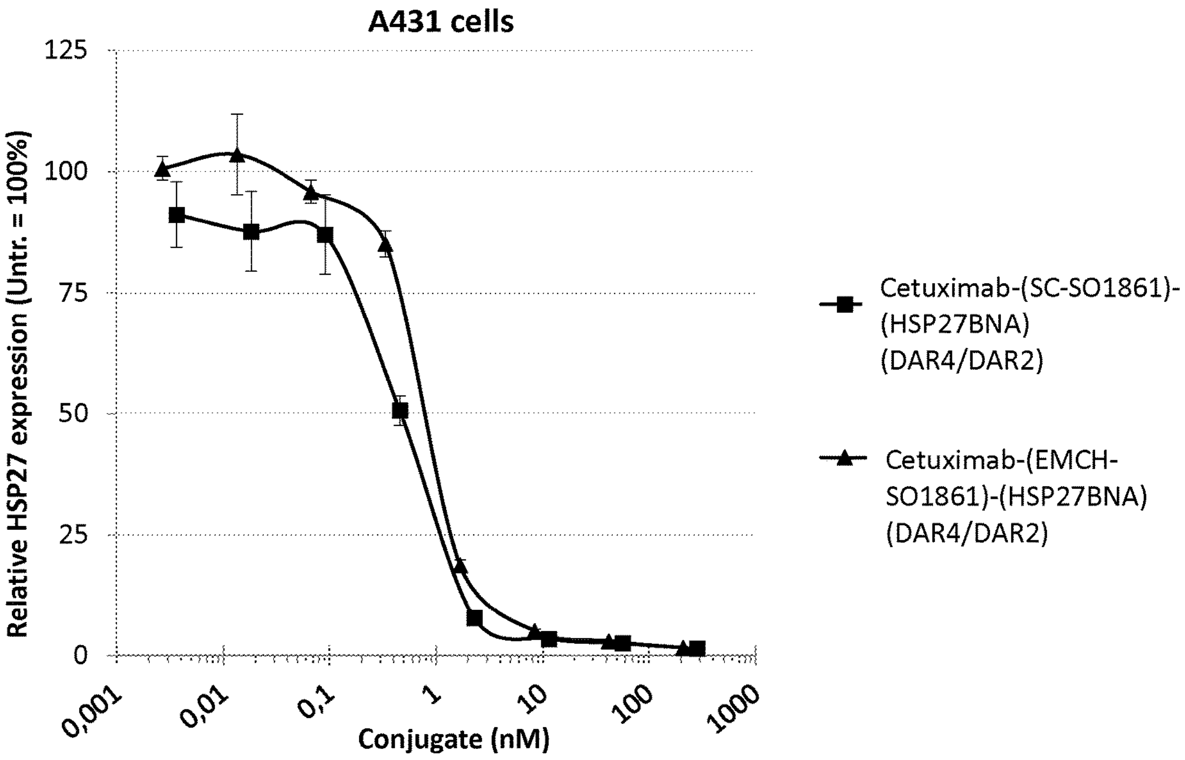
FIG. 18: HSP27 mRNA expression levels in A431 cells. Displayed is the relative HSP27 expression in A431 cells contacted with Cetuximab-(SC-SO1861)-HSP27 (DAR4/DAR2) and Cetuximab-(EMCH-SO1861)-HSP27 (DAR4/DAR2). The conjugates comprise two BNA molecules (DAR 2) and four SO1861 moieties (DAR 4).

Cetuximab-(SC-SO1861)-(HSP27BNA) (DAR4 for the SO1861 moieties/DAR2 for the HSP27 BNA molecule) (FIG. 40) and Cetuximab-(EMCH-SO1861)-(HSP27BNA) (DAR4 for SO1861/DAR2 for the BNA) were produced and potency compared on A431 cells ($EGFR^{++}$). This revealed that Cetuximab-(SC-SO1861)-(HSP27BNA) (DAR4/DAR2) showed improved potency (IC50=0.5 nM) compared to Cetuximab-(EMCH-SO1861)-(HSP27BNA) (DAR4/DAR2) (IC50=1 nM), indicating that after uptake of the conjugate upon binding of the antibody to the target cell-receptor, in the endosome improved release of SO1861 from the antibody enhances the potency of the Cetuximab-(SC-SO1861)-(HSP27BNA) conjugate (DAR4/DAR2) (FIG. 18).

Example 2

Materials and Methods

Abbreviations

- AEM N-(2-Aminoethyl)maleimide trifluoroacetate salt
- AMPD 2-Amino-2-methyl-1,3-propanediol
- BOP (Benzotriazol-1-yloxy)tris(dimethylamino)phosphonium hexafluorophosphate
- DIPEA N,N-diisopropylethylamine
- DMF N,N-dimethylformamide
- DTME dithiobismaleimidoethane
- DTT dithiothreitol
- EDCI·HCl 3-((ethylimino)methyleneamino)-N,N-dimethylpropan-1-aminium chloride
- EDTA ethylenediaminetetraacetic acid
- EMCH·TFA N-(ε-maleimidocaproic acid) hydrazide, trifluoroacetic acid salt
- HATU 1-[Bis(dimethylamino)methylene]-1H-1,2,3-triazolo[4,5-b]pyridinium 3-oxide hexafluorophosphate
- min minutes
- NMM 4-methylmorpholine
- r.t. retention time
- SEC size exclusion chromatography
- TBEU (Tris-(hydroxymethyl)-aminomethan)-Borat-EDTA-Urea
- TCEP tris(2-carboxyethyl)phosphine hydrochloride
- Temp temperature
- TFA trifluoroacetic acid
- TFL trifunctional linker Analytical Methods LC-MS Method 1

Apparatus: Waters IClass; Bin. Pump: UPIBSM, SM: UPISMFTN with SO; UPCMA, PDA: UPPDATC, 210-320 nm, SQD: ACQ-SQD2 ESI, mass ranges depending on the molecular weight of the product:

neg or neg/pos within in a range of 1500-2400 or 2000-3000; ELSD: gas pressure 40 psi, drift tube temp: 50° C.; column: Acquity C18, 50×2.1 mm, 1.7 μm Temp: 60° C., Flow: 0.6 mL/min, lin. Gradient depending on the polarity of the product:

$^{A}t_0$=2% A, $t_{5.0\ min}$=50% A, $t_{6.0\ min}$=98% A $^{B}t_0$=2% A, $t_{5.0\ min}$=98% A, $t_{6.0\ min}$=98% A Posttime: 1.0 min, Eluent A: acetonitrile, Eluent B: 10 mM ammonium bicarbonate in water (pH=9.5).

LC-MS Method 2

Apparatus: Waters IClass; Bin. Pump: UPIBSM, SM: UPISMFTN with SO; UPCMA, PDA: UPPDATC, 210-320 nm, SQD: ACQ-SQD2 ESI, mass ranges depending on the molecular weight of the product: pos/neg 100-800 or neg 2000-3000; ELSD: gas pressure 40 psi, drift tube temp: 50° C.; column: Waters XSelect™ CSH C18, 50×2.1 mm, 2.5 μm, Temp: 25° C., Flow: 0.5 mL/min, Gradient: $t_{0\ min}$=5% A, $t_{2.0\ min}$=98% A, $t_{2.7\ min}$=98% A, Posttime: 0.3 min, Eluent A: acetonitrile, Eluent B: 10 mM ammonium bicarbonate in water (pH=9.5).

LC-MS Method 3

Apparatus: Waters IClass; Bin. Pump: UPIBSM, SM: UPISMFTN with SO; UPCMA, PDA: UPPDATC, 210-320 nm, SQD: ACQ-SQD2 ESI, mass ranges depending on the molecular weight of the product pos/neg 105-800, 500-1200 or 1500-2500; ELSD: gas pressure 40 psi, drift tube temp: 50° C.; column: Waters XSelect™ CSH C18, 50×2.1 mm, 2.5 μm, Temp: 40° C., Flow: 0.5 mL/min, Gradient: $t_{0\ min}$=5% A, $t_{2.0\ min}$=98% A, $t_{2.7\ min}$=98% A, Posttime: 0.3 min, Eluent A: 0.1% formic acid in acetonitrile, Eluent B: 0.1% formic acid in water.

LC-MS Method 4

Apparatus: Waters IClass; Bin. Pump: UPIBSM, SM: UPISMFTN with SO; UPCMA, PDA: UPPDATC, 210-320 nm, SQD: ACQ-SQD2 ESI, mass ranges depending on the molecular weight of the product: pos/neg 100-800 or neg 2000-3000; ELSD: gas pressure 40 psi, drift tube temp: 50° C. column: Waters Acquity Shield RP18, 50×2.1 mm, 1.7 μm, Temp: 25° C., Flow: 0.5 mL/min, Gradient: $t_{0\ min}$=5% A, $t_{2.0\ min}$=98% A, $t_{2.7\ min}$=98% A, Posttime: 0.3 min, Eluent A: acetonitrile, Eluent B: 10 mM ammonium bicarbonate in water (pH=9.5).

Preparative Methods

Preparative MP-LC Method 1

Instrument type: Reveleris™ prep MPLC; column: Waters XSelect™ CSH C18 (145×25 mm, 10 μm); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient:

$^{A}t_{0\ min}$=5% B, $t_{1\ min}$=5% B, $t_{2\ min}$=10% B, $t_{17\ min}$=50% B, $t_{18\ min}$=100% B, $t_{23\ min}$=100% B $^{A}t_{0\ min}$=5% B, $t_{1\ min}$=5% B, $t_{2\ min}$=20% B, $t_{17\ min}$=60% B, $t_{18\ min}$=100% B, $t_{23\ min}$=100% B;

Detection UV: 210, 235, 254 nm and ELSD.

Preparative MP-LC Method 2

Instrument type: Reveleris™ prep MPLC; Column: Phenomenex LUNA C18(3) (150×25 mm, 10 μm); Flow: 40 mL/min; Column temp: room temperature; Eluent A: 0.1% (v/v) Formic acid in water, Eluent B: 0.1% (v/v) Formic acid in acetonitrile; Gradient:

$^{A}t_{0\ min}$=5% B, $t_{1\ min}$=5% B, $t_{2\ min}$=20% B, $t_{17\ min}$=60% B, $t_{18\ min}$=100% B, $t_{23\ min}$=100% B $^{B}t_{0\ min}$=2% B, $t_{1\ min}$=2% B, $t_{2\ min}$=2% B, $t_{17\ min}$=30% B, $t_{18\ min}$=100% B, $t_{23\ min}$=100% B $^{C}t_{0\ min}$=5% B, $t_{1\ min}$=5% B, $t_{2\ min}$=10% B, $t_{17\ min}$=50% B, $t_{18\ min}$=100% B, $t_{23\ min}$=100% B $^{D}t_{0\ min}$=5% B, $t_{1\ min}$=5% B, $t_{2\ min}$=5% B, $t_{17\ min}$=40% B, $t_{18\ min}$=100% B, $t_{23\ min}$=100% B;

Detection UV: 210, 235, 254 nm and ELSD.

Preparative LC-MS Method 3

MS instrument type: Agilent Technologies G6130B Quadrupole; HPLC instrument type: Agilent Technologies 1290 preparative LC; Column: Waters XSelect™ CSH (C18, 150×19 mm, 10 μm); Flow: 25 ml/min; Column temp: room temperature; Eluent A: 100% acetonitrile; Eluent B: 10 mM ammonium bicarbonate in water pH=9.0; Gradient:

$^{A}t_{0}$=20% A, $t_{2.5\ min}$=20% A, $t_{11\ min}$=60% A, $t_{13\ min}$=100% A, $t_{17\ min}$=100% A $^{B}t_{0}$=5% A, $t_{2.5\ min}$=5% A, $t_{11\ min}$=40% A, $t_{13\ min}$=100% A, $t_{17\ min}$=100% A;

Detection: DAD (210 nm); Detection: MSD (ESI pos/neg) mass range: 100-800; Fraction collection based on DAD.

Preparative LC-MS Method 4

MS instrument type: Agilent Technologies G6130B Quadrupole; HPLC instrument type: Agilent Technologies 1290 preparative LC; Column: Waters XBridge Protein (C4, 150×19 mm, 10 μm); Flow: 25 ml/min; Column temp: room temperature; Eluent A: 100% acetonitrile; Eluent B: 10 mM ammonium bicarbonate in water pH=9.0; Gradient:

$^{A}t_{0}$=2% A, $t_{2.5\ min}$=2% A, $t_{11\ min}$=30% A, $t_{13\ min}$=100% A, $t_{17\ min}$=100% A $^{B}t_{0}$=10% A, $t_{2.5\ min}$=10% A, $t_{11\ min}$=50% A, $t_{13\ min}$=100% A, $t_{17\ min}$=100% A $^{C}t_{0}$=5% A, $t_{2.5\ min}$=5% A, $t_{11\ min}$=40% A, $t_{13\ min}$=100% A, $t_{17\ min}$=100% A;

Detection: DAD (210 nm); Detection: MSD (ESI pos/neg) mass range: 100-800; Fraction collection based on DAD Flash Chromatography Grace Reveleris X2® C-815 Flash; Solvent delivery system: 3-piston pump with auto-priming, 4 independent channels with up to 4 solvents in a single run, auto-switches lines when solvent depletes; maximum pump flow rate 250 mL/min; maximum pressure 50 bar (725 psi); Detection: UV 200-400 nm, combination of up to 4 UV signals and scan of entire UV range, ELSD; Column sizes: 4-330 g on instrument, luer type, 750 g up to 3000 g with optional holder.

UV-Vis Spectrophotometry

Protein concentrations were determined using a Thermo Nanodrop 2000 spectrometer and the following mass ε280 values ((mg/ml)-1 cm-1); Oligo concentrations were determined using a molar ε260 value of 153,000 M-1 cm-1.

Ellman's assay was carried out using a Perkin Elmer Lambda 25 Spectrophotometer and a literature molar ε412 value of 14150 M-1 cm-1 for TNB. Experimentally determined molar ε495=58,700 M-1 cm-1 and Rz280:495=0.428 were used for SAMSA-fluorescein.

SEC

The conjugates were analysed by SEC using an Akta purifier 10 system and Biosep SEC-s3000 column eluting with DPBS:IPA (85:15). Conjugate purity was determined by integration of the Conjugate peak with respect to impurities/aggregate forms.

SDS-PAGE and Western Blotting

Native proteins and conjugates were analysed under heat denaturing non-reducing and reducing conditions by SDS-PAGE against a protein ladder using a 4-12% bis-tris gel and MES as running buffer (200V, ~40 minutes). Samples were prepared to 0.5 mg/ml, comprising LDS sample buffer and MOPS running buffer as diluent. For reducing samples, DTT was added to a final concentration of 50 mM. Samples were heat treated for 2 minutes at 90-95° C. and 5 μg (10 μl) added to each well. Protein ladder (10 μl) was loaded without pre-treatment. Empty lines were filled with 1×LDS sample buffer (10 μl). After the gel was run, it was washed thrice with DI water (100 ml) with shaking (15 minutes, 200 rpm). Coomassie staining was performed by shaker-incubating the gel with PAGEBlue protein stain (30 ml) (60 minutes, 200 rpm). Excess staining solution was removed, rinsed twice with DI water (100 ml) and destained with DI water (100 ml) (60 minutes, 200 rpm). The resulting gel was imaged and processed using ImageJ (Rasband, W. S., ImageJ, U. S. National Institutes of Health, Bethesda, Maryland, USA).

TBEU-PAGE

Native protein, conjugates and BNA standard were analysed under heat denaturing non-reducing and reducing conditions by TBEU-PAGE against an oligo ladder using a 15% TBE-Urea gel and TBE as running buffer (180V, ~60 minutes). Samples were prepared to 0.5 mg/ml, and BNA standard was prepared to 20 μg/ml, respectively, all comprising TBE Urea sample buffer and purified $H_2O$ as diluent. Samples and standards were heat treated for 3 minutes at 70° C. and 10 μl added to each well, equating to 5 μg of protein and conjugate samples, and 0.2 μg of BNA, per lane. Oligo ladder reconstituted to 0.1 μg/band/ml in TE pH 7.5 (2 μl) was loaded without pre-treatment. After the gel was run, it was stained with freshly prepared ethidium bromide solution (1 μg/ml) with shaking (40 minutes, 200 rpm). The resulting gel was visualised by UV epi-illumination (254 nm), imaged and processed using ImageJ.

MALDI-TOF-MS

MALDI-TOF spectra were recorded on a MALDI-Mass Spectrometer (Bruker Ultrafex III). Typically, the sample dissolved in MilliQ water in nanomolar to micromolar range was spotted on the target (MTP 384 target plate polished steel T F, Bruker Daltons) using either super-DHB (99%, Fluka) or sinapinic acid (SA, 99%, Sigma-Aldrich) as the matrix dissolved in acetonitrile (MADLI-TOF-MS tested, Sigma)/0.1% TFA (7:3 v/v) via the dried-droplet-method. PepMix (Peptide Calibration Standard, Bruker Daltons) or ProteMass (Protein Calibration Standard, Sigma-Aldrich) served as calibration standards.

Figure 31:
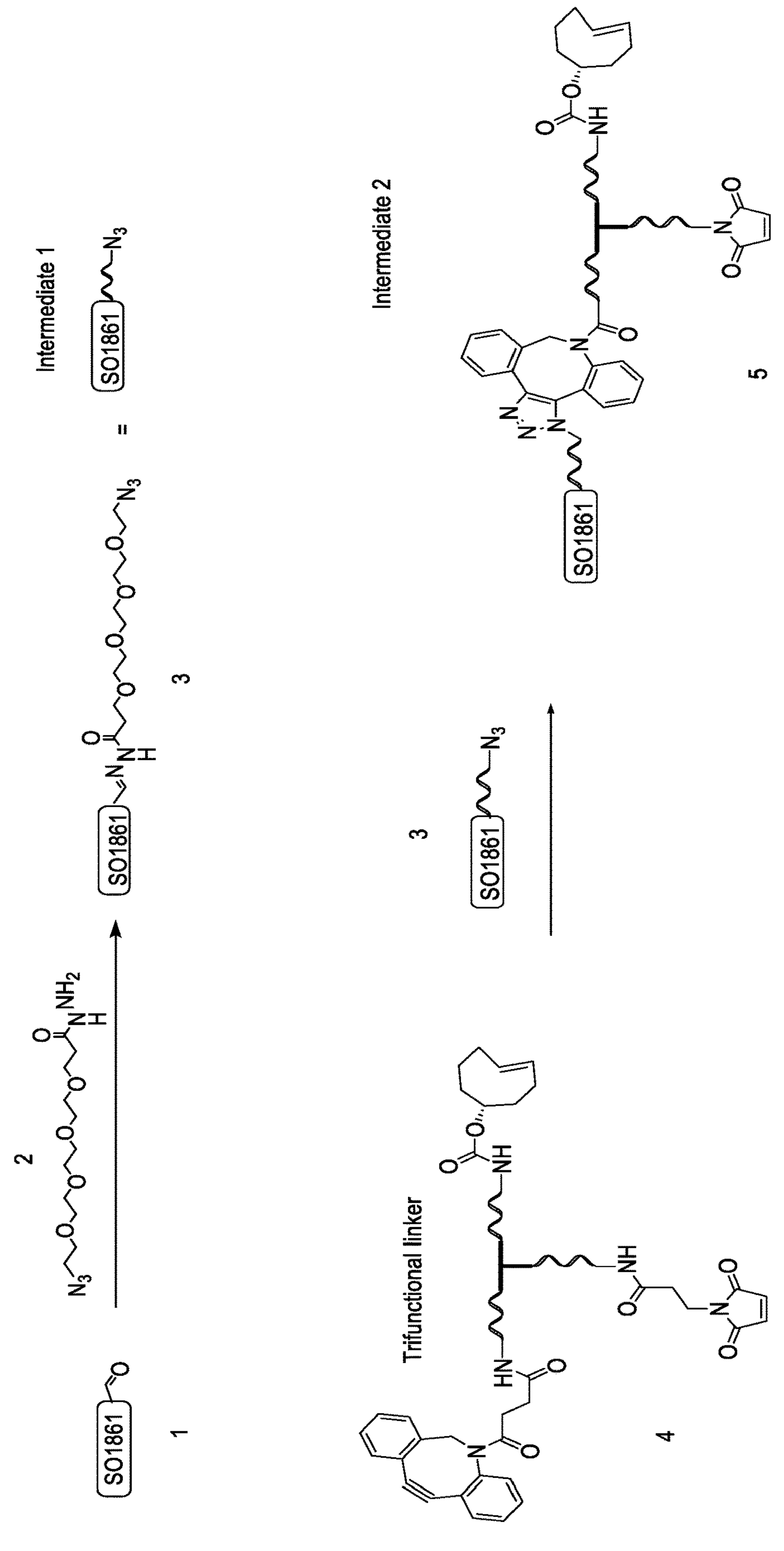
FIG. 31A-D: Trifunctional linker-(L-hydrazone-SO1861)-(L-BNA oligo)-(Trivalent-GalNAc) synthesis
Figure 31:
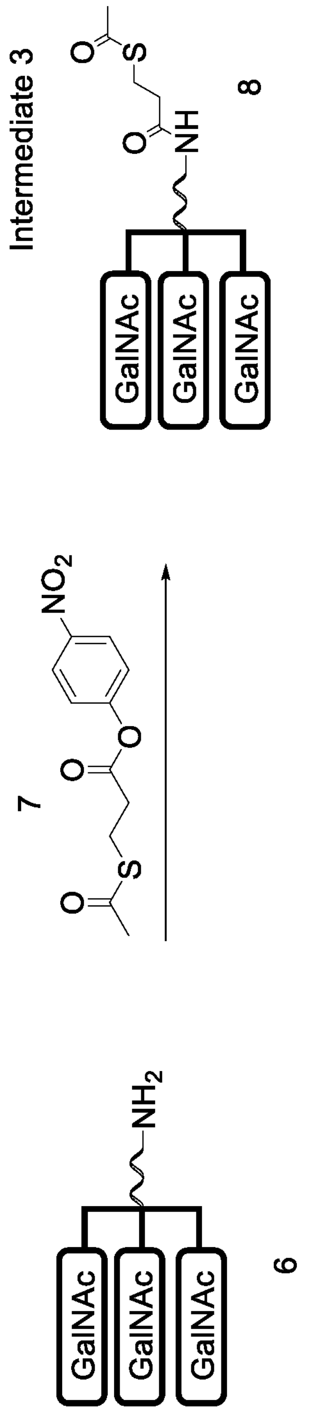
Figure 31:
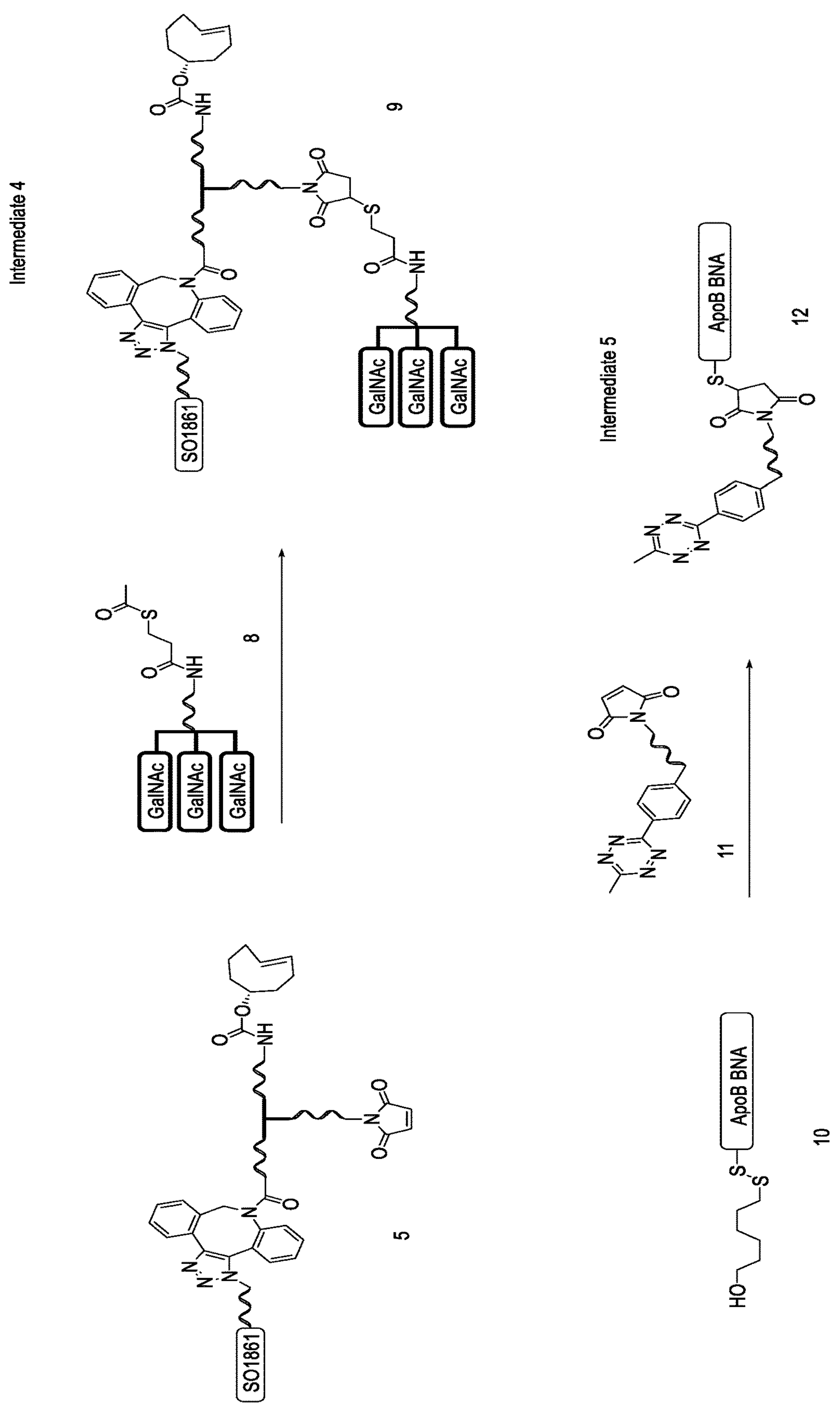
Figure 31:
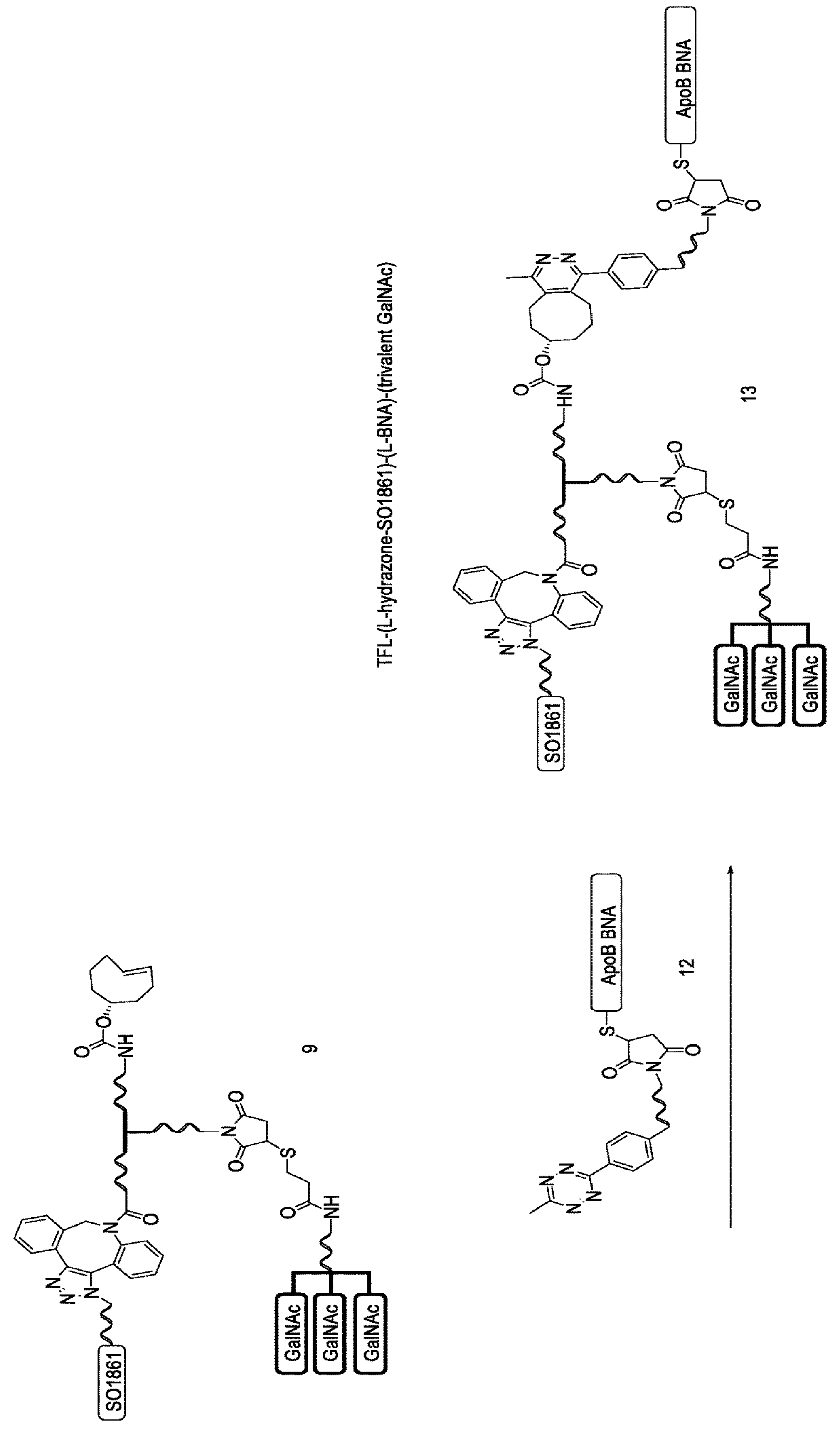

Trifunctional Linker-(L-Hydrazone-SO1861)-(L-BNA oligo)-(Trivalent-GalNAc) Synthesis (FIG. 31)

The trifunctional linker (TFL) has the IUPAC name: 5,8,11,18,21,24,27-Heptaoxa-2,14,30-triazatritriacontanoic acid, 14-[16-(11,12-didehydrodibenz[b,f]azocin-5(6H)-yl)-13,16-dioxo-3,6,9-trioxa-12-azahexadec-1-yl]-33-(2,5-dihydro-2,5-dioxo-1H-pyrrol-1-yl)-15,31-dioxo-, (1R,4E)-4-cycloocten-1-yl ester. The trifunctional linker has the following formula (XXI):

(XXI)

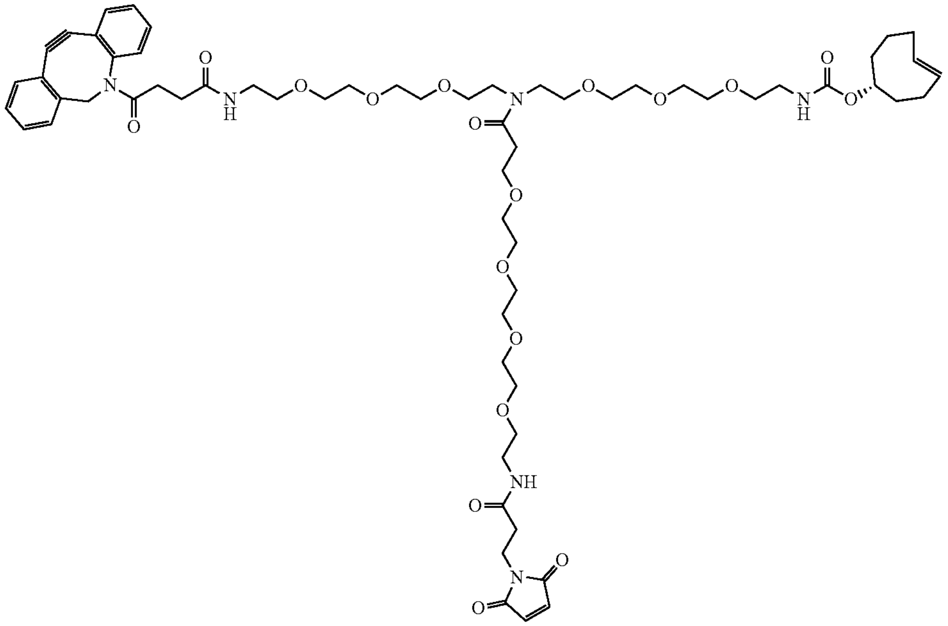

Intermediate 1

SO1861-L-Hydrazone-Azide (Molecule 3)

To SO1861 (60 mg, 0.032 mmol, molecule 1) and 1-azido-3,6,9,12-tetraoxapentadecane-15-hydrazide (39.3 mg, 0.129 mmol, molecule 2) was added methanol (extra dry, 1.00 mL) and TFA (9.86 μl, 0.129 mmol) and the reaction mixture was shaken for 1 min and left standing at room temperature. After 2 hours the reaction mixture was subjected to preparative MP-LC.[1] Fractions corresponding to the product were immediately pooled together, frozen and lyophilized overnight to give the title compound (58.4 mg, 84%) as a white fluffy solid. Purity based on LC-MS 99%.

LRMS (m/z): 2150 $[M-H]^{1-}$

LC-MS r.t. (min): 1.10[3B]

Intermediate 2

Trifunctional Linker-(L-Hydrazone-SO1861)-(TCO)-(Maleimide) (Molecule 5)

A solution of TFL-(DBCO)-(TCO)-(Maleimide) (15 mg, 12.5 μmol, molecule 4) in DMF (2.0 mL) was added to SO1861-L-hydrazone-azide (26.8 mg, 12.5 μmol, molecule 3). The reaction mixture was shaken for 30 min and left standing at room temperature. After 30 min the reaction mixture was submitted to preparative MP-LC.[1C] Fractions corresponding to the product were immediately pooled together, frozen and lyophilized overnight to give the title compound (31.4 mg, 75%) as a white fluffy solid. Purity based on LC-MS 96%.

MS (m/z): 3354 $[M-H]^{1-}$

Intermediate 3

Trivalent GalNAc-Thioacetate (Molecule 8)

Trivalent GalNAc-amine formate (18.7 mg, 11.0 μmol, molecule 6) and 4-nitrophenyl 3-(acetylthio)propanoate (5.90 mg, 21.9 μmol, molecule 7) were dissolved in a solution of NMM (2.41 μL, 21.9 μmol) in DMF (0.50 mL). The reaction mixture was shaken for 1 min and left standing at room temperature. After 2 hours the reaction mixture was evaporated in vacuo and the residue was dissolved in a mixture of 0.1% formic acid in water and 0.1% formic acid in acetonitrile (9:1, v/v, 1 mL). The resulting solution was directly subjected to preparative MP-LC.[2B] Fractions corresponding to the product were immediately pooled together, frozen and lyophilized overnight to give the title compound (13.0 mg, 66%) as a white solid. Purity based on LC-MS 100%.

LRMS (m/z): 1749 $[M-43]^{1-}$, 1792 $[M-H]^{1}$

LC-MS r.t. (min): 1.24[1B]

Intermediate 4

Trifunctional Linker-(L-SO1861)-(TCO)-(Trivalent GalNAc) (Molecule 9)

Trivalent GalNAc-thioacetate (13.0 mg, 7.25 μmol, molecule 8) was dissolved in methanol (0.50 mL). Next, a 1 M solution of sodium hydroxide (7.98 μL, 7.98 μmol) was added. The reaction mixture was shaken for 1 min and left standing at room temperature. After 30 min the reaction mixture was added to a freshly prepared solution of TFL-(DBCO)-(TCO)-(Maleimide) (20.6 mg, 6.13 μmol, molecule 5) in 20 mM ammonium bicarbonate/acetonitrile (3:1, v/v, 2.00 mL).

The resulting mixture was shaken for 1 min and left standing at room temperature. After 2 hours the reaction mixture was subjected to preparative MP-LC.[2A] Fractions corresponding to the product were immediately pooled together, frozen and lyophilized overnight to give the title compound (3.83 mg, 21%) as a white solid. Purity based on LC-MS 89%.

MS (m/z): 5106 $[M+H]^{+}$

Intermediate 5

Methyltetrazine-L-ApoB BNA Oligo (Molecule 12)

To ApoB BNA oligo disulfide (3.3 mg, 0.686 μmol, molecule 10) was added a solution of 20 mM ammonium bicarbonate with 2.5 mM TCEP (1.00 mL, 2.5 μmol). The reaction mixture was shaken for 1 min and left standing at room temperature. After 1 hour the reaction mixture was filtered by using a centrifugal filter with a molecular weight cut-off of 3000 Da (5000×g for 30 min, 2×0.50 mL). Next, the residue solution was washed twice with a solution of 20 mM ammonium bicarbonate with 2.5 mM TCEP (0.50 mL), each time filtered under the same conditions described above. As next, the residue solution was diluted with 20 mM ammonium bicarbonate (1.50 mL) and the resulting mixture was directly added to a solution of (E)-1-(4-((2-(6-(2,5-dioxo-2,5-dihydro-1H-pyrrol-1-yl)hexanoyl)hydraziney-lidene)methyl)benzamido)-N-(4-(6-methyl-1,2,4,5-tetrazin-3-yl)benzyl)-3,6,9,12-tetraoxapentadecan-15-amide (1.36 mg, 1.73 μmol, molecule 11) in acetonitrile (0.5 mL). The reaction mixture was shaken for 1 min and left standing at room temperature. After 30 min the reaction mixture was frozen and lyophilized overnight to yield the crude title product as a pink fluffy solid. To the crude product was added a solution of 20 mM ammonium bicarbonate (1.50 mL) and the resulting suspension was filtered over a 0.45 μm syringe filter. The filtrate was lyophilized overnight to yield the title product (3.4 mg, 89%) as a pink fluffy solid. Purity based on LC-MS 90%.

MS (m/z): 5579 $[M+Na]^+$

Trifunctional Linker-(L-Hydrazone-SO1861)-(L-BNA Oligo)-(Trivalent GalNAc) (Molecule 13)

TFL-(L-hydrazone-SO1861)-(TCO)-(trivalent GalNAc) (16.1 mg, 3.15 μmol, molecule 9) and Methyltetrazine-BNA oligo (10.2 mg, 1.83 μmol, molecule 12) were dissolved in a solution of 20 mM ammonium bicarbonate/acetonitrile (3:1, v/v, 1.00 mL). The reaction mixture was shaken for 1 min and left standing at room temperature. After 3 hours the reaction mixture was frozen and lyophilized overnight. The crude product was dissolved in 20 mM ammonium bicarbonate (1 mL) and the resulting solution was directly subjected to preparative LC-MS.[1B] Fractions corresponding to the product were immediately pooled together, frozen and lyophilized overnight to give the title compound (27.2 mg, 81%) as a white fluffy solid. Purity based on LC-MS 91%.

MS (m/z): 10660 $[M+H]^+$

Using a similar approach as for synthesis of Trifunctional linker-(L-hydrazone-SO1861)-(L-BNA oligo)-(trivalent GalNAc) (molecule 13); a conjugate in which the ApoB BNA was replaced for a BNA with a scrambled ApoB nucleic acid sequence (molecule 12 a), was synthesized (molecule 13a).

Figure 32:
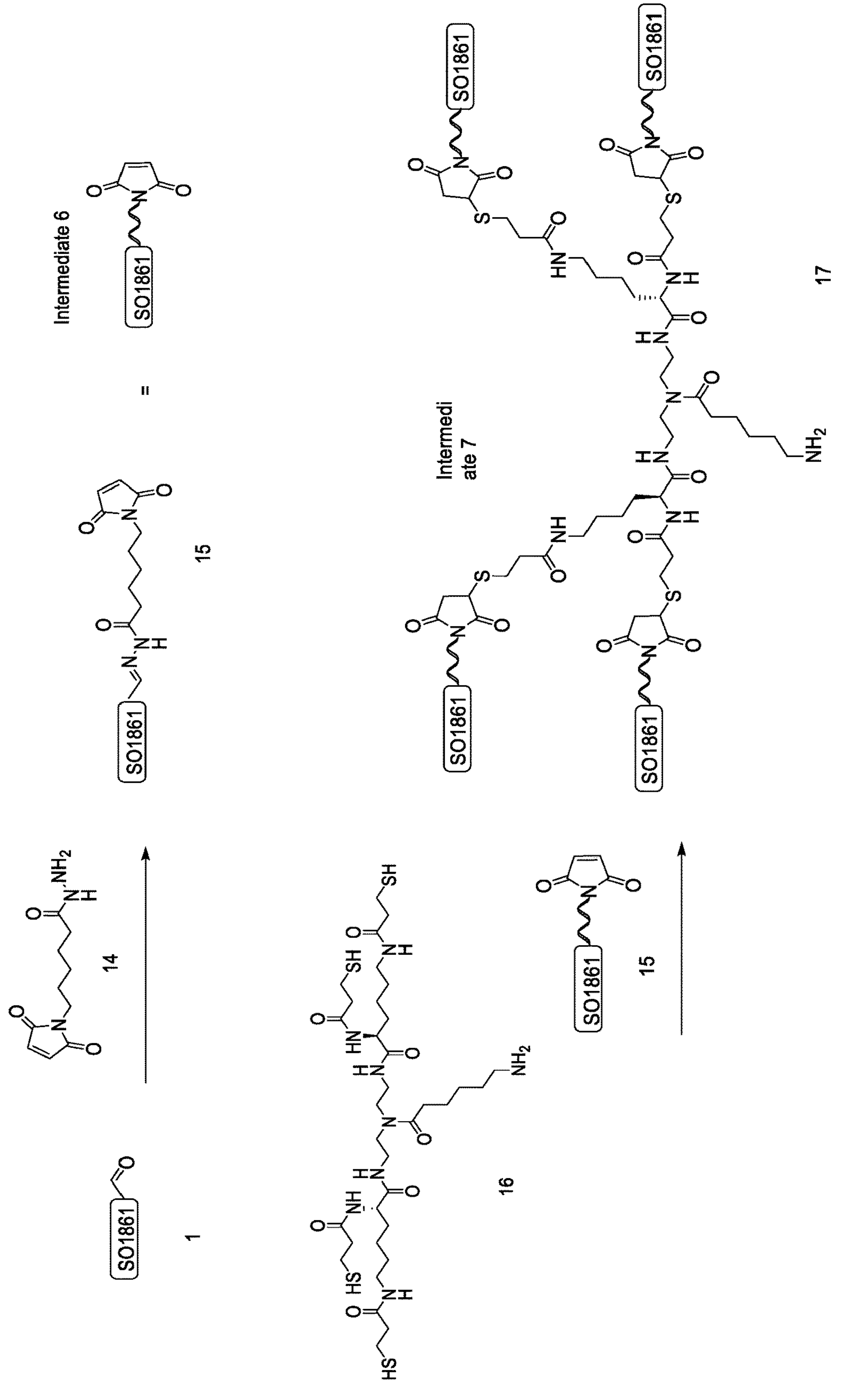
FIG. 32A-E: Trifunctional linker-(dendron(-L-hydrazone-SO1861)4)-(L-BNA oligo)-(Trivalent-GalNAc) synthesis. Note that the drawing of FIG. 32 E encompasses two sheets, labelled FIG. 32 E and FIG. 32 E (continued), which two sheets together display the conjugation of molecule 21 with molecule 19, therewith forming conjugate molecule 22.
Figure 32:
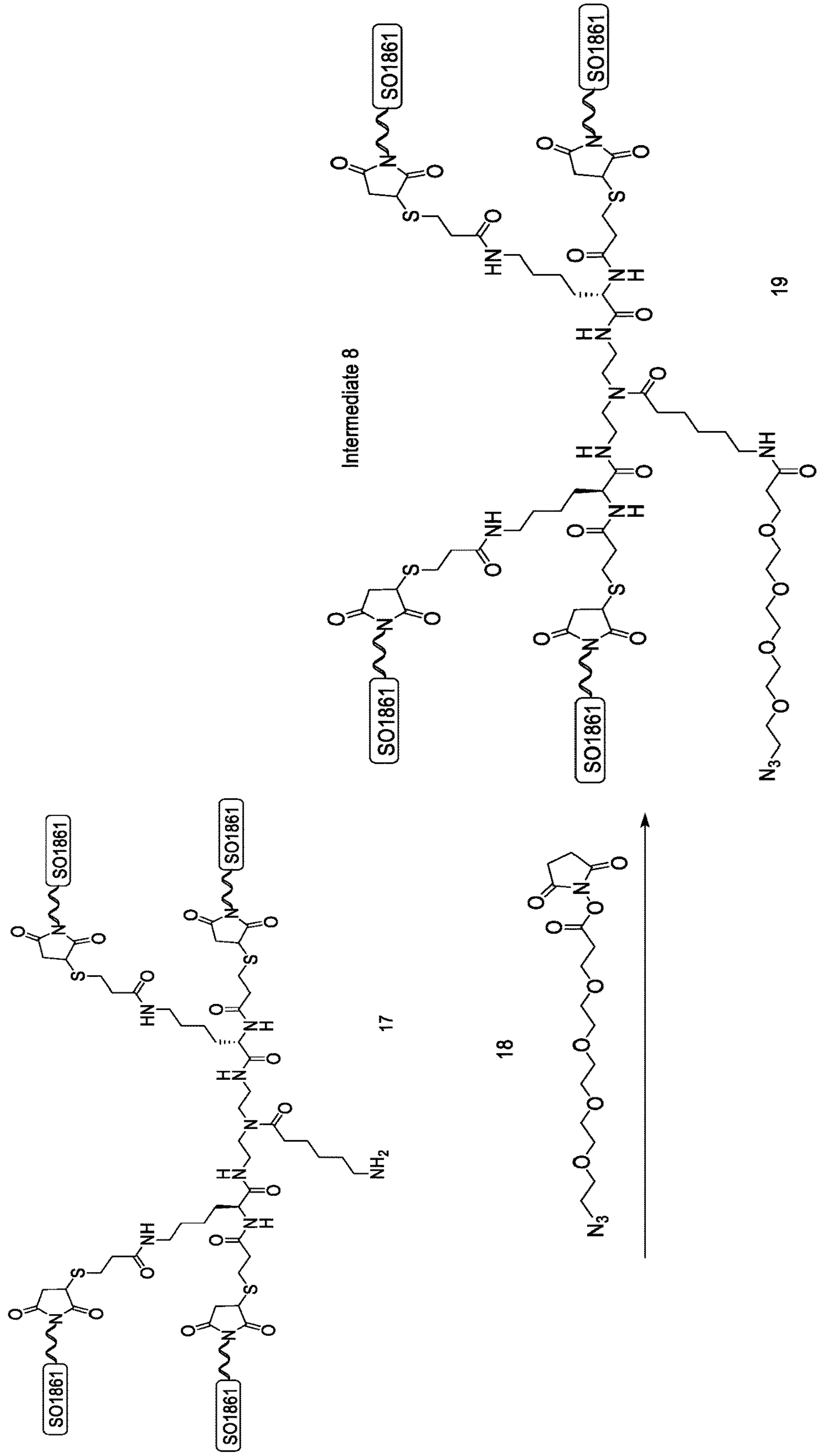
Figure 32:
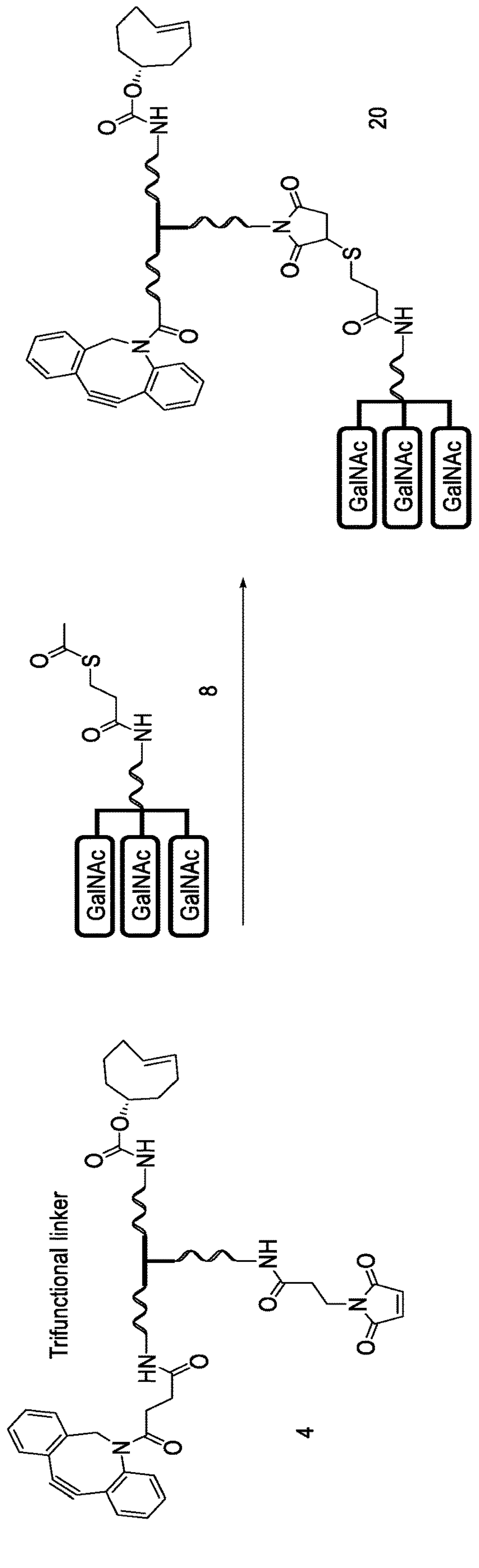
Figure 32:
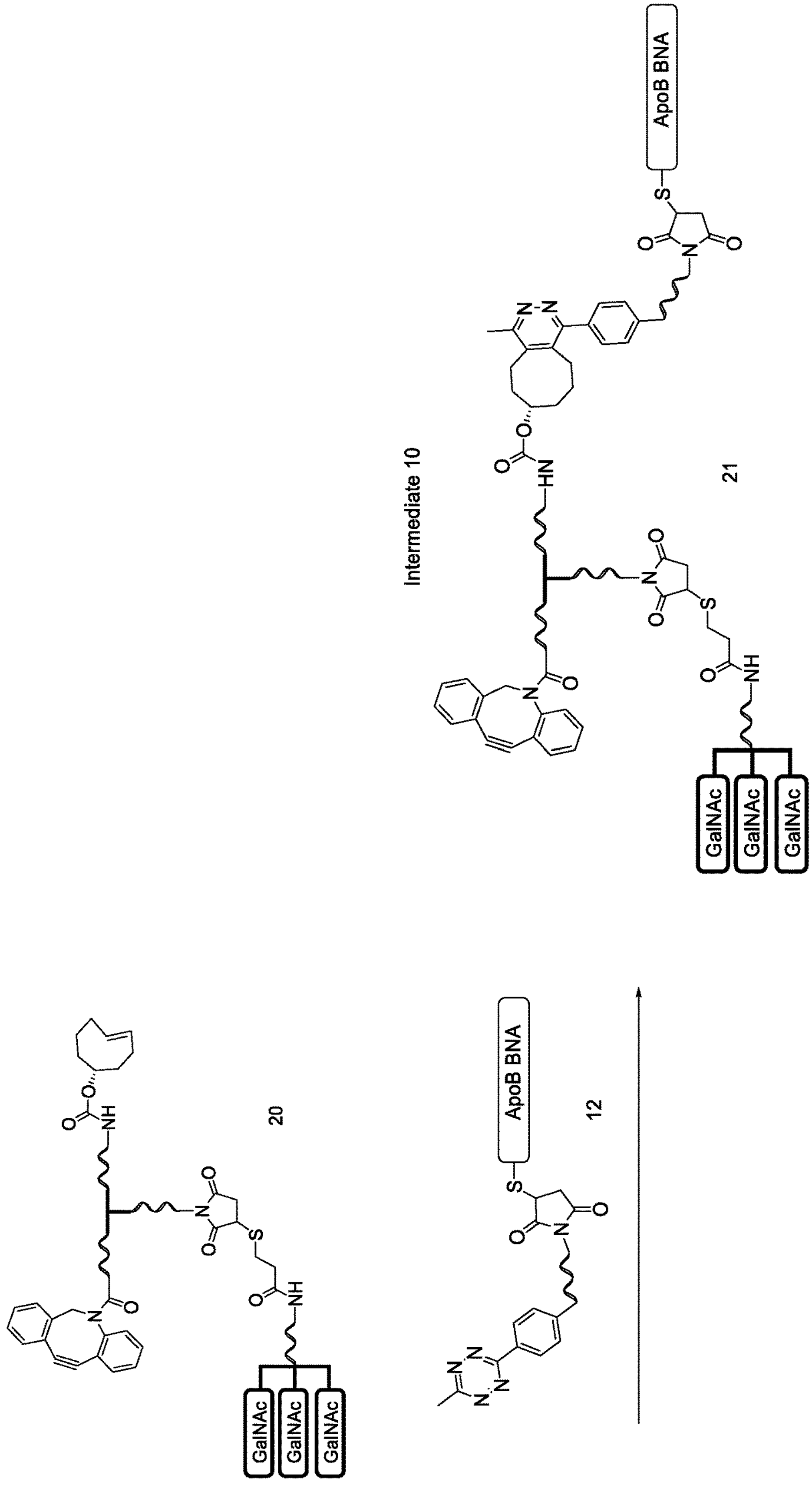
Figure 32:
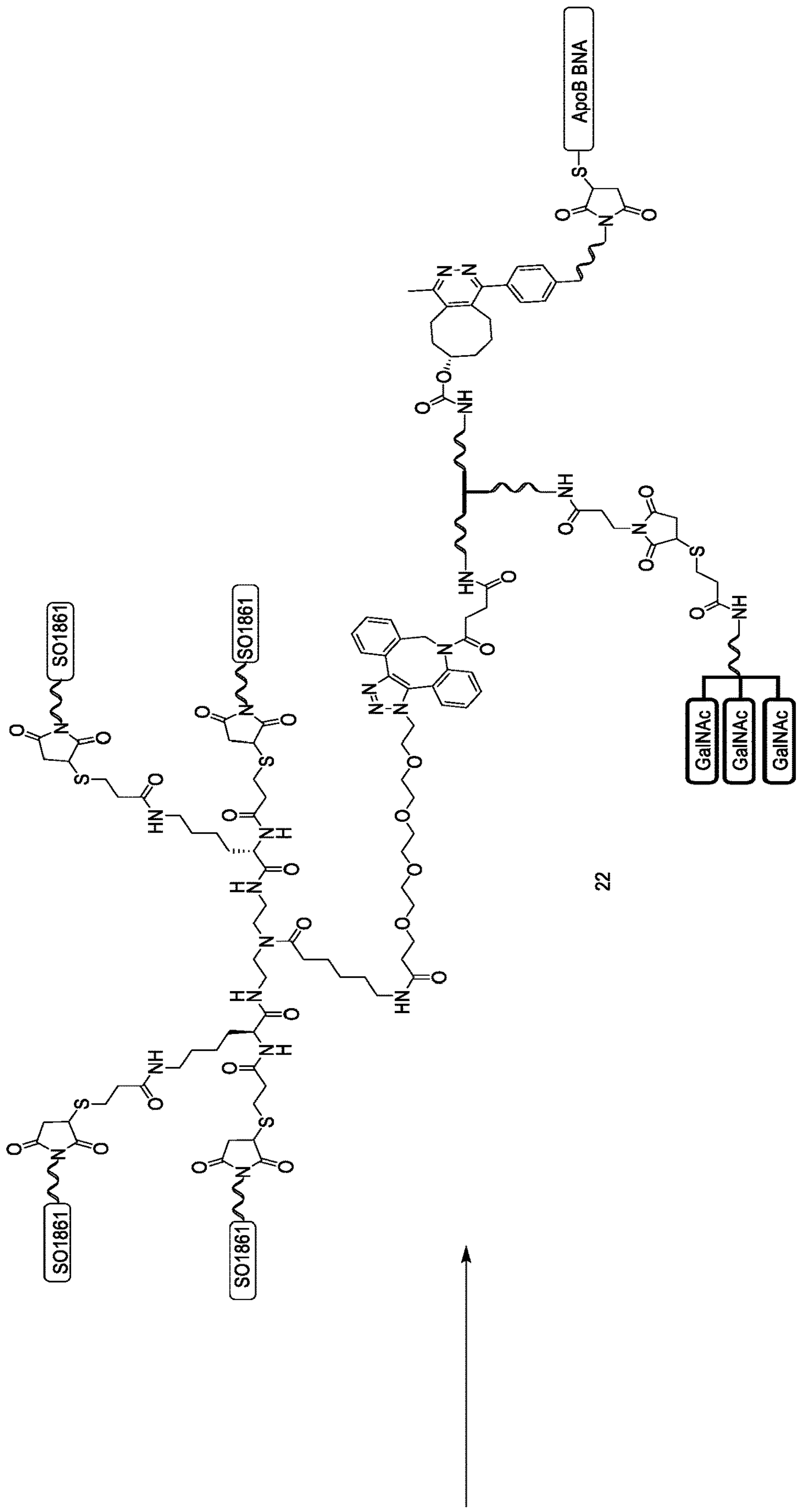
Figure 32:
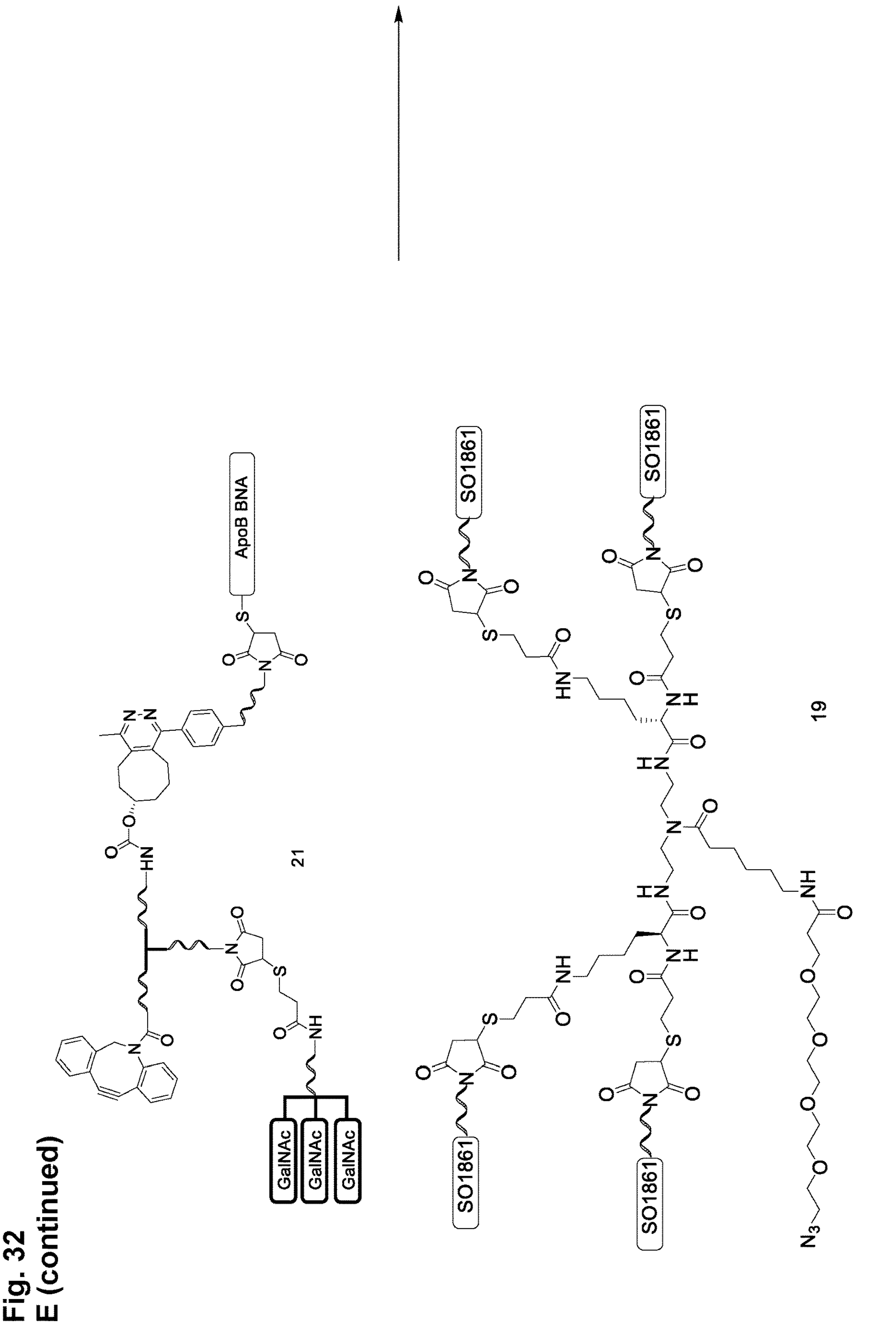

Trifunctional Linker-(dendron(-L-hydrazone-SO1861)4)-(L-BNA oligo)-(Trivalent-GalNAc) Synthesis (FIG. 32)

Intermediate 6

SO1861-EMCH (Molecule 15)

To SO1861 (121 mg, 0.065 mmol, molecule 1) and EMCH·TFA (110 mg, 0.325 mmol, molecule 14) was added methanol (extra dry, 3.00 mL) and TFA (0.020 mL, 0.260 mmol). The reaction mixture stirred at room temperature. After 1.5 hours the reaction mixture was subjected to preparative MP-LC.1 Fractions corresponding to the product were immediately pooled together, frozen and lyophilized overnight to give the title compound (120 mg, 90%) as a white fluffy solid. Purity based on LC-MS 96%.

LRMS (m/z): 2069 [M−1]1−

LC-MS r.t. (min): 1.084

Intermediate 7

Dendron(-L-SO1861)$_4$-Amine (Molecule 17)

N,N'-((9S,19S)-14-(6-aminohexanoyl)-1-mercapto-9-(3-mercaptopropanamido)-3,10,18-trioxo-4,11,14,17-tetraaza-tricosane-19,23-diyl)bis(3-mercaptopropanamide) formate (2.73 mg, 3.13 μmol, molecule 16) was dissolved in a mixture of 20 mM $NH_4HCO_3$ with 0.5 mM TCEP/acetonitrile (3:1, v/v, 3.00 mL). Next, SO1861-EMCH (29.2 mg, 0.014 mmol, molecule 15) was added and the reaction mixture was stirred at room temperature. After 1.5 hours the reaction mixture was subjected to preparative LC-MS.[3B] Fractions corresponding to the product were immediately pooled together, frozen and lyophilized overnight to give the title compound (12.3 mg, 43%) as a white fluffy solid. Purity based on LC-MS 97%.

LRMS (m/z): 1517 $[M-6]^{6-}$, 1821 $[M-5]^{5-}$, 2276 $[M-4]^{4-}$

LC-MS r.t. (min): 4.39[5A]

Intermediate 8

Dendron(-L-SO1861)$_4$-Azide (Molecule 19)

Dendron(SO1861)$_4$-amine (6.81 mg, 0.748 μmol, molecule 17) and 2,5-dioxopyrrolidin-1-yl 1-azido-3,6,9,12-tetraoxapentadecan-15-oate (2.90 mg, 7.48 μmol, molecule 18), were dissolved in DMF (1.00 mL). Next, DIPEA (1.302 μL, 7.48 μmol) was added and the mixture was shaken for 1 min and left standing at room temperature. After 2 hours the reaction mixture was subjected to preparative LC-MS.[3C] Fractions corresponding to the product were immediately pooled together, frozen and lyophilized overnight to give the title compound (5.86 mg, 84%) as a white fluffy solid. Purity based on LC-MS 90%.

LRMS (m/z): 2344 $[M-4]^{4-}$

LC-MS r.t. (min): 4.78[5B]

Intermediate 9

Trifunctional Linker (DBCO)-(TCO)-(Trivalent GalNAc) (Molecule 20)

Trivalent GalNAc-thioacetate (13.0 mg, 7.25 μmol, molecule 8) was dissolved in methanol (0.50 mL). Next, a 1 M solution of sodium hydroxide (7.98 μL, 7.98 μmol) was added. The reaction mixture was shaken for 1 min and left standing at room temperature. After 30 min the reaction mixture was added to a freshly prepared solution of trifunctional linker (7.39 mg, 6.13 μmol, molecule 4) in 20 mM ammonium bicarbonate/acetonitrile (3:1, v/v, 2.00 mL). The resulting mixture was shaken for 1 min and left standing at room temperature. After 2 hours the reaction mixture was subjected to preparative MP-LC.[2A] Fractions corresponding to the product were immediately pooled together, frozen and lyophilized overnight to give the title compound (3.83 mg, 21%) as a white solid. Purity based on LC-MS 89%.

LRMS (m/z): 2409 $[M-546]^{1-}$, 2955 $[M-1]^{1-}$

LC-MS r.t. (min): 2.66[1B]

Intermediate 10

Trifunctional Linker (DBCO)-(L-ApoB BNA Oligo)-(Trivalent GalNAc) (Molecule 21)

To methyltetrazine-L-ApoB BNA oligo (5.82 mg, 0.684 μmol, molecule 12) and TFL-(DBCO)-(TCO)-(trivalent GalNAc) (2.03 mg, 0.687 μmol, molecule 20) was added 20 mM ammonium bicarbonate/acetonitrile (3:1, v/v, 1.00 mL). The reaction mixture was shaken for 1 min and left standing at room temperature. After 2 hours the reaction mixture was subjected to preparative LC-MS.[4C] Fractions corresponding to the product were immediately pooled together, frozen and lyophilized overnight to give the title compound (3.73 mg, 64%) as a white fluffy solid. LC-MS shows multiple broad peaks with the correct m/z values.

MS (m/z): 8511 $[M+H]^+$

Trifunctional Linker (Dendron(-L-Hydrazone-SO1861)$_4$)-(L-ApoB BNA Oligo)-(Trivalent GalNAc Synthesis) (Molecule 22)

To TFL-(DBCO)-(L-ApoB BNA oligo)-(trivalent GalNAc) (1.16 mg, 0.137 μmol; molecule 21) and dendron(-L-SO1861)$_4$-azide (1.39 mg, 0.142 μmol; molecule 19) was added 20 mM ammonium bicarbonate/acetonitrile (3:1, v/v, 0.5 mL). The reaction mixture was shaken for 1 min and left standing at room temperature. After 3 hours the reaction mixture was subjected to preparative LC-MS.[4B] Fractions corresponding to the product were immediately pooled together, frozen and lyophilized overnight to give the title compound (1.36 mg, 54%) as a white fluffy solid. Purity based on LC-MS 92% (very broad peak).

MS (m/z): 18336 $[M+H]^+$

Using a similar approach as for synthesis of Trifunctional linker (Dendron(-L-hydrazone-SO1861)4)-(L-ApoB BNA oligo)-(trivalent GalNAc synthesis) (molecule 22); a conjugate in which the ApoB BNA was replaced for a BNA with a scrambled ApoB nucleic acid sequence (molecule 12 a), was synthesized (molecule 22a).

Figure 33:
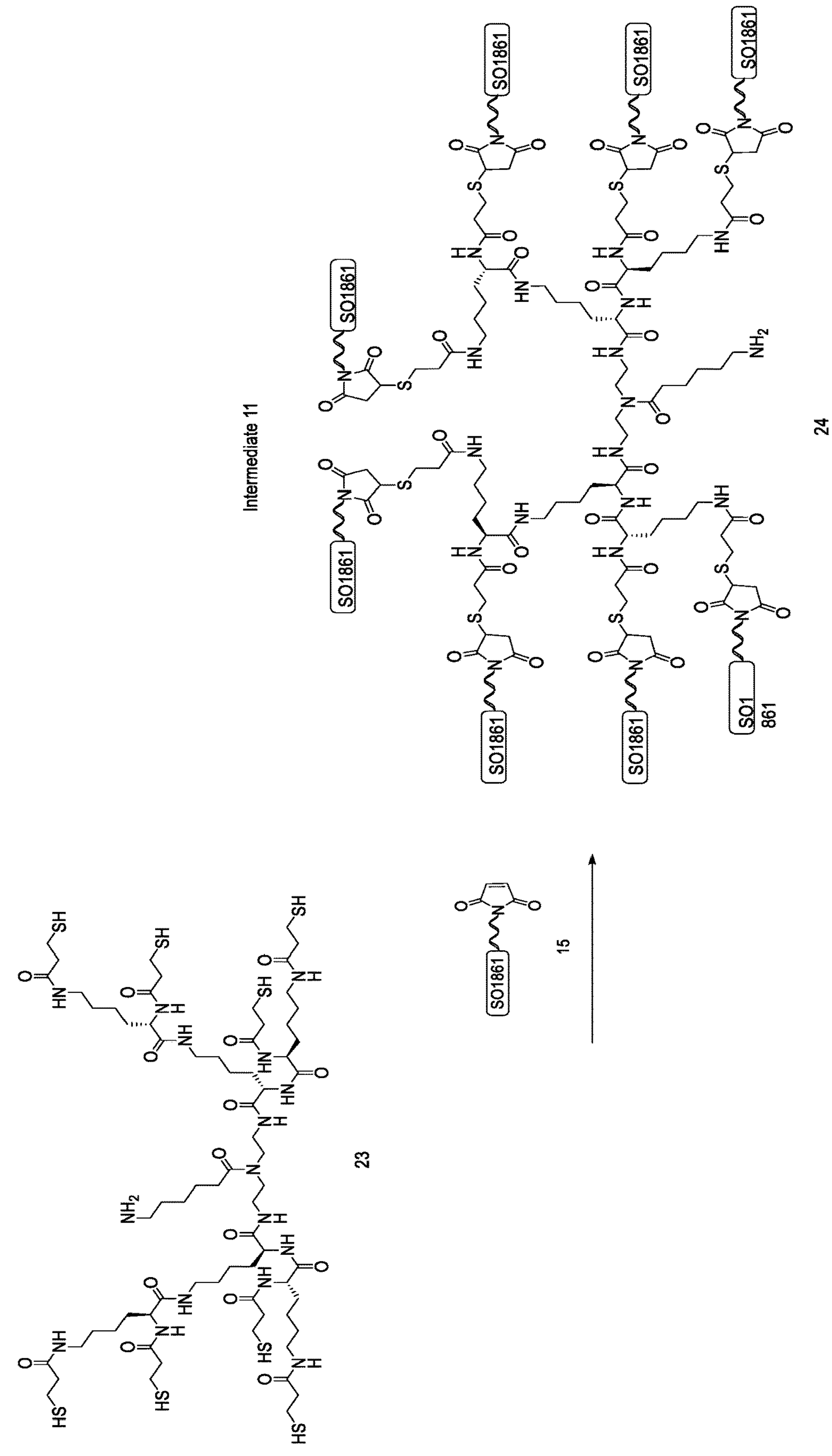
FIG. 33A-C: Trifunctional linker-(dendron(-L-hydrazone-SO1861)8)-(BNA oligo)-(Trivalent-GalNAc) synthesis. Note that the drawing of FIG. 33 B encompasses two sheets, labelled FIG. 33 B and FIG. 33 B (continued), which two sheets together display the conjugation of molecule 24 with molecule 18, therewith forming conjugate molecule 25 (intermediate 12). Note that the drawing of FIG. 33 C encompasses two sheets, labelled FIG. 33 C and FIG. 33 C (continued), which two sheets together display the conjugation of molecule 25 with molecule 21, therewith forming conjugate molecule 26.
Figure 33:
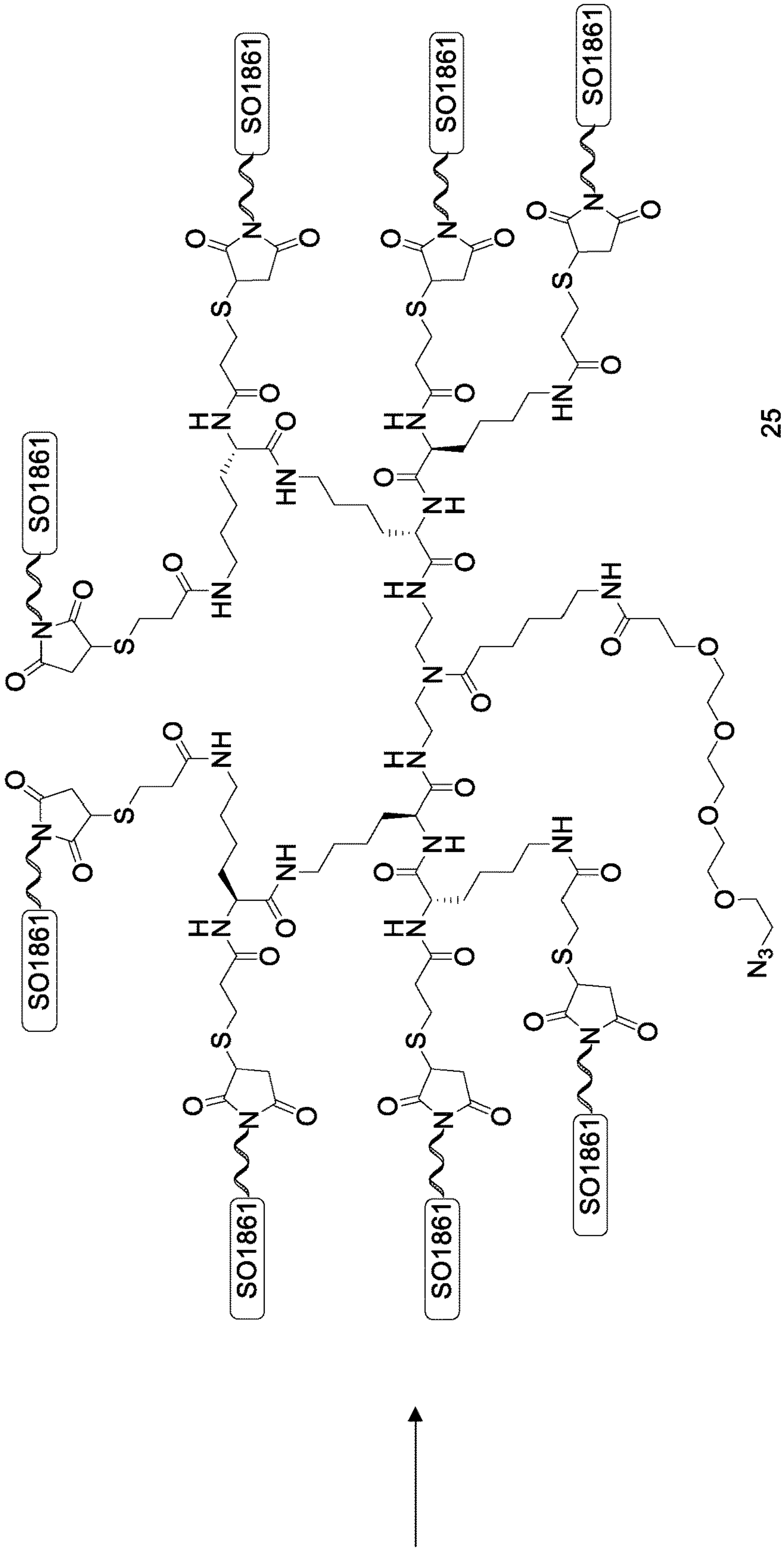
Figure 33:
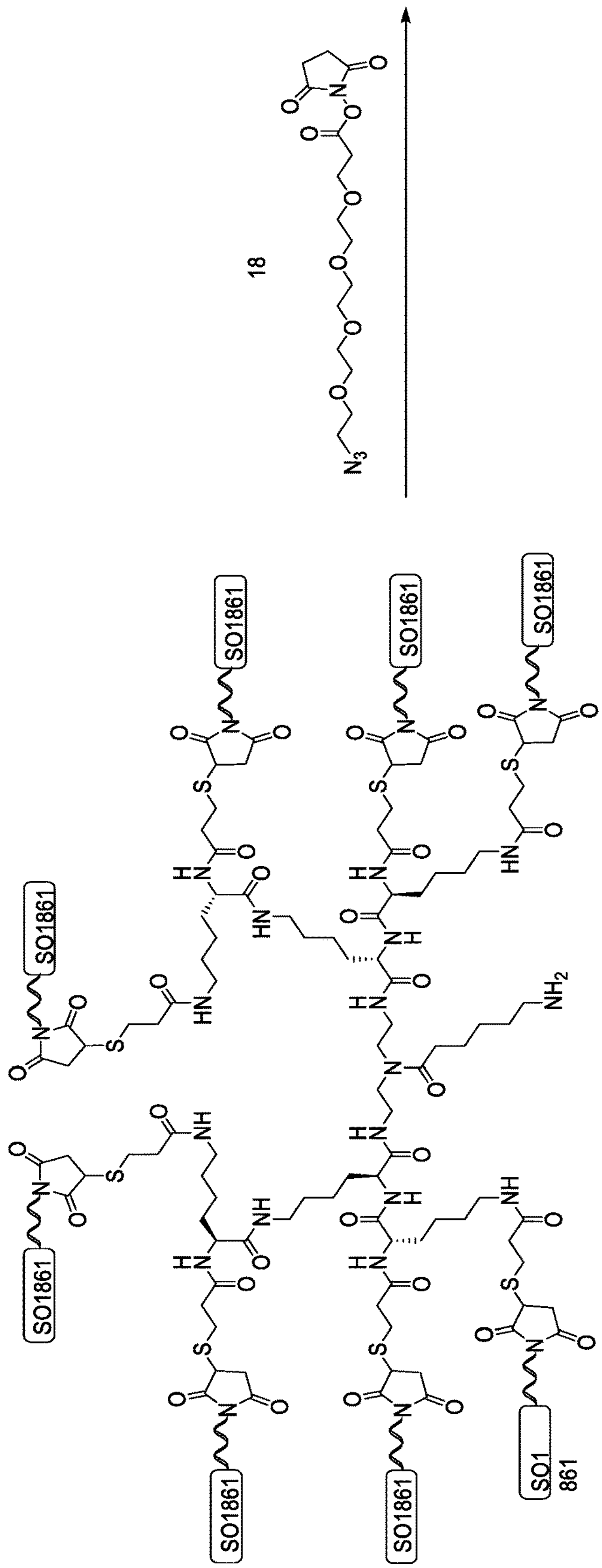
Figure 33:
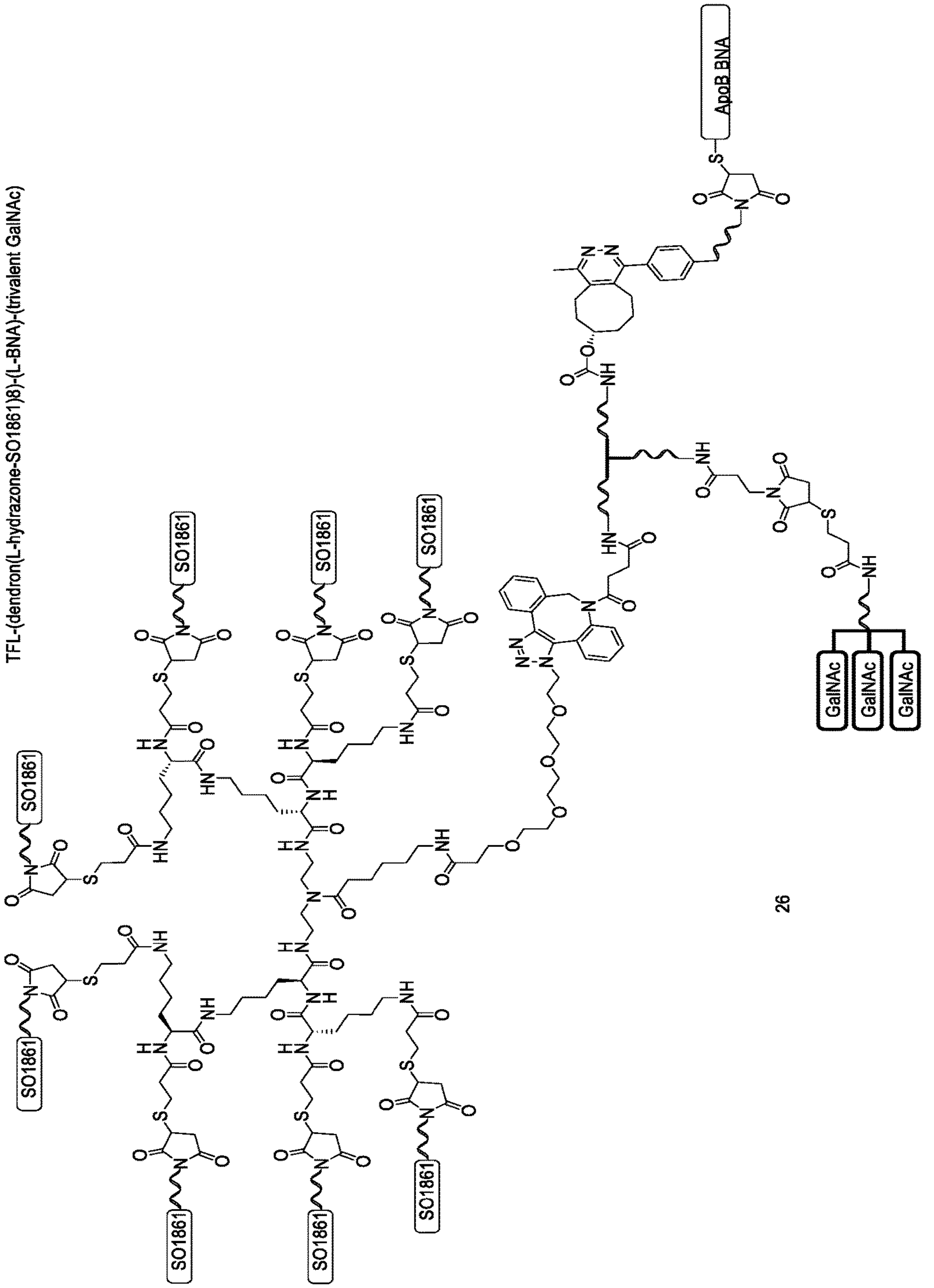
Figure 33:
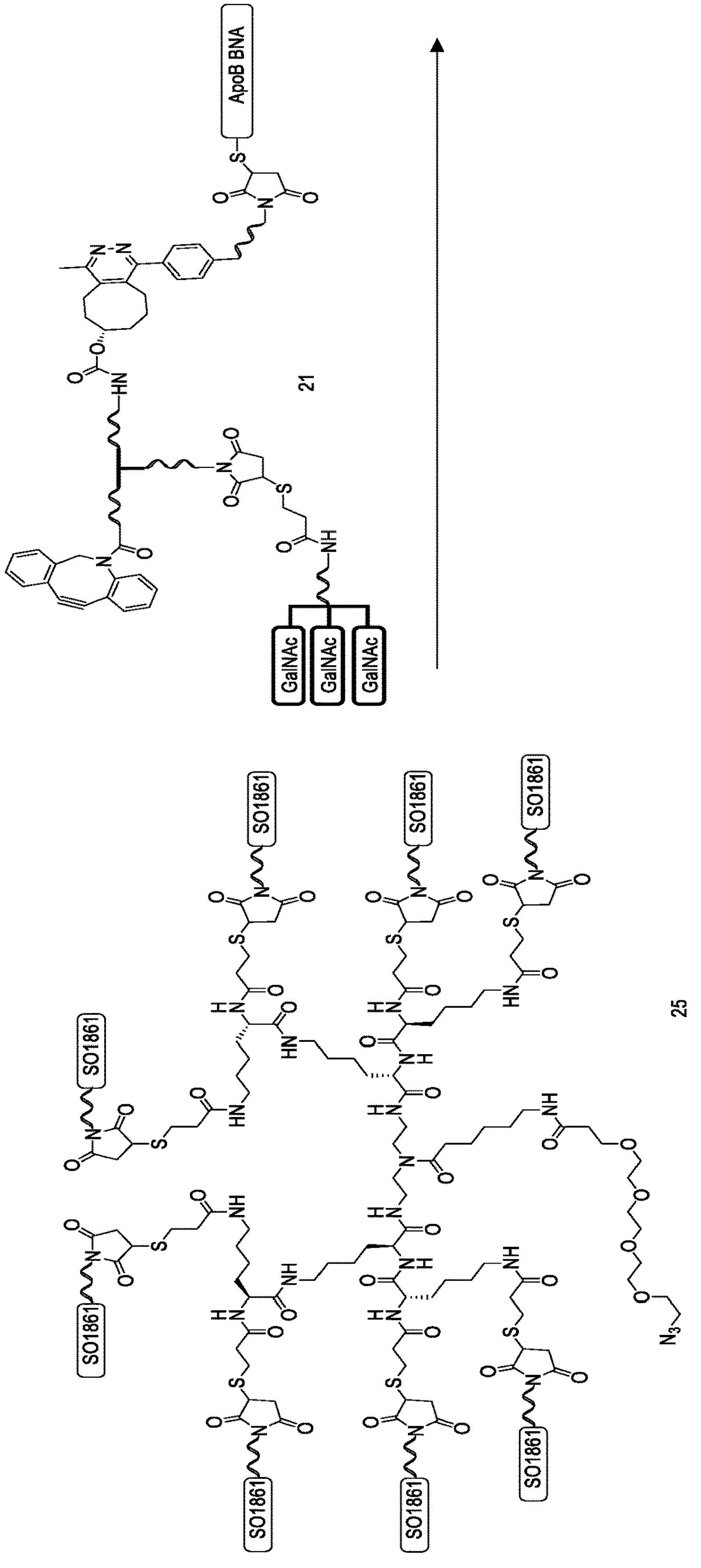

Trifunctional Linker-(Dendron(-L-Hydrazone-SO1861)8)-(BNA Oligo)-(Trivalent-GalNAc) Synthesis (FIG. 33)

Intermediate 11

Dendron(-L-SO1861)$_8$-Amine (Molecule 24)

(2S)—N-[(1 S)-1-{[2-(6-amino-N-{2-[(2S)-2,6-bis[(2S)-2,6-bis(3-sulfanylpropanamido)hexanamido]hexanamido] ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate (0.52 mg, 0.299 μmol, molecule 23) and SO1861-EMCH (29.2 mg, 0.014 mmol, molecule 15) were dissolved in a mixture of 20 mM $NH_4HCO_3$ with 0.5 mM TCEP/acetonitrile (3:1, v/v, 1.00 mL) and the resulting mixture was shaken for 1 min and left standing at room temperature. After 30 min TCEP (0.30 mg, 1.05 μmol) was added and the reaction mixture was shaken for 1 min. Next, the mixture was directly subjected to preparative LC-MS.[3B] Fractions corresponding to the product were immediately pooled together, frozen and lyophilized overnight to give the title compound (2.17 mg, 40%) as a white fluffy solid. Purity based on LC-MS 97%.

LRMS (m/z): 2282 $[M-8]^{8-}$, 2607 $[M-7]^{7-}$

LC-MS r.t. (min): 4.41[5A]

Intermediate 12

Dendron(-L-SO1861)$_8$-Azide (Molecule 25)

Dendron(-L-SO1861)$_8$-amine (19.6 mg, 1.08 μmol, molecule 24) and 2,5-dioxopyrrolidin-1-yl 1-azido-3,6,9,12-tetraoxapentadecan-15-oate (4.17 mg, 10.8 μmol, molecule 18) were dissolved in DMF (1.50 mL). Next, DIPEA (1.87 μL, 10.8 μmol) was added and the mixture was shaken for 1 min and left standing overnight at room temperature. The reaction mixture was subjected to preparative LC-MS.[4B] Fractions corresponding to the product were immediately pooled together, frozen and lyophilized overnight to give the title compound (11.7 mg, 59%) as a white fluffy solid. Purity based on LC-MS 92% (very broad peak).

LRMS (m/z): 2316 $[M-8]^{8-}$): 2647 $[M-7]^{7-}$

LC-MS r.t. (min): 4.29[1A]

Trifunctional Linker (Dendron(-L-Hydrazone-SO1861)$_8$)-(L-ApoB BNA Oligo)-(Trivalent GalNAc Synthesis) (Molecule 26)

To TFL-(DBCO)-(L-ApoB BNA oligo)-(trivalent GalNAc) (1.16 mg, 0.137 μmol; molecule 21) and dendron(-L-SO1861)$_8$-azide (2.72 mg, 0.142 μmol; molecule 25) was added 20 mM ammonium bicarbonate/acetonitrile (3:1, v/v, 0.5 mL). The reaction mixture was shaken for 1 min and left standing at room temperature. After 3 hours the reaction mixture was subjected to preparative LC-MS.[4B] Fractions corresponding to the product were immediately pooled together, frozen and lyophilized overnight to give the title compound (1.6 mg, 42%) as a white fluffy solid. Purity based on LC-MS 93% (very broad peak).

MS (m/z): 27655 $[M+H]^+$

Using a similar approach as for synthesis of Trifunctional linker (Dendron(-L-hydrazone-SO1861)8)-(L-ApoB BNA oligo)-(trivalent GalNAc synthesis) (molecule 26); a conjugate in which the ApoB BNA was replaced for a BNA with a scrambled ApoB nucleic acid sequence (molecule 12 a), was synthesized (molecule 26a).

Figure 34:
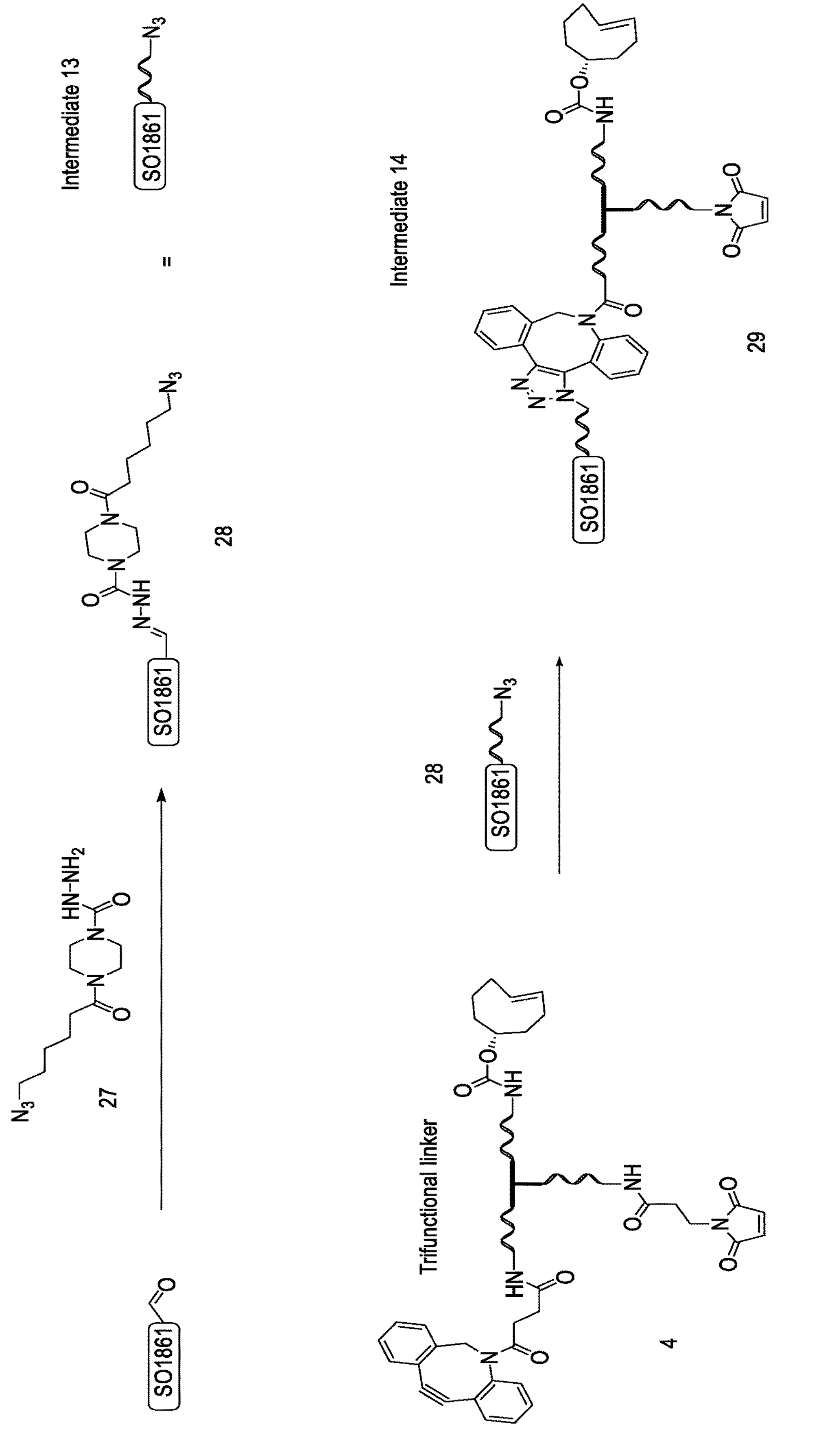
FIG. 34A-C: Trifunctional linker-(L-semicarbazone-SO1861)-(BNA oligo)-(Trivalent-GalNAc) synthesis.
Figure 34:
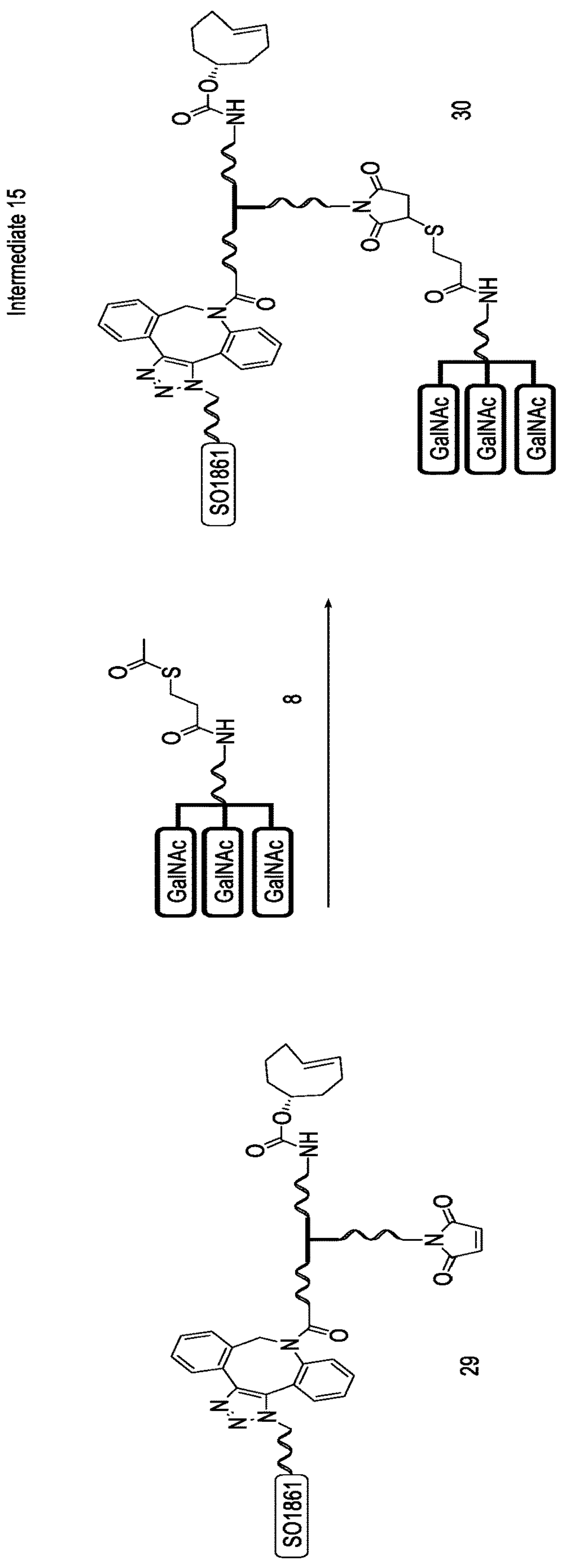
Figure 34:
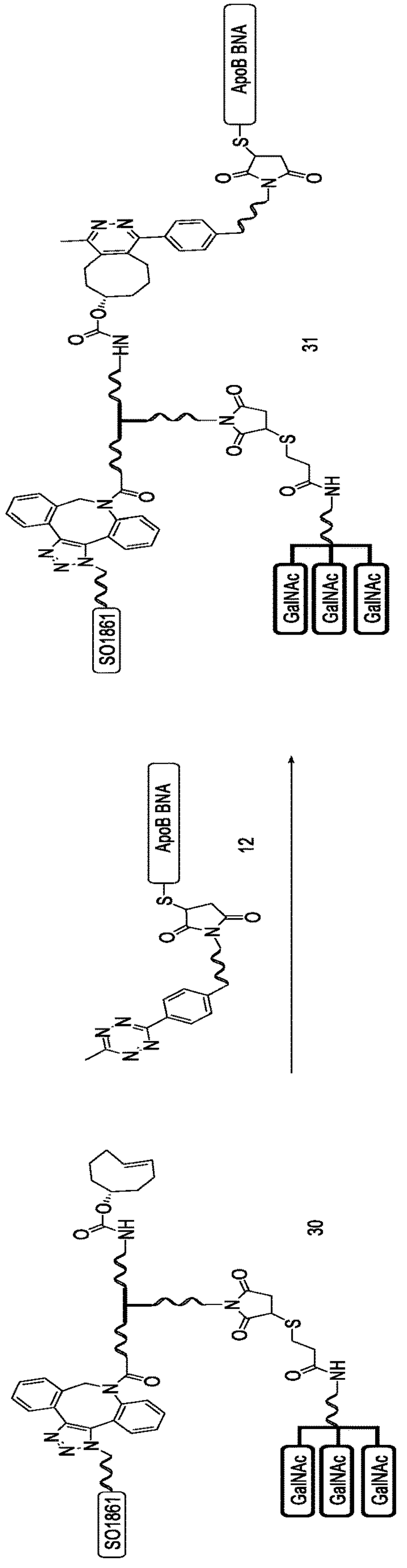

Trifunctional Linker-(L-Semicarbazone-SO1861)-(BNA Oligo)-(Trivalent-GalNAc Synthesis) (FIG. 34)

Intermediate 13

SO1861-L-Semicarbazone-Azide (Molecule 28)

To SO1861 (60 mg, 0.032 mmol, molecule 1) and 4-(6-azidohexanoyl)piperazine-1-carbohydrazide (36.5 mg, 0.129 mmol, molecule 27) was added methanol (extra dry, 1.00 mL) and TFA (9.86 μl, 0.129 mmol) and the reaction mixture was shaken for 1 min and left standing at room temperature. After 2 hours the reaction mixture was subjected to preparative MP-LC.[1] Fractions corresponding to the product were immediately pooled together, frozen and lyophilized overnight to give the title compound (30 mg, 44%) as a white fluffy solid. Purity based on LC-MS 99%.

MS (m/z): 2126 [M−1][1]

Intermediate 14

Trifunctional Linker-(L-Semicarbazone-SO1861)-(TCO)-(Maleimide) (Molecule 29)

A solution of TFL-(DBCO)-(TCO)-(Maleimide) (15 mg, 12.5 μmol, molecule 4) in DMF (2.0 mL) was added to SO1861-L-azide (26.6 mg, 12.5 μmol, molecule 28). The reaction mixture was shaken for 30 min and left standing at room temperature. After 30 min the reaction mixture was submitted to preparative MP-LC.[1C] Fractions corresponding to the product were immediately pooled together, frozen and lyophilized overnight to give the title compound (27.5 mg, 66%) as a white fluffy solid. Purity based on LC-MS 96%.

MS (m/z): 3331 $[M-1]^{1-}$

Intermediate 15

Trifunctional Linker-(L-Semicarbazone-SO1861)-(TCO)-(Trivalent GalNAc) (Molecule 30)

Trivalent GalNAc-thioacetate (13.0 mg, 7.25 μmol, molecule 8) was dissolved in methanol (0.50 mL). Next, a 1 M solution of sodium hydroxide (7.98 μL, 7.98 μmol) was added. The reaction mixture was shaken for 1 min and left standing at room temperature. After 30 min the reaction mixture was added to a freshly prepared solution of TFL-(L-semicarbazone-SO1861)-(TCO)-(maleimide) (20.4 mg, 6.13 μmol, molecule 29) in 20 mM ammonium bicarbonate/acetonitrile (3:1, v/v, 2.00 mL).

The resulting mixture was shaken for 1 min and left standing at room temperature. After 2 hours the reaction mixture was subjected to preparative MP-LC.[2A] Fractions corresponding to the product were immediately pooled together, frozen and lyophilized overnight to give the title compound (16.7 mg, 54%) as a white solid. Purity based on LC-MS 94%.

MS (m/z): 5081 $[M-1]^{1-}$

Trifunctional Linker-(L-Semicarbazone-SO1861)-(L-BNA Oligo)-(Trivalent GalNAc) (Molecule 31)

TFL-(L-semicarbazone-SO1861)-(TCO)-(trivalent GalNAc) (16 mg, 3.15 μmol, molecule 30) and Methyltetrazine-BNA oligo (10.2 mg, 1.83 μmol, molecule 12) were dissolved in a solution of 20 mM ammonium bicarbonate/acetonitrile (3:1, v/v, 1.00 mL). The reaction mixture was shaken for 1 min and left standing at room temperature. After 3 hours the reaction mixture was frozen and lyophilized overnight. The crude product was dissolved in 20 mM ammonium bicarbonate (1 mL) and the resulting solution was directly subjected to preparative LC-MS.[1B] Fractions corresponding to the product were immediately pooled together, frozen and lyophilized overnight to give the title compound (11.3 mg, 59%) as a white fluffy solid. Purity based on LC-MS 92%.

MS (m/z): 10638 $[M+H]^+$

Using a similar approach as for synthesis of Trifunctional linker-(L-semicarbazone-SO1861)-(L-BNA oligo)-(trivalent GalNAc) (molecule 31); a conjugate in which the ApoB BNA was replaced for a BNA with a scrambled ApoB nucleic acid sequence (molecule 12 a), can be synthesized (molecule 31a)

Figure 35:
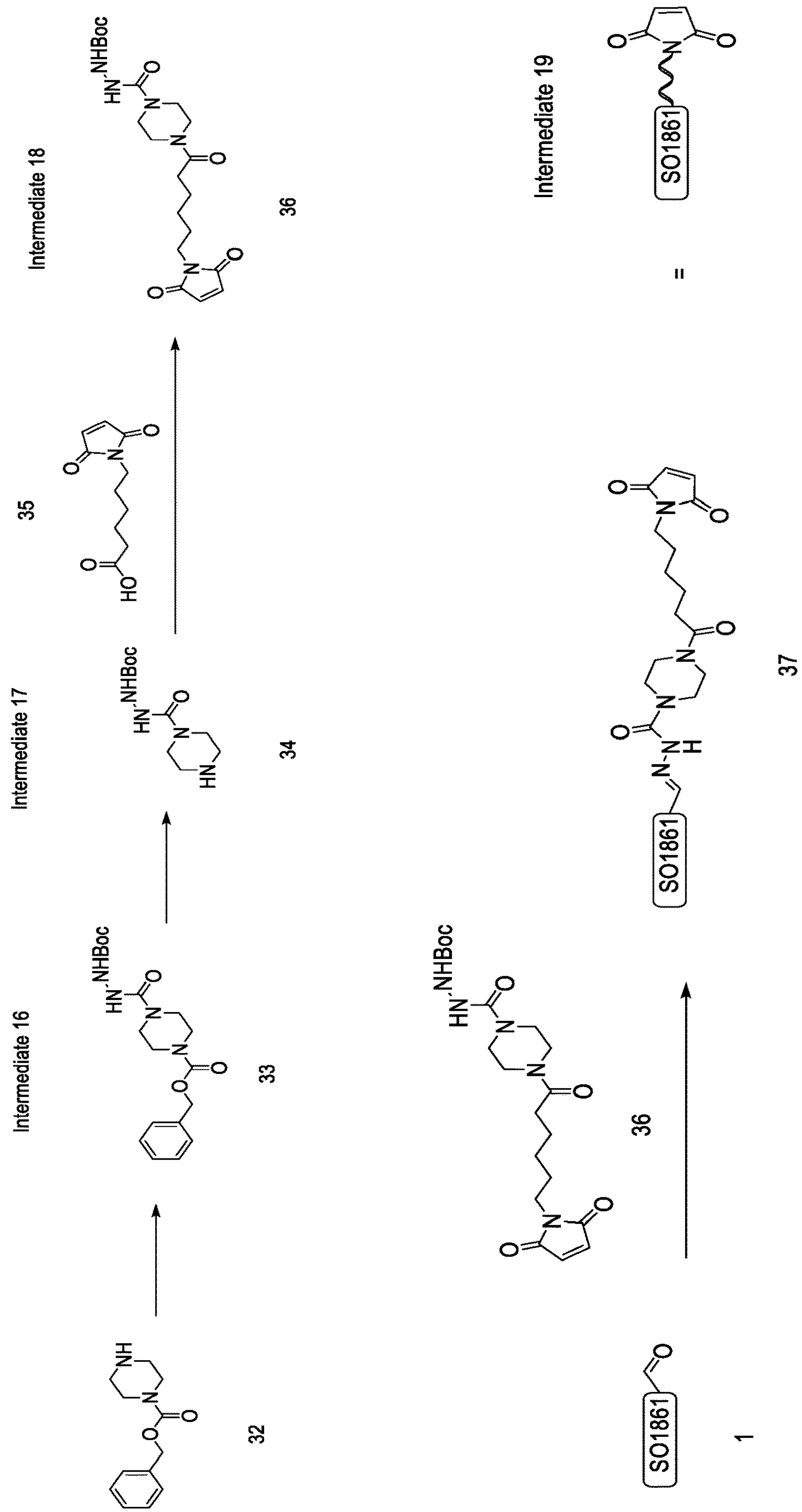
FIG. 35A-F: Trifunctional linker-(dendron(L-semicarbazone-SO1861)4)-(L-BNA oligo)-(Trivalent-GalNAc) synthesis. Note that the drawing of FIG. 35 E encompasses two sheets, labelled FIG. 35 E and FIG. 35 E (continued), which two sheets together display the conjugation of molecule 40 with molecule 20, therewith forming conjugate intermediate 24.
Figure 35:
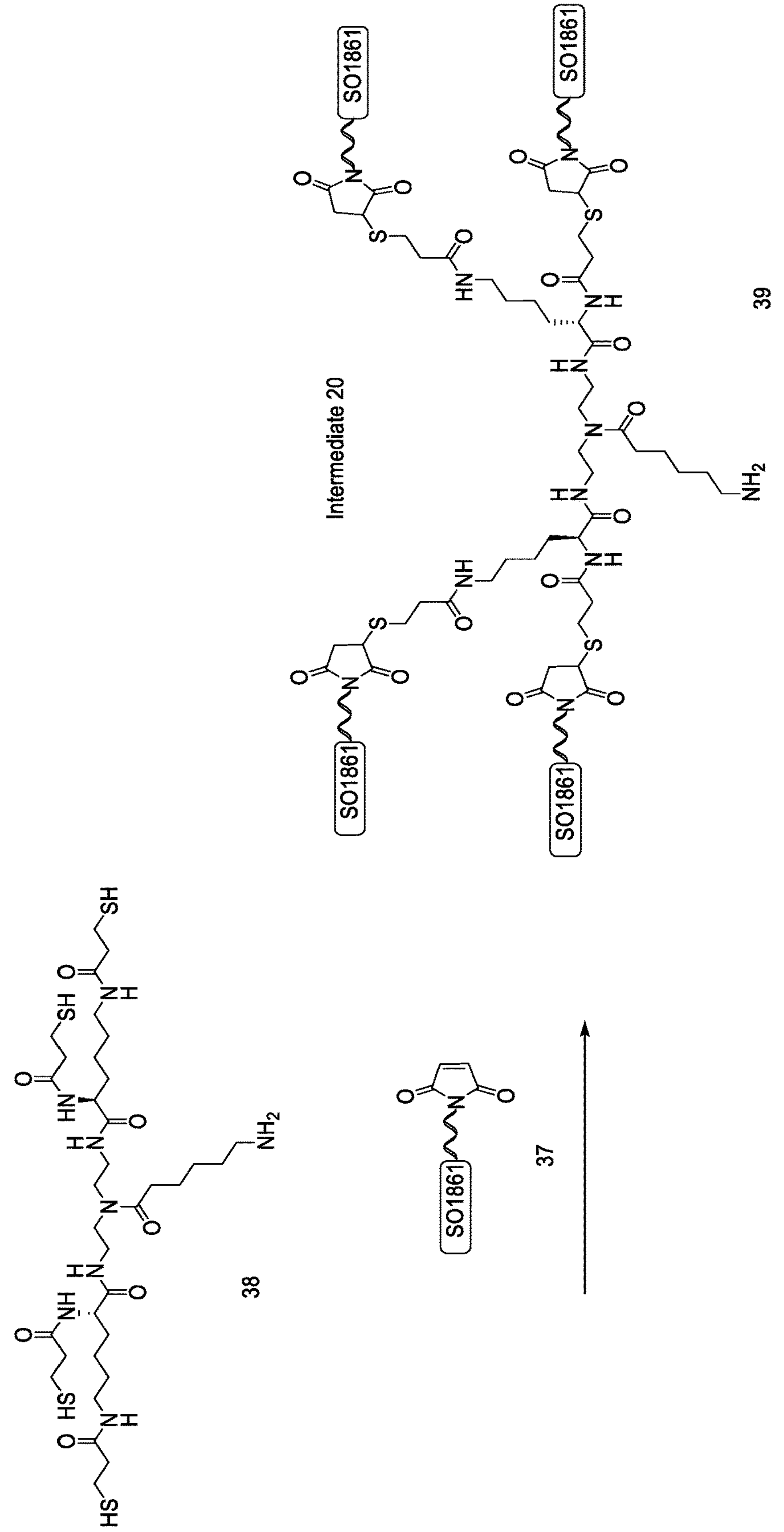
Figure 35:
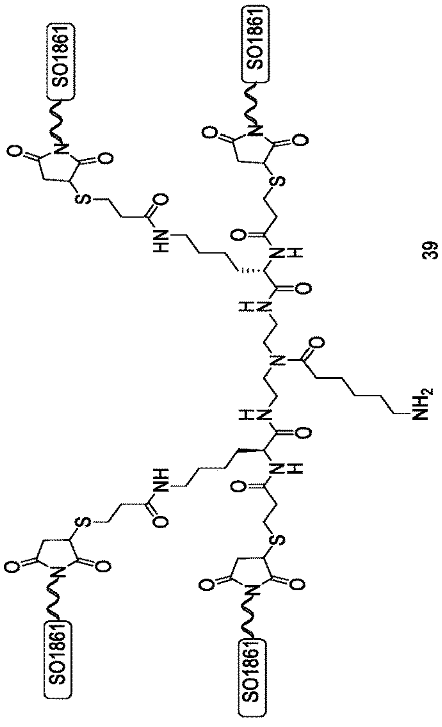
Figure 35:
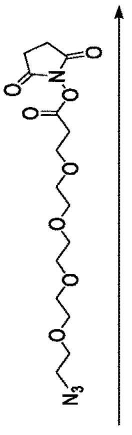
Figure 35:
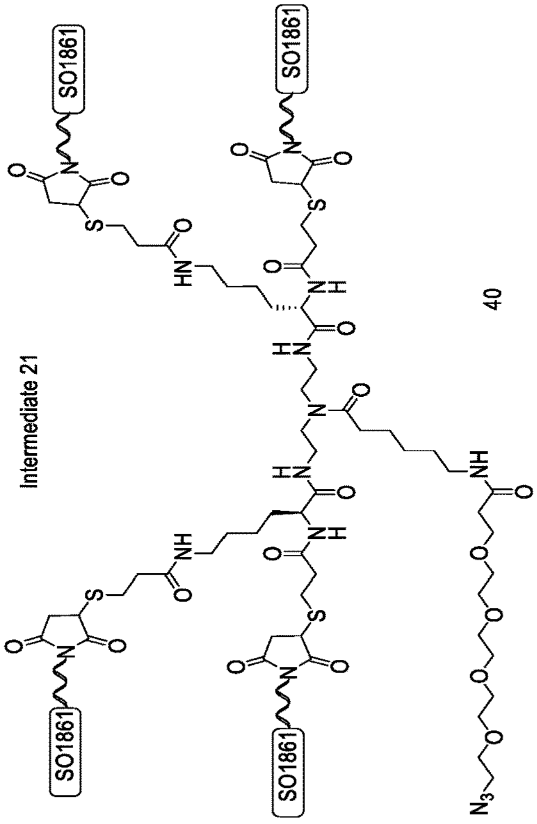
Figure 35:
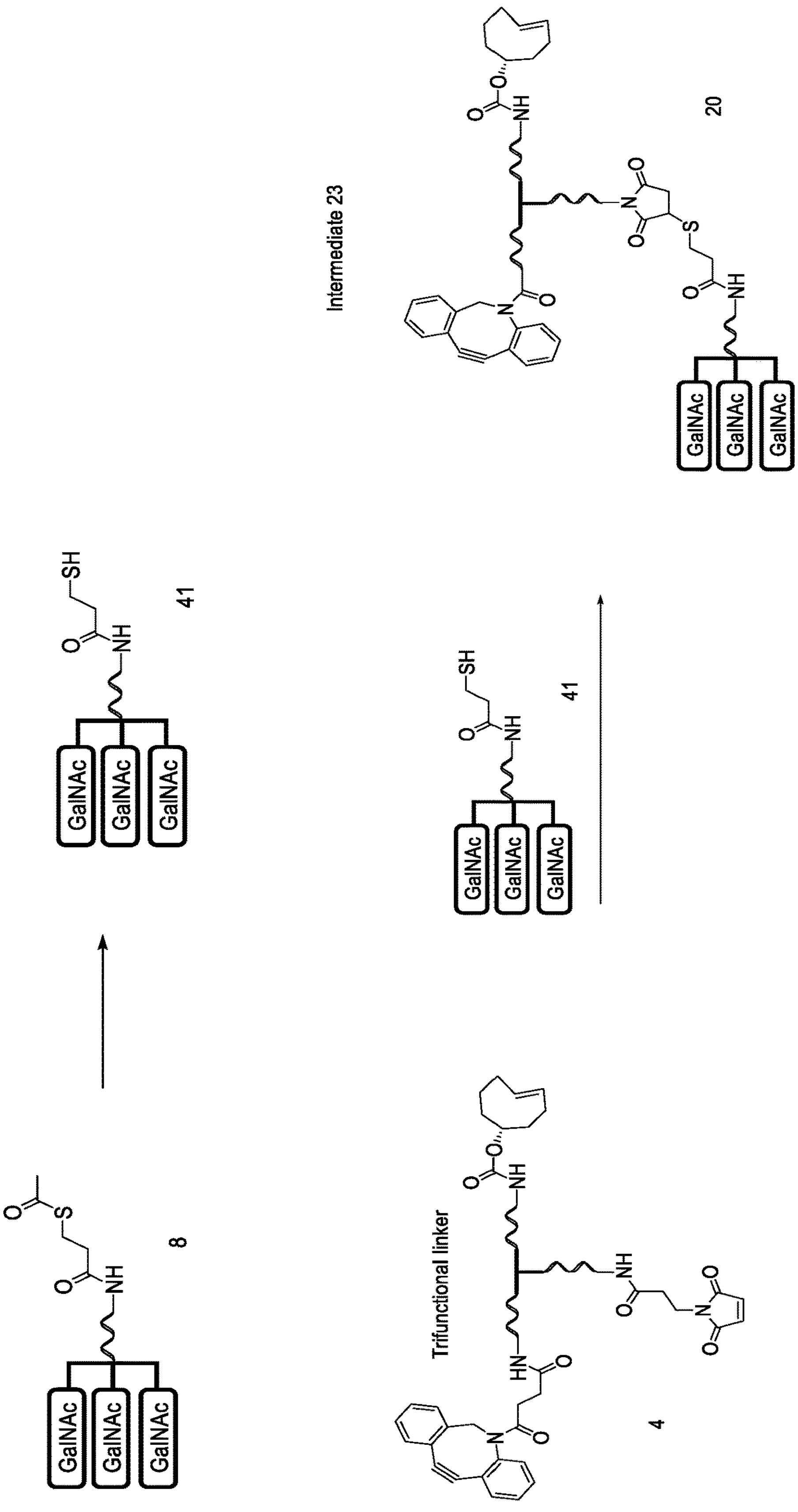
Figure 35:
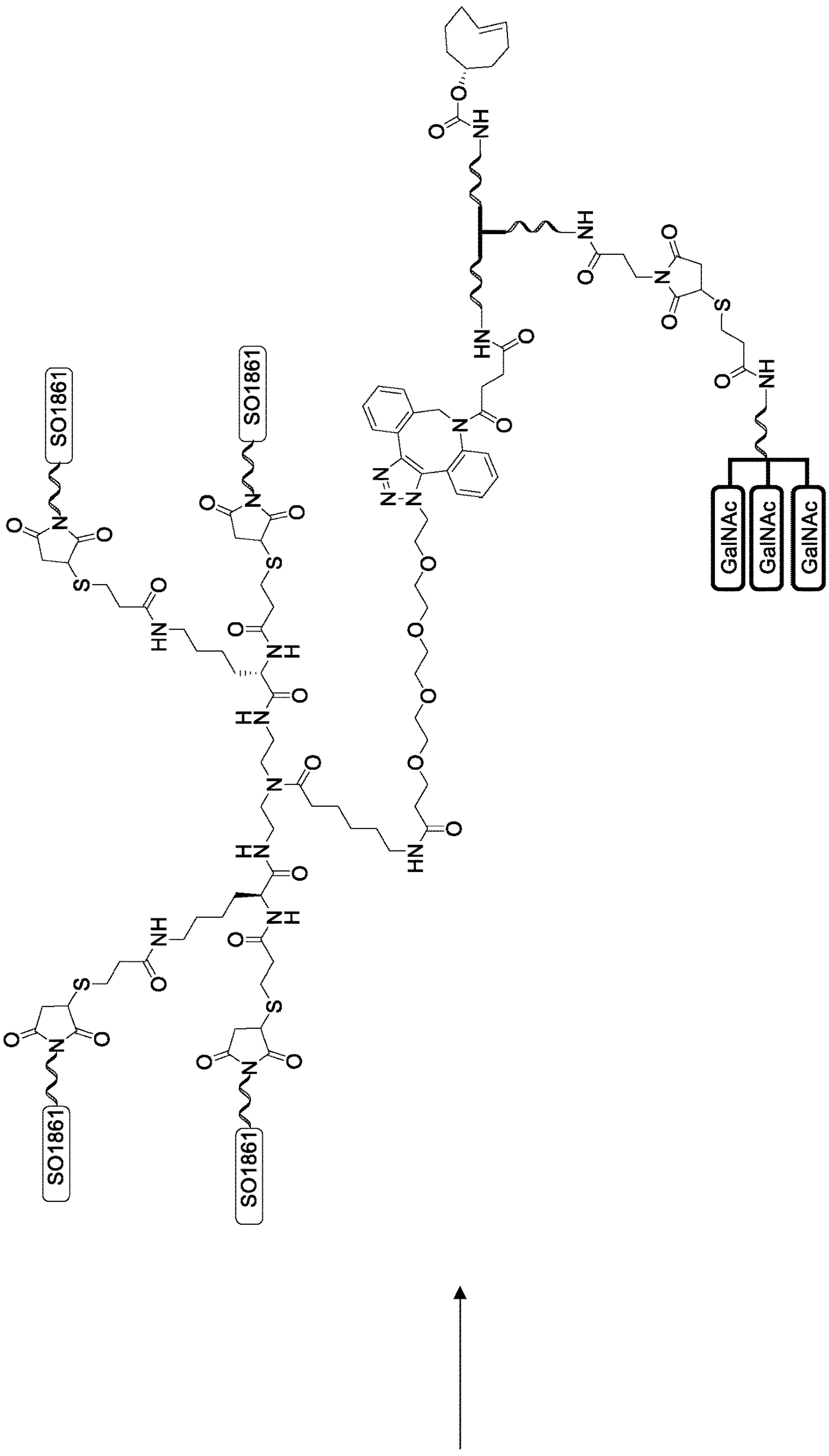
Figure 35:
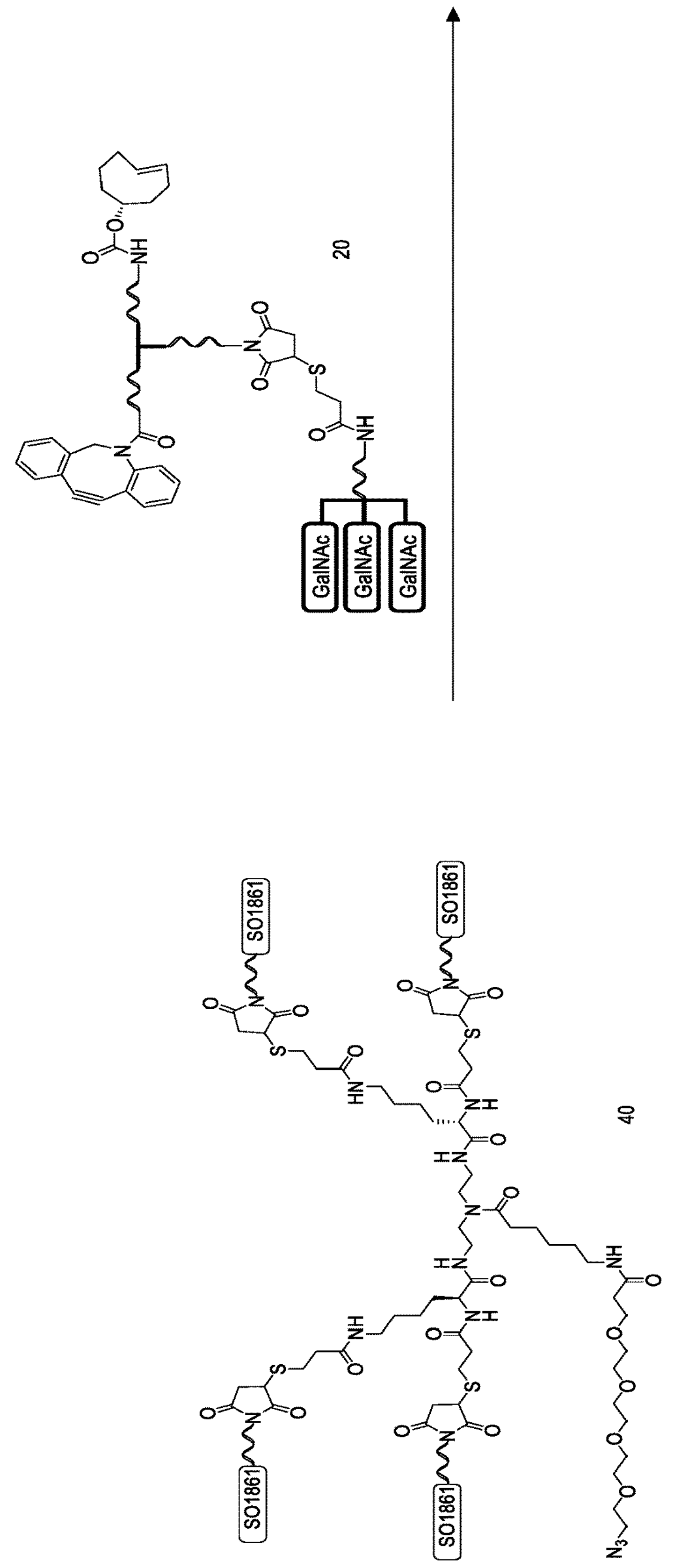
Figure 35:
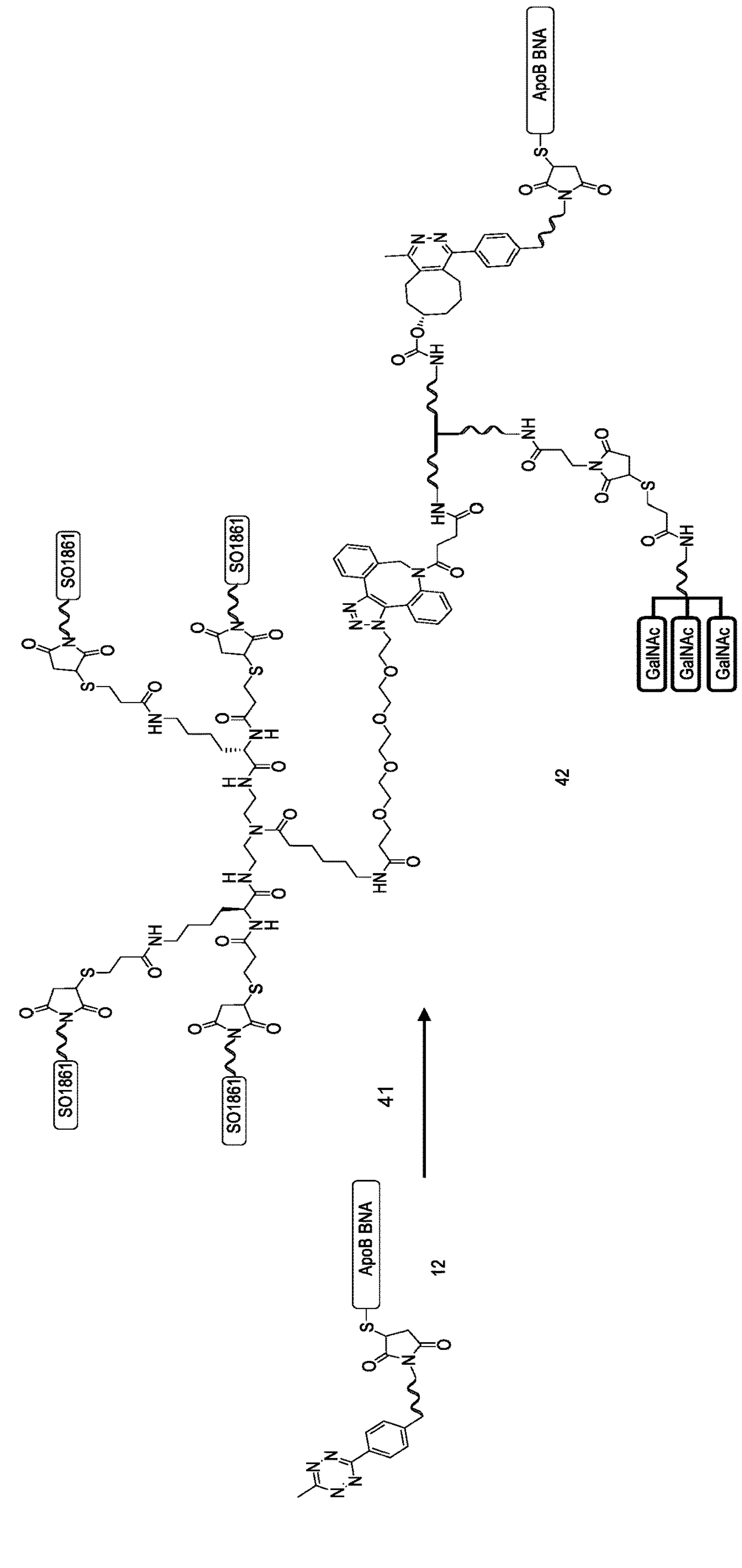

Trifunctional Linker-Dendron(L-Semicarbazone-SO1861) 4-(L-BNA Oligo)-(Trivalent-GalNAc) Synthesis (FIG. 35)

Intermediate 16 benzyl 4-(2-(tert-butoxycarbonyl)hydrazine-1-carbonyl)piperazine-1-carboxylate (Molecule 33)

To a stirring solution of phosgene in toluene (20%, w/w, 15.8 mL, 30.0 mmol) at 0° C. was added slowly (10 min) a solution of 1-Cbz-piperazine (1.93 mL, 10.0 mmol, molecule 1) in dichloromethane (25 mL) and DIPEA (3.83 mL, 22.0 mmol). The reaction mixture was stirred at room temperature. After 30 min the reaction mixture was evaporated in vacuo and co-evaporated with dichloromethane (2×50 mL). Next, the residue was dissolved in dichloromethane (100 mL) and resulting solution was stirred at 0° C. A solution of Boc hydrazine (2.33 mL, 15.0 mmol) in dichloromethane (20 mL) and DiPEA (3.83 mL, 22.0 mL) was added and the reaction mixture was stirred overnight at room temperature. The reaction mixture was diluted with dichloromethane (100 mL) and the resulting solution was washed with 0.5 N potassium bisulphate solution (2×100 mL) and brine (100 mL), dried over $Na_2SO_4$, filtered and evaporated in vacuo. The residue was purified by flash chromatography (first by an ethyl acetate-heptane gradient, 5:95 (v/v) rising to 100% ethyl acetate followed by a flush with 10% methanol in DCM (v/v)) to give the title compound (2.42 g, 64%) as a white solid. Purity based on LC-MS 100%.

LRMS (m/z): 279/323/401 $[M-99/M-55/M+23]^{1+}$

LC-MS r.t. (min): 1.271

Intermediate 17 tert-butyl 2-(piperazine-1-carbonyl)hydrazine-1-carboxylate (Molecule 34)

To benzyl 4-(2-(tert-butoxycarbonyl)hydrazine-1-carbonyl)piperazine-1-carboxylate (2.42 g, 6.39 mmol, molecule 33) was added methanol (50 mL). The mixture was heated to obtain a clear solution. Next, palladium (10% on activated carbon, 50% wet with water, 1.50 g) was added and the resulting mixture was stirred under a hydrogen atmosphere by using a balloon. After 1 hour the reaction mixture was filtered over celite and the filtrate evaporated in vacuo to give the title product (1.56 g, quant.) as a white solid.

LRMS (m/z): 189/245 $[M-55/M+1]^{1+}$

Intermediate 18 tert-butyl 2-(4-(6-(2,5-dioxo-2,5-dihydro-1H-pyrrol-1-yl)hexanoyl)piperazine-1-carbonyl)hydrazine-1-carboxylate (Molecule 36)

6-maleimidocaproic acid (810 mg, 3.84 mmol, molecule 35), tert-butyl 2-(piperazine-1-carbonyl)hydrazine-1-carboxylate (781 mg, 3.20 mmol, molecule 34), EDCI·HCl (735 mg, 3.84 mmol) and Oxyma Pure (591 mg, 4.16 mmol) were dissolved in a mixture of dichloromethane (25 mL) and DIPEA (835 μL, 4.80 mmol) and the reaction mixture was stirred at room temperature. After 2 hours the reaction mixture was evaporated in vacuo and the residue was dissolved in ethyl acetate (50 mL). The resulting solution was washed with 0.5 N potassium bisulphate solution (50 mL), saturated sodium bicarbonate solution (2×50 mL) and brine (50 mL), dried over $Na_2SO_4$, filtered and evaporated in vacuo. The residue was purified by flash chromatography (DCM—10% methanol in DCM (v/v) gradient 100:0 rising to 40:60) to give the title compound (634 mg, 45%) as a white solid. Purity based on LC-MS 97%.

LRMS (m/z): 338/382/460 $[M-99/M-55/M+23]^{1+}$

LC-MS r.t. (min): 1.02[1]

Intermediate 19

SO1861-SC-Mal (Molecule 37)

tert-butyl 2-(4-(6-(2,5-dioxo-2,5-dihydro-1H-pyrrol-1-yl)hexanoyl)piperazine-1-carbonyl)hydrazine-1-carboxylate (25.0 mg, 57.1 μmol, molecule 36) was dissolved in a mixture of dichloromethane (500 μL) and TFA (500 μL) and the reaction mixture was stirred at room temperature. After 30 min the reaction mixture was evaporated in vacuo and co-evaporated with dichloromethane (3×5 mL) and methanol (5 mL). The residue and SO1861 (21.3 mg, 11.4 μmol, molecule 1) were dissolved in methanol (extra dry, 1.00 mL) and the resulting mixture was shaken for 1 min and left standing at room temperature. After 4 hours the reaction mixture was subjected to preparative MP-LC.[2] Fractions corresponding to the product were immediately pooled together, frozen and lyophilized overnight to yield the title compound (13.7 mg, 55%) as a white fluffy solid. Purity based on LC-MS 97%.

LRMS (m/z): 2181 $[M-1]^{1-}$

LC-MS r.t. (min): 2.133

Intermediate 20

Dendron(L-Semicarbazone-SO1861)$_4$-Amine (Molecule 39)

N,N'-((9S,19S)-14-(6-aminohexanoyl)-1-mercapto-9-(3-mercaptopropanamido)-3,10,18-trioxo-4,11,14,17-tetraazatricosane-19,23-diyl)bis(3-mercaptopropanamide) formate (2.73 mg, 3.13 μmol, molecule 38) was dissolved in a mixture of 1M NaOH and MeOH (1:1, v/v, 3.00 mL) and stirred for 30 min. Next, 5 mL of Trimethylphosphine (9.5 mg, 125 μmol) dissolved in THE was added and the mixture was stirred for 30 min. Next, SO1861-SC-Mal (30.54 mg, 0.014 mmol, molecule 37) dissolved in 20 mM $NH_4HCO_3$ with acetonitrile (3:1, v/v, 3.00 mL) was added and the reaction mixture was stirred at room temperature. After 1.5 hours the reaction mixture was subjected to preparative LC-MS.[3B] Fractions corresponding to the product were immediately pooled together, frozen and lyophilized overnight to give the title compound (19 mg, 64%) as a white fluffy solid. Purity based on LC-MS 95%.

MS (m/z): 9553 $[M+H]^+$

Intermediate 21

Dendron(-L-SO1861)$^4$-Azide (Molecule 40)

Dendron(L-semicarbazone-SO1861)$_4$-amine (7.1 mg, 0.748 μmol, molecule 39) and 2,5-dioxopyrrolidin-1-yl 1-azido-3,6,9,12-tetraoxapentadecan-15-oate (2.90 mg, 7.48 μmol, molecule 18) were dissolved in DMF (1.00 mL). Next, DIPEA (1.302 μL, 7.48 μmol) was added and the mixture was shaken for 1 min and left standing at room temperature. After 2 hours the reaction mixture was subjected to preparative LC-MS.[3C] Fractions corresponding to the product were immediately pooled together, frozen and lyophilized overnight to give the title compound (6.4 mg, 87%) as a white fluffy solid. Purity based on LC-MS 93%.

MS (m/z): 9826 $[M+H]^+$

Intermediate 22

Trivalent GalNAc-Thiol (Molecule 41)

Trivalent GalNAc-thioacetate (16.2 mg, 9.02 μmol, molecule 8) was dissolved in methanol (500 μL). Next, a 1.00 M solution of sodium hydroxide (11.0 μL, 11.0 μmol) was added. The reaction mixture was shaken for 1 min and left standing at room temperature. After 30 min the reaction mixture was submitted to preparative MP-LC.[1A] Fractions corresponding to the product were immediately pooled together, frozen and lyophilized overnight to give the title compound (13.1 mg, 83%) as a white solid. Purity based on LC-MS 98%.

LRMS (m/z): 1748 $[M-H]^{1-}$

LC-MS r.t. (min): 1.78[1A]

Intermediate 23

TFL-(DBCO)-(TCO)-(Trivalent GalNAc) (Molecule 20)

TFL-(DBCO)-(TCO)-(Mal) (15.0 mg, 12.4 μmol, molecule 4) was dissolved in acetonitrile (0.50 mL). Next, a solution of 20 mM ammonium bicarbonate (1.50 mL) was added and the resulting solution was directly transferred to trivalent GalNAc-thiol (22.7 mg, 13.0 μmol, molecule 41). The reaction mixture was shaken for 1 min and left standing at room temperature. After 1 hour the reaction mixture was frozen and lyophilized overnight to yield the crude title product as a white solid. Purity based on LC-MS 84%.

LRMS (m/z): 2409 $[M-546]^{1-}$, 2955 $[M-1]^{1-}$

LC-MS r.t. (min): 2.63[1B]

Intermediate 24

TFL-(Dendron(L-Semicarbazone-SO1861)4)-(TCO)-(Trivalent GalNAc) (Molecule 41)

Dendron(L-semicarbazone-SO1861)$_4$-azide (5.2 mg, 0.529 μmol, molecule 40) and TFL-(DBCO)-(TCO)-(trivalent GalNAc) (1.5 mg, 0.5 μmol, molecule 20) were dissolved in DMF (2.00 mL). The mixture was shaken for 10 min and left standing at room temperature. After 2 hours the reaction mixture was subjected to preparative LC-MS.[3C] Fractions corresponding to the product were immediately pooled together, frozen and lyophilized overnight to give the title compound (6.1 mg, 90%) as a white fluffy solid. Purity based on LC-MS 93%.

MS (m/z): 12781 $[M+H]^+$

TFL-(-Dendron(L-Semicarbazone-SO1861)4)-(L-BNA Oligo)-(Trivalent GalNAc) (Molecule 42)

TFL-(dendron(L-semicarbazone-SO1861)4)-(TCO)-(trivalent GalNAc) (5.2 mg, 0.41 μmol, molecule 41) and Methyltetrazine-BNA oligo (2.7 mg, 0.5 μmol, molecule 12) were dissolved in a solution of 20 mM ammonium bicarbonate/acetonitrile (3:1, v/v, 1.00 mL). The reaction mixture was shaken for 1 min and left standing at room temperature. After 3 hours the reaction mixture was frozen and lyophilized overnight. The crude product was dissolved in 20 mM ammonium bicarbonate (1 mL) and the resulting solution was directly subjected to preparative LC-MS.[1B] Fractions corresponding to the product were immediately pooled together, frozen and lyophilized overnight to give the title compound (1.8 mg, 24%) as a white fluffy solid. Purity based on LC-MS 96% (multiple (broad) peaks due to regio-isomers).

MS (m/z): 18336 $[M+H]^+$

Using a similar approach as for synthesis of Trifunctional linker (Dendron(-L-semicarbazone-SO1861)4)-(L-ApoB BNA oligo)-(trivalent GalNAc synthesis) (molecule 42); a conjugate in which the ApoB BNA was replaced for a BNA with a scrambled ApoB nucleic acid sequence (molecule 12 a), can be synthesized (molecule 42a).

Figure 36:
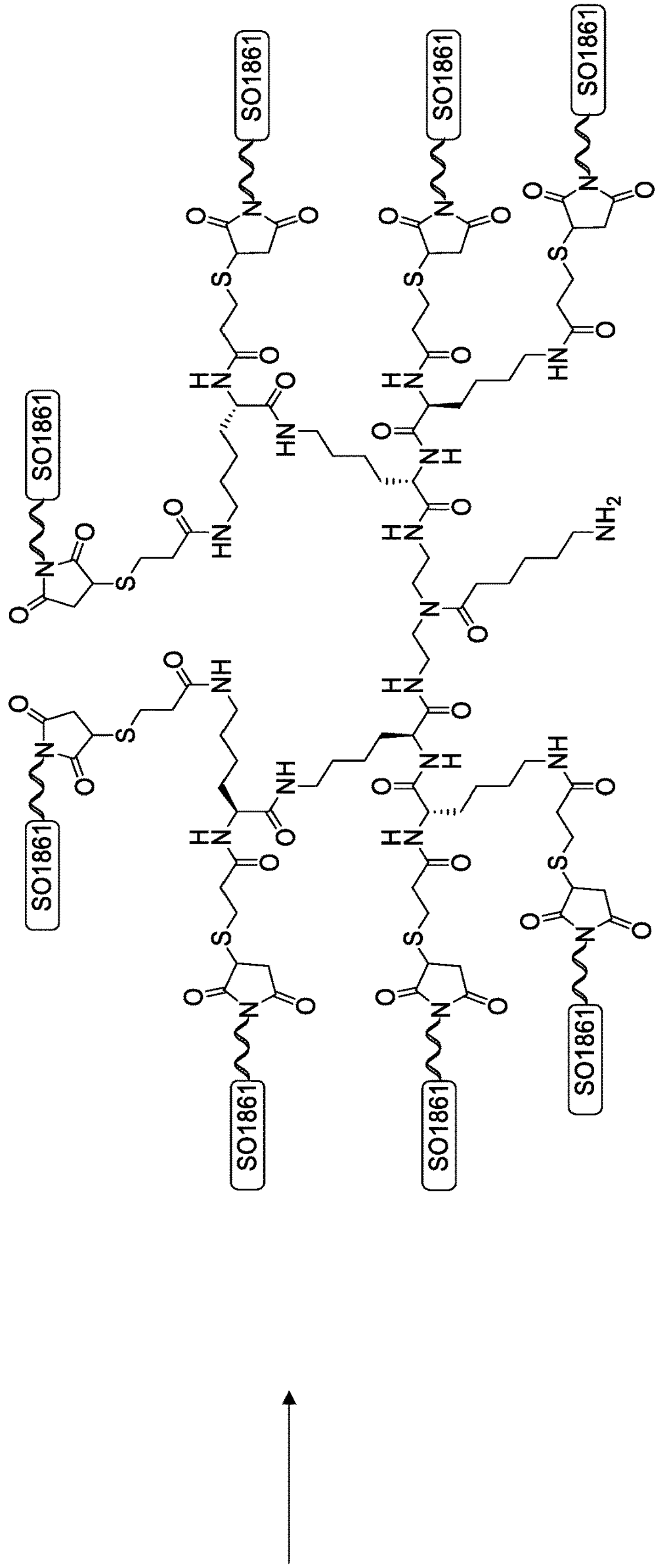
FIG. 36A-D: Trifunctional linker-(dendron(L-semicarbazone-SO1861)8)-(L-BNA oligo)-(Trivalent-GalNAc) synthesis. Note that the drawing of FIG. 36 A encompasses two sheets, labelled FIG. 36 A and FIG. 36 A (continued), which two sheets together display the conjugation of molecule 43 with molecule 37, therewith forming conjugate (molecule 44) intermediate 25. Note that the drawing of FIG. 36 B encompasses two sheets, labelled FIG. 36 B and FIG. 36 B (continued), which two sheets together display the conjugation of molecule 44 with molecule 18, therewith forming conjugate molecule 45 (intermediate 26). Note that the drawing of FIG. 36 C encompasses two sheets, labelled FIG. 36 C and FIG. 36 C (continued), which two sheets together display the conjugation of molecule 45 with molecule 20, therewith forming conjugate molecule 46 (intermediate 27).
Figure 36:
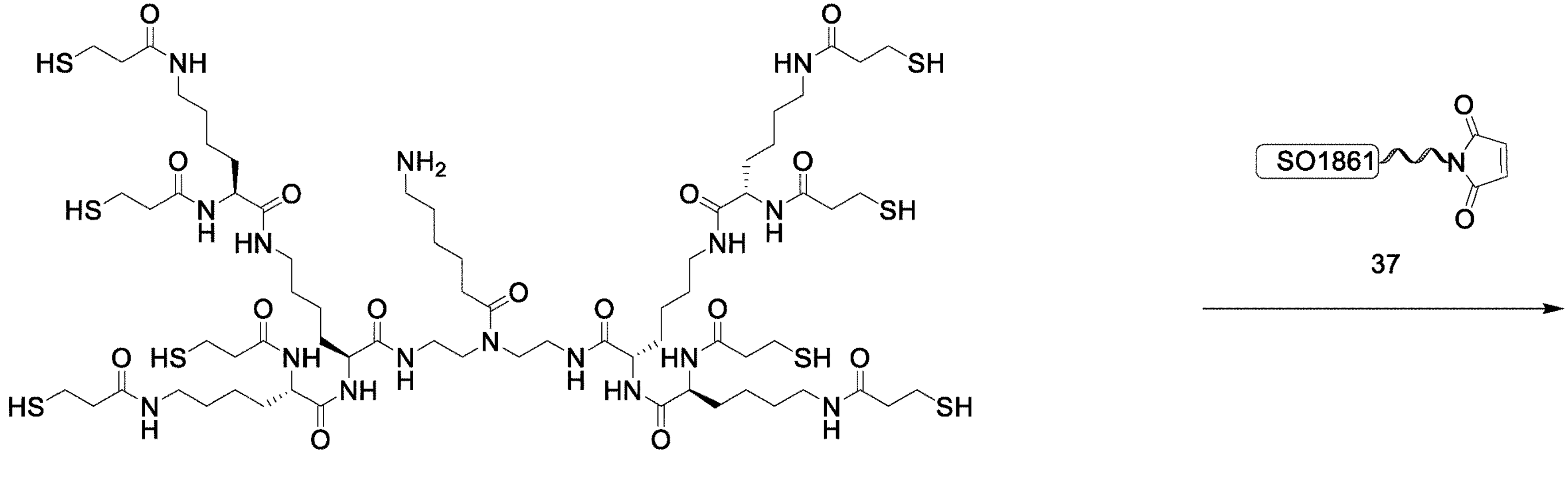
Figure 36:
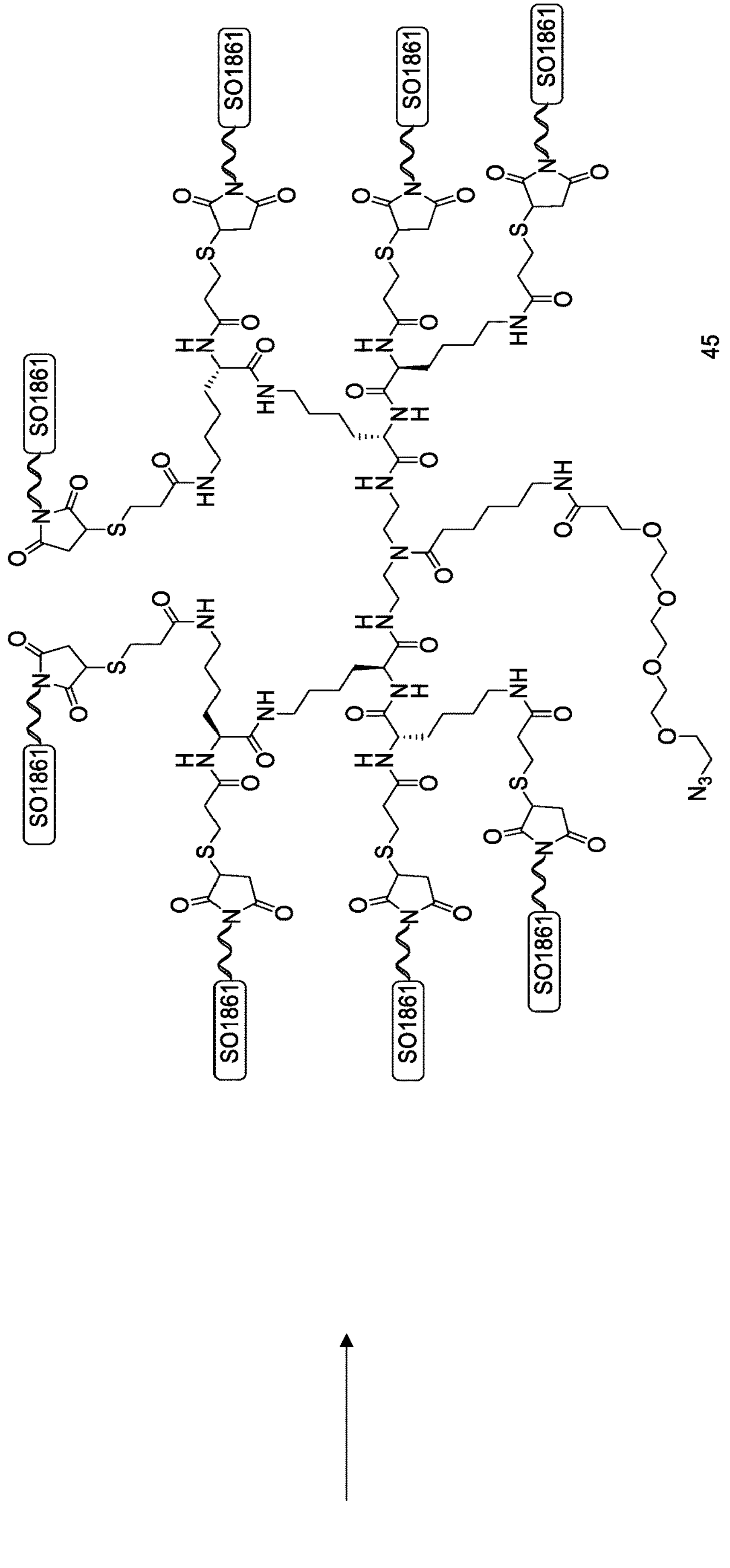
Figure 36:
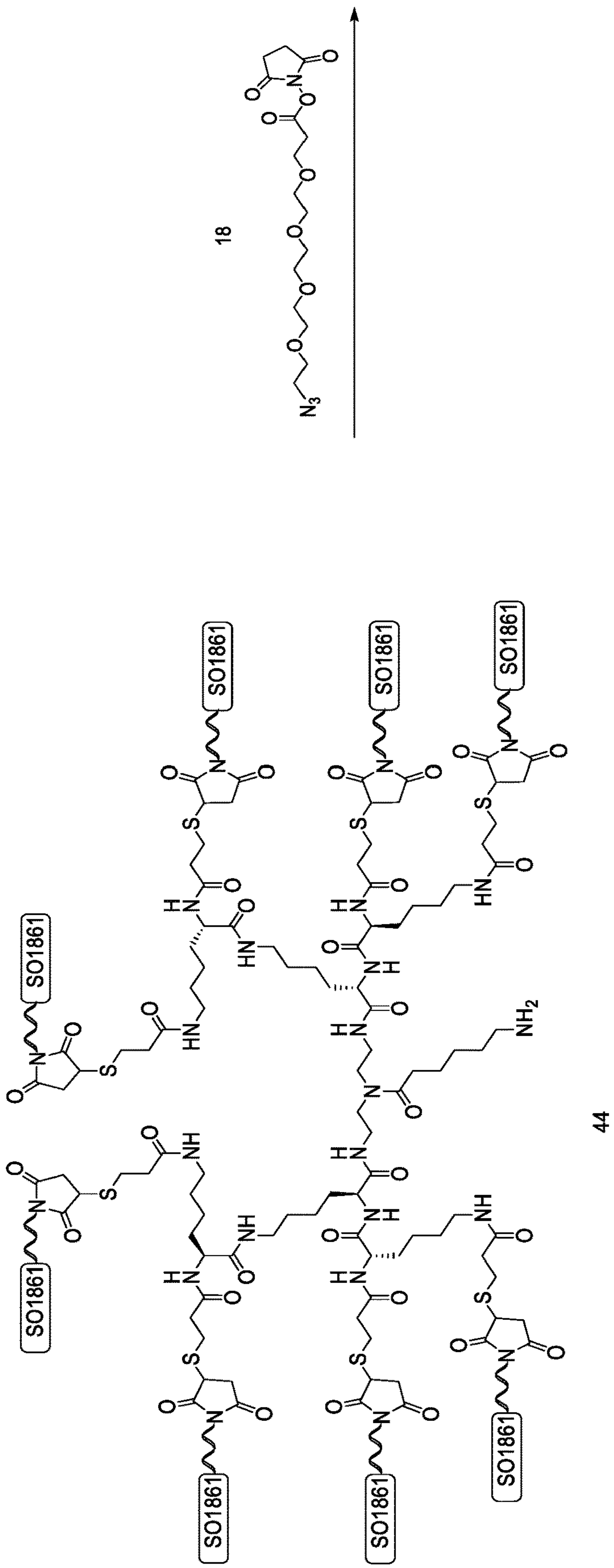
Figure 36:
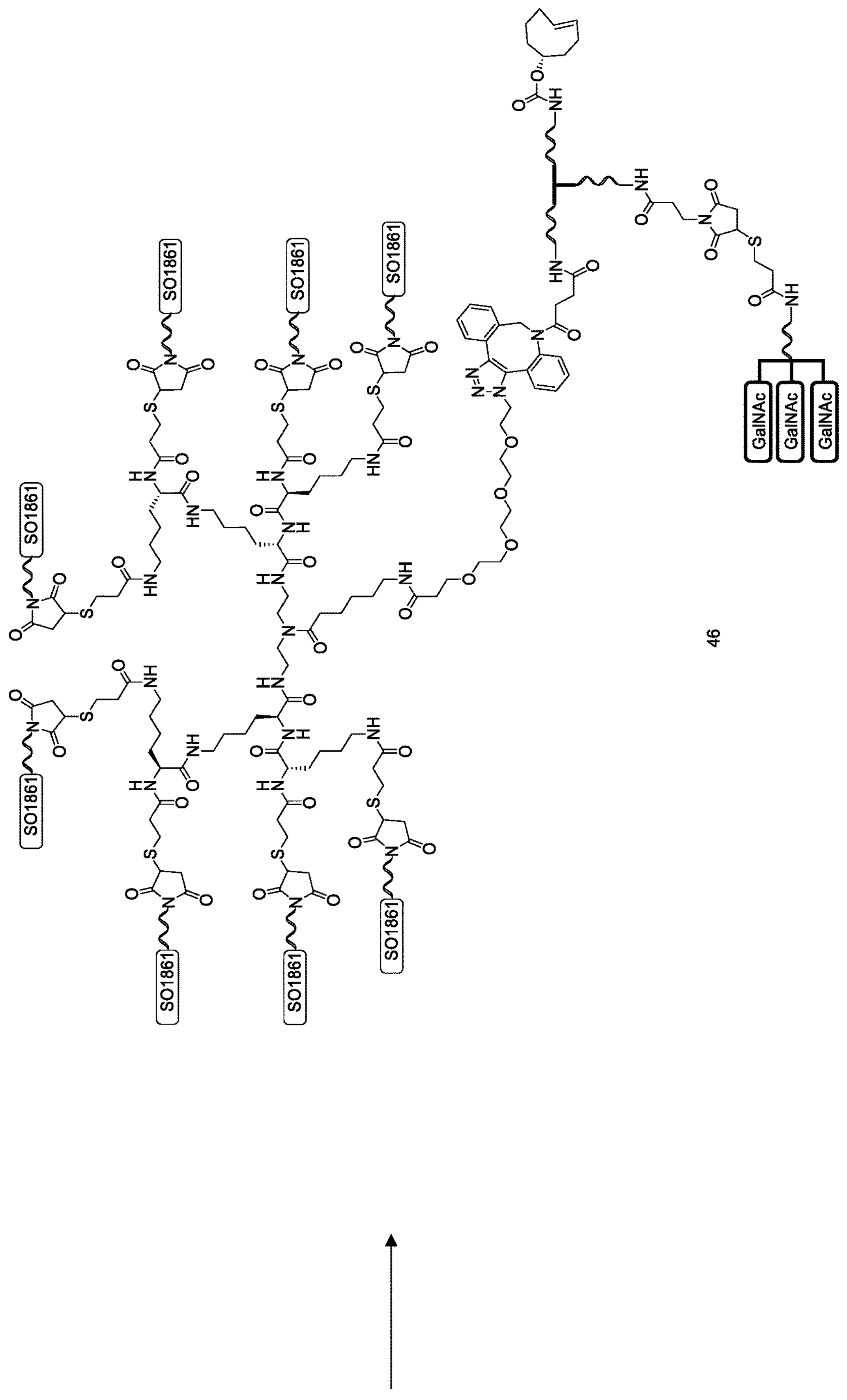
Figure 36:
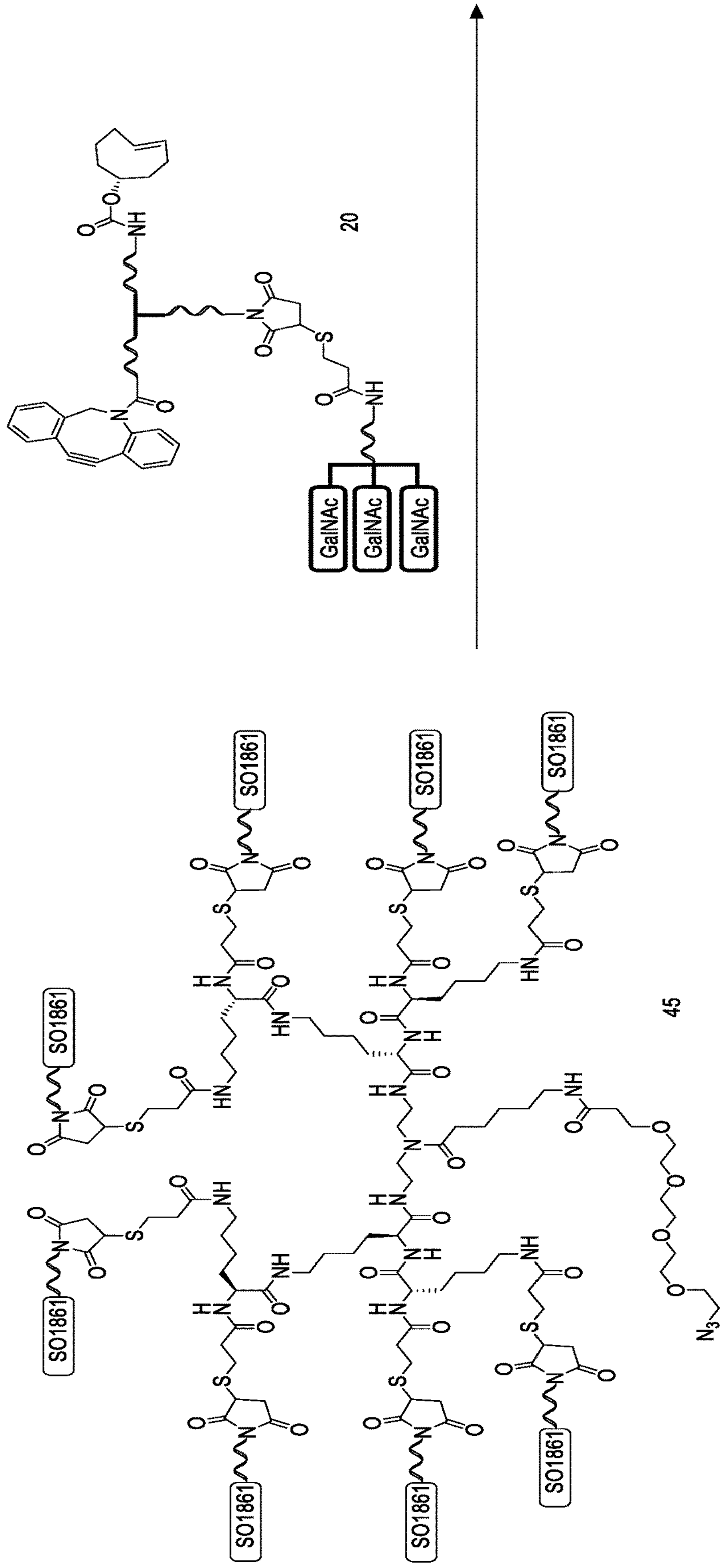
Figure 36:
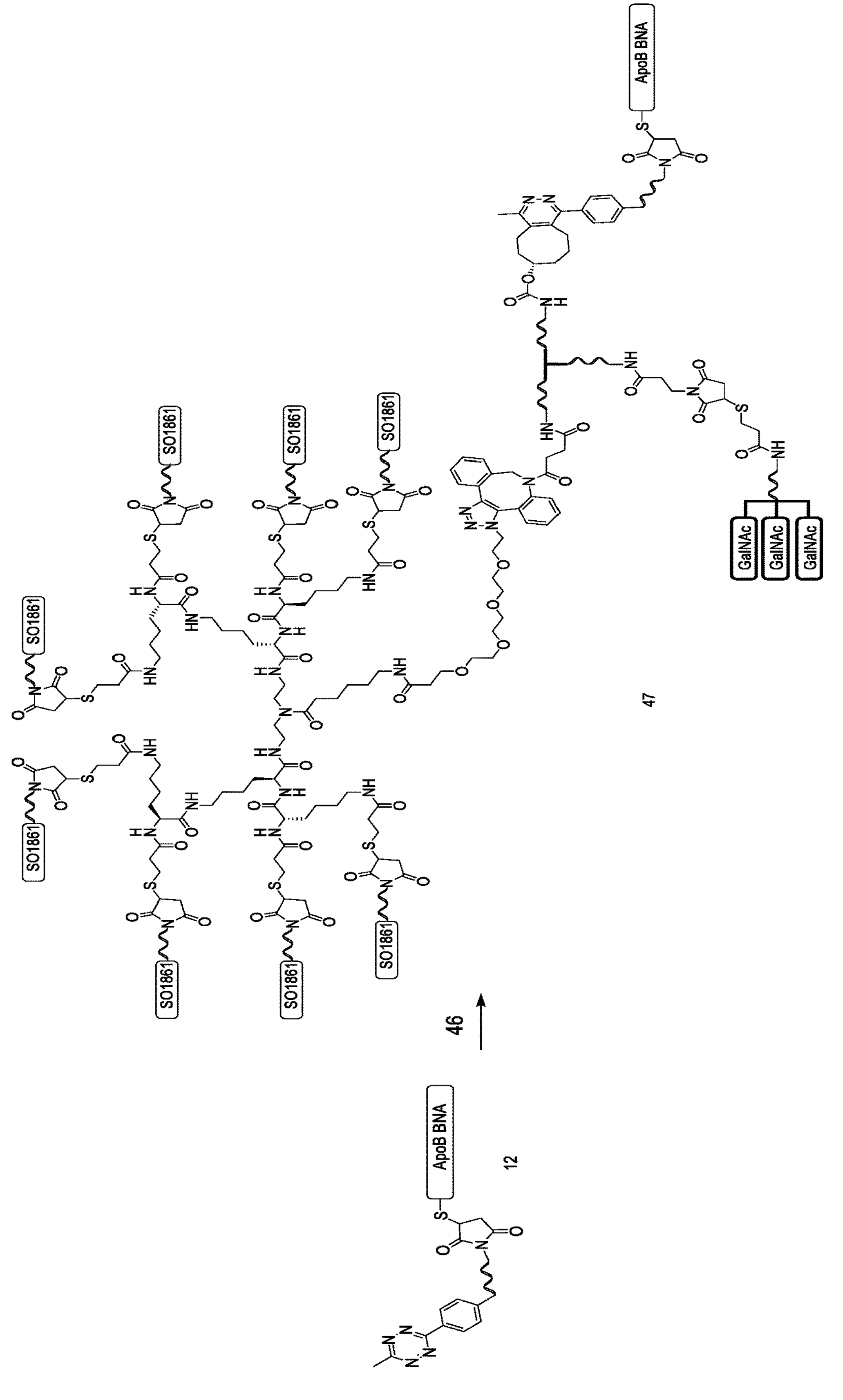

Trifunctional Linker-(Dendron(-L-Semicarbazone-SO1861)8)-BNA Oligo-Trivalent-GalNAc Synthesis (FIG. 36)

Intermediate 25

Dendron(L-Semicarbazone-SO1861)$^8$-Amine (Molecule 44)

(2S)—N-[(1 S)-1-{[2-(6-amino-N-{2-[(2S)-2,6-bis[(2S)-2,6-bis(3-sulfanylpropanamido)hexanamido]hexanamido]ethyl}hexanamido)ethyl]carbamoyl}-5-[(2S)-2,6-bis(3-sulfanylpropanamido)hexanamido]pentyl]-2,6-bis(3-sulfanylpropanamido)hexanamide formate (0.61 mg, 0.299 μmol, molecule 43) was dissolved in a mixture of 1M NaOH and MeOH (1:1, v/v, 3.00 mL) and stirred for 30 min. Next, 5 mL of Trimethylphosphine (2 mg, 24 μmol) dissolved in THE was added and the mixture was stirred for 30 min. Next, SO1861-SC-Mal (30.54 mg, 0.014 mmol, molecule 37) dissolved in 20 mM $NH_4HCO_3$ with acetonitrile (3:1, v/v, 3.00 mL) was added and the reaction mixture was stirred at room temperature. After 1.5 hours the reaction mixture was subjected to preparative LC-MS.[3B] Fractions corresponding to the product were immediately pooled together, frozen and lyophilized overnight to give the title compound (4.6 mg, 81%) as a white fluffy solid. Purity based on LC-MS 95%.

MS (m/z): 19146 $[M+H]^+$

Intermediate 26

Dendron(-L-SO1861)$^8$-Azide (Molecule 45)

Dendron(L-semicarbazone-SO1861)$_8$-amine (5.4 mg, 0.28 μmol, molecule 44) and 2,5-dioxopyrrolidin-1-yl 1-azido-3,6,9,12-tetraoxapentadecan-15-oate (1.1 mg, 2.8 μmol, molecule 18) were dissolved in DMF (1.00 mL). Next, DIPEA (1.302 μL) was added and the mixture was shaken for 1 min and left standing at room temperature. After 2 hours the reaction mixture was subjected to preparative LC-MS.[3C] Fractions corresponding to the product were immediately pooled together, frozen and lyophilized overnight to give the title compound (4.35 mg, 80%) as a white fluffy solid. Purity based on LC-MS 93%.

MS (m/z): 19420 $[M+H]^+$

Intermediate 27

TFL-(Dendron(L-Semicarbazone-SO1861)8)-(TCO)-(Trivalent GalNAc) (Molecule 46)

Dendron(L-semicarbazone-SO1861)$_8$-azide (10.3 mg, 0.529 μmol, molecule 45) and TFL-(DBCO)-(TCO)-(trivalent GalNAc) (1.5 mg, 0.5 μmol, molecule 20) were dissolved in DMF (2.00 mL). The mixture was shaken for 10 min and left standing at room temperature. After 2 hours the reaction mixture was subjected to preparative LC-MS.[3C] Fractions corresponding to the product were immediately pooled together, frozen and lyophilized overnight to give the title compound (8.75 mg, 74%) as a white fluffy solid. Purity based on LC-MS 91%.

MS (m/z): 22373 $[M+H]^+$

TFL-(Dendron(-L-Semicarbazone-SO1861)8)-(L-BNA Oligo)-(Trivalent GalNAc) (Molecule 47)

TFL-(dendron(L-semicarbazone-SO1861)8)-(TCO)-(trivalent GalNAc) (9.2 mg, 0.41 μmol, molecule 46) and Methyltetrazine-BNA oligo (2.8 mg, 0.5 μmol, molecule 12) were dissolved in a solution of 20 mM ammonium bicarbonate/acetonitrile (3:1, v/v, 1.00 mL). The reaction mixture was shaken for 1 min and left standing at room temperature. After 3 hours the reaction mixture was frozen and lyophilized overnight. The crude product was dissolved in 20 mM ammonium bicarbonate (1 mL) and the resulting solution was directly subjected to preparative LC-MS.[1B] Fractions corresponding to the product were immediately pooled together, frozen and lyophilized overnight to give the title compound (1.26 mg, 11%) as a white fluffy solid. Purity based on LC-MS 97%.

MS (m/z): 27928 $[M+H]^+$

Using a similar approach as for synthesis of Trifunctional linker (Dendron(-L-semicarbazone-SO1861)8)-(L-ApoB BNA oligo)-(trivalent GalNAc synthesis) (molecule 47); a conjugate in which the ApoB BNA was replaced for a BNA with a scrambled ApoB nucleic acid sequence (molecule 12 a), can be synthesized (molecule 47a).

Figure 37:
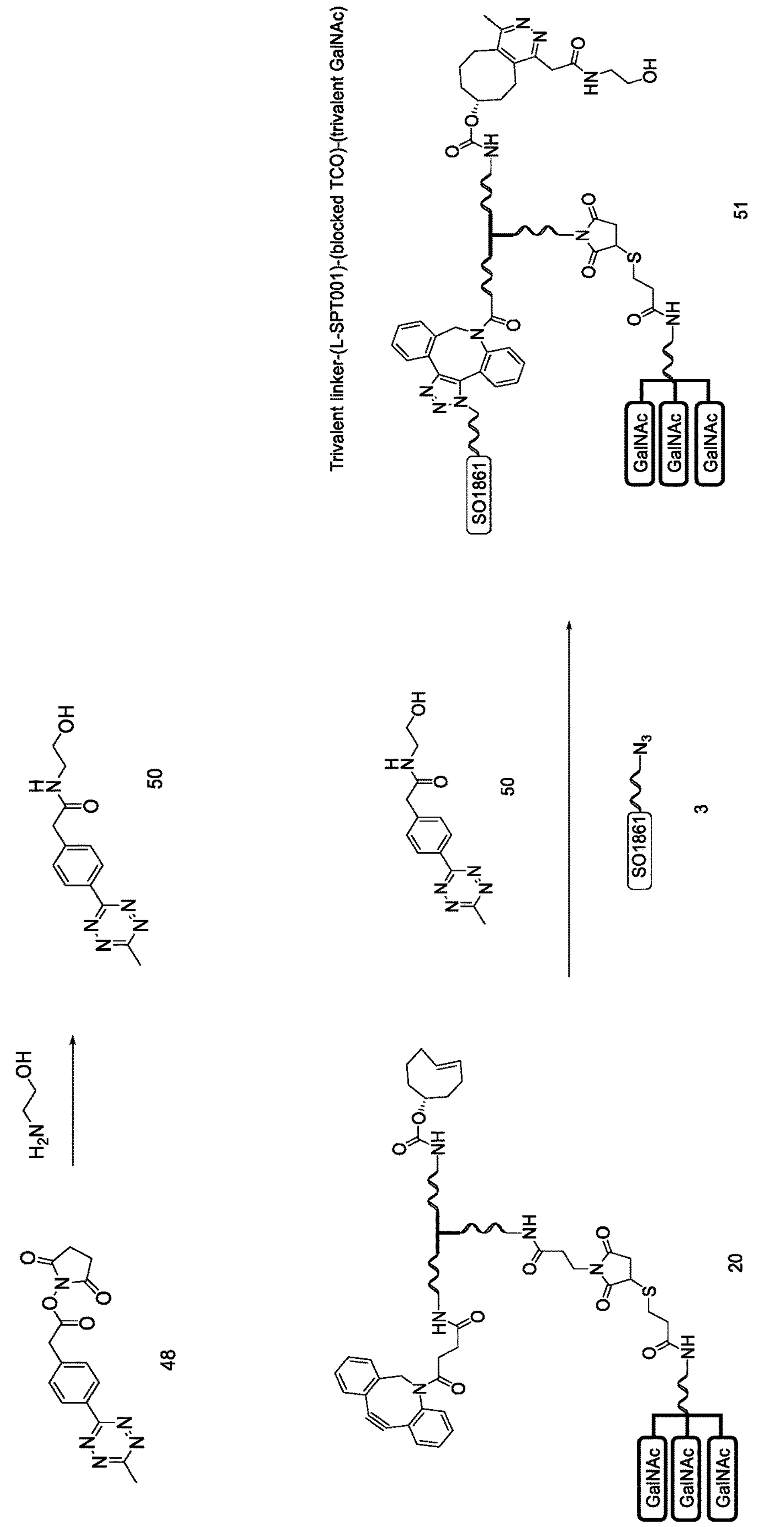
FIG. 37: Trivalent linker-(L-SPT001)-(blocked TCO)-(trivalent GalNAc) synthesis

Trivalent Linker-(L-SPT001)-(Blocked TCO)-(Trivalent GalNAc) Synthesis (FIG. 37)

Intermediate 28

N-(2-hydroxyethyl)-2-(4-(6-methyl-1,2,4,5-tetrazin-3-yl)phenyl)acetamide (Molecule 50)

To a solution of methyltetrazine-NHS ester (30.0 mg, 91.7 μmol, molecule 48) in DMF (1.00 mL) was added ethanolamine (11.1 μL, 0.184 mmol, molecule 49) and triethylamine (25.5 μL, 0.183 mmol). The reaction mixture was shaken for 1 min and left standing at room temperature. After 1 hour the reaction mixture was submitted to preparative MP-LC.[1B] Fractions corresponding to the product were immediately pooled together, frozen and lyophilized overnight to give the title compound (19.2 mg, 77%) as a purple solid. Purity based on LC-MS 89%.

LRMS (m/z): 274 $[M+1]^{1+}$

LC-MS r.t. (min): 0.85[2]

TCO blocking on TFL has been performed on the following conjugates:

- TFL-(L-hydrazone-SPT001)-(blocked TCO)-(trivalent GalNAc) (molecule 51)
- TFL-(dendron (L-hydrazone-SPT001)4)-(blocked TCO)-(trivalent GalNAc) (molecule 52)
- TFL-(dendron-(L-hydrazone-SPT001)8)-(blocked TCO)-(trivalent GalNAc) (molecule 53)
- TFL-(L-semicarbazone-SPT001)-(blocked TCO)-(trivalent GalNAc) (molecule 54)
- TFL-(dendron((L-semicarbazone-SPT001)4)-(blocked TCO)-(trivalent GalNAc) (molecule 55)
- TFL-(dendron(L-semicarbazone-SPT001)8)-(blocked TCO)-(trivalent GalNAc) (molecule 56)

The procedure is exemplary described for TFL-(L-hydrazone-SPT001)-(blocked TCO)-(trivalent GalNAc) (molecule 51):

TFL-(L-Hydrazone-SPT001)-(Blocked TCO)-(Trivalent GalNAc) (Molecule 51)

A solution of TLF-(DBCO)-(TCO)-(trivalent GalNAc) (36.8 mg, 12.5 μmol, molecule 20) in DMF (2.0 mL) was added to SO1861-L-hydrazone-azide (26.8 mg, 12.5 μmol, molecule 3). The reaction mixture was shaken for 1 min and left standing at room temperature. After 30 min N-(2-hydroxyethyl)-2-(4-(6-methyl-1,2,4,5-tetrazin-3-yl)phenyl)

acetamide (4.08 mg, 14.9 μmol, molecule 50) was added. The reaction mixture was shaken for 1 min and left standing at room temperature. After 30 min the reaction mixture was submitted to preparative MP-LC.[1C] Fractions corresponding to the product were immediately pooled together, frozen and lyophilized overnight to give the title compound (37.3 mg, 56%) as a white fluffy solid. Purity based on LC-MS 96% (double peaks due to regioisomers).

LRMS (m/z): 2676 $[M-2]^2$

LC-MS r.t. (min): 2.23[1B]

Figure 38:
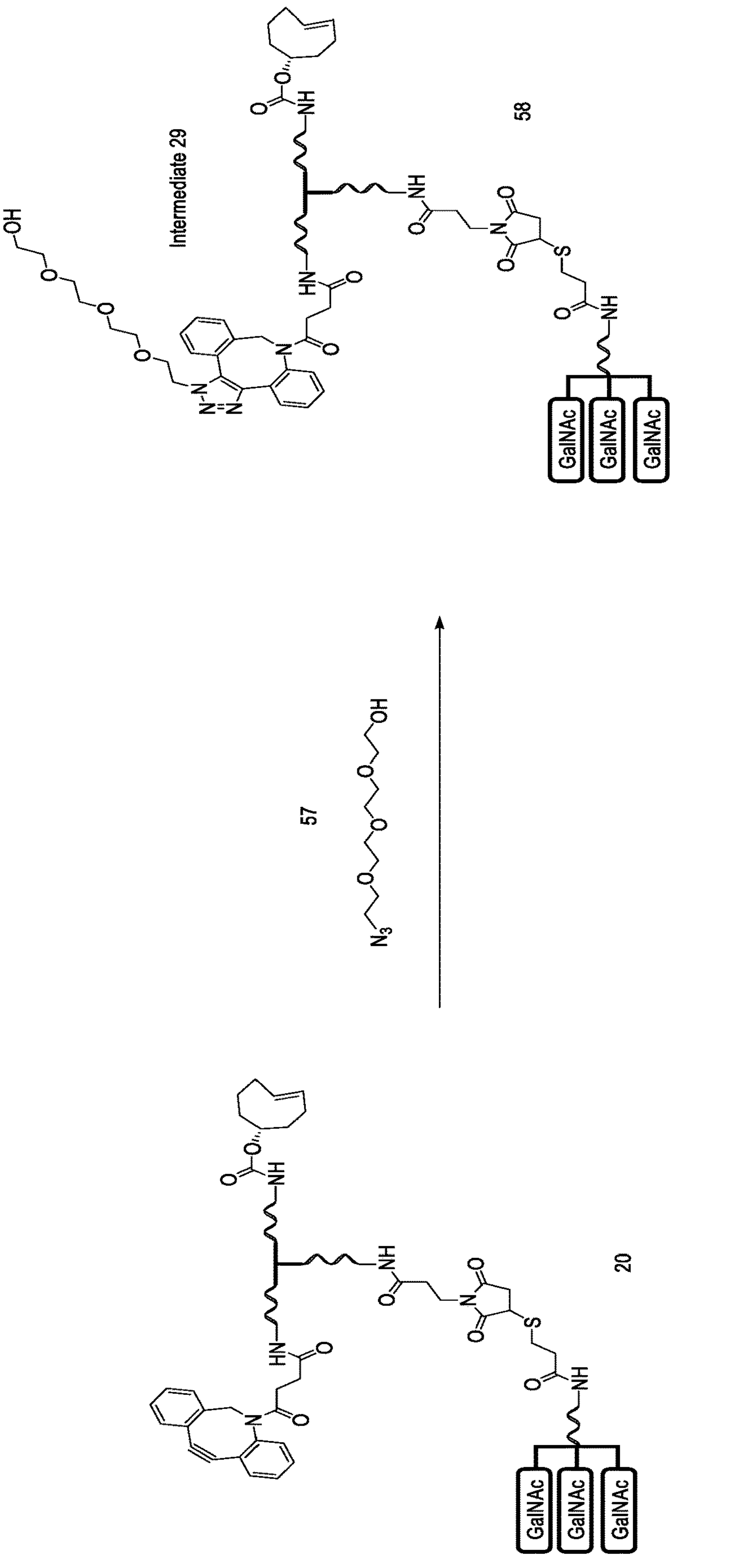
FIG. 38A-B: Trivalent linker-(blocked DBCO)-(L-BNA oligo)-(trivalent GalNAc) synthesis
Figure 38:
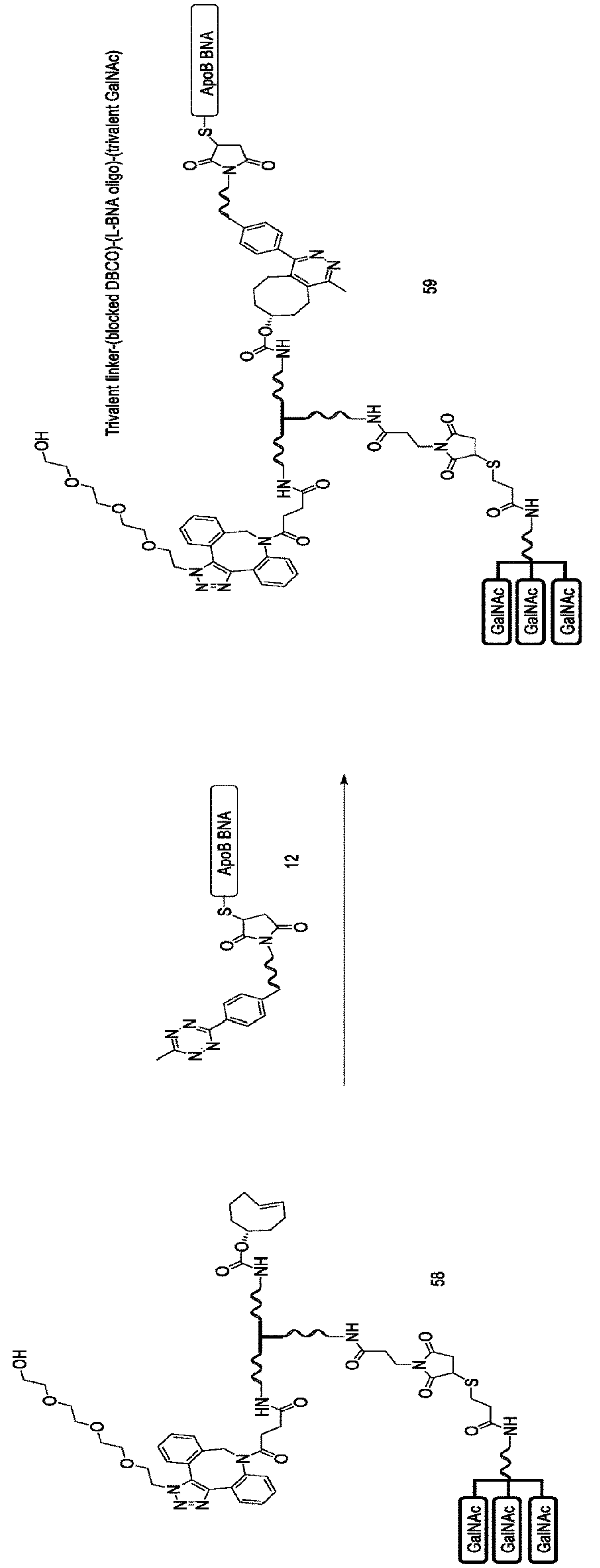

Trifunctional linker-(blocked DBCO)-(L-BNA oligo)-(trivalent GalNAc) Synthesis (FIG. 38)

Intermediate 29

TFL-(blocked DBCO)-(TCO)-(trivalent GalNAc) (Molecule 58)

A solution of 1-azido-3,6,9-trioxaundecane-11-ol (2.17 mg, 9.88 μmol, molecule 57) in DMF (0.50 mL) was added to TFL-(DBCO)-(TCO)-(trivalent GalNAc) (14.6 mg, 4.94 μmol, molecule 20). The reaction mixture was shaken for 1 min and left standing at room temperature. After 2 hours the reaction mixture was submitted to preparative MP-LC.[1C] Fractions corresponding to the product were immediately pooled together, frozen and lyophilized overnight to give the title compound (10.00 mg, 64%) as a white solid. Purity based on LC-MS 98%.

MS (m/z): 3175 $[M+H]^+$

LC-MS r.t. (min): 2.33[1B]

Trifunctional Linker-(Blocked DBCO)-(BNA Oligo)-(Trivalent GalNAc) (Molecule 59)

TFL-(blocked DBCO)-(TCO)-(trivalent GalNAc) (10.0 mg, 3.15 μmol, molecule 58) and Methyltetrazine-BNA oligo (10.0 mg, 1.83 μmol, molecule 12) were dissolved in a solution of 20 mM ammonium bicarbonate/acetonitrile (3:1, v/v, 1.00 mL). The reaction mixture was shaken for 1 min and left standing at room temperature. After 3 hours the reaction mixture was frozen and lyophilized overnight. The crude product was dissolved in 20 mM ammonium bicarbonate (1 mL) and the resulting solution was directly subjected to preparative LC-MS.[1B] Fractions corresponding to the product were immediately pooled together, frozen and lyophilized overnight to give the title compound (11.3 mg, 72%) as a white fluffy solid. Purity based on LC-MS 95%.

LRMS (m/z): 2149 $[M-4]^{4-}$, 2866 $[M-3]^{3-}$

LC-MS r.t. (min): 2.92[1A]

Using a similar approach as for synthesis of Trifunctional linker-(blocked DBCO)-(BNA oligo)-(trivalent GalNAc) (molecule 59); a conjugate in which the ApoB BNA was replaced for a BNA with a scrambled ApoB nucleic acid sequence (molecule 12 a), can be synthesized (molecule 59 a).

Figure 39:
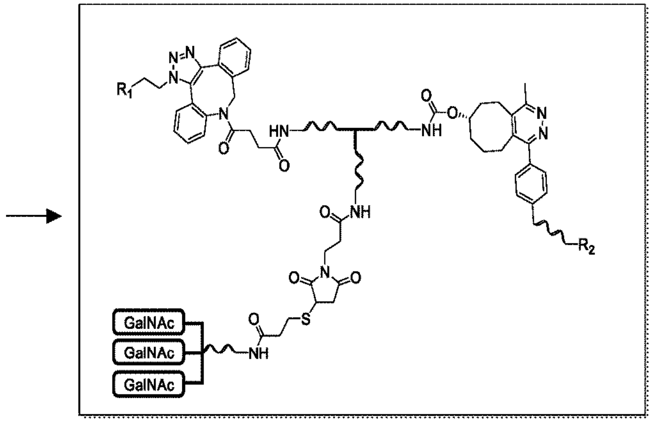
FIG. 39: Overview of conjugates obtainable by applying TFL methodology. Note that the drawing of FIG. 39 encompasses two sheets, labelled FIG. 39 and FIG. 39 (continued), which two sheets together display the conjugation of Trifunctional linker labelled molecule 4 with Targeting ligand labelled molecule 41, Effector labelled molecule 12, and one of the Enhancers labelled molecule 3, 19, 25, 28, 40 and 45 or one of the Blocking agents for controls labelled molecule 5, 12a and 50, therewith forming a conjugate with the general conjugate structure as depicted in the box, comprising group R1 and group R2, wherein R1 is any one of the groups depicted next to the boxed conjugate and R2 is any one of the groups depicted next to the boxed conjugate.
Figure 39:
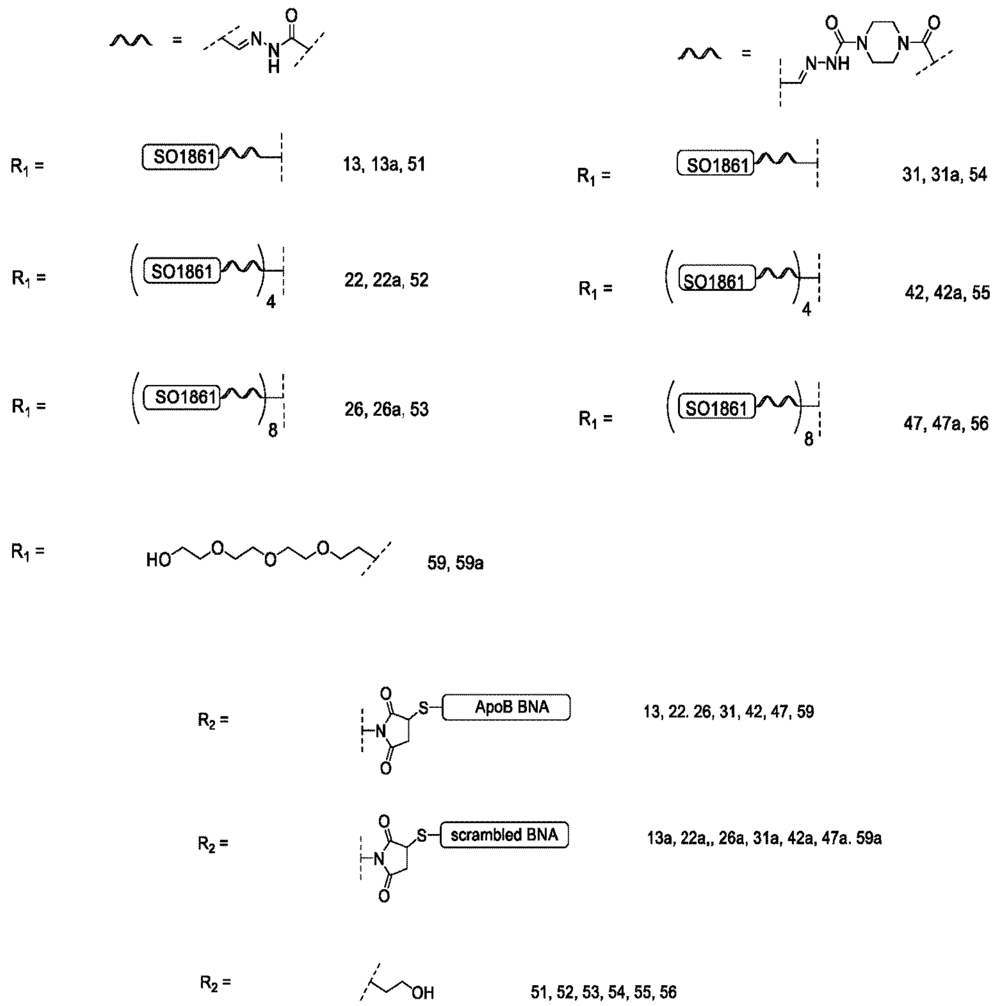
Figure 39:
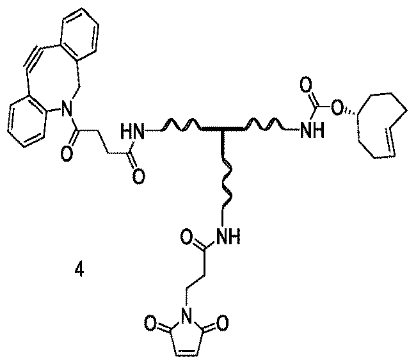
Figure 39:
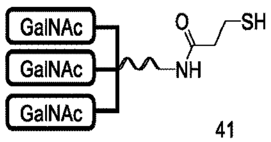
Figure 39:
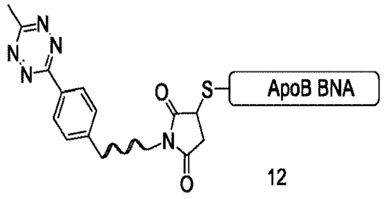
Figure 39:
Figure 39:
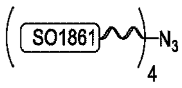
Figure 39:
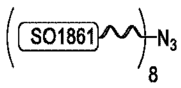
Figure 39:
Figure 39:
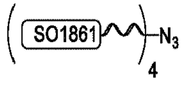
Figure 39:
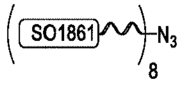
Figure 39:
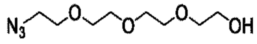
Figure 39:
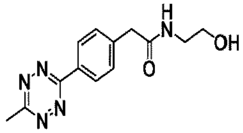
Figure 39:
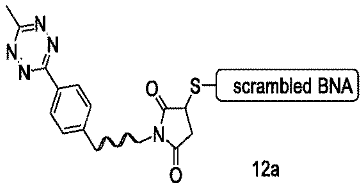

An overview of all conjugates 'CONJUGATE C' (as depicted in the box; the conjugate comprising one of the listed groups for $R^1$ and comprising one of the listed groups $R^2$) produced by applying the Trifunctional linker (TFL) methodology, is shown in FIG. 39. In addition, a conjugate according to the invention, comprising a single GalNAc moiety, has been synthesized and tested.

Cell Viability Assay (CTG)

After treatment the cells were incubated for 72 hr at 37° C. before the cell viability was determined by a CTG-assay, performed according to the manufacturer's instruction (CellTiter-Glo® 2.0 Cell Viability Assay, Promega). Briefly, the cell plate was first equilibrated to RT for 30 minutes. Next, to each well containing 120 μL treatment media 120 μL CTG solution was added. The plate briefly mixed (10 sec, 600 rpm) and incubated for approximately 10 minutes in the dark at RT. Subsequently, the luminescence signal was measured on a Spectramax ID5 plate reader (Molecular Devices). For quantification, the background signal of 'medium only' wells was subtracted from all other wells before the cell viability percentage of treated/untreated cells was calculated by dividing the background corrected signal of treated wells over the background corrected signal of the untreated wells (×100).

Human Primary Hepatocyte Treatment

Cryopreserved primary human hepatocytes (Cytes Biotechnologies S.L., Spain) were thawed in hepatocyte thawing media (Cytes Biotechnologies S.L., Spain). Cells were re-suspended in hepatocyte plating media (Cytes Biotechnologies S.L., Spain). Cells were seeded onto collagen-1 coated plates at a density of 215.600 cells/well or 66.600 cells/well for the 48 or 96-well plates (Greiner BioOne). Cells were pre-cultured for 4-6 hrs at 37° C. allowing for cell attachment to cell culture plates before the start of treatment. Plating medium was replaced by 315 μl or 108 μl maintenance media (Cytes Biotechnologies S.L., Spain), after which conjugates were added from a 10× concentrated stock solution in PBS. Plates were incubated for 72 hr at 37° C. being harvested for gene expression and cell viability analysis.

HSP27BNA, ApoB and $ApoB_{scrambled}$, and ApoB #02 Oligo Sequences

HSP27 (5'-GGCacagccagtgGCG-3') [SEQ ID NO: 1]: antisense BNA (HSP27) was a bridged-nucleic acid (BNA) oligonucleotide, more specifically $BNA^{NC}$, with sequence 5'-GGCacagccagtgGCG-3' modified from Zhang et al. (2011) [Y Zhang, Z Qu, S Kim, V Shi, B Liao1, P Kraft, R Bandaru, Y Wu, L M Greenberger and I D Horak, *Down-modulation of cancer targets using locked nucleic acid (LNA)-based antisense oligonucleotides without transfection, Gene Therapy* (2011) 18, 326-333]); the apoB-targeting oligonucleotideApoB-(5'-GCCTCagtctgcttcGCACC-3') [SEQ ID NO: 8] and the control $ApoB_{scrambled}$ (5'-GGCCTctctacaccgCTCGT-3') [SEQ ID NO: 9], and murine and human sequence-compatible ApoB #02 (5'-GCattggtat-TCA-3') [SEQ ID NO: 14] were all $BNA^{NC}$ oligonucleotides and ordered with 5'-Thiol C6 linker at Bio-Synthesis Inc (Lewisville, Texas), with $BNA^{NC}$ bases in capitals, and fully phosphorothioated backbones.

FACS Analysis

Cells were seeded in DMEM (PAN-Biotech GmbH) supplemented with 10% fetal bovine serum (PAN-Biotech GmbH) and 1% penicillin/streptomycin (PAN-Biotech GmbH), in T75 flasks at appropriate density for each cell-line and incubated for 72-96 hrs (5% $CO_2$, 37° C.), until a confluency of 90% was reached. Next, the cells were trypsinized (TrypIE Express, Gibco Thermo Scientific) to single cells, transferred to a 15 mL falcon tube, and centrifuged (1,400 rpm, 3 min). The supernatant was discarded while leaving the cell pellet submerged. 500.000 Cells were transferred to round bottom FACS tubes and the washed with 3 mL cold DPBS ($Mg^{2+}$ and $Ca^{2+}$ free, 2% FBS). The cells were centrifuged at 1800 rpm, 3 min 4° C. and resuspended in 200 μL cold DPBS ($Mg^{2+}$ and $Ca^{2+}$ free, 2% FBS) or 200 μL antibody solution; containing 5 μL antibody in 195 μL cold DPBS ($Mg^{2+}$ and $Ca^{2+}$ free, 2% FBS). PE anti-human CD71 (#334106, Biolegend) was used to stain the transferrin receptor, PE Mouse IgG2a, κ Isotype Ctrl FC (#400212, Biolegend) was used as its matched isotype control. PE anti-human ASGPR1 (#130-122-963, Miltenyi) was used to stain the ASGPR1 receptor and PE Mouse IgG1, Isotype Ctrl (#130-113-762, Miltenyi) was used as its matched isotype control. Samples were incubated for 30 min. at 4° C. Afterwards, the cells were washed 2× with cold DPBS ($Mg^{2+}$ and $Ca^{2+}$ free, 2% FBS) and fixated for 20 min at room temperature using a 2% PFA solution in DPBS ($Mg^{2+}$ and $Ca^{2+}$ free, 2% FBS). Cells were washed 1× with cold DPBS, and resuspended in 1000 μL cold DPBS for FACS analysis. Samples were analyzed with a Sysmex Cube 8 flow cytometry system (Sysmex) and FCS Express 7 Research edition software. Results of the FACS analyses are summarized in Table A3.

TABLE A3

Cell membrane receptor expression levels of ASGPR1 and CD71 of HepG2 and Huh7 cells

| Cell line | ASGPR1 expression level (MFI) | CD71 expression level (MFI) |
|---|---|---|
| HepG2 | 8.8 | 74.7 |
| Huh7 | 1.6 | 109 |

RNA Isolation and Gene Expression Analysis from Primary Mouse and Human Hepatocytes RNA from cells was isolated using TRI Reagent® Solution (Thermo Scientific) according to the manufacturer's instruction. Conversion into cDNA was performed using iScript™ cDNA Synthesis Kit (BioRad) using standard protocols. ApoB expression levels and levels of specific hepatocyte housekeeping genes were determined using quantitative real-time PCR assays (qRT-PCR) using iTaq™ Universal SYBR® Green Supermix (BioRad) and the Light Cycler 480 (Roche Diagnostics, Rotkreuz, Switzerland) with specific DNA primers, listed in Table A4. Analysis was done by the ΔCt method to determine ApoB expression relative to 2 hepatocyte-specific housekeeping control mRNAs. Each analysis reaction was performed in triplicate.

TABLE A4

Primers used in qPCR analysis of mouse cells/liver tissue (study A)

| | | |
|---|---|---|
| ApoB#02 | Forward | GCTAACACTAAGAACCAGAAGATC [SEQ ID NO: 15] |
| | Reverse | TGTCCGTCTAAGGATCCTGC [SEQ ID NO: 16] |
| Mm PPIA | Forward | GCGGCAGGTCCATCTACG [SEQ ID NO: 17] |
| | Reverse | GCCATCCAGCCATTCAGTC [SEQ ID NO: 18] |
| Mm SDHA | Forward | GAGGAAGCACACCCTCTCAT [SEQ ID NO: 19] |
| | Reverse | GGAGCGGATAGCAGGAGGTA [SEQ ID NO: 20] |

In Vivo Tolerability and Efficacy of Trivalent GalNAc-Conjugates in a C57BL/6J Model Dose administration and in-life phase. Per group, 8 C57BL/6J male mice for treatment groups (in study A, 14 mice in vehicle control group), approximately 6-7 weeks at arrival and 8-9 weeks at dosing, were dosed. The compounds, formulated in PBS or PBS alone (vehicle) according to Table A5 and Table A6, were dosed at 5 ml/kg in the tail vain (intravenously, iv), with dose volumes corresponding to the individual body-weights. Where applicable, trivalent (GalNAc)3-SO1861 (EMCH) was co-administered at 5 ml/kg in the tail vain (iv) right after the trivalent GalNAc-ApoB conjugate. Animals were weighed weekly and clinical observations were performed 2-3 times daily within the first 48 hrs, and at least once daily thereafter until study end.

Sampling of serum, liver, and kidney tissue. Blood was sampled before dosing (predose) and at indicated post-dose timepoints (eg, 24 hrs, 72 hrs, 196 hrs, 336 hrs, 672 hrs post dose), and serum was generated from the collected blood for biomarker analysis, using standard procedures. At the relevant inter-study post-dose time-points, 3 animals per timepoint per treatment group (6 animals in the vehicle control group in study A) were sacrificed to collect terminal bleeds and collect relevant organs, such as liver and kidney tissues for further analyses. At end of study, the remaining 2 animals (4 in the control group in study A) per group were sacrificed. One half of the liver and one kidney was frozen and used for tissue RNA analysis.

TABLE A5

Experimental design in vivo tolerability and efficacy of trivalent GalNAc-conjugates (study A)

| Group | Conjugate | Dose [mg/kg] | Relative BNA dose administered [mg/kg] | Co-administered trivalent GalNAc-SO1861-EMCH dose [mg/kg] |
|---|---|---|---|---|
| 1 | PBS (vehicle) | N/A | 0 | N/A |
| 2 | ApoB#02 BNA | 0.1 | 0.1 | N/A |
| 3 | ApoB#02 BNA | 1 | 1 | N/A |
| 4 | ApoB#02 BNA | 2 | 2 | N/A |
| 5 | (GalNAc)3-ApoB#02 BNA | 0.1 | 0.054 | N/A |
| 6 | (GalNAc)3-ApoB#02 BNA | 1 | 0.54 | N/A |
| 7 | (GalNAc)3-ApoB#02 BNA | 0.01 | 0.0054 | 5 |
| 8 | (GalNAc)3-ApoBBNA#02 | 0.1 | 0.054 | 5 |
| 9 | (GalNAc)3-SO1861 ApoB#02 (EMCH) BNA | 1 | 0.44 | N/A |
| 10 | (GalNAc)3-SO1861 ApoB#02 (sc) BNA | 1 | 0.44 | N/A |

TABLE A6

Experimental design in vivo tolerability and efficacy of trivalent GalNAc-conjugates (study B)

| Group | Conjugate | Dose [mg/kg] | Relative BNA dose administered [mg/kg] | Co-administered trivalent GalNAc-SO1861-EMCH dose [mg/kg] |
|---|---|---|---|---|
| 1 | PBS (vehicle) | N/A | 0 | N/A |
| 2 | ApoB#02 BNA | 2 | 2 | N/A |

TABLE A6-continued

Experimental design in vivo tolerability and efficacy of trivalent GalNAc-conjugates (study B)

| Group | Conjugate | Dose [mg/kg] | Relative BNA dose administered [mg/kg] | Co-administered trivalent GalNAc-SO1861-EMCH dose [mg/kg] |
|---|---|---|---|---|
| 3 | (GalNAc)3-SO1861 ApoB#02 (sc) BNA | 1 | 0.44 | N/A |
| 4 | (GalNAc)3-SO1861 ApoB#02 (sc) BNA | 0.1 | 0.044 | N/A |
| 5 | (GalNAc)3-dSPT4-ApoB#02 (sc) BNA | 0.173 | 0.044 | N/A |
| 6 | (GalNAc)3-dSPT8-ApoB#02 (sc) BNA | 0.265 | 0.044 | N/A |
| 7 | (GalNAc)3-ApoB#02 BNA | 1 | 1 | 0.1 |
| 8 | (GalNAc)3-ApoBBNA#02 | 0.1 | 0.1 | 0.1 |

Biomarker RNA Analysis in Liver Tissue

The mRNA was isolated from frozen liver tissue using TRizol® Reagent (Thermo Scientific) according to the manufacturer's instruction. Conversion into cDNA was performed using iScript™ cDNA Synthesis Kit (BioRad). ApoB expression levels and levels of specific liver housekeeping genes were determined using quantitative real-time PCR assays (qRT-PCR) using iTaq™ Universal SYBR® Green Supermix (BioRad) and the Light Cycler 480 (Roche Diagnostics, Rotkreuz, Switzerland) with specific DNA primers, listed in Table A4 (study A) and Table A7 (study B), respectively. Analysis was done by the ΔCt method to determine ApoB expression relative to 2 liver-specific housekeeping control mRNAs. Each analysis reaction was performed in triplicate.

TABLE A7

Primers used in qPCR analysis of liver tissue (study B)

| | | |
|---|---|---|
| ApoB#02 | Forward | GCTAACACTAAGAACCAGAAGATC [SEQ ID NO: 15] |
| | Reverse | TGTCCGTCTAAGGATCCTGC [SEQ ID NO: 16] |
| Mm RPS17 | Forward | GTGCGAGGAGATCGCCATTA [SEQ ID NO: 21] |
| | Reverse | ATCCGCTTCATCAGATGCGT [SEQ ID NO: 22] |
| Mm PPIA | Forward | GCGGCAGGTCCATCTACG [SEQ ID NO: 17] |
| | Reverse | GCCATCCAGCCATTCAGTC [SEQ ID NO: 18] |

Biomarker RNA Analysis in Liver Tissue

The mRNA was isolated from frozen liver tissue using TRizol® Reagent (Thermo Scientific) according to the manufacturer's instruction. Conversion into cDNA was performed using iScript™ cDNA Synthesis Kit (BioRad). ApoB expression levels and levels of specific liver housekeeping genes were determined using quantitative real-time PCR assays (qRT-PCR) using iTaq™ Universal SYBR® Green Supermix (BioRad) and the Light Cycler 480 (Roche Diagnostics, Rotkreuz, Switzerland) with specific DNA primers, listed in Table A4 (study A) and Table A7 (study B). Analysis was done by the ΔCt method to determine apoB expression relative to 2 liver-specific housekeeping control mRNAs. Each analysis reaction was performed in triplicate.

Biomarker Analysis ApoB Protein

ApoB protein levels in mouse serum was determined using an ApoB ELISA (ab230932, Abcam, Cambridge, UK), according to the manufacturer's instruction.

Biomarker Analysis LDL Cholesterol

LDL-cholesterol was measured in mouse serum, using an LDL-cholesterol specific two-step AU480 assay kit, respectively, from Beckman Coulter, with a photometric measurement according to the manufacturer's instructions.

Biomarker ALT Level Analysis

Serum alanine transaminase (ALT) levels was measured using an AU480 assay kit from Beckman Coulter (photometric measurements), according to the manufacturer's instructions.

Results

In Vitro Potency of (GalNAc)3-SO1861-ApoB #02 BNA

Figure 19:
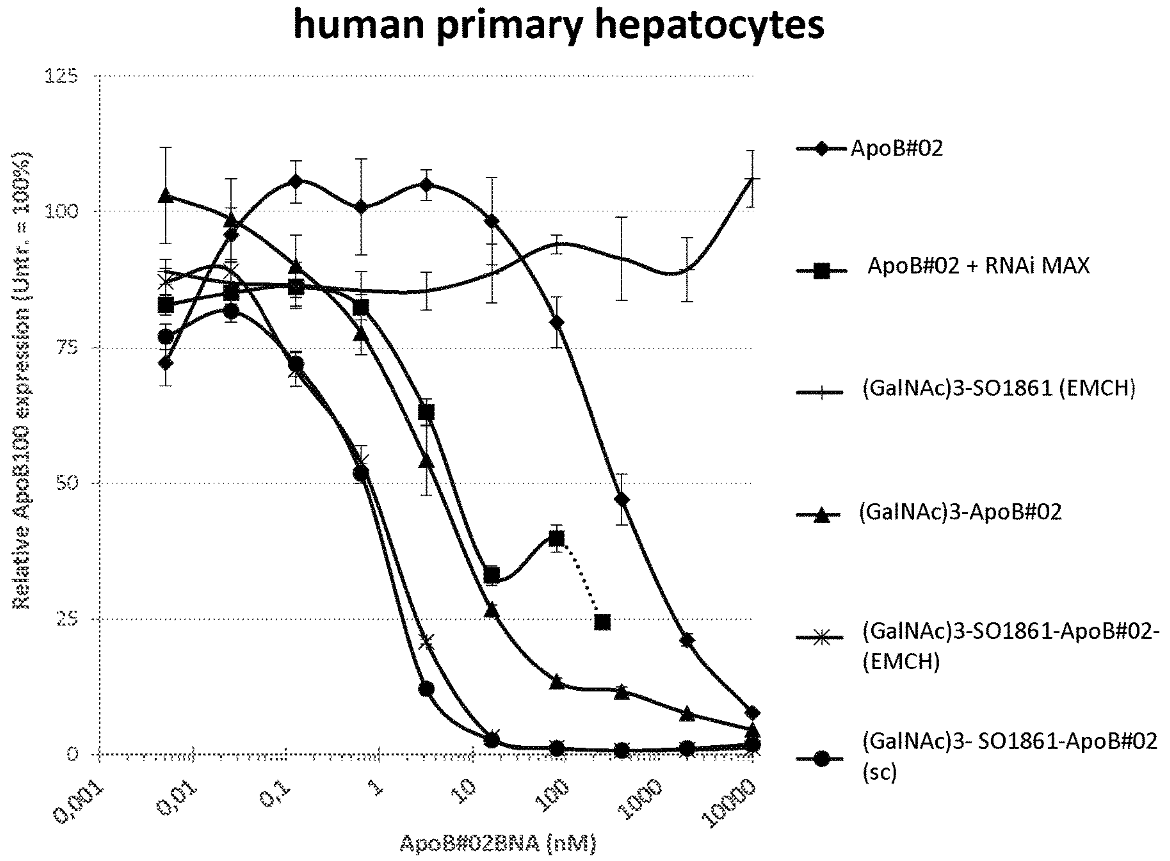
FIG. 19: Relative apoB (ApoB100) expression analysis on primary human hepatocytes (A), HepG2 cell line (B), and Huh7 cell line (C) for different ApoB #02 conjugates.
Figure 19:
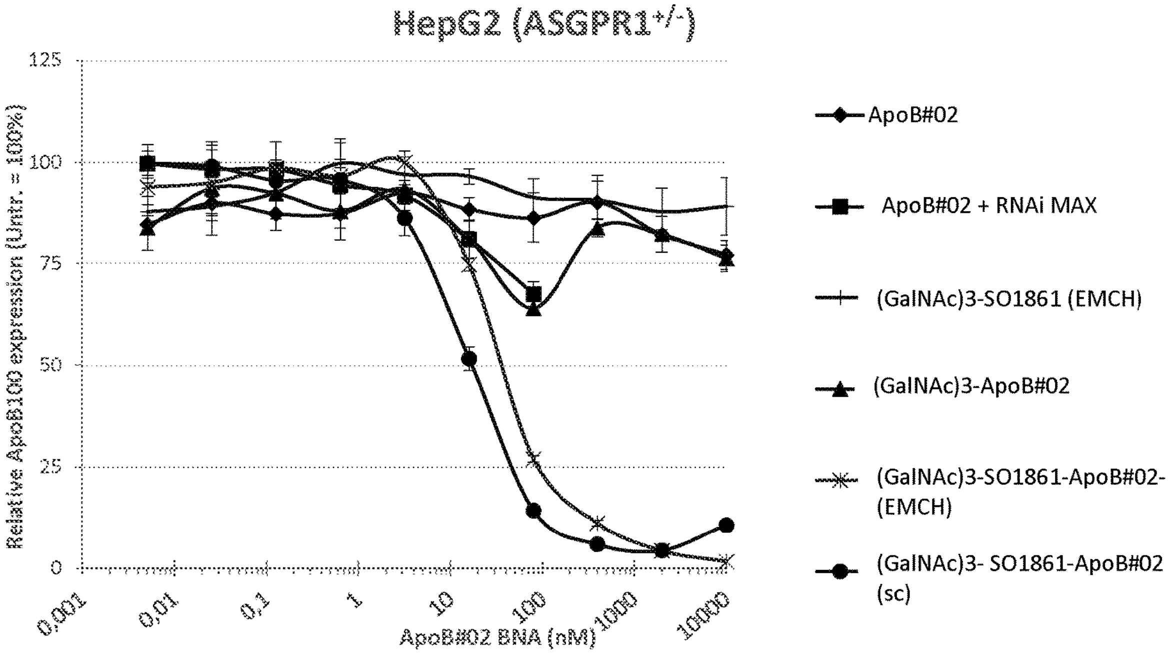
Figure 19:
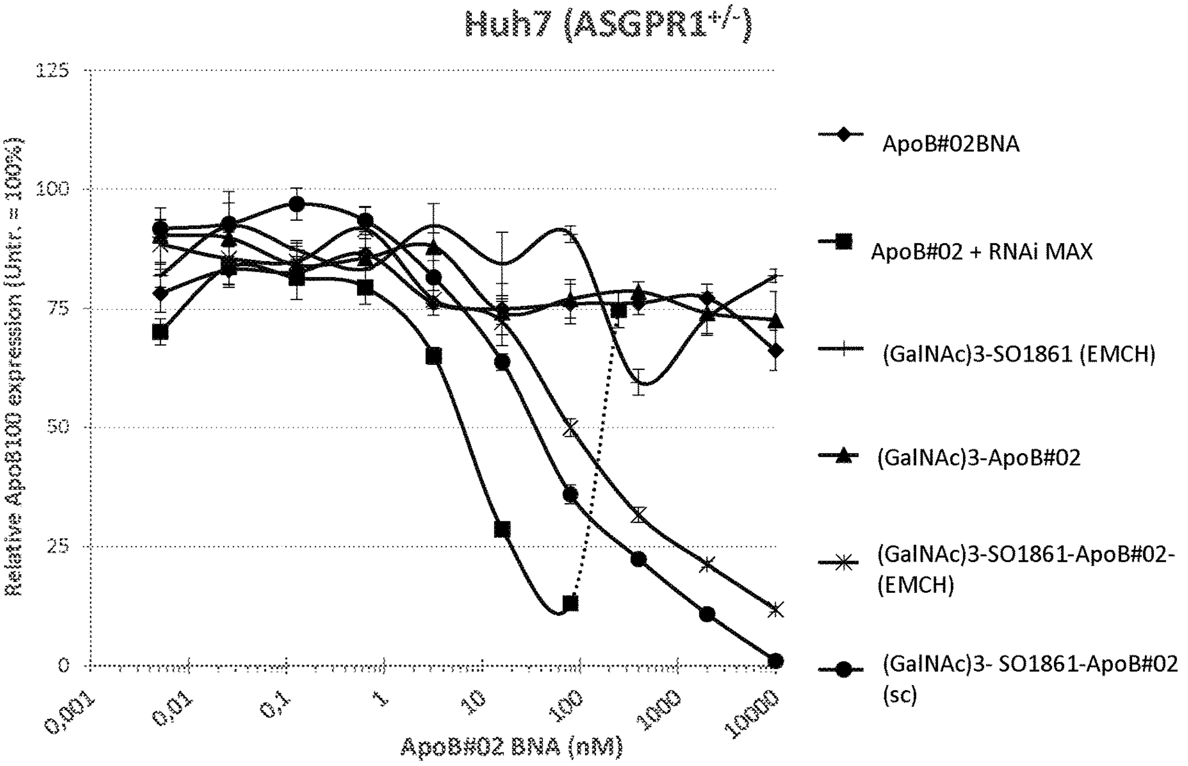
Figure 29:
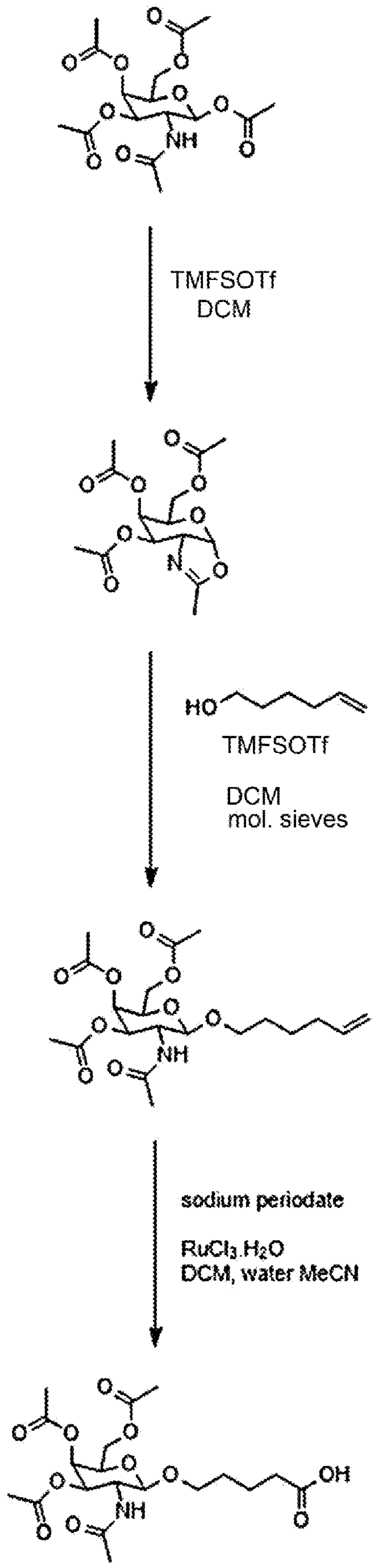
FIG. 29A-C: synthesis of trivalent GalNAc
Figure 29:
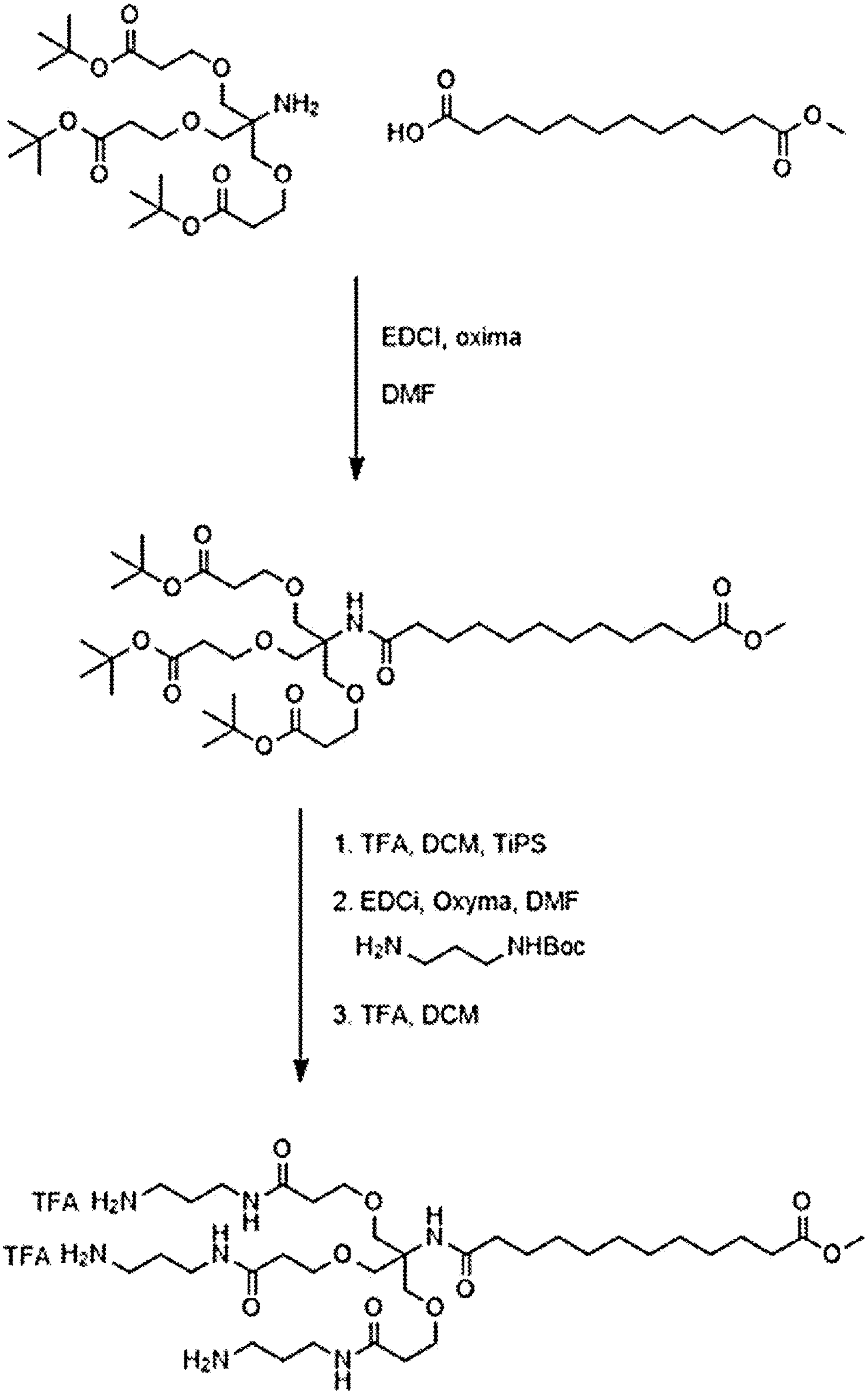
Figure 29:
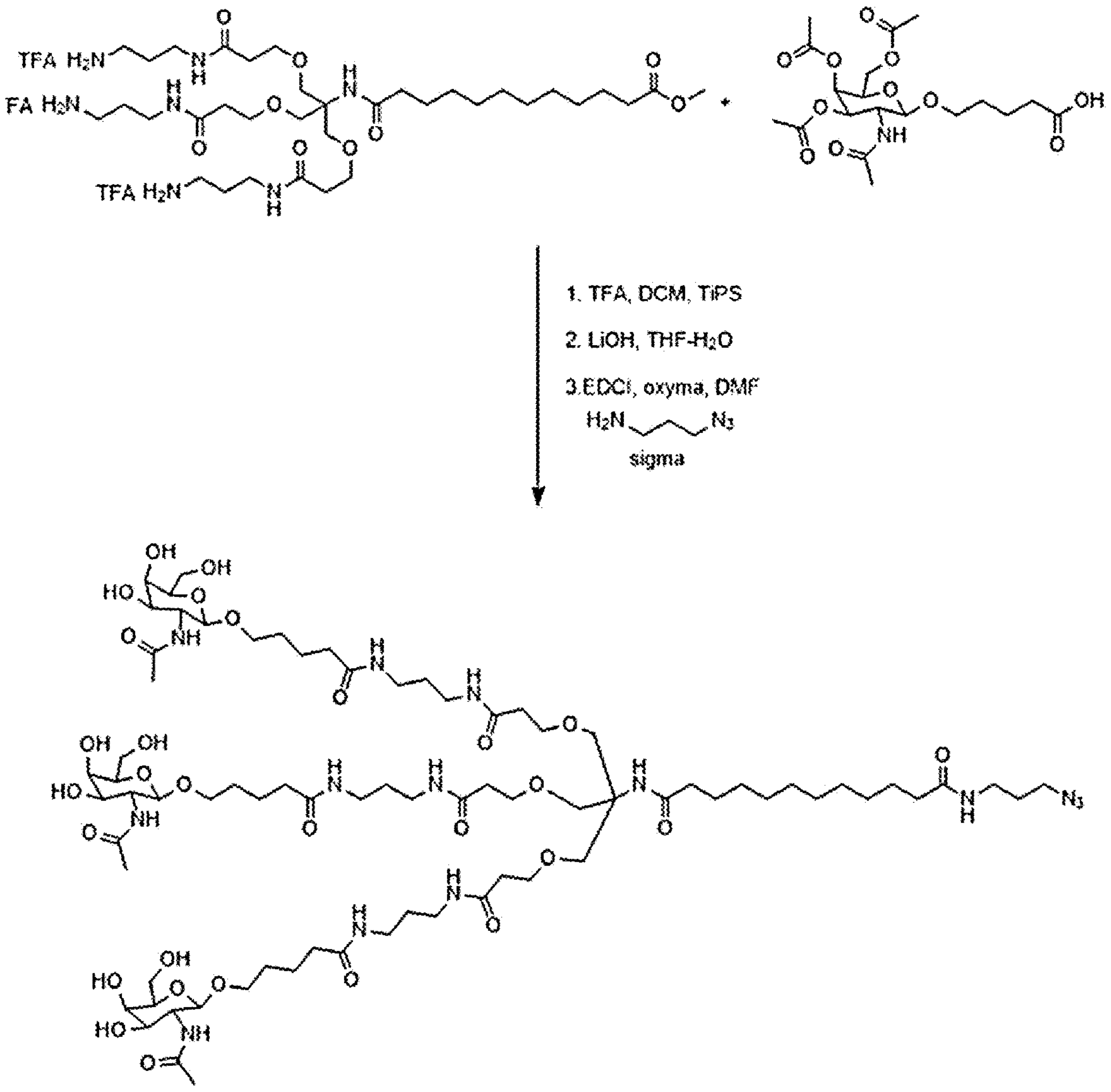
Figure 30:
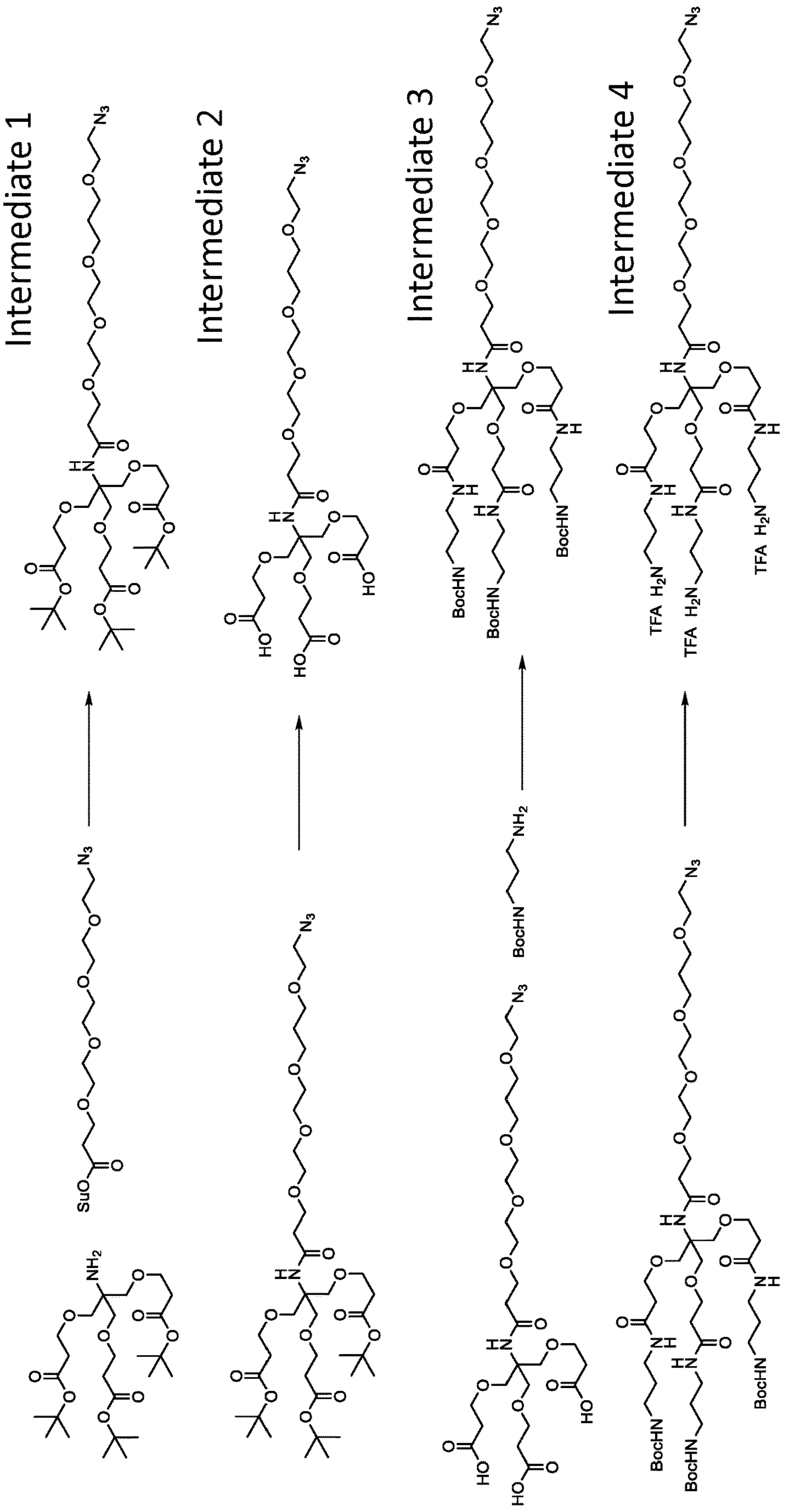
FIG. 30A-D: synthesis of trivalent GalNAc.
Figure 30:
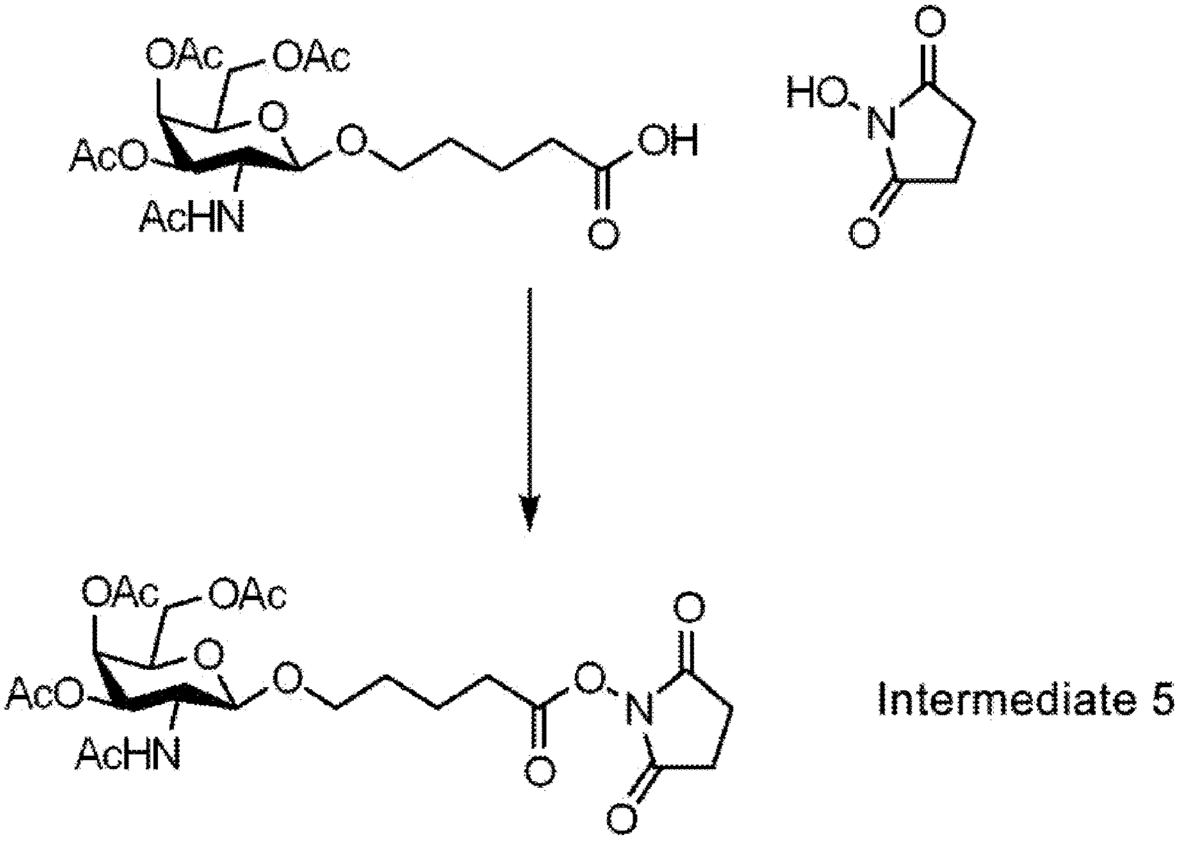
Figure 30:
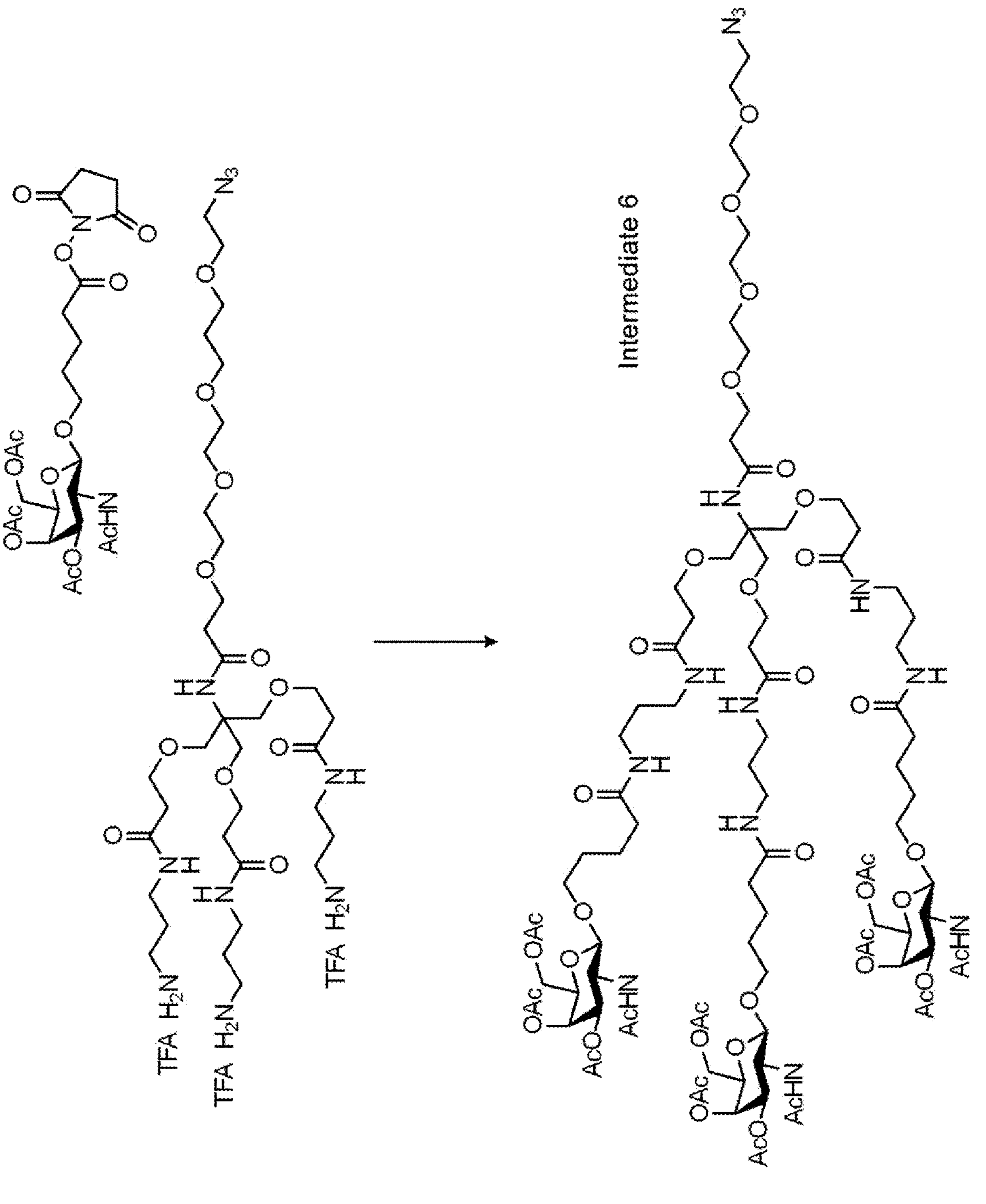
Figure 30:
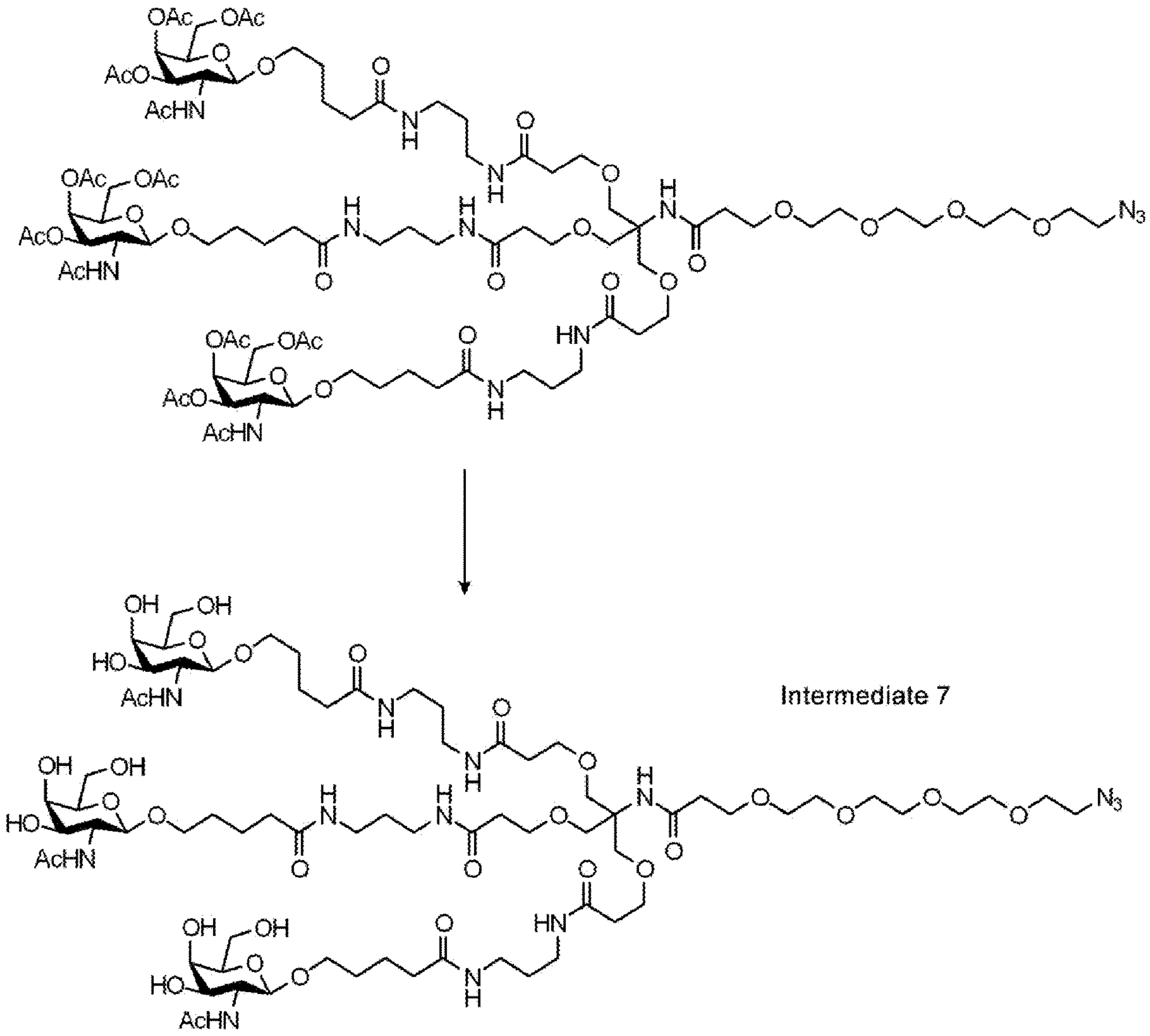
Figure 30:
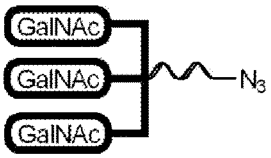

An apoB-targeting BNA, ApoB #02 (SEQ ID NO: 14), and SO1861-EMCH or SO1861-sc-Mal was conjugated to trivalent-GalNAc ((GalNAc)3) (FIG. 29, FIG. 30) to produce (GalNAc)3-SO1861-ApoB #02 (EMCH) (FIG. 31) and (GalNAc)3-SO1861-ApoB #02 (sc) (FIG. 34), (GalNAc)3-SO1861 (FIG. 37; referred to as 'Trivalent linker-(L-SPT001)-(blocked TCO)-(trivalent GalNAc)', FIG. 39) and (GalNAc)3-ApoB #02 BNA (FIG. 38; referred to as 'Trivalent linker-(blocked DBCO)-(L-BNA oligo)-(trivalent GalNAc)', FIG. 39) and conjugates were tested on primary human hepatocytes, as well as HepG2 ($ASGPR^{+}$) and Huh7 ($ASGPR^{+/-}$) cell lines to assess their effect on apoB RNA levels. In primary hepatocytes, this assessment revealed that (GalNAc)3-SO1861-ApoB #02 (EMCH) and (GalNAc)3-SO1861-ApoB #02 (sc) showed an IC50 of 1 nM (relative ApoB #02 BNA concentration), whereas (GalNAc)3-ApoB #02 BNA without SO1861 showed an IC50=7 nM (relative ApoB #02 BNA concentration), and ApoB #02 BNA transfection with RNAi-MAX showed an IC50=8 nM; ApoB #02 alone (without any transfection agent) showed an IC50=400 nM, while (GalNAc)3-SO1861 had no effect on apoB RNA levels (FIG. 19A). All this shows that (GalNAc)3-SO1861-ApoB #02 enhances the cytoplasmic delivery of the ApoB #02 BNA in human primary hepatocytes, resulting in around 10-fold improved potency at low nM levels of ApoB #02 BNA oligonucleotide. Covalent binding of the saponin to the GalNAc/oligonucleotide conjugate via a semicarbazone bond thus results in increased efficacy when relative apoB RNA levels are considered and compared with levels measured in cells which were contacted with a conjugate comprising saponin linked via a hydrazone bond to the GalNAc/oligonucleotide conjugate. Without wishing to be bound by any theory, improved efficacy of the release of free saponin from the conjugate, when the conjugate is transferred into the endosome, is at the basis for the improved potency of the oligonucleotide, as obtained with the conjugate comprising saponin bound via semicarbazone.

For HepG2 cells ($ASGPR1^{+}$), only ((GalNAc)3-SO1861-ApoB #02 (EMCH) and (GalNAc)3-SO1861-ApoB #02 (sc) showed activity at the concentrations tested (IC50=40 nM and IC50=20 nM, respectively) (FIG. 19B), whereas in Huh7 cells ($ASGPR1^{+/-}$), (GalNAc)3-SO1861-ApoB #02

(EMCH) showed activity at IC50=100 nM and (GalNAc)3-SO1861-ApoB #02 (sc) showed activity at IC50=40 nM (FIG. 19C).

In Vivo Efficacy of (GalNAc)3-SO1861-ApoB #02 in C57BL/6J Mice (Study A)

In study A, C57BL/6J mice were treated as described and dosed according to Table A5. The conjugates used in this study, (GalNAc)3-ApoB #02 (FIG. 38; referred to as 'Trivalent linker-(blocked DBCO)-(L-BNA oligo)-(trivalent GalNAc)', FIG. 39), (GalNAc)3-SO1861 (FIG. 37; referred to as 'Trivalent linker-(L-SPT001)-(blocked TCO)-(trivalent GalNAc)', FIG. 39), (GalNAc)3-SO1861-ApoB #02 (EMCH) (FIG. 31) and (GalNAc)3-SO1861-ApoB #02 (sc) (FIG. 34) were produced. Clinical observations were recorded and different biomarkers of efficacy and tolerability were analysed.

Figure 20:
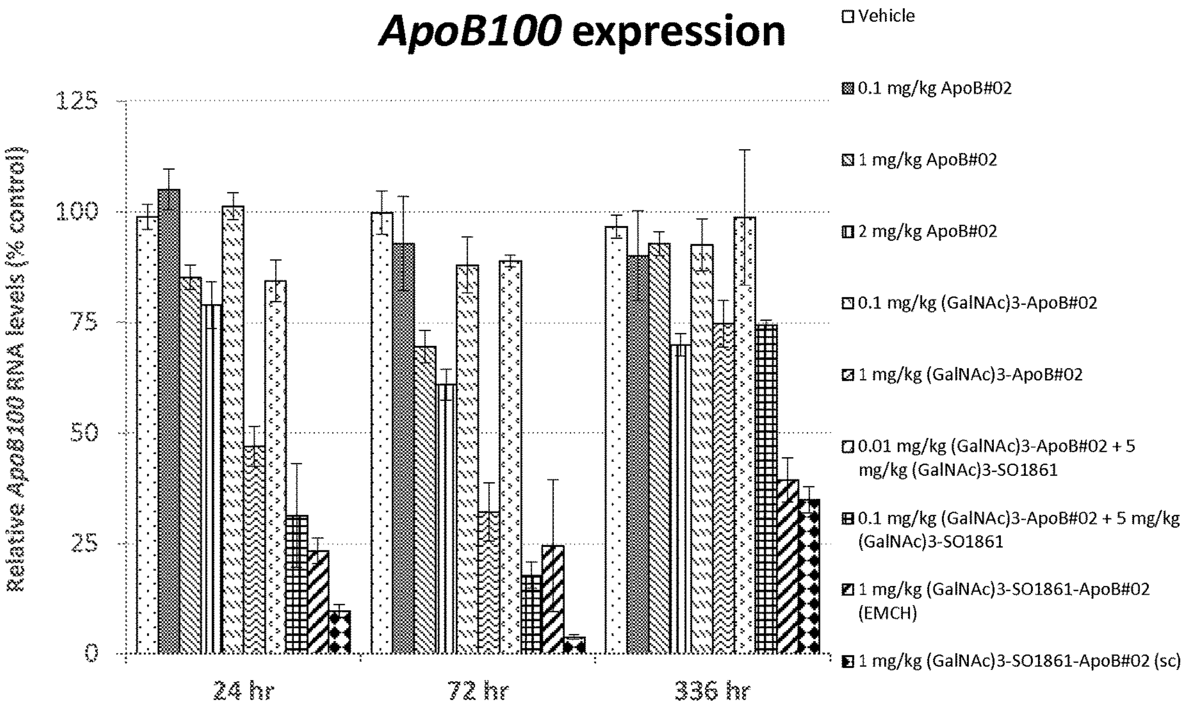
FIG. 20: Relative apoB expression analysis in liver tissue of C57BL/6J mice.

As FIG. 20 shows, after 24 hrs, the apoB RNA levels, i.e. gene expression, was not noticeably reduced in animals treated with 0.1 mg/kg ApoB #02 BNA (ApoB #02), and ca 15% and 21% reduced in groups dosed with 1 mg/kg or 2 mg/kg ApoB #02 BNA, respectively (all n=3 animals per group), compared to the vehicle-dosed group (n=5 animals). Likewise, (GalNAc)3-ApoB #02, at a dose of 1 mg/kg (corresponding to 0.54 mg/kg ApoB #02 BNA) reduced apoB expression by ca. 53% (n=3 animals) compared to the vehicle control after 24 hrs, while 0.1 mg/kg (GalNAc)3-ApoB #02 alone did not show a noticeable reduction (n=3) compared to vehicle. In contrast, when 0.1 mg/kg (GalNAc)3-ApoB #02 was co-administered with 5 mg/kg (GalNAc)3-SO1861, apoB expression was readily reduced by ca 69% (n=2 animals) already after 24 hrs; while 0.01 mg/kg (GalNAc)3-ApoB #02, when co-administered with 5 mg/kg (GalNAc)3-SO1861 still show a minor reduction of 16% (n=2 animals), compared to vehicle. Most notably, treatment with 1 mg/kg (GalNAc)3-SO1861-ApoB #02 BNA (corresponding to 0.44 mg/kg ApoB #02 BNA) resulted in a ca. 77% reduction for (GalNAc)3-SO1861-ApoB #02 BNA (EMCH) and even more, namely a 90% reduction, for (GalNAc)3-SO1861-ApoB #02 BNA (sc), compared to control already 24 hrs post dosing (n=3 animals in both groups each). Covalent binding of the saponin to the GalNAc/oligonucleotide conjugate via a semicarbazone bond thus results in increased efficacy when relative apoB RNA levels are considered and compared with levels measured for control animals which were treated with conjugate comprising saponin linked via a hydrazone bond to the GalNAc/oligonucleotide conjugate. Without wishing to be bound by any theory, improved efficacy of the release of free saponin from the conjugate, when the conjugate is transferred into the endosome, is at the basis for the improved potency of the oligonucleotide, as obtained with the conjugate comprising saponin bound via semicarbazone.

Figure 21:
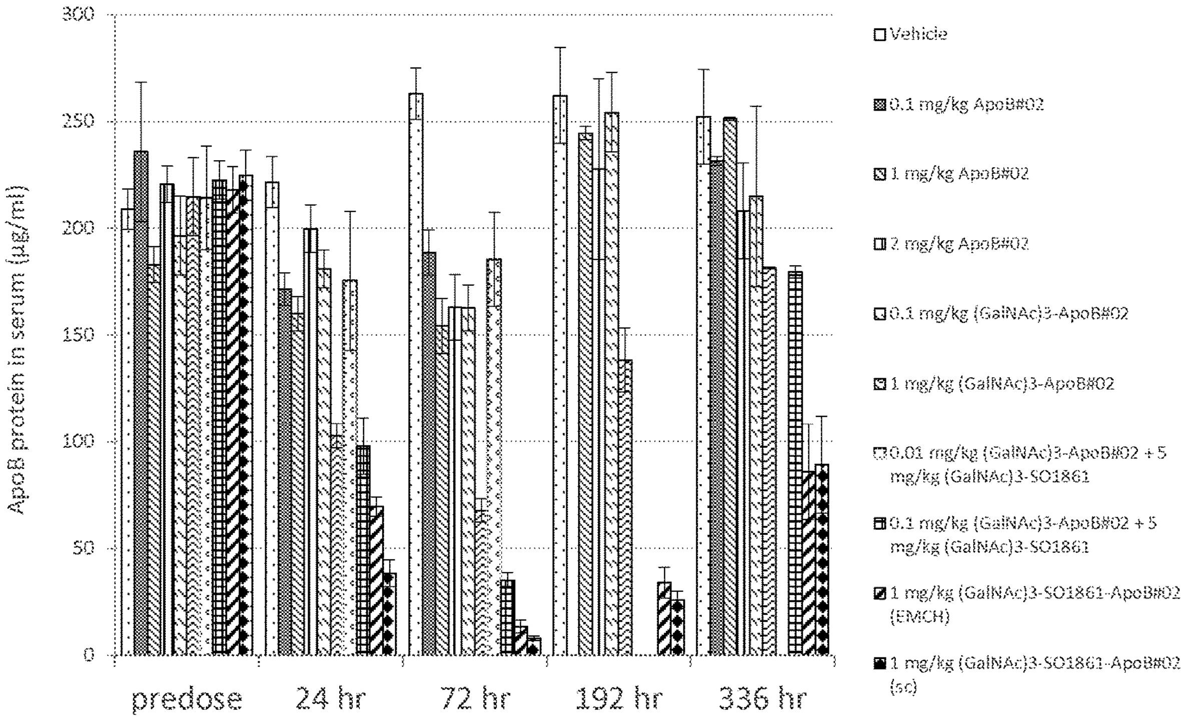
FIG. 21: Serum apoB protein analysis C57BL/6J mice. NB, levels for 0.1 mg/kg ApoB #02 (196 hrs), 0.01 mg/kg $(GalNAc)_3$-ApoB+5 mg/kg $(GalNAc)_3$-SO1861 (196 hrs and 336 hrs) and 0.1 mg/kg $(GalNAc)_3$-ApoB+5 mg/kg $(GalNAc)_3$-SO1861 (196 hrs) are not reported.

After 72 hrs, the highest dose of ApoB #02 BNA administered (2 mg/kg) showed a maximal reduction of 39% (n=3 animals) compared to vehicle (n=5 animals), while 1 mg/kg (GalNAc)3-ApoB #02 resulted in a 68% reduction of apoB expression (n=3 animals). Again, in contrast, the 10-fold lower dose of 0.1 mg/kg (GalNAc)3-ApoB #02, when co-administered with 5 mg/kg (GalNAc)3-SO1861, resulted in even 82% reduction of apoB expression levels (n=3 animals), while 0.1 mg/kg (GalNAc)3-ApoB #02 alone only shows 12% reduction (n=3 animals). Here, treatment with 1 mg/kg (GalNAc)3-SO1861-ApoB #02 BNA resulted in ca. 76% reduction for (GalNAc)3-SO1861-ApoB #02 BNA (EMCH) and even a 96% reduction for (GalNAc)3-SO1861-ApoB #02 BNA (sc) (n=3 animals in both groups each). The effect was durable, and after 336 hrs, apoB expression levels were reduced by 30% for 2 mg/kg ApoB #2 BNA (n=2 animals) and 25% for 1 mg/kg (GalNAc)3-ApoB #02. The co-administration group of 10-fold less payload (i.e., 0.1 mg/kg (GalNAc)3-ApoB #02+5 mg/kg (GalNAc)3-SO1861 still showed 25% decrease. Treatment with 1 mg/kg (GalNAc)3-SO1861-ApoB #02 BNA resulted in ca. 61% reduction for (GalNAc)3-SO1861-ApoB #02 BNA (EMCH) and a 65% reduction for (GalNAc)3-SO1861-ApoB #02 BNA (sc) (n=3 animals in both groups each). In conclusion, conjugation of SO1861 markedly improves potency, and specifically, conjugates with SC-SO1861, meaning (GalNAc)3-SO1861-ApoB #02 BNA (sc), result in the most potent down-modulation at the same payload (ApoB BNA) dose per kg. As FIG. 21 shows, the apoB RNA down-modulation in the liver (shown in FIG. 20) also translated to apoB protein reduction in serum. After 24 hrs, the apoB protein levels were reduced by over 50% for both, the 1 mg/kg (GalNAc)3-ApoB #02 (n=8 animals, 54% reduction) and equally so for the co-administration group with 10-fold less (GalNAc)3-ApoB #02+5 mg/kg (GalNAc)3-SO1861, i.e., 0.1 mg/kg (GalNAc)3-ApoB #02+5 mg/kg (GalNAc)3-SO1861 (n=8 animals, 56% reduction); most notably, apoB protein levels were reduced for 1 mg/kg (GalNAc)3-SO1861-ApoB #02 (EMCH) group (n=8 animals, 69% reduction) and to an even higher extent of 83% for 1 mg/kg (GalNAc)3-SO1861-ApoB #02 (sc) group (n=8 animals) compared to controls (n=14 animals). After 72 hours, while all treatment groups showed reduction in apoB protein, compared to vehicle controls, the most pronounced effect was observed for 1 mg/kg (GalNAc)3-SO1861-ApoB #02 (EMCH) group (n=5 animals, 95% reduction) and, to an even higher extent, for the 1 mg/kg (GalNAc)3-SO1861-ApoB #02 (sc) group (n=5 animals, as much as 97% reduction) or when co-administering 0.1 mg/kg (GalNAc)3-ApoB #02 with 5 mg/kg (GalNAc)3-SO1861, resulting in an apoB reduction of almost 90% (n=5 animals). Even 0.01 mg/kg (GalNAc)3-ApoB #02 reduced apoB protein by ca. 25% when co-administering it with 5 mg/kg (GalNAc)3-SO1861 (n=4 animals), while the 10-fold higher dose of 0.1 mg/kg (GalNAc)3-ApoB #02 alone reduced apoB protein by 35% (n=animals) after 72 hrs post-dose. The effect was durable and apoB protein reduction was still observable at 192 hrs and 336 hrs for all treatment groups analyzed; NB, levels for 0.1 mg/kg ApoB #02 (196 hrs), 0.01 mg/kg (GalNAc)3-ApoB+5 mg/kg (GalNAc)3-SO1861 (196 hrs and 336 hrs) and 0.1 mg/kg (GalNAc)3-ApoB+5 mg/kg (GalNAc)3-SO1861 (196 hrs) are not reported. At 192 hrs, 0.1 mg/kg (GalNAc)3-ApoB #02+5 mg/kg (GalNAc)3-SO1861 showed 55% reduction (n=2 animals), 1 mg/kg (GalNAc)3-ApoB #02 showed 47% reduction (n=2 animals) but 1 mg/kg (GalNAc)3-SO1861-ApoB #02 (EMCH) and 1 mg/kg (GalNAc)3-SO1861-ApoB #02 (sc) showed 87% and 90% reduction, respectively (n=2 animals per group). At 336 hrs, 0.1 mg/kg (GalNAc)3-ApoB #02 with 5 mg/kg (GalNAc)3-SO1861 showed still 29% reduction (n=2 animals), 1 mg/kg (GalNAc)3-ApoB #02 showed 28% reduction (n=2 animals) but 1 mg/kg (GalNAc)3-SO1861-ApoB #02 (EMCH) and 1 mg/kg (GalNAc)3-SO1861-ApoB #02 (sc) showed still 66% and 65% reduction, respectively (n=2 animals per group). Similar to the results obtained with testing for apoB gene expression, covalent binding of the saponin to the GalNAc/oligonucleotide conjugate via a semicarbazone bond thus results in increased efficacy when relative apoB protein levels in serum are considered and compared with levels measured for animals which were treated with conjugate comprising saponin linked via a hydrazone bond to the GalNAc/oligonucleotide conjugate.

Without wishing to be bound by any theory, improved efficacy of the release of free saponin from the conjugate, when the conjugate is transferred into the endosome, is at the basis for the improved potency of the oligonucleotide, as obtained with the conjugate comprising saponin bound via semicarbazone.

Figure 22:
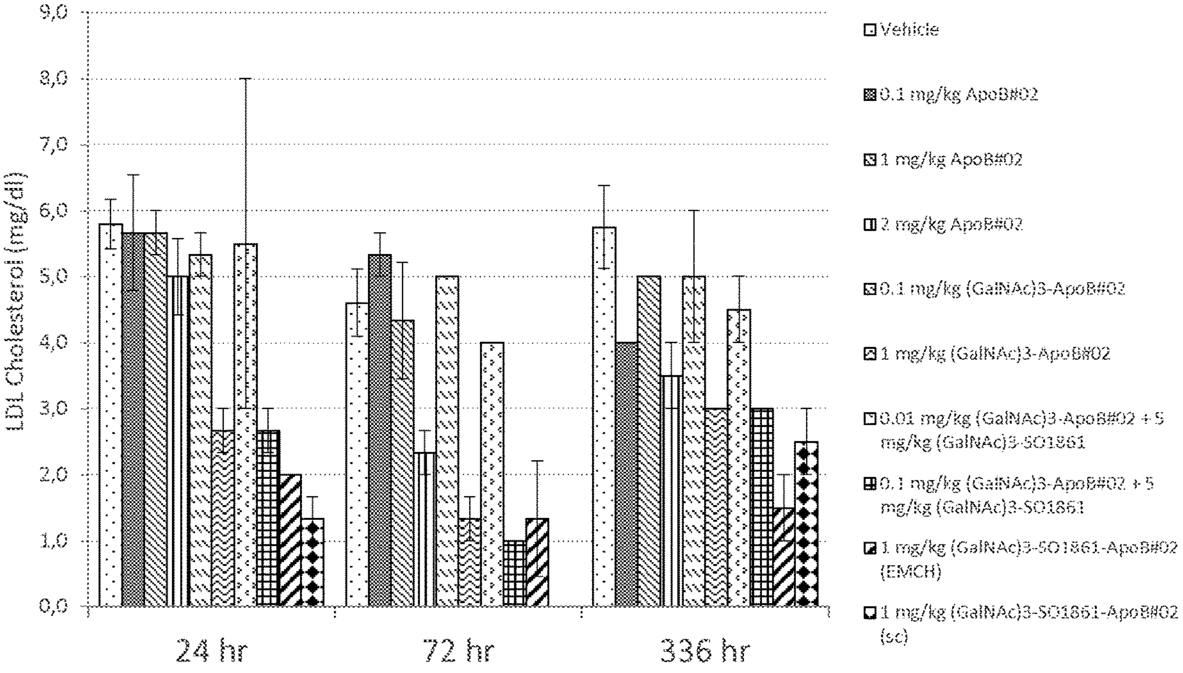
FIG. 22: Serum LDL-cholesterol (LDL-C) analysis in C57BL/6J mice.

As FIG. 22 shows, the observed serum apoB protein reduction (shown in FIG. 21) translated also to a reduction in serum LDL-cholesterol (LDL-C) levels. After 24 hrs, LDL-C levels were not noticeably reduced in animals treated with either 0.1, 1, or 2 mg/kg ApoB #02 BNA (n=3 animals per group) compared to vehicle (n=5 animals). Targeted (GalNAc)3-ApoB #02 at a dose of 1 mg/kg reduced LDL-C to an average of 2.7 mg/dl within 24 hrs already (n=3 animals), i.e., a 53% reduction compared to vehicle and ApoB #02 BNA groups. The same reduction of LDL-C to an average of 2.7 mg/dl within 24 hrs (n=3 animals), i.e. a 53% reduction, was already observed with a 10-fold lower dose of 0.1 mg/kg (GalNAc)3-ApoB #02 when co-administering it with 5 mg/kg (GalNAc)3-SO1861, while 1 mg/kg (GalNAc)3-SO1861-ApoB #02 (EMCH) and 1 mg/kg (GalNAc)3-SO1861-ApoB #02 (sc) showed a reduction of 66% and even as high as 77%, respectively. After 72 hrs, the highest dose of ApoB #02 BNA (2 mg/kg) showed a ca. 50% reduction (n=3 animals) in LDL-C compared to vehicle (n=5 animals), while for the 1 mg/kg (GalNAc)3-ApoB #02 group, LDL-C was 72% reduced (n=3 animals), and the 10-fold lower dose of 0.1 mg/kg (GalNAc)3-ApoB #02+5 mg/kg (GalNAc)3-SO1861 was even 78% reduced (n=3 animals); 1 mg/kg (GalNAc)3-SO1861-ApoB #02 (EMCH) showed 72% reduction, while in the 1 mg/kg (GalNAc)3-SO1861-ApoB #02 (sc), no LDL-C above limit of detection (i.e., zero) remained measurable, i.e., a surprisingly high extent of 100% reduction in apoB protein compared to control (all n=3 animals). The effect was durable, and after 336 hrs, LDL-C levels were still reduced (in n=2 animals for all groups) by ca. 40% for 2 mg/kg ApoB #02 BNA, and 48% for both, the 1 mg/kg (GalNAc)3-ApoB #02 and for the co-administration group of 0.1 mg/kg (GalNAc)3-ApoB #02+5 mg/kg (GalNAc)3-SO1861, showing a 10-fold improved LDL-C reduction based in administered payload in the latter. Again, the most pronounced reductions were observed in the groups with 1 mg/kg (GalNAc)3-SO1861-ApoB #02 (EMCH) with 74% reduction and 1 mg/kg (GalNAc)3-SO1861-ApoB #02 (sc) showed a reduction of 57%.

In conclusion, this shows that in combination with SO1861, and specifically also SC-SO1861, the potency of ApoB #02 is markedly increased and is effectively inducing apoB RNA reduction, i.e., gene silencing in the livers of C57BL/6J mice, and reduction of all 'downstream' serum biomarkers of efficacy, such as apoB protein and LDL-cholesterol.

In Vivo Tolerability of (GalNAc)3-SO1861-ApoB #02 in C57BL/6J Mice

The conjugates used in this study, (GalNAc)3-ApoB #02 (FIG. 38, FIG. 39), (GalNAc)3-SO1861 (FIG. 37, FIG. 39), (GalNAc)3-SO1861-ApoB #02 (EMCH) (FIG. 31) and (GalNAc)3-SO1861-ApoB #02 (sc) (FIG. 34) were produced.

Figure 23:
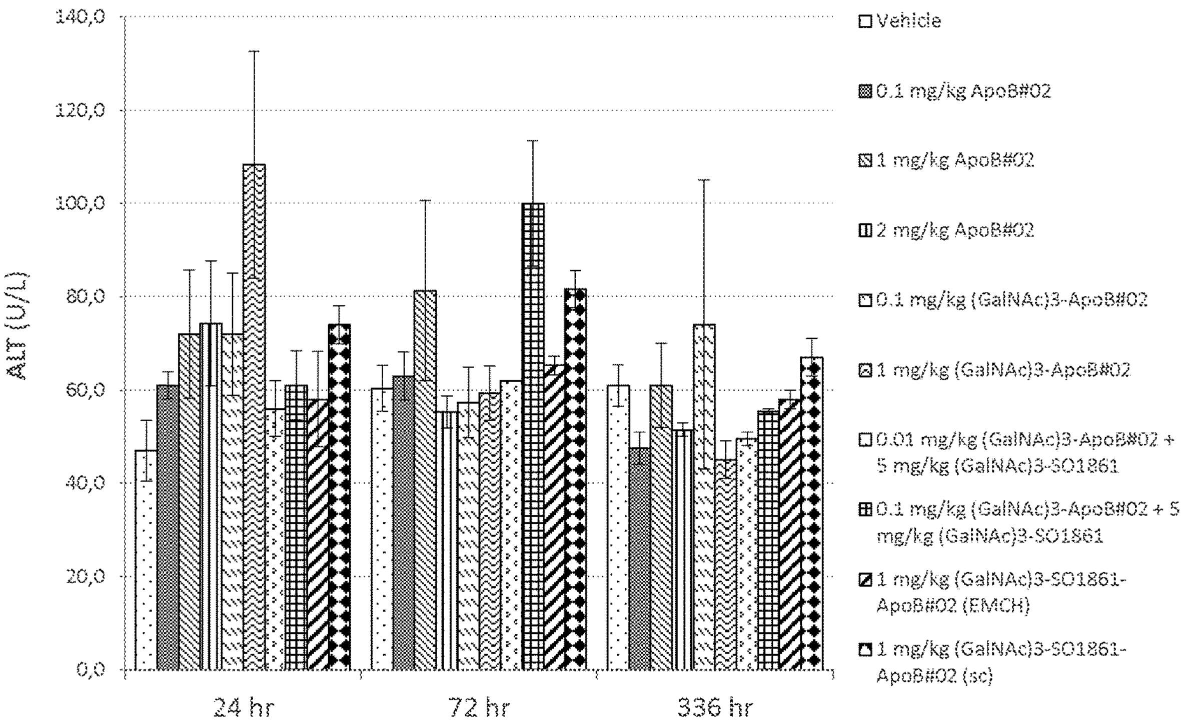
FIG. 23: Serum ALT analysis in C57BL/6J mice.

During the course of the study, all treatments, doses, and dose regimens as described in Table A5 were well tolerated and showed no treatment-specific adverse findings or any specific clinical observations indicative of the conjugates not being tolerated. The mice in treatment groups gained weight comparable to the mice receiving vehicle. Serum ALT levels were determined and results are shown in FIG. 23. During the study period, ALT levels for vehicle mice ranged from an average 47 to 61 U/L per group (n=5 animals for vehicle). Levels of ALT transiently increased in the different dose groups at different time points, with sometimes large per-animal variation per group, without showing specific compound or dose relationship (n=3 for all groups at 24 hrs and 72 hrs, respectively, except for 0.01 mg/kg (GalNAc)3-ApoB #02+5 mg/kg (GalNAc)3-SO1861, where n=2 for both time points). Notably, after 336 hrs, ALT levels in all dosing groups were back to baseline and comparable to vehicle controls (n=2 for all groups).

In conclusion, this shows that ApoB #02, (GalNAc)3-ApoB #02, (GalNAc)3-SO1861 (alone or in combination with (GalNAc)3-ApoB #02), and (GalNAc)3-SO1861-ApoB #02 (EMCH) and (GalNAc)3-SO1861-ApoB #02 (sc) are well tolerated in the doses and dose regimen applied, and particularly, that administration of SO1861-containing conjugates (GalNAc)3-SO1861-ApoB #02 (EMCH) and (GalNAc)3-SO1861-ApoB #02 (sc) as well as co-administration of (GalNAc)3-SO1861 with (GalNAc)3-ApoB #02 has no immediate tolerability issues, while showing high potency in the C57BL/6J mouse model.

In Vitro Potency of (GalNAc)3-d(SO1861)8-ApoB #02

Figure 24:
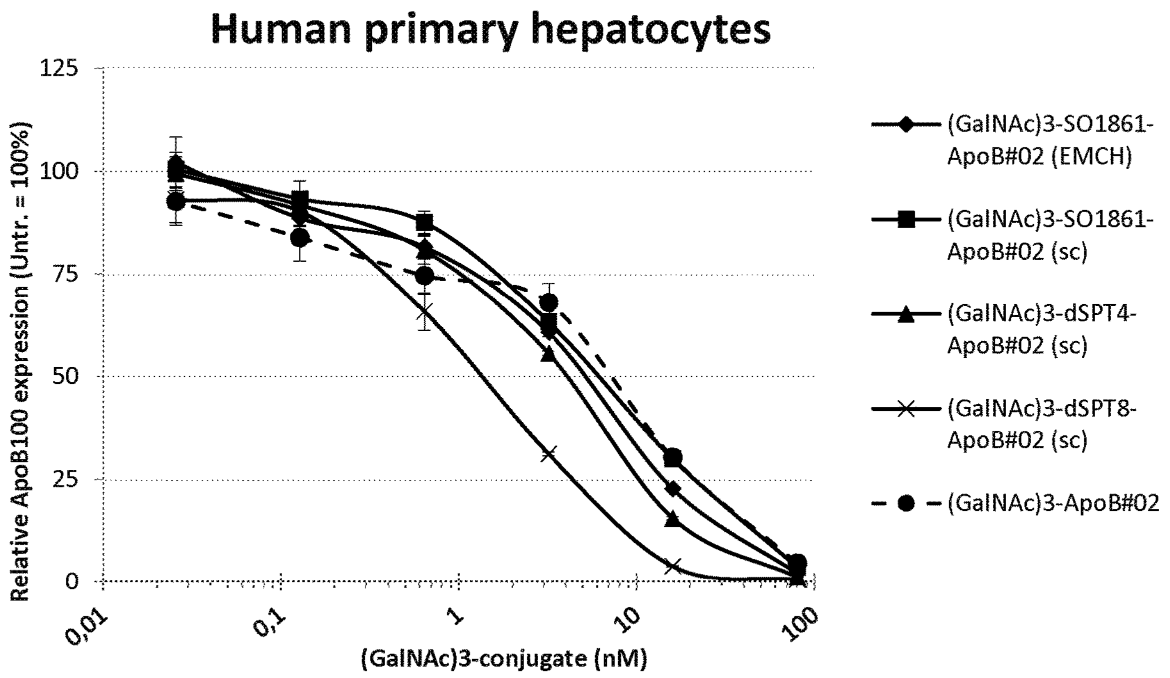
FIG. 24: ApoB expression analysis and cell viability assay on primary human hepatocytes for ApoB #02 conjugates

An apoB-targeting BNA, ApoB #02 (SEQ ID NO: 14), and SO1861-EMCH or SO1861-sc-Mal was conjugated to trivalent-GalNAc ((GalNAc)3) (FIG. 29, FIG. 30) to produce (GalNAc)3-SO1861-ApoB #02 (EMCH) (FIG. 31), (GalNAc)3-SO1861-ApoB #02 (sc) (FIG. 34), (GalNAc)3-d(SO1861)4-ApoB #02 (sc) (FIG. 35), (GalNAc)3-d(SO1861)8-ApoB #02 (sc) (FIG. 36, also named (GalNAc)3-dSPT8-ApoB #02)) and (GalNAc)3-ApoB #02 BNA (FIG. 38, (GalNAc)3-dSPT8-ApoB #02)) and conjugates were tested on primary human hepatocytes to assess their effect on apoB RNA levels. In primary hepatocytes, this assessment revealed that (GalNAc)3-d(SO1861)8-ApoB #02 (sc) showed an IC50 of 1.5 nM (relative conjugate concentration), whereas (GalNAc)3-SO1861-ApoB #02 (EMCH), (GalNAc)3-SO1861-ApoB #02 (sc), (GalNAc)3-d(SO1861)4-ApoB #02 (sc) or (GalNAc)3-ApoB #02 were less potent (IC50 between 5-8 nM) (FIG. 24). All this shows that increased numbers of SO1861 molecules per GalNAc conjugate enhances the potency of the conjugate thereby reducing the amounts of ApoB #02 BNA payload that is needed to reduce the levels of apoB mRNA. This is in favor of a broadened therapeutic window when the potency of the oligonucleotide is considered, under influence of an increased number of saponin moieties present in the conjugate comprising saponin, oligonucleotide and a target-cell ligand (GalNAc).

In Vivo Efficacy of $(GalNAc)_3$-SO1861-ApoB #02 in C57BL/6J Mice (Study B)

In study B, C57BL/6J mice were treated as described and dosed according to Table A6. The conjugates used in this study, (GalNAc)3-SO1861-ApoB #02 (sc), (GalNAc)3-d(SO1861)4-ApoB #02 (sc), (GalNAc)3-d(SO1861)8-ApoB #02 (sc), (GalNAc)3-ApoB #02 and (GalNAc)3-SO1861) were produced as described in FIG. 34, FIG. 35, FIG. 36, FIG. 37, FIG. 38 Clinical observations were recorded and different biomarkers of efficacy and tolerability were analysed.

Figure 25:
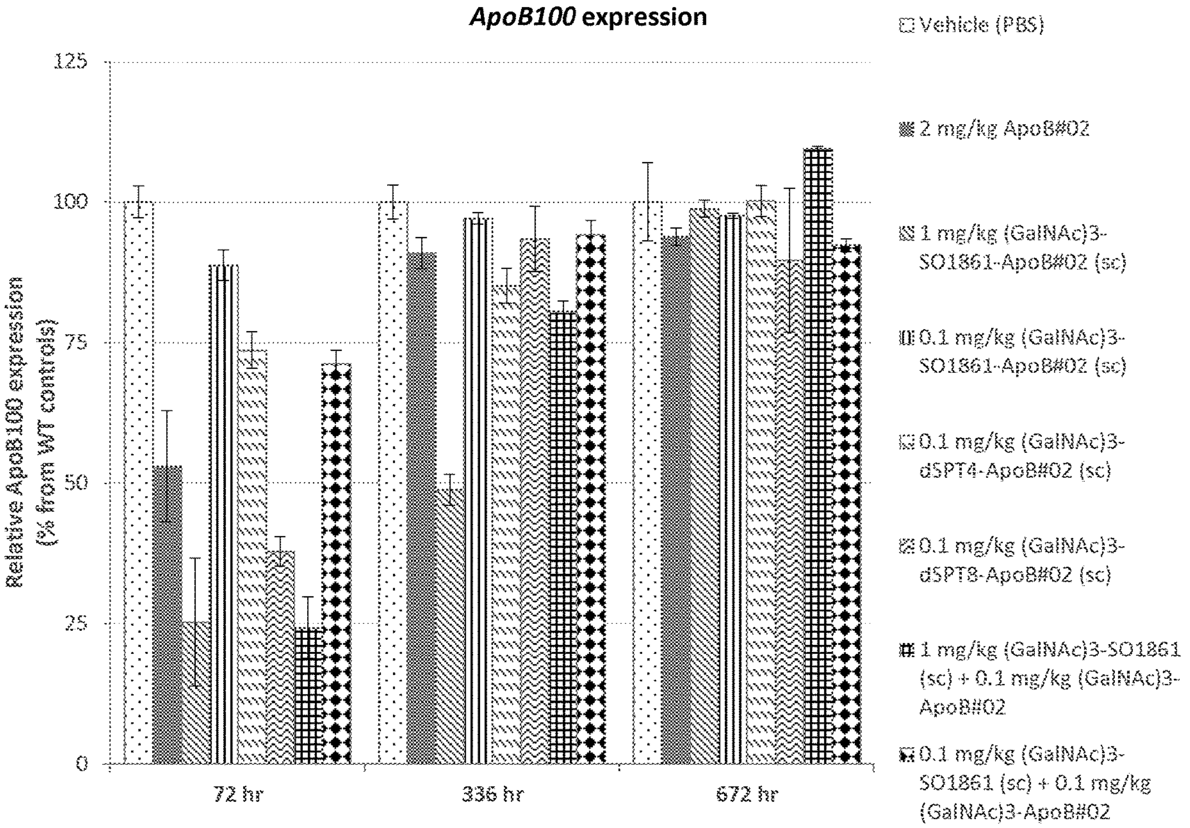
FIG. 25: Relative apoB expression analysis in liver tissue of C57BL/6J mice.

As FIG. 25 shows, after 72 hrs, the apoB RNA levels, i.e. gene expression, was reduced in animals treated with the benchmark 2 mg/kg ApoB #02 BNA (53% from control), but was even more reduced (to 24% and 21% of vehicle control, respectively) in the groups dosed with (1 mg/kg (GalNAc)3-ApoB #02+0.1 mg/kg (GalNAc)3-SO1861) and with 1 mg/kg (GalNAc)3-SO1861-ApoB #02 (sc), respectively, showing the markedly improved potency when adding SO1861 to the conjugate (n=3 animals per group). Moreover, when increasing the saponin-per-payload, by dosing 10-times less payload (0.173 mg/kg (GalNAc)3-d(SO1861)4-ApoB #02 (sc), (for brevity reasons, in the FIG. 25 the dose is displayed as 0.1 mg/kg) also named (GalNAc)3-dSPT4-ApoB #02 (sc) or 0.265 mg/kg (GalNAc)3-d(SO1861)8-ApoB #02 (sc), also named $GalNAc)_3$-dSPT8-ApoB #02 (sc)), corresponding to the same payload doses (i.e., 0.044 mg/kg ApoB #02 BNA) contained in 0.1 mg/kg (GalNAc)3-SO1861-ApoB #02 (sc), but 4-times and 8-times more SO1861, respectively, apoB expression was reduced to 74% and 38%, respectively, while it was 89% of control for 0.1 mg/kg (GalNAc)3-SO1861-ApoB #02 (sc), showing that an increase of saponin markedly increases potency of the conjugate. A decrease of saponin amount (0.1 mg/kg $(GalNAc)_3$-SO1861 (sc)+0.1 mg/kg (GalNAc)3-ApoB #02) yielded less potency (71% apoB expression compared to vehicle). After 336 hrs, the effect of expression downmodulation was still preserved in the 1 mg/kg (GalNAc)3-SO1861-ApoB #02 (sc) dose group and was 49% of vehicle control (n=3 mice).

Figure 26:
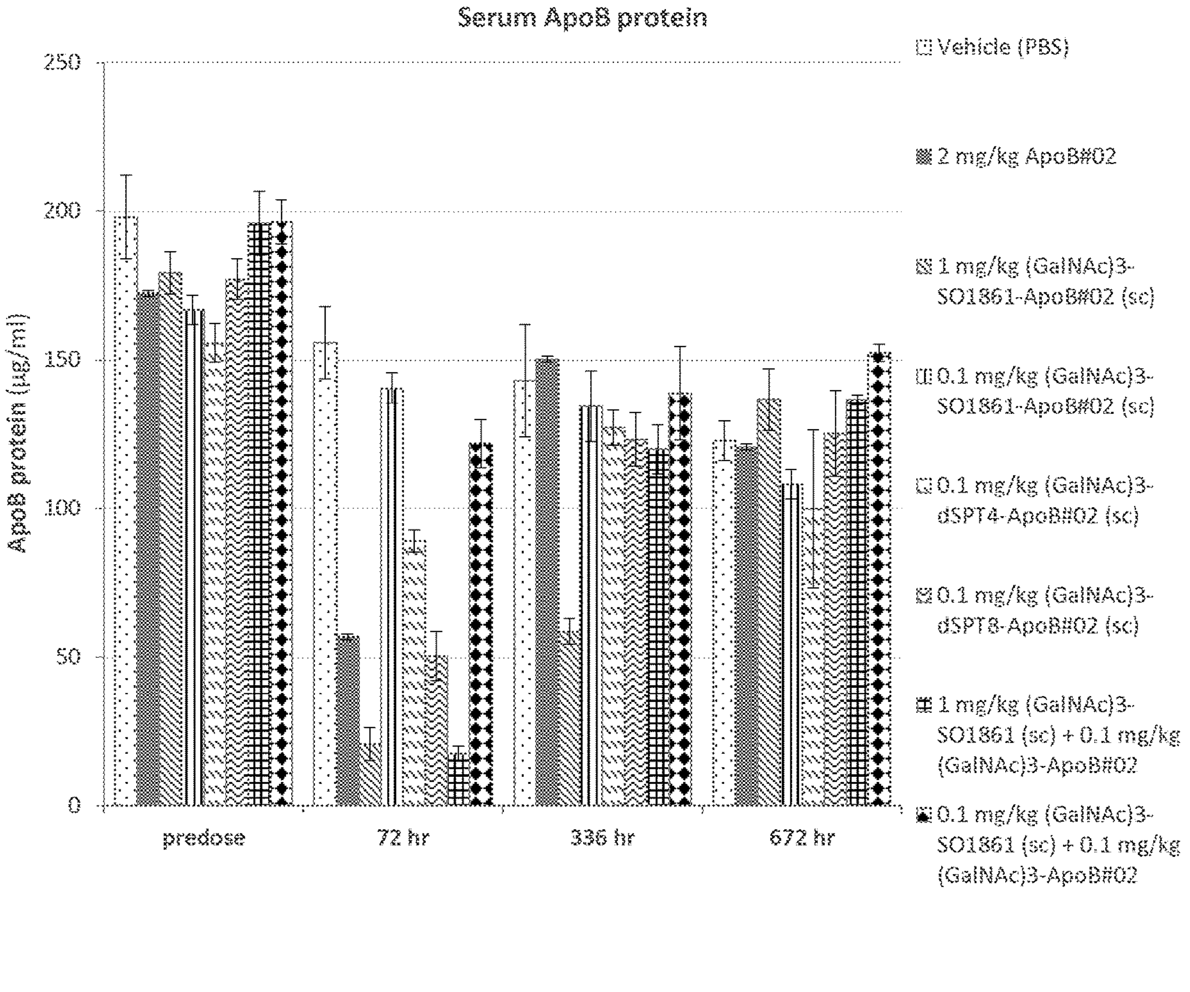
FIG. 26: Serum apoB protein analysis in C57BL/6J mice.

As FIG. 26 shows, the apoB RNA down-modulation in the liver (shown in FIG. 25) also translated to apoB protein reduction in serum. Predose levels ranged from 156-198 μg/ml over the groups (n=8 per group). At 72 hrs post-dose, the apoB protein levels were reduced in animals treated with the benchmark 2 mg/kg ApoB #02 BNA (57 μg/ml average compared to 156 μg/ml of the vehicle control), but was even more reduced (to 18 μg/ml and 21 μg/ml of vehicle control, respectively) in the groups dosed with (1 mg/kg (GalNAc)3-ApoB #02+0.1 mg/kg (GalNAc)3-SO1861) and with 1 mg/kg (GalNAc)3-SO1861-ApoB #02 (sc), respectively, showing the markedly improved potency when adding SO1861 to the conjugate (n=8 animals per group). As with the RNA levels, when increasing the saponin-per-payload, by dosing 0.173 mg/kg (GalNAc)3-d(SO1861)4-ApoB #02 (sc) or 0.265 mg/kg (GalNAc)3-d(SO1861)8-ApoB #02 (sc), respectively, serum apoB protein was reduced to 89 μg/ml and 50 μg/ml, respectively, while it was 141 μg/ml for 0.1 mg/kg (GalNAc)3-SO1861-ApoB #02 (sc), showing that an increase of saponin markedly increases potency of the conjugate in reducing apoB protein. A decrease of saponin amount (0.1 mg/kg (GalNAc)3-SO1861 (sc)+0.1 mg/kg (GalNAc)3-ApoB #02) yielded less potency (122 μg/ml apoB protein). After 336 hrs, the effect of protein reduction was still preserved in the 1 mg/kg (GalNAc)3-SO1861-ApoB #02 (sc) dose group and was 59 μg/ml, compared to 143 μg/ml in the vehicle control (n=5 mice in all groups); at 672 hrs, apoB protein levels varied between 100-152 μg/ml in all groups (n=2 mice).

Figure 27:
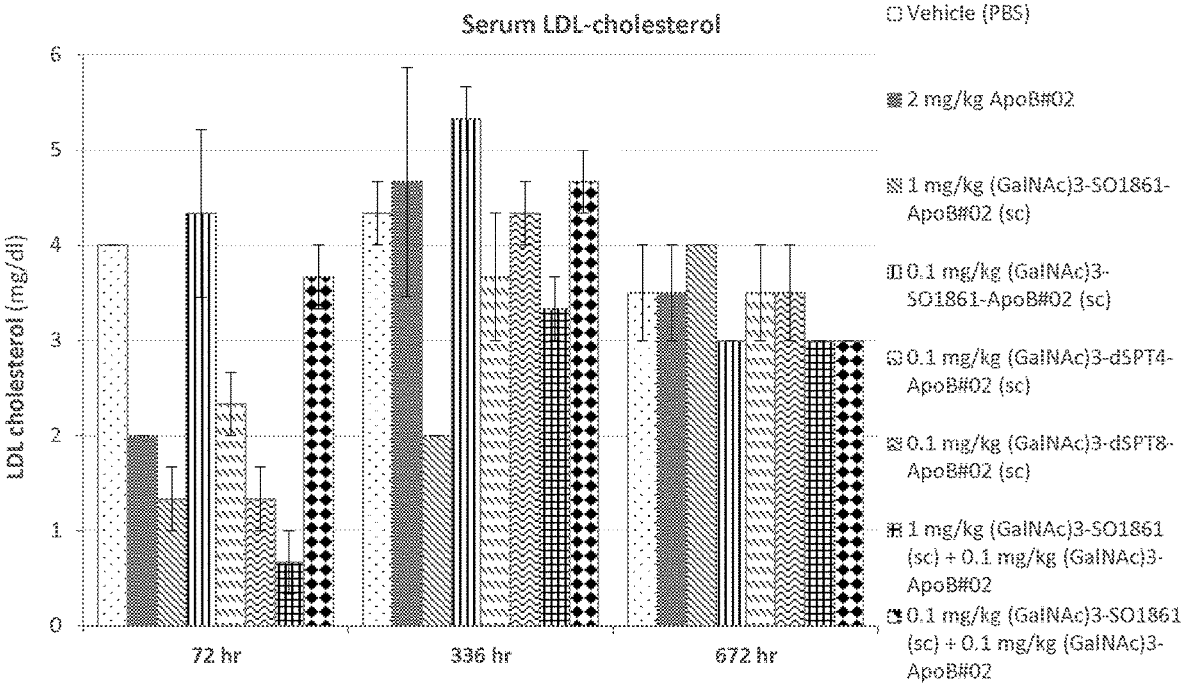
FIG. 27: Serum LDL-cholesterol (LDL-C) analysis in C57BL/6J mice.

As FIG. 27 shows, the observed serum apoB protein reduction (shown in FIG. 26) translated well to serum LDL-cholesterol (LDL-C) levels. At 72 hrs post-dose, the LDL-C levels were reduced in animals treated with the benchmark 2 mg/kg ApoB #02 BNA (2 mg/dl compared to 4 mg/dl of the vehicle control), but was even more reduced (to 0.7 mg/dl and 1.3 mg/dl μg/ml, respectively) in the groups dosed with (1 mg/kg (GalNAc)3-ApoB #02+0.1 mg/kg (GalNAc)3-SO1861) and with 1 mg/kg (GalNAc)3-SO1861-ApoB #02 (sc), respectively, showing the markedly improved potency when adding SO1861 to the conjugate (n=3 animals per group). As with the RNA and apoB protein levels, when increasing the saponin-per-payload, by dosing 0.173 mg/kg (GalNAc)3-d(SO1861)4-ApoB #02 (sc) or 0.265 mg/kg (GalNAc)3-d(SO1861)8-ApoB #02 (sc), respectively, LDL-C was reduced, to 2.3 mg/dl and 1.3 mg/dl, respectively, while it was 4.3 mg/dl for 0.1 mg/kg $(GalNAc)_3$-SO1861-ApoB #02 (sc), showing that an increase of saponin markedly increases potency of the conjugate in reducing LDL-C. A decrease of saponin amount (0.1 mg/kg $(GalNAc)_3$-SO1861 (sc)+0.1 mg/kg (GalNAc)3-ApoB #02) yielded less potency (3.7 mg/dl LDL-C). After 336 hrs, the effect of LDL-C reduction was still preserved in the 1 mg/kg (GalNAc)3-SO1861-ApoB #02 (sc) dose group (2 mg/dl; n=3 animals) and in the (1 mg/kg (GalNAc)3-ApoB #02+0.1 mg/kg (GalNAc)3-SO1861), where it was 3.3 mg/dl (n=3 animals). Showing the durability of the effect; at 672 hrs, LDL-C levels varied between 3-4 mg/dl in all grops (n=2 mice).

In conclusion, this shows that in combination with SO1861, the potency of ApoB #02 is markedly increased, and mostly for the SC-SO1861-containing conjugates, and is effectively inducing apoB RNA down-modulation, i.e., gene silencing in the livers of C57BL/6J mice, and of all 'downstream' serum biomarkers of efficacy measured, such as apoB protein and LDL-cholesterol.

In Vivo Tolerability of (GalNAc)3-SO1861-ApoB #02 in C57BL/6J Mice (Study B)

The conjugates used in this study, (GalNAc)3-SO1861-ApoB #02 (sc), (GalNAc)3-d(SO1861)4-ApoB #02 (sc), (GalNAc)3-d(SO1861)8-ApoB #02 (sc), (GalNAc)3-ApoB #02 and (GalNAc)3-SO1861) were produced as described in FIG. 34, FIG. 35, FIG. 36, FIG. 37, FIG. 38.

Figure 28:
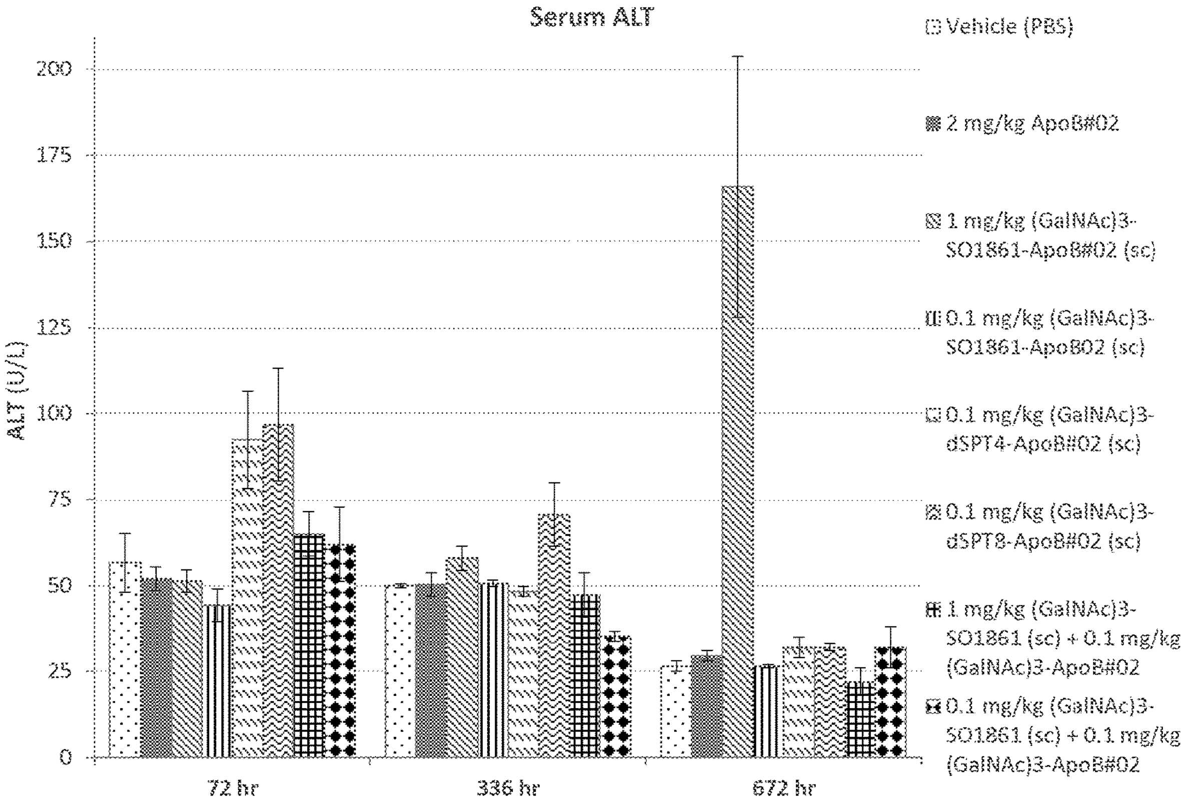
FIG. 28: Serum ALT analysis in C57BL/6J mice.

During the course of the study, all treatments, doses, and dose regimens as described in Table A6 were well tolerated and showed no treatment-specific adverse findings or any specific clinical observations or gross organ morphology indicative of the conjugates not being tolerated. The mice in treatment groups gained weight comparable to the mice receiving vehicle. Serum ALT levels were determined and results are shown in FIG. 28. Levels of ALT appeared to transiently increase in the 0.173 mg/kg (GalNAc)3-d(SO1861)4-ApoB #02 (sc) group at 72 hrs but returned to levels of vehicle control by 336 hrs post-dose; likewise, it increased in the 0.265 mg/kg (GalNAc)3-d(SO1861)4-ApoB #02 (sc) group, but returned to vehicle levels at later timepoints post-dose. Notably, 1 mg/kg (GalNAc)3-SO1861-ApoB #02 (sc) showed no elevation post-dose up to 336 hrs but was measured at 166 U/L at 672 hrs (n=2 mice).

In conclusion, this data shows that the saponin conjugates are well tolerated in the doses and dose regimen applied, and particularly, that administration of SO1861-containing conjugates (GalNAc)3-SO1861-ApoB #02 (sc), (GalNAc)3-d(SO1861)4-ApoB #02 (sc), and (GalNAc)3-d(SO1861)8-ApoB #02 (sc), as well as co-administration of (GalNAc)3-SO1861 with (GalNAc)3-ApoB #02 has no immediate tolerability issues, while showing high potency in the C57BL/6J mouse model.

The invention claimed is:

1. A saponin derivative based on a saponin comprising a triterpene aglycone core structure and at least one of a first saccharide chain '$R^1$' and a second saccharide chain '$R^2$' linked to the aglycone core structure, wherein the saponin derivative comprises an aglycone core structure comprising an aldehyde group, wherein the saponin on which the saponin derivative is based is a or bi-desmosidic triterpene saponin belonging to the type of a 12,13-dehydrooleanane with the aldehyde group in position C-23, and wherein the aldehyde group is transformed into a semicarbazone functional group according to formula (I)

(I)

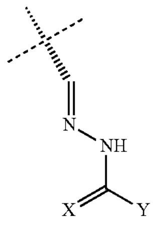

wherein:

$R^1$ and $R^2$ are independently selected from a monosaccharide, a linear oligosaccharide, and a branched oligosaccharide, X=O, P, or S, and Y=$NR^3R^4$, wherein $R^3$ and $R^4$ independently represent H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker; or

Y=

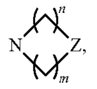

wherein n and m each are an integer independently selected from 1, 2, or 3,

Z=$CH_2$, O, S, P or $NR^5$, and wherein $R^5$ represents H, an unsubstituted C1-C10 straight chain, branched or cyclic alkyl, an unsubstituted C2-C10 straight chain, branched or cyclic alkenyl, an unsubstituted C2-C10 straight chain or branched alkynyl, or a covalently bound linker, or a maleimide moiety according to formula (II)a or formula (II)b (II)a

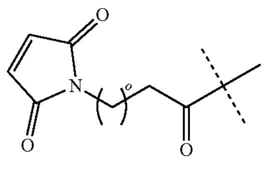

(II)b

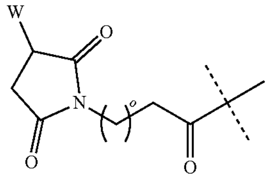

or an azide moiety according to formula (II)c (II)c

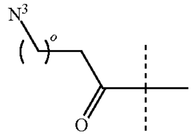

wherein o is an integer selected from 0-10, and W is a group according to formula (III)

(III)

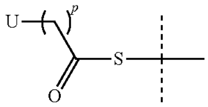

wherein U=SH, $NH_2$ or OH and p is an integer selected from 0-4.

2. The saponin derivative according to claim 1, wherein the saponin on which the saponin derivative is based comprises a glucuronic acid group in a carbohydrate substituent at the C-3beta-OH position of the saponin.

3. The saponin derivative according to claim 1, wherein:

Y=

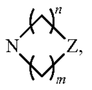

n and m each are an integer independently selected from 1, 2 or 3; and

Z=$CH_2$, O, S, P or $NR^5$; and wherein $R^5$ represents H, an unsubstituted C1-C10 straight chain, branched or cyclic alkyl, an unsubstituted C2-C10 straight chain, branched or cyclic alkenyl or an unsubstituted C2-C10 straight chain or branched alkynyl, or a covalently bound linker, or a maleimide moiety according to formula (II)a or formula (II)b (II)a

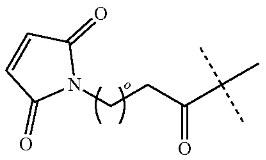

(II)b

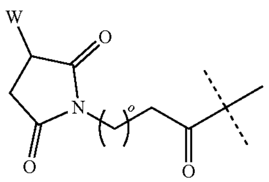

or an azide moiety according to formula (II)c (II)c

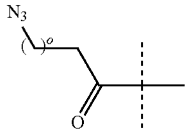

wherein o is an integer selected from 0-10 and W is a group according to formula (III)

(III)

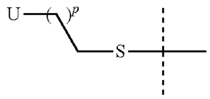

wherein U=SH, $NH_2$ or OH and p is an integer selected from 0-4.

4. The saponin derivative according to claim 1, wherein $R^1$ is selected from:

GlcA-,
Glc-,
Gal-,
Rha-(1→2)-Ara-,
Gal-(1→2)-[Xyl-(1→3)]-GlcA-,
Glc-(1→2)-[Glc-(1→4)]-GlcA-,
Glc-(1→2)-Ara-(1→3)-[Gal-(1→2)]-GlcA-,
Xyl-(1→2)-Ara-(1→3)-[Gal-(1→2)]-GlcA-,
Glc-(1→3)-Gal-(1→2)-[Xyl-(1→3)]-Glc-(1→4)-Gal-,
Rha-(1→2)-Gal-(1→3)-[Glc-(1→2)]-GlcA-,
Ara-(1→4)-Rha-(1→2)-Glc-(1→2)-Rha-(1→2)-GlcA-,
Ara-(1→4)-Fuc-(1→2)-Glc-(1→2)-Rha-(1→2)-GlcA-,
Ara-(1→4)-Rha-(1→2)-Gal-(1→2)-Rha-(1→2)-GlcA-,
Ara-(1→4)-Fuc-(1→2)-Gal-(1→2)-Rha-(1→2)-GlcA-,
Ara-(1→4)-Rha-(1→2)-Glc-(1→2)-Fuc-(1→2)-GlcA-,
Ara-(1→4)-Fuc-(1→2)-Glc-(1→2)-Fuc-(1→2)-GlcA-,
Ara-(1→4)-Rha-(1→2)-Gal-(1→2)-Fuc-(1→2)-GlcA-,
Ara-(1→4)-Fuc-(1→2)-Gal-(1→2)-Fuc-(1→2)-GlcA-,
Xyl-(1→4)-Rha-(1→2)-Glc-(1→2)-Rha-(1→2)-GlcA-,
Xyl-(1→4)-Fuc-(1→2)-Glc-(1→2)-Rha-(1→2)-GlcA-,
Xyl-(1→4)-Rha-(1→2)-Gal-(1→2)-Rha-(1→2)-GlcA-,
Xyl-(1→4)-Fuc-(1→2)-Gal-(1→2)-Rha-(1→2)-GlcA-,
Xyl-(1→4)-Rha-(1→2)-Glc-(1→2)-Fuc-(1→2)-GlcA-,
Xyl-(1→4)-Fuc-(1→2)-Glc-(1→2)-Fuc-(1→2)-GlcA-,
Xyl-(1→4)-Rha-(1→2)-Gal-(1→2)-Fuc-(1→2)-GlcA-,
Xyl-(1→4)-Fuc-(1→2)-Gal-(1→2)-Fuc-(1→2)-GlcA-, and
derivatives thereof, and $R^2$ is selected from:

Glc-,
Gal-,
Rha-(1→2)-[Xyl-(1→4)]-Rha-,
Rha-(1→2)-[Ara-(1→3)-Xyl-(1→4)]-Rha-,
Ara-,
Xyl-,
Xyl-(1→4)-Rha-(1→2)-[R1-(→4)]-Fuc- wherein R1 is 4E-Methoxycinnamic acid,
Xyl-(1→4)-Rha-(1→2)-[R2-(→4)]-Fuc- wherein R2 is 4Z-Methoxycinnamic acid,
Xyl-(1→4)-[Gal-(1→3)]-Rha-(1→2)-4-OAc-Fuc-,
Xyl-(1→4)-[Glc-(1→3)]-Rha-(1→2)-3,4-di-OAc-Fuc-,
Xyl-(1→4)-[Glc-(1→3)]-Rha-(1→2)-[$R^6$-(→4)]-3-OAc-Fuc- wherein $R^6$ is 4E-Methoxycinnamic acid,
Glc-(1→3)-Xyl-(1→4)-[Glc-(1→3)]-Rha-(1→2)-4-OAc-Fuc-,
Glc-(1→3)-Xyl-(1→4)-Rha-(1→2)-4-OAc-Fuc-,
(Ara- or Xyl-)(1→3)-(Ara- or Xyl-)(1→4)-(Rha- or Fuc-)(1→2)-[4-OAc-(Rha- or Fuc-)(1→4)]-(Rha- or Fuc-),
Xyl-(1→3)-Xyl-(1→4)-Rha-(1→2)-[Qui-(1→4)]-Fuc-,
Api-(1→3)-Xyl-(1→4)-[Glc-(1→3)]-Rha-(1→2)-Fuc-, Xyl-(1→4)-[Gal-(1→3)]-Rha-(1→2)-Fuc-,
Xyl-(1→4)-[Glc-(1→3)]-Rha-(1→2)-Fuc-,
Ara/Xyl-(1→4)-Rha/Fuc-(1→4)-[Glc/Gal-(1→2)]-Fuc-,
Api-(1→3)-Xyl-(1→4)-[Glc-(1→3)]-Rha-(1→2)-[$R^7$-(→4)]-Fuc- wherein $R^7$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^8$-(→4)]-Fuc- wherein $R^8$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[Rha-(1→3)]-4-OAc-Fuc-,
Api-(1→3)-Xyl-(1→4)-[Glc-(1→3)]-Rha-(1→2)-[Rha-(1→3)]-4-OAc-Fuc-,
6-OAc-Glc-(1→3)-Xyl-(1→4)-Rha-(1→2)-[3-OAc-Rha-(1→3)]-Fuc-,
Glc-(1→3)-Xyl-(1→4)-Rha-(1→2)-[3-OAc-Rha-(1→3)]-Fuc-,
Xyl-(1→3)-Xyl-(1→4)-Rha-(1→2)-[Qui-(1→4)]-Fuc-,
Glc-(1→3)-[Xyl-(1→4)]-Rha-(1→2)-[Qui-(1→4)]-Fuc-,
Glc-(1→3)-Xyl-(1→4)-Rha-(1→2)-[Xyl-(1→3)-4-OAc-Qui-(1→4)]-Fuc-,
Xyl-(1→3)-Xyl-(1→4)-Rha-(1→2)-[3,4-di-OAc-Qui-(1→4)]-Fuc-,
Glc-(1→3)-[Xyl-(1→4)]-Rha-(1→2)-Fuc-,
6-OAc-Glc-(1→3)-[Xyl-(1→4)]-Rha-(1→2)-Fuc-,
Glc-(1→3)-[Xyl-(1→3)-Xyl-(1→4)]-Rha-(1→2)-Fuc-,
Xyl-(1→3)-Xyl-(1→4)-Rha-(1→2)-[Xyl-(1→3)-4-OAc-Qui-(1→4)]-Fuc-,
Api/Xyl-(1→3)-Xyl-(1→4)-[Glc-(1→3)]-Rha-(1→2)-[Rha-(1→3)]-4OAc-Fuc-,
Api-(1→3)-Xyl-(1→4)-[Glc-(1→3)]-Rha-(1→2)-[Rha-(1→3)]-4OAc-Fuc-,
Api/Xyl-(1→3)-Xyl-(1→4)-[Glc-(1→3)]-Rha-(1→2)-[$R^9$-(→4)]-Fuc- wherein $R^9$ is 5-O-[5-O-Rha-(1→2)-Ara/Api-3,5-dihydroxy-6-methyl-octanoyl]-3,5-dihydroxy-6-methyl-octanoic acid), Api/Xyl-(1→3)-Xyl-(1→4)-[Glc-(1→3)]-Rha-(1→2)-[$R^{10}$-(→4)]-Fuc- wherein $R^{10}$ is 5-O-[5-O-Ara/Api-3,5-dihydroxy-6-methyl-octanoyl]-3,5-dihydroxy-6-methyl-octanoic acid),
Api/Xyl-(1→3)-Xyl-(1→4)-[Glc-(1→3)]-Rha-(1→2)-[$R^{11}$-(→4)]-Fuc- wherein $R^{11}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{12}$-(→4)]-Fuc- wherein $R^{12}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{13}$-(→4)]-Fuc- wherein $R^{13}$ is 5-O-[5-O-Ara/Api-3,5-dihydroxy-6-methyl-octanoyl]-3,5-dihydroxy-6-methyl-octanoic acid),
Api-(1→3)-Xyl-(1→4)-Rha-(1→2)-[$R^{14}$-(→3)]-Fuc- wherein $R^{14}$ is 5-O-[5-O-Ara/Api-3,5-dihydroxy-6-methyl-octanoyl]-3,5-dihydroxy-6-methyl-octanoic acid),
Xyl-(1→3)-Xyl-(1→4)-Rha-(1→2)-[$R^{15}$-(→3)]-Fuc- wherein $R^{15}$ is 5-O-[5-O-Ara/Api-3,5-dihydroxy-6-methyl-octanoyl]-3,5-dihydroxy-6-methyl-octanoic acid)
Glc-(1→3)-[Glc-(1→6)]-Gal-, and
derivatives thereof.

5. The saponin derivative according to claim 1, wherein the saponin derivative is a derivative of a saponin selected from the group of saponins consisting of: *Quillaja* bark saponin, NP-017777, NP-017778, NP-017774, NP-018110, NP-017772, NP-018109, NP-017888, NP-017889, NP-018108, SA1641, AE X55, NP-017674, NP-017810, AG1, NP-003881, NP-017676, NP-017677, NP-017706, NP-017705, NP-017773, NP-017775, SA1657, AG2, SO1861, GE1741, SO1542, SO1584, SO1658, SO1674, SO1832, SO1904, SO1862, QS-7, QS1861, QS-7 api, QS1862, QS-17, QS-18, QS-21 A-apio, QS-21 A-xylo, QS-21 B-apio, and QS-21 B-xylo.

6. The saponin derivative according to claim 1, wherein the saponin derivative is according to Molecule (V), Molecule (VII) or Molecule (VIII):

Molecule (V)

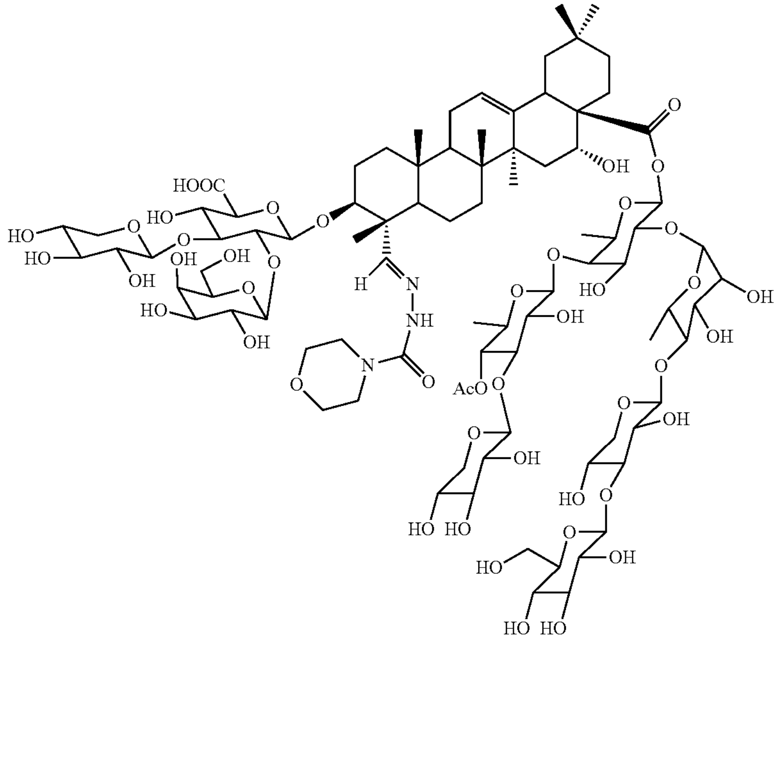

-continued
Molecule (VII)
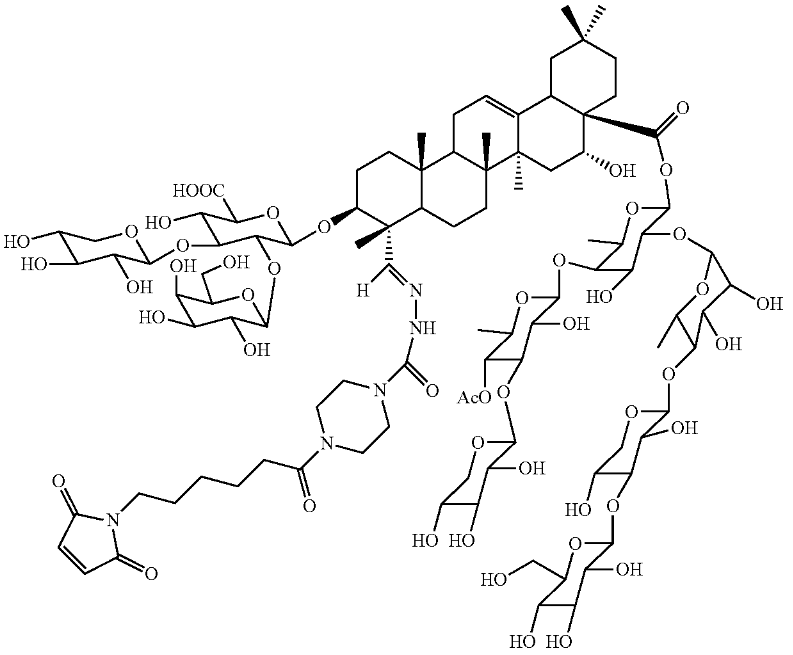
Molecule (VIII)
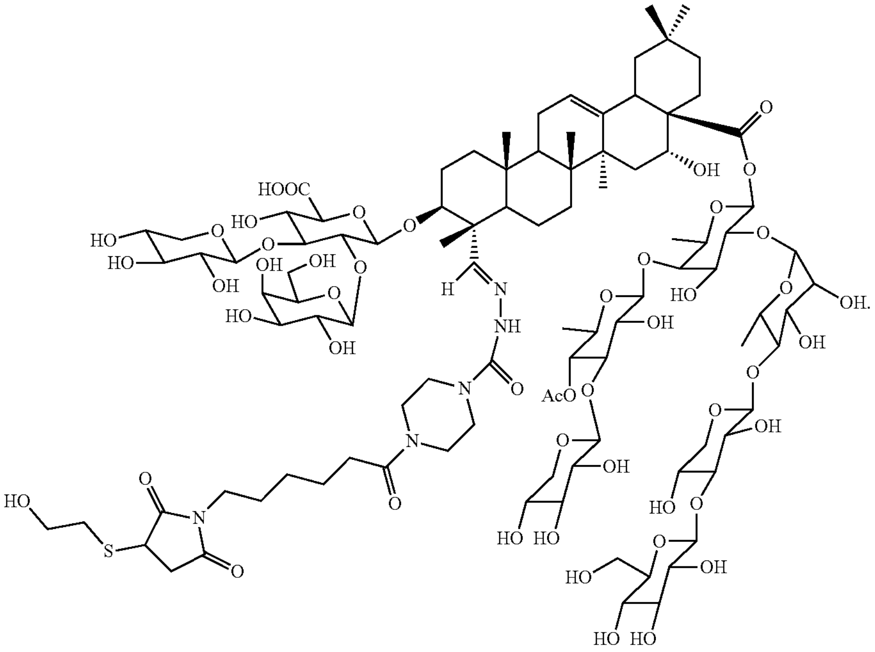

7. A first pharmaceutical composition comprising the saponin derivative according to claim 1.

8. A saponin conjugate based on a saponin derivative according to claim 1, wherein the aldehyde group is transformed into a semicarbazone group according to formula (IX)

(IX)

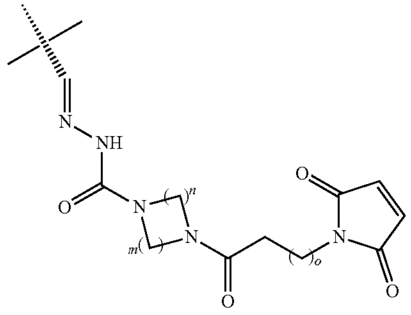

wherein n and m each are an integer independently selected from 1, 2, or 3;

o is an integer selected from 0-10;

and wherein the maleimide group is further transformed into a thioether bond through reaction with a first proteinaceous molecule ('proteinaceous molecule 1') comprising a thiol group according to formula (X)

(X)

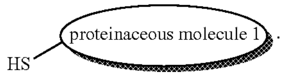

9. The saponin conjugate according to claim 8, wherein the proteinaceous molecule 1 comprises a cell-surface molecule binding-molecule comprising a first binding site for binding to a first epitope of a first cell-surface molecule.

10. The saponin conjugate according to claim 8, wherein the proteinaceous molecule 1 comprises a covalently bound effector moiety.

11. The saponin derivative according to claim 1, wherein the semicarbazone group of formula (I) is hydrolysable under acidic conditions, wherein hydrolysis of said semicarbazone group provides an aldehyde group.

* * * * *

SEQUENCE LISTING

<160> NUMBER OF SEQ ID NOS: 22

<210> SEQ ID NO 1
<211> LENGTH: 16
<212> TYPE: DNA
<213> ORGANISM: Artificial Sequence
<220> FEATURE:
<223> OTHER INFORMATION: Antisense BNA (HSP27) oligo nucleic acid sequence

<400> SEQUENCE: 1
ggcacagcca gtggcg 16

<210> SEQ ID NO 2
<211> LENGTH: 20
<212> TYPE: DNA
<213> ORGANISM: Artificial Sequence
<220> FEATURE:
<223> OTHER INFORMATION: HSP27 primer forward sequence

<400> SEQUENCE: 2
gcagtccaac gagatcacca 20

<210> SEQ ID NO 3
<211> LENGTH: 20
<212> TYPE: DNA
<213> ORGANISM: Artificial Sequence
<220> FEATURE:
<223> OTHER INFORMATION: HSP27 primer reverse sequence

<400> SEQUENCE: 3
taaggcttta cttggcggca 20

<210> SEQ ID NO 4
<211> LENGTH: 20
<212> TYPE: DNA
<213> ORGANISM: Artificial Sequence
<220> FEATURE:
<223> OTHER INFORMATION: HBMS primer forward sequence

<400> SEQUENCE: 4
cacccacaca cagcctactt 20

<210> SEQ ID NO 5
<211> LENGTH: 20
<212> TYPE: DNA
<213> ORGANISM: Artificial Sequence
<220> FEATURE:
<223> OTHER INFORMATION: HBMS primer reverse sequence

<400> SEQUENCE: 5
gtacccacgc gaatcactct 20

<210> SEQ ID NO 6
<211> LENGTH: 22
<212> TYPE: DNA
<213> ORGANISM: Artificial Sequence
<220> FEATURE:
<223> OTHER INFORMATION: GUSB primer forward sequence

<400> SEQUENCE: 6
gaaaatacgt ggttggagag ct 22

<210> SEQ ID NO 7
<211> LENGTH: 22
<212> TYPE: DNA

```
<213> ORGANISM: Artificial Sequence
<220> FEATURE:
<223> OTHER INFORMATION: GUSB primer reverse sequence

<400> SEQUENCE: 7

ccgagtgaag atccccttttt ta                                          22


<210> SEQ ID NO 8
<211> LENGTH: 20
<212> TYPE: DNA
<213> ORGANISM: Artificial Sequence
<220> FEATURE:
<223> OTHER INFORMATION: APOB BNA oligo

<400> SEQUENCE: 8

gcctcagtct gcttcgcacc                                              20


<210> SEQ ID NO 9
<211> LENGTH: 20
<212> TYPE: DNA
<213> ORGANISM: Artificial Sequence
<220> FEATURE:
<223> OTHER INFORMATION: APOB scrambled BNA oligo

<400> SEQUENCE: 9

ggcctctcta caccgctcgt                                              20


<210> SEQ ID NO 10
<211> LENGTH: 20
<212> TYPE: DNA
<213> ORGANISM: Artificial Sequence
<220> FEATURE:
<223> OTHER INFORMATION: HSP27 primer forward sequence

<400> SEQUENCE: 10

gcagtccaac gagatcacca                                              20


<210> SEQ ID NO 11
<211> LENGTH: 20
<212> TYPE: DNA
<213> ORGANISM: Artificial Sequence
<220> FEATURE:
<223> OTHER INFORMATION: HSP27 primer reverse sequence

<400> SEQUENCE: 11

taaggcttta cttggcggca                                              20


<210> SEQ ID NO 12
<211> LENGTH: 20
<212> TYPE: DNA
<213> ORGANISM: Artificial Sequence
<220> FEATURE:
<223> OTHER INFORMATION: ApoB primer forward sequence

<400> SEQUENCE: 12

agggtccggg aatctgatga                                              20


<210> SEQ ID NO 13
<211> LENGTH: 21
<212> TYPE: DNA
<213> ORGANISM: Artificial Sequence
<220> FEATURE:
<223> OTHER INFORMATION: ApoB primer reverse sequence

<400> SEQUENCE: 13

tgggcacgtt gtctttcaga g                                            21
```

<210> SEQ ID NO 14
<211> LENGTH: 13
<212> TYPE: DNA
<213> ORGANISM: Artificial Sequence
<220> FEATURE:
<223> OTHER INFORMATION: ApoB#02

<400> SEQUENCE: 14
gcattggtat tca 13

<210> SEQ ID NO 15
<211> LENGTH: 24
<212> TYPE: DNA
<213> ORGANISM: Artificial Sequence
<220> FEATURE:
<223> OTHER INFORMATION: ApoB#02 forward primer

<400> SEQUENCE: 15
gctaacacta agaaccagaa gatc 24

<210> SEQ ID NO 16
<211> LENGTH: 20
<212> TYPE: DNA
<213> ORGANISM: Artificial Sequence
<220> FEATURE:
<223> OTHER INFORMATION: ApoB#02 reverse primer

<400> SEQUENCE: 16
tgtccgtcta aggatcctgc 20

<210> SEQ ID NO 17
<211> LENGTH: 18
<212> TYPE: DNA
<213> ORGANISM: Artificial Sequence
<220> FEATURE:
<223> OTHER INFORMATION: Mm PPIA forward primer

<400> SEQUENCE: 17
gcggcaggtc catctacg 18

<210> SEQ ID NO 18
<211> LENGTH: 19
<212> TYPE: DNA
<213> ORGANISM: Artificial Sequence
<220> FEATURE:
<223> OTHER INFORMATION: Mm PPIA reverse primer

<400> SEQUENCE: 18
gccatccagc cattcagtc 19

<210> SEQ ID NO 19
<211> LENGTH: 20
<212> TYPE: DNA
<213> ORGANISM: Artificial Sequence
<220> FEATURE:
<223> OTHER INFORMATION: Mm SDHA forward primer

<400> SEQUENCE: 19
gaggaagcac accctctcat 20

<210> SEQ ID NO 20
<211> LENGTH: 20
<212> TYPE: DNA
<213> ORGANISM: Artificial Sequence
<220> FEATURE:

-continued

<223> OTHER INFORMATION: Mm SDHA reverse primer

<400> SEQUENCE: 20
ggagcggata gcaggaggta 20

<210> SEQ ID NO 21
<211> LENGTH: 20
<212> TYPE: DNA
<213> ORGANISM: Artificial Sequence
<220> FEATURE:
<223> OTHER INFORMATION: Mm RPS17 forward primer

<400> SEQUENCE: 21
gtgcgaggag atcgccatta 20

<210> SEQ ID NO 22
<211> LENGTH: 20
<212> TYPE: DNA
<213> ORGANISM: Artificial Sequence
<220> FEATURE:
<223> OTHER INFORMATION: Mm RPS17 reverse primer

<400> SEQUENCE: 22
atccgcttca tcagatgcgt 20